US011965001B2

(12) United States Patent
Piraner et al.

(10) Patent No.: US 11,965,001 B2
(45) Date of Patent: Apr. 23, 2024

(54) MODULAR DIMERIZATION THERMOSWITCHES AND RELATED MONOMERS, DIMERS, CONSTRUCTS, DIMERIC COMPLEXES, VECTORS, CELLS, SURFACES, DEVICES COMPOSITIONS, METHODS AND SYSTEMS

(71) Applicant: California Institute of Technology, Pasadena, CA (US)

(72) Inventors: Dan I. Piraner, San Francisco, CA (US); Mikhail Shapiro, Pasadena, CA (US)

(73) Assignee: California Institute of Technology, Pasadena, CA (US)

(*) Notice: Subject to any disclaimer, the term of this patent is extended or adjusted under 35 U.S.C. 154(b) by 378 days.

(21) Appl. No.: 16/927,590

(22) Filed: Jul. 13, 2020

(65) Prior Publication Data
US 2021/0040161 A1 Feb. 11, 2021

Related U.S. Application Data

(60) Provisional application No. 62/873,482, filed on Jul. 12, 2019.

(51) Int. Cl.
*C07K 14/255* (2006.01)

(52) U.S. Cl.
CPC ........ *C07K 14/255* (2013.01); *C07K 2319/73* (2013.01)

(58) Field of Classification Search
CPC ....... B01L 7/52; C12N 15/00; C12N 15/1055; C12N 15/63; C12N 15/8217; C12Q 1/6804; C12Q 1/6825; C12Q 2522/101; C12Q 2525/30; C12Q 2527/101; G01N 33/53; C07K 14/255; C07K 2319/73; C07K 17/00; C07K 2319/00
See application file for complete search history.

(56) References Cited

U.S. PATENT DOCUMENTS 9,284,562 B2 3/2016 Collins et al.
9,487,787 B2 11/2016 Wandless et al.
(Continued)

FOREIGN PATENT DOCUMENTS

CN 114401996 A 4/2022
EP 3997110 A1 5/2022
(Continued)

OTHER PUBLICATIONS

GenBank: EBL0439264.1, DZB26_25160, partial [*Salmonella enterica*], Submitted Aug. 10, 2018, 312 aa, also available at https://www.ncbi.nlm.nih.gov/protein/EBL0439264.1 (last visited Jul. 5, 2022) (Year: 2018).*
(Continued)

*Primary Examiner* — Randall L Beane
(74) *Attorney, Agent, or Firm* — Sheppard, Mullin, Richter & Hampton LLP

(57) ABSTRACT

Provided herein are thermomer monomer, thermomer dimers, thermomer monomeric constructs, thermomer dimeric complexes, and related gene expression cassette vectors, cells, surfaces devices, compositions methods and systems, that provide a thermobioswitch suitable to control location and/or binding of cargo moiety of interest in a temperature regulated manner.

10 Claims, 22 Drawing Sheets

Figure 1:
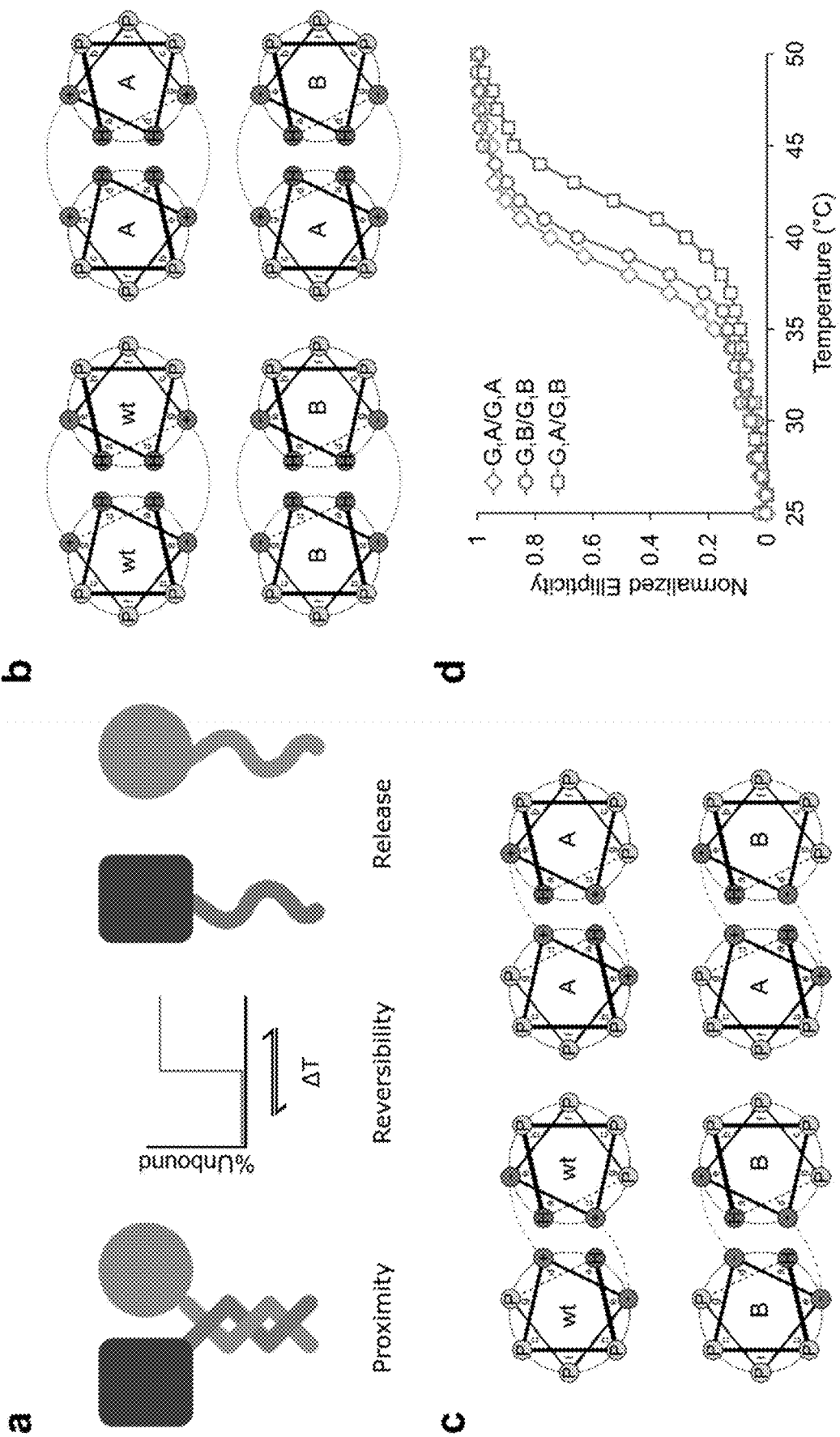

Specification includes a Sequence Listing.

(56) References Cited

U.S. PATENT DOCUMENTS

| | | | |
|---|---|---|---|
| 10,975,420 | B2* | 4/2021 | Shapiro ............... C12Q 1/6825 |
| 2007/0037133 | A1 | 2/2007 | Brott et al. |
| 2012/0252077 | A1 | 10/2012 | Figge et al. |
| 2013/0089903 | A1 | 4/2013 | Dischert et al. |
| 2015/0191735 | A1 | 7/2015 | Williams et al. |
| 2016/0312215 | A1 | 10/2016 | Murray et al. |
| 2016/0333326 | A1 | 11/2016 | Falb et al. |
| 2017/0232043 | A1 | 8/2017 | Falb et al. |
| 2017/0253862 | A1 | 9/2017 | Falb et al. |
| 2017/0298425 | A1* | 10/2017 | Shapiro ............... C12N 15/63 |
| 2018/0004890 | A1 | 1/2018 | Ganjam |
| 2021/0040161 | A1 | 2/2021 | Piraner et al. |
| 2021/0277453 | A1 | 9/2021 | Shapiro et al. |

FOREIGN PATENT DOCUMENTS

| | | |
|---|---|---|
| WO | 2011/130540 A1 | 10/2011 |
| WO | 2012/088461 A2 | 6/2012 |
| WO | 2016/098078 A2 | 6/2016 |
| WO | 2021/011474 A1 | 1/2021 |

OTHER PUBLICATIONS

GenBank: KUA86919.1, ncbi.nlm.gov, alpha-helical coiled-coil protein [*Salmonella enterica* subsp. *enterica* serovar Kentucky], 2 pages (Dec. 22, 2015), also available at https://www.ncbi.nlm.nih.gov/protein/KUA86919.1 (last visited Feb. 3, 2023) (Year: 2015).*

GenBank: AAA74964.1, NCBI.nlm.nih.gov/protein, TlpA [*Salmonella enterica* subsp. *enterica* serovar Typhimurium], 2 pages (Aug. 30, 1995), available at https://www.ncbi.nlm.nih.gov/protein/968911 (last visited Aug. 15, 2023); hereafter "AAA74964"). (Year: 1995).*

Ai, H.W., et al., "Hue-shifted monomeric variants of Clavularia cyan fluorescent protein: identification of the molecular determinants of color and applications in fluorescence imaging", BMC Biology 6, 13-25, (2008). 13 pages.

Al-Bataineh, O., et al., "Clinical and future applications of high intensity focused ultrasound in cancer", Cancer treatment reviews, 38(5), 346-353, 2012.

"Salt bridge (protein and supramolecular)" Wikipedia Definition. Accessed online on Jul. 27, 2020 on https://en.wikipedia.org/wiki/Salt_bridge_(protein_and_supramolecular). Pages.

Altschul, S.F., et al., "Gapped BLAST and PSI-BLAST: a new generation of protein database search programs." Nucleic Acids Research 25(17), 3389-3402, (1997). 14 pages.

Apostolovic, B., et al., "Coiled Coils: Attractive Protein Folding Motifs for the Fabrication of Self-Assembled, Responsive and Bioactive Materials," Chem. Soc. Rev. Feb. 23, 2010, 39, 3541-3575. https://doi.org/10.1039/b914339b.37 Pages.

Azuma, Y., et al., "Controlling leucine-zipper partner recognition in cells through modification of a-g Interactions," Chem Commun (Camb), 2014. 50(48): p. 6364-6367. 5 Pages.

Berggard, T., et al., "Methods for the Detection and Analysis of Protein-Protein Interactions," Proteomics, 2007, 7, 2833-2842. https://doi.org/10.1002/pmic.200700131.12 pages.

Berman, H.M., et al., "The Protein Data Bank." Acta Crystallographica Section D: Biological Crystallography 58(6), 899-907, (2002). 9 pages.

Bertram, R., et al., "The application of Tet repressor in prokaryotic gene regulation and expression." Microbial Biotechnology 1(1), 2-16, (2008). 15 pages.

Bohme, K., et al., "Concerted Actions of a Thermo-Labile Regulator and a Unique Intergenic RNA Thermosensor Control Yersinia Virulence." PLoS Pathogens 8(2), e1002518, (2012). Doi:10.1371/journal.ppat.1002518. 23 pages.

"Bioconjugation", Wikipedia Definition. Accessed on Jul. 23, 2020. 13 Pages. Available from :https://en.wikipedia.org/wiki/Bioconjugation.

Brenowitz, M., et al., "Quantitative DNase footprint titration: A method for studying protein-DNA interactions", Methods in Enzymology. vol. 130.; 1985:132-181. doi:10.1016/0076-6879(86)30011-9.

Bugaj, L. J., et al., "Optogenetic protein clustering and signaling activation in mammalian cells," Nature Methods, Published online Feb. 3, 2013, 10 (3), pp. 249-252. https://doi.org/10.1038/nmeth.2360. 7 Pages.

Carpenter, A.E., et al., "CellProfiler: image analysis software for identifying and quantifying cell phenotypes," Genome Biol, Oct. 31, 2006. 7(10): p. R100. 12 pages.

Casadesus, J., et al., "The virulence plasmids of *Salmonella*." International Microbiology 2(3), 177-184, (1999). Doi: 10.2436/im/v2i3.9210. 8 pages.

Chao, Y.P., et al., "Construction and characterization of thermo-inducible vectors derived from heat-sensitive lacI genes in combination with the T7 A1 promoter", Biotechnology and bioengineering, 79(1), 1-8, 2002.

Chappell, J., et al., "The centrality of RNA for engineering gene expression." Biotechnology Journal 8(12), 1379-1395, (2013). 18 pages.

Chen, X., et al., "Fusion Protein Linkers: Property, Design and Functionality." Advanced Drug Delivery Reviews 65(10), 1357-1369, (2013). 32 pages.

Cooper, T. M., et al., "The effect of conformation on the CD of interacting helices: A theoretical study of tropomyosin," Biopolymers, vol. 30, Issue 7-8, pp. 657-676. First Published in 1990. 21 Pages.

Cox, V. T., et al., "Specification of Individual Slouch Muscle Progenitors in *Drosophila* Requires Sequential Wingless Signaling," Development 2005, 132, 713-724. https://doi.org/10.1242/dev.01610. 13 Pages.

Dasika, M.S. et al. "OptCircuit: An optimization based method for computational design of genetic circuits", BMC Systems Biology, Mar. 3, 2008, 2:24 doi:10.1186/1752-0509-2-24. http://www.biomedcentral/1752-0509/2/24. 19 pages.

De Marco, A., et al., "Native folding of aggregation-prone recombinant proteins in *Escherichia coli* by osmolytes, plasmid- or benzyl alcohol-overexpressed molecular chaperones." Cell Stress & Chaperones 10(4), 329-339, (2005). 11 pages.

Debiec, K., et al., "Evaluating the Strength of Salt Bridges: A Comparison of Current Biomolecular Force Fields," *J. Phys. Chem. B*,2014, 118, 24, 6561-6569. Published on Apr. 5, 2014. Available online at https://pubs.acs.org/doi/10.1021/jp500958r. 9 Pages.

Deckers, R., et al., Image-guided, noninvasive, spatiotemporal control of gene expression. PNAS 106(4), 1175-1180, (2009). 6 pages.

Del Vecchio, D., Murray, R.M. "Biomolecular Feedback Systems", bfs-pupss, dated Jun. 13, 2014. 280 pages. Published 2015 by Princeton University Press, 6 Oxford Street, Woodstock, Oxfordshire OX20 ITW, United Kingdom.

Delviks, K.A., et al., "Effect of Distance between Homologous Sequences and 3' Homology on the Frequency of Retroviral Reverse Transcriptase Template Switching," *Journal of Virology*,1999. 73(10): p. 7923-7932. 11 Pages.

DeRose, R., et al., et al., "Manipulating Signaling at Will: Chemically-Inducible Dimerization (CID) Techniques Resolve Problems in Cell Biology," Pflügers Arch.—Eur. J Physiol. 2013, 465 (3), 409-417. https://doi.org/10.1007/s00424-012-1208-6. 10 Pages.

Dimaio, F. et al. "Refinement of Protein Structures into Low-Resolution Density Maps using Rosetta", J Mol Biol., Sep. 11, 2009, 392(1); 181-190. doi:10.1016/j.jmb.2009.07.008. 18 pages.

Drozdetskiy, A., et al., "JPred4: a protein secondary structure prediction server." Nucleic Acids Research 43, W389-W394, (2015). 6 pages.

Duplantis, Barry N. et al., Temperature-sensitive *Salmonella enterica* serovar enteritidis PT13a expressing essential proteins of psychrophilic bacteria, Applied and Environmental Microbiology, 2015, vol. 81, No. 19, pp. 6757-6766.

Elias, W.J., et al., "A Pilot Study of Focused Ultrasound Thalamotomy for Essential Tremor." New England Journal of Medicine 369(7), 640-648, (2013). 9 pages.

Elowitz, M.B., et al., A synthetic oscillatory network of transcriptional regulators. Nature 403(6767), 335-338, (2000). 4 pages.

(56) References Cited

OTHER PUBLICATIONS

Final Office Action for U.S. Appl. No. 15/384,254, filed Dec. 19, 2016 on behalf of California Institute of Technology dated Jun. 18, 2019 21 pages.
Fite, B.Z., et al., "Magnetic Resonance Thermometry at 7T for Real-Time Monitoring and Correction of Ultrasound Induced Mild Hyperthermia." PloS One 7(4), e35509, (2012). 10 pages.
Flynn, R.L., et al., "Oligonucleotide/Oligosaccharide-Binding Fold Proteins: A Growing Family of Genome Guardians." Critical Reviews in Biochemistry and Molecular Biology, 45(4), 266-275, (2010). 17 pages.
Gaitanaris, G., et al., Renaturation of Denatured λ Repressor Requires Heat Shock Proteins. Cell. 1990;61:1013-1020.
Gal-Mor, O., et al., "The temperature-sensing protein TlpA is repressed by PhoP and dispensable for virulence of *Salmonella enterica* serovar Typhimurium in mice." Microbes Infection 8(8), 2154-2162, (2006). Doi:10.1016/j.micinf.2006.04.015. 9 pages.
Ganguly, T., et al., "A Point Mutation at the C-Terminal Half of the Repressor of Temperate Mycobacteriophage L1 Affects Its Binding to the Operator DNA." Journal of Biochemistry and Molecular Biology 37(6), 709-714, (2004). 6 pages.
García-Quintanilla, M, et al., "Bile-Induced Curing of the Virulence Plasmid in *Salmonella enterica* Serovar Typhimurium." Journal of Bacteriology 188(22), 7963-7965, (2006). Doi: 10.1128/JB.00995-06. 3 pages.
Gardner, T.S., et al., "Construction of a genetic toggle switch in *Escherichia coli*." Nature 403(6767), 339-342, (2000). 4 pages.
Gelly, J.-C., et al., "iPBA: a tool for protein structure comparison using sequence alignment strategies." Nucleic Acids Research 39(suppl 2), W18-W23, (2011). 6 pages.
Greenfield, N.J., "Using circular dichroism collected as a function of temperature to determine the thermodynamics of protein unfolding and binding interactions," Nat Protoc, 2006. 1(6): p. 2527-2535. 10 pages.
Grigoryan, G., et al., "Structural specificity in coiled-coil interactions." Current Opinion in Structural Biology 18(4), 477-483, (2008). 13 pages.
Guilhon, E., et al., "Spatial and temporal control of Transgene expression in vivo using a heat-sensitive promoter and MRI-Guided Focused Ultrasound," J. Gene Med. 2003, 5(4), 333-342. https://doi.org/10.1002/jgm.345.11 Pages.
Haar, G.T. et al., "High intensity focused ultrasound: physical principles and devices", Int J Hyperthermia, 23(2), 89-104, 2007.
Heinrich, J., et al., "The cl repressor of bacteriophage P1 operator-repressor interaction of wild-type and mutant repressor proteins", Nucleic acids research, 17(19), 7681-7692, 1989.
Herbst, K., et al., "Intrinsic Thermal Sensing Controls Proteolysis of Yersinia Virulence Regulator RovA." PLoS Pathogens 5(5), e1000435, (2009). 16 pages.
Hoe, N.P., et al., "Temperature Sensing in Yersinia pestis: Translation of the LcrF Activator Protein is Thermally Regulated." Journal of Bacteriology 175(24), 7901-7909, (1993). 9 pages. http://www.pubmedcentral.nih.gov/articlerender.fcgi?artid=206968&tool=pmcentrez&rendertype=abstract.
Hooshangi, S., et al., "Ultrasensitivity and noise propagation in a synthetic transcriptional cascade." PNAS 102(10), 3581-3586, (2005). 6 pages.
"How Big is the Average Protein," downloaded from http://book.bionumbers.org/how-big-is-the-average-protein/ on Jul. 27, 2020. 6 Pages.
Hu, et al., "Sequence requirements for coiled-coils: analysis with repressor-GCN4 leucine zipper fusions", Science 250, 1400-1403, 1990.
Huang, D., et al., "A genetic bistable switch utilizing nonlinear protein degradation." Journal of Biological Engineering 6(9), p. 1, (2012). 13 pages.
Humphris, E.L., et al., "Prediction of Protein-Protein Interface Sequence Diversity Using Flexible Backbone Computational Protein Design." Structure 16(12), 1777-1788, (2008). 12 pages.
Hurme, R., et al., "A Proteinaceous Gene Regulatory Thermometer in *Salmonella*." Cell 90(1), 55-64, (1997). 10 pages.
Hurme, R., et al., "DNA Binding exerted by a bacterial gene regulator with an extensive coiled-coil domain", J Biol Chem, 271 (21), 12626-31. 1996. 8 pages.
Hurme, R., et al., "Intermediate filament-like network formed in vitro by a bacterial coiled coil Protein," *J Biol Chem*,1994. 269(14): p. 10675-10682. 9 Pages.
Ilinkin, I., et al., "Multiple structure alignment and consensus identification for proteins." BMC Bioinformatics 11(1), p. 71, (2010). 8 pages.
International Search Report and Written Opinion for International Application No. PCT/US2020/041812 filed on Jul. 13, 2020 on behalf of California Institute of Technology, dated Nov. 17, 2020. 11 pages.
Jensen, P.R., et al., "The use of lac-type promoters in control analysis." European Journal of Biochemistry 211(1-2), 181-191, (1993). 11 pages.
Justia Patent Search for U.S. Pat. No. 8,828,658. Published May 26, 2009, accessed on Jul. 27, 2020 on https://patents.justia.com/patent/8828658. 47 Pages.
Kamp, H.D., et al., "A Protein Thermometer Controls Temperature-Dependent Transcription of Flagellar Motility Genes in Listeria monocytogenes." PLoS Pathogens 7(8), e1002153, (2011). 15 pages.
Kawe, M., et al., "Facile promoter deletion in *Escherichia coli* in response to leaky expression of very robust and benign proteins from common expression vectors," *Microb Cell Fact*,2009. 8 (8), 1-8. https://doi.org/10.1186/1475-2859-8-8. 9 Pages.
Khalil et al. in "Synthetic biology: applications come of age" (Nature Reviews/Genetics, May 2010, vol. 11, pp. 367-379). (Year : 2010).
Klinkert, B., et al., "Microbial thermosensors", Cell Mol Life Sci 66(16), 2661-2676, (2009), doi:10.1007/s00018-009-0041-3.
Kortmann, J., et al., "Translation on demand by a simple RNA-based thermosensor." Nucleic Acids Research 39(7), 2855-2868. (2011). Doi:10.1093/nar/gkq1252. 14 pages.
Koski, P., et al., "A New alpha-Helical Coiled Coil Protein Encoded by the *Salmonella typhimurium* Virulence Plasmid." Journal of Biological Chemistry 267(17), 12258-12265, (1992). 8 pages.
Kotula, J.W., et al., "Programmable bacteria detect and record an environmental signal in the mammalian gut." PNAS111(13), 4838-4843, Apr. 1, 2014. Doi:10.1073/pnas.1321321111. 6pages.
Krajewski, S. S., et al., "Temperature-Driven Differential Gene Expression by RNA Thermosensors," *Biochim. Biophys. Acta—Gene Regul. Mech*.Mar. 21, 2014, 1839(10), 978-988. https://doi.org/10.1016/j.bbagrm.2014.03.006.12 Pages.
Kuhlman, B., et al., "Design of a Novel Globular Protein Fold with Atomic-Level Accuracy." Science 302(5649), 1364-1368, (2003). 6 pages.
Kyte, J, et al., "A Simple Method for Displaying the Hydropathic Character of a Protein." Journal of Molecular Biology 157(1), 105-132, (1982). 28 pages.
Lam, K.S., "Mini-review. Application of combinatorial library methods in cancer research and drug discovery." Anti-Cancer Drug Design 12(3), 145-167, (1997). 23 pages.
Laub M. et al., "Genes directly controlled by CtrA, a master regulator of the Caulobacter cell cycle" *PNAS*, vol. 99, No. 7, 4632-4637. Apr. 2002 6 pages.
Lauck, F., et al., "RosettaBackrub—a web server for flexible backbone protein structure modeling and design." Nucleic Acids Research 38(suppl 2), W569-W575, (2010). 7 pages.
Liu, R. Y., et al. "Regulation of Chemical Stress-Induced Hsp70 Gene Expression in Murine L929 Cells," *J.Cell Sci*.1994, 107, 2209-2214. 7 Pages.
Lohse, M.B., et al., "Identification and characterization of a previously undescribed family of sequence-specific DNA-binding domains." PNAS 110(19), 7660-7665, (2013). 6 pages.
Love, C.A., et al., "Stable high-copy-number bacteriophage lambda promoter vectors for overproduction of proteins in *Escherichia coli*", Gene. 1996;176(1-2):49-53. doi:10.1016/0378-1119(96)00208-9.
Lupas, A., et al., "Predicting Coiled Coils from Protein Sequences." Science 252(5009), 1162-1164, (1991). 3 pages.

(56) References Cited

OTHER PUBLICATIONS

Lutz, R., et al., "Independent and tight regulation of transcriptional units in *Escherichia coli* via the LacR/O, the TetR/O and AraC/I1-I2 regulatory elements." Nucleic Acids Research 25(6), 1203-1210, (1997). Doi:10.1093/nar/25.6.1203. 8 pages.
Maiti, R., et al., "SuperPose: a simple server for sophisticated structural superposition." Nucleic Acids Research 32(suppl 2), W590-W594, (2004). 5 pages.
Mangan, S., et al., "Structure and function of the feed-forward loop network motif." PNAS 100(21): p. 11980-11985, (2003). 6 pages.
Marr, M.T., et al., "Promoter recognition as measured by binding of polymerase to nontemplate strand oligonucleotide", Science, 276(5316), 1258-60, 1997.
Mason, J.M., et al., "Coiled coil domains: stability, specificity, and biological Implications," ChemBioChem, 2004. 5(2): p. 170-176. 8 Pages.
Mastop, M., et al., "Characterization of a spectrally diverse set of fluorescent proteins as FRET acceptors for mTurquoise2," Sci Rep, 2017. 7(1): p. 11999. 19 pages.
McCabe, K.M., et al., "LacI(Ts)-Regulated Expression as an In Situ Intracellular Biomolecular Thermometer." Applied Environmental Microbiology 77(9), 2863-2868, (2011). 6 pages.
McDannold, N., et al., "MRI Investigation of the Threshold for Thermally Induced Blood-Brain Barrier Disruption and Brain Tissue Damage in the Rabbit Brain." Magnetic Resonance in Medicine 51(5), 913-923, (2004). 11 pages.
McDannold, N.J., et al., "Usefulness of MR Imaging-Derived Thermometry and Dosimetry in Determining the Threshold for Tissue Damage Induced by Thermal Surgery in Rabbits 1", Radiology 216(2), 517-523, 2000.
McDonnell, A.V., et al., "Paircoil2: improved prediction of coiled coils from sequence." Bioinformatics 22(3), 356-358, (2006). 3 pages.
Moser, B. A., et al., "A Photoactivatable Innate Immune Receptor for Optogenetic Inflammation," ACS Chem. Biol. 2017, 12 (2), 347-350. https://doi.org/10.1021/acschembio.6b01012. 5 pages.
Muller, K. M., et al., "Protein Fusions to Coiled-Coil Domains," *In Methods in Enzymology*;2000; vol. 328, pp. 261-282. https://doi.org/10.1016/S0076-6879(00)28402-4. 23 pages.
Muthuswamy, S. K., "Controlled Dimerization of ErbB Receptors Provides Evidence for Differential Signaling by Homo- and Heterodimers," Mol. Cell. Biol. Oct. 1999, 19 (10), 6845-6857. 14 Pages.
Myers, C.J. et al. "iBioSim: a tool for the analysis and design of genetic circuits", Bioinformatics, vol. 25, No. 21, 2009, pp. 2848-2849. Doi:10.1093/bioinformatics/btp457.
Neupert, J., et al., Design of simple synthetic RNA thermometers for temperature controlled gene expression in *Escherichia coli*. Nucleic Acids Research 36(19), e124, (2008). Doi:10.1093/nar/gkn545. 9 pages.
Niederholtmeyer, H., Sun, Z.Z., et al. "Rapid cell-free forward engineering of novel genetic ring oscillators", eLIFE, Research Article Oct. 2, 2015, doi: 10.7554.eLife.09771. Downloaded: Dec. 15, 2019. 59 pages.
Non-Final Office Action for U.S. Appl. No. 15/384,254, filed Dec. 19, 2016 on behalf of California Institute of Technology dated May 29, 2020 26 pages.
Non-Final Office Action for U.S. Appl. No. 15/384,254, filed Dec. 19, 2016, on behalf of California Institute of Technology, dated Sep. 10, 2018. 25 pgs.
Notice of Allowance for U.S. Appl. No. 15/384,254, filed Dec. 19, 2016, on behalf of California Institute of Technology, dated Dec. 11, 2020. 12 Pages.
Pabo, C.O., et al., "The operator-binding domain of lambda repressor: structure and DNA recognition", Nature, 298, 443-447, 1982.
Patyar, S., et al., "Bacteria in cancer therapy: a novel experimental strategy." Journal of Biomedical Science 17, p. 21, (2010). 9 pages.
Pinero-Lambea, C., et al., "Engineered bacteria as therapeutic agents", Curr Opin Biotechnol. 2015;35:94-102. doi:10.1016/j.copbio.2015.05.004.
Piraner, D. I., et al., Going Deeper: Biomolecular Tools for Acoustic and Magnetic Imaging and Control of Cellular Function. Biochemistry 2017, 56 (39), pp. 5202-5209. https://doi.org/10.1021/acs.biochem.7b00443. 9 Pages.
Piraner, D. I., et al., "Modular Thermal Control of Protein Dimerization, "Publicly posted on Jul. 13, 2019. 7 Pages. bioRxiv preprint doi: //doi.org/10.1101/694448.
Piraner, D. I., et al., "Tunable Thermal Bioswitches for in Vivo Control of Microbial Therapeutics," Nat. Chem. Biol.2017, 13 (1), 75-80. https://doi.org/10.1038/nchembio.2233. 9 pages.
Piraner, D.I., et al., "Tunable thermal bioswitches for in vivo control of microbial therapeutics." Nature Chemical Biology, (2016). 13 pages. (Note: doi:10.1038/NCHEMBIO.2233).
Pogorzala, L., et al., "The Cellular Code for Mammalian Thermosensation." The Journal of Neuroscience 33(13), 5533-5541, (2013). Doi:10.1523/JNUEROSCI.5788-12.2013. 9 pages.
Pritchard, M.T., et al., "Protocols for simulating the thermal component of fever: preclinical and clinical experience", Methods 32(1), 54-62, 2004.
Renfrew, P.D., et al., "Incorporation of Noncanonical Amino Acids into Rosetta and Use in Computational Protein-Peptide Interface Design." PLoS One 7(3), e32637, (2012). 15 pages.
Restriction Requirement for U.S. Appl. No. 15/384,254, filed Dec. 19, 2016, on behalf of California Institute of Technology, dated Jan. 25, 2018. 9 pages.
Rohl, C.A. et al "[4] Protein Structure Prediction Using Rosetta" Methods in Enzymology, vol. 383, 2004, pp. 66-93.
Rosetta Commons: The hub for Rosetta modeling software. Sep. 29, 2015. 16 pages. http://www.rosettacommons.org.
Royal, D. C., et al., "Temperature-Sensitive Mutant of the Caenorhabditis Elegans Neurotoxic MEC-4(d) DEG/ENaC Channel Identifies a Site Required for Trafficking or Surface Maintenance," J. Biol. Chem. Dec. 23, 2005, 280 (51), 41976-41986. https://doi.org/10.1074/jbc.M510732200. 13 Pages.
Rudaya, A.Y., et al., "Thermoregulatory responses to lipopolysaccharide in the mouse: dependence on the dose and ambient temperature." American Journal of Physiology—Regulatory, Integrative and Comparative Physiology 289(5), R1244-1252, (2005). 9 pages.
Sadeghi, S. et al., Length-dependent force characteristics of coiled coils. Physical Review E, 80, 061909, 2009. 061909-1 to 061909-9.
Scott, M. et al. "Deterministic characterization of stochastic genetic circuits" PNAS, vol. 104, No. 18, May 1, 2007, pp. 7402-7407.
Servant, P., et al., "The RheA repressor is the thermosensor of the HSP18 heat shock response in Streptomyces albus." PNAS 97(7), 3538-3543, (2000). 6 pages.
Shaner, N.C., et al., "Improved monomeric red, orange and yellow fluorescent proteins derived from *Discosoma* sp. red fluorescent protein." Nature Biotechnology 22(12), 1567-1572, (2004). 6 pages.
Shin, J., et al., "An *E. coli* cell-free expression toolbox: application to synthetic gene circuits and artificial cells", ACS Synth Biol, 1(1), 29-41, 2012.
Silva, F., et al.,"Evaluating metabolic stress and plasmid stability in plasmid DNA production by *Escherichia coli*.," Biotechnol Adv, 2012. 30(3): p. 691-708. 19 Pages.
Skurnik M., et al., LcrF is the Temperature-Regulated Activator of the yadA Gene of Yersinia enterocolitica and Yersinia pseudotuberculosis. Journal of Bacteriology 174(6), 2047-2051, (1992). 5 pages. http://www.pubmedcentral.nih.gov/articlerender.fcgi?artid=206968&tool=pmcentrez&rendertype=abstract.
Spencer, D. M., et al., "Controlling Signal Transduction with Synthetic Ligands," Science, 1993, 262 (5136), 1019-1024. 8 Pages.
Sprinzak, D. et al. "Reconstruction of genetic circuits" Nature, vol. 438, Nov. 24, 2005, pp. 443-448.
Stayrook, S., et al., "Crystal structure of the lambda repressor and a model for pairwise cooperative operator binding." Nature 452, 1022-1025, (2008). 5 pages.
Steidler, L., et al., "Treatment of Murine Colitis by Lactococcus lactis Secreting Interleukin-10." Science (80- ) 289(5483), 1352-1355, (2000). Doi:10.1126/science.289.5483.1352. 4 pages.
Storz in "An RNA thermometer" (Genes & Development 1999 vol. 13 : pp. 633-636). (Year : 1999).

(56) References Cited

OTHER PUBLICATIONS

Tan et al in "An essential transcription factor, SciP, enhances robustness of Caulobacter cell cycle regulation" PNAS, vol. 107, No. 44, 18985-18990. Nov. 2, 2010. 7 pages.
"Stoke's Law" Wikipedia Definition. Accessed on Jul. 27, 2020 from https://en.wikipedia.org/wiki/Stokes%27_law. 7 Pages.
Tripet, B., et al.,"Engineering a de novo-designed coiled-coil heterodimerization domain for the rapid detection, purification and characterization of recombinantly expressed peptides and proteins," *Protein Eng*,1996. 9(11): p. 1029-1042. 16 pages.
Valdez-Cruz, N.A.., et al., "Production of recombinant proteins in *E. coli* by the heat inducible expression system based on the phage lambda pL and/or pR promoters." Microbial Cell Factories 9, p. 18, (2010). 16 pages.
Vincent, T.L., et al., "Logicoil—multi-state prediction of coiled-coil oligomeric state." Bioinformatics 29(1), 69-76, (2013). 8 pages.
Vogel, J., et al., "Temperature-Sensitive Mutations in the Bacteriophage Mu c Repressor Locate a 63-Amino-Acid DNA-Binding Domain." Journal of Bacteriology 173(20), 6568-6577, (1991). 10 pages.
Waldminghaus, T., et al., "Generation of synthetic RNA-based thermosensors." Biological Chemistry 389(10), 1319-1326, (2008). Doi:10.1515/BC.2008.150. 9 pages.
Weiss, R., et al., "Genetic circuit building blocks for cellular computation, communciations, and signal processing." Natural Computing 2(1), 47-84, (2003). Doi:10.1023/A:1023307812034. 38 pages.
Wielgus-Kutrowska, B., et al., "Folding and unfolding of a non-fluorescent mutant of green fluorescent protein." Journal of Physics: Condensed Matter 19(28), 285223, (2007). 9 pages.
Wilson, C.J., et al., "The lactose repressor system: paradigms for regulation, allosteric behavior and protein folding", Cell Mol Life Sci, 64(1), 3-16, 2007.
Wissmann, A., et al., "Selection of Tn10 Tet Repressor Binding to tet Operator in *Escherichia coli*: Isolation of Temperature-Sensitive Mutants and Combinatorial Mutagenesis in the DNA Binding Motif." Genetics 128(2), 225-232, (1991). 8 pages.
Wood, C.W., et al., "CCBuilder: an interactive web-based tool for building, designing and accessing coiled-coil protein assemblies", Bioinformatics, vol. 30, No. 21, 2014, pp. 3029-3035. Doi: 10.1093/bioinformatics/btu502.
Woolley, G. A., et al. "Reversible photocontrol of DNA binding by a designed GCN4-bZIP protein." Biochemistry 45(19): 6075-6084. 2006. 11 pages.
Written Opinion for International Application No. PCT/US2020/041812 filed on Jul. 13, 2020 on behalf of California Institute of Technology dated Nov. 17, 2020 5 pages.
Wu, C.-Y., et al. "Remote Control of Therapeutic T Cells through a Small Molecule-Gated Chimeric Receptor," Science, Oct. 16, 2015, 350 (6258). https://doi.org/10.1126/science.aab4077.13 Pages.
Wu, C.-Y., et al., "Synthetic Biology Approaches to Engineer T Cells". Curr. Opin. Immunol. 2015, 35, 123-130. https://doi.org/10.1016/j.coi.2015.06.015. 9 pages.
Ye, Y., et al., "Flexible structure alignment by chaining aligned fragment pairs allowing twists." Bioinformatics 19(suppl 2), ii246-ii255, (2003). 10 pages.
Yuzawa, S., et al., "Activating an Enzyme by an Engineered Coiled Coil Switch," Chem. Eur. J. 2006, 12, 7345-7352. https://doi.org/10.1002/chem.200600007. 9 pages.
Zhao, K., et al., "The Global Transcriptional Response of *Escherichia coli* to Induced Sigma32 Protein Involves Sigma32 Regulon Activation Followed by Inactivation and Degradation of Sigma32 in Vivo." The Journal of Biological Chemistry 280(18), 17758-17768, (2005). 12 pages.
Zhou, NE., et al., "Synthetic model proteins: the relative contribution of leucine residues at the nonequivalent positions of the 3-4 hydrophobic repeat to the stability of the two-stranded alpha-helical coiled-coil." *Biochemistry*,1992, 31, 5739-5746. 9 Pages.

Zong, C., et al. "Lysogen stability is determined by the frequency of activity bursts from the fate-determining gene" Molecular Systems Biology, 6, Article No. 440, pp. 1-12, 2010. doi:10.1038/msb.2010.96.
Dan Piraner, "Thesis: Tunable Thermal Bioswitches as a Control Modality for Next Generation Therapeutics", Caltech Institute of Technology, Defended Feb. 26, 2019. 190 pages.
Dan Piraner, "Tunable Thermal Bioswitches for In Vivo Control of Cell-Based Therapeutics", Presented on Sep. 22, 2018 at Society for Biological Engineering Cell Therapies and Bioengineering Conference. 11 pages.
Aronsson, C., et al., "Self-sorting heterodimeric coiled coil peptides with defined and tuneable self-assembly properties," Sci. Rep. 5, 14063; doi: 10.1038/srep14063. 2015. 10 Pages.
International Preliminary Report on Patentability for International Application No. PCT/US2020/041812 filed on Jul. 13, 2020 on behalf of California Institute of Technology, dated Jan. 27, 2022. 8 Pages.
Thermo Scientific Crosslinking Technical Handbook: Easy Molecular Bonding Crosslinking Technology. Thermo Scientific, 2012. 56 Pages.
Thompson, K. E., et al., "SYNZIP Protein Interaction Toolbox: in Vitro and in Vivo Specifications of Heterospecific Coiled-Coil Interaction Domains," *ACS Synth. Biol.* 2012, 1, 4, 118-129, Feb. 2, 2012. Website: doi.org/10.1021/sb200015u.
Ai, Hui-wang, et al. "Hue-shifted monomeric variants of Clavularia cyan fluorescent protein: identification of the molecular determinants of color and applications in fluorescence imaging." BMC biology 6 (2008): 1-13.
Duplantis, Barry N., et al. "Temperature-sensitive *Salmonella enterica* serovar enteritidis PT13a expressing essential proteins of psychrophilic bacteria." Applied and Environmental Microbiology 81.19 (2015): 6757-6766.
Final Office Action for U.S. Appl. No. 16/927,590, filed Jul. 13, 2020, on behalf of California Institute of Technology, dated Aug. 21, 2023. 33 pgs.
Genebank: AAA74964.1, TlpA [*Salmonella enterica* subsp. *enterica* serovar Typhimurium], 2 pages (Aug. 30, 1995), available at https://www.ncbi.nlm.nih.gov/protein/AAA74964.1 (last visited Oct. 5, 2023).
Genebank: KUA86919.1, DE34_22565, partial [*Salmonella enterica*], Submitted Feb. 28, 2015, 371 aa, also available at https://www.ncbi.nlm.nih.gov/protein/KUA86919.1 (last visited Jul. 11, 2023).
Genebank: EBL0439264.1, DZB26_25160, partial [*Salmonella enterica*], Submitted Aug. 10, 2018, 312 aa, also available at https://www.ncbi.nlm.nih.gov/protein/EBL0439264.1 (last visited Oct. 5, 2023) 2 Pages.
Non-Final Office Action for U.S. Appl. No. 16/927,590, filed Jul. 13, 2020, on behalf of California Institute of Technology, dated Feb. 9, 2023. 39 pgs.
Non-Final Office Action for U.S. Appl. No. 17/204,782, filed Mar. 17, 2021, on behalf of California Institute of Technology, dated May 10, 2023. 11 pgs.
Notice of Allowance for U.S. Appl. No. 17/204,782, filed Mar. 17, 2021, on behalf of California Institute of Technology, dated Sep. 29, 2023. 11 pgs.
Patyar, S., et al. "Bacteria in cancer therapy: a novel experimental strategy." Journal of biomedical science 17.1 (2010): 1-9.
Restriction Requirement for U.S. Appl. No. 16/927,590, filed Jul. 13, 2020 on behalf of California Institute of Technology dated Jul. 12, 2022 20 pages.
Rotger, Rafael, and Casadesús, Josep "The virulence plasmids of *Salmonella*." International Microbiology 2 (1999): 177-184.
Wikipedia "Salt bridge (protein and supramolecular)" Accessed online on Oct. 5, 2023 available at: https://en.wikipedia.org/wiki/Salt_bridge_(protein_and_supramolecular). 7 Pages.
Extended European search report for EP application No. 20840339.4 issued by European Patent Office dated May 4, 2023, 11 pages.
Gilbert et al., "Biological Engineered Living Materials: Growing Functional Materials with Genetically Programmable Properties," ACS Synth Biol. 2019, 8, 1-15, first published Dec. 21, 2018.

(56) References Cited

OTHER PUBLICATIONS

Maresca et al., "Biomolecular Ultrasound and Sonogenetics," Annu Rev Chem Biomol Eng. 2018. 9: 229-252. First published as a Review in Advance on Mar. 26, 2018.

Naik et al., "The thermostability of an ex-helical coiled-coil protein and its potential use in sensor applications," Biosensors & Bioelectronics 16 (2001) 1051-1057.

Piraner et al., "Tunable Thermal Bioswitches for In Vivo Control of Cell-Based Therapeutics," Poster, Presented on Jun. 9, 2019, at Gordon Immunology Research Seminar, 4 pages.

Piraner et al., "Modular Thermal Control of Protein Dimerization," ACS Synthetic Biology, vol. 8, No. 10, Sep. 6, 2019, pp. 2256-2262, XP093034190, Washington DC, USA.

Stanton et al., "Chemically induced proximity in biology and medicine," Science, 359 (6380), Mar. 9, 2018, 11 pages.

\* cited by examiner

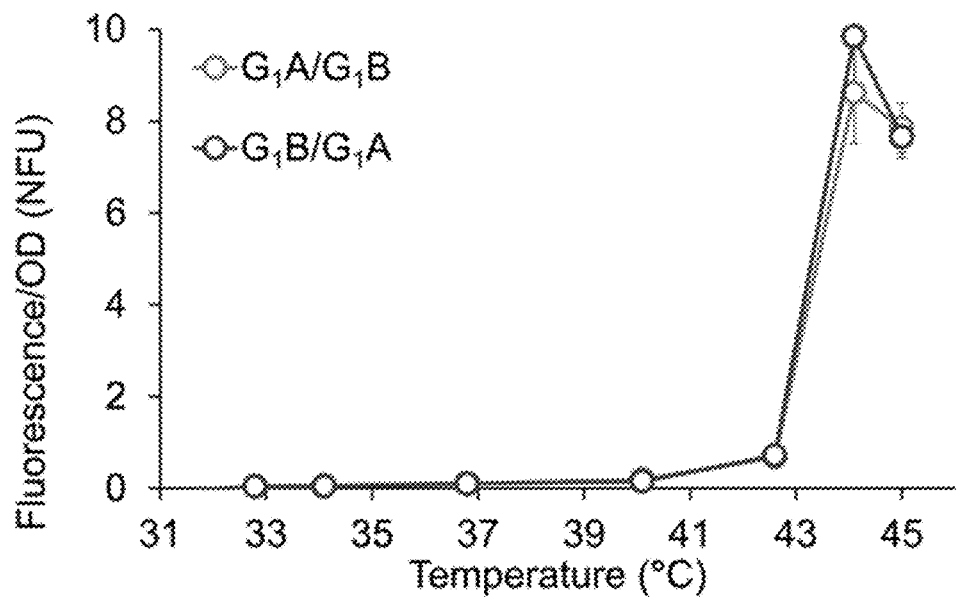
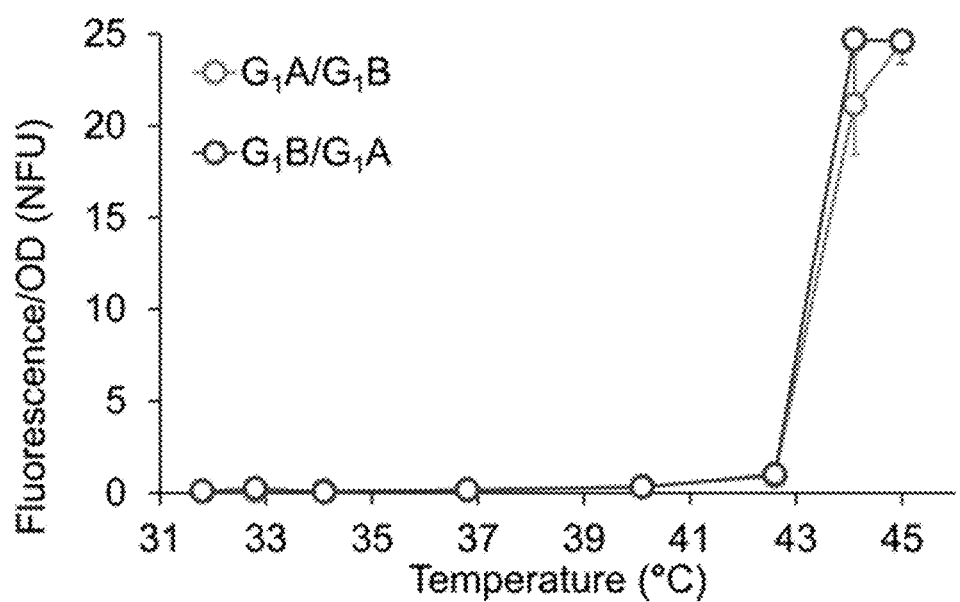
FIG. 7

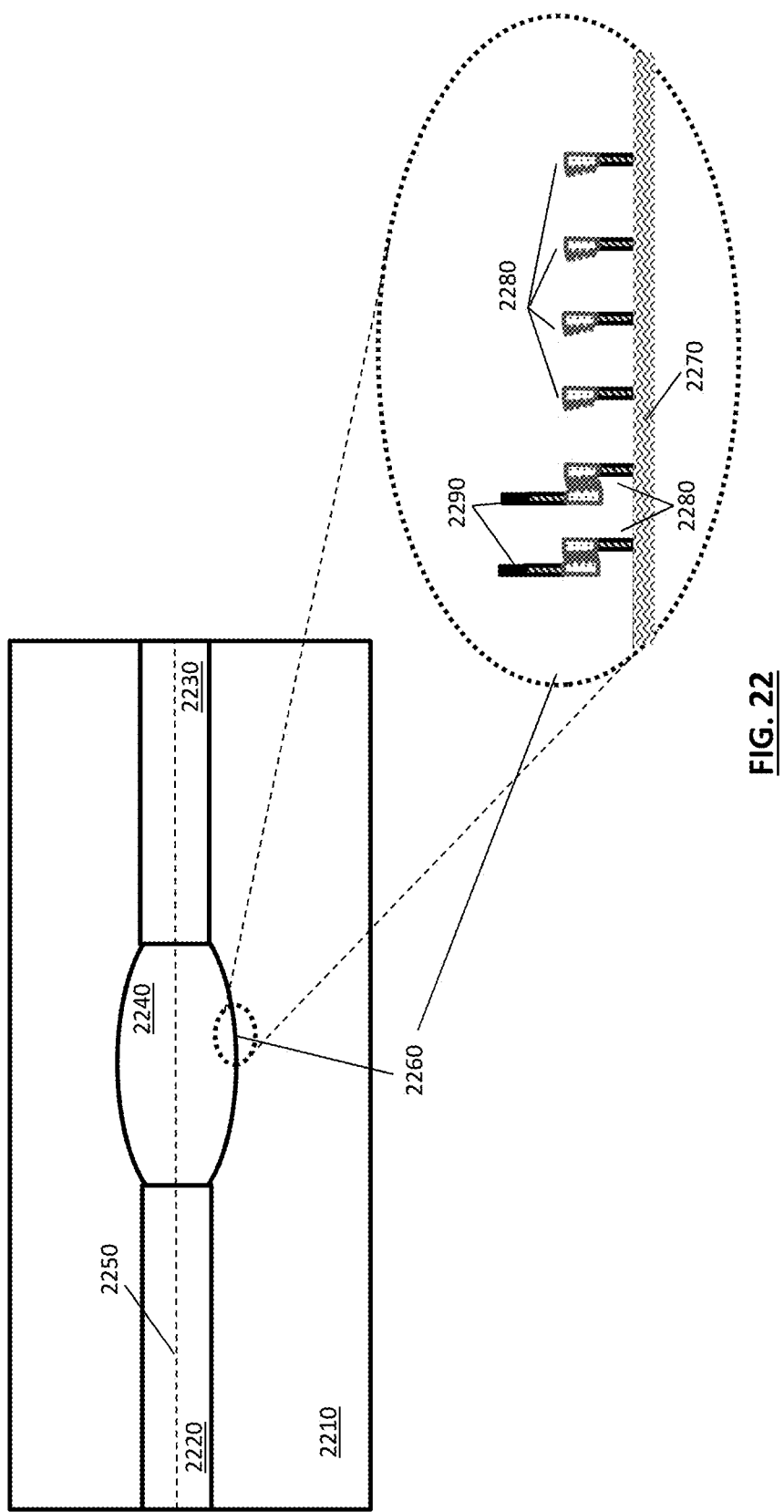

MODULAR DIMERIZATION THERMOSWITCHES AND RELATED MONOMERS, DIMERS, CONSTRUCTS, DIMERIC COMPLEXES, VECTORS, CELLS, SURFACES, DEVICES COMPOSITIONS, METHODS AND SYSTEMS

CROSS REFERENCE TO RELATED APPLICATIONS

The present application claims priority to U.S. Provisional Application No. 62/873,482, entitled "Modular Temperature Dependent Protein Association Domains" filed on Jul. 12, 2019, which is incorporated herein by reference in its entirety.

STATEMENT OF INTEREST

This invention was made with government support under Grant No. W911NF-19-D-0001 awarded by the Army and Grant No. HR0011-14-1-0780 (DOI: D14AP0050) awarded by DARPA. The government has certain rights in the invention.

FIELD

The present disclosure relates to modular dimerization thermoswitches and related monomers, dimers, constructs, dimeric complexes, vectors, cells, surfaces and devices as well as related compositions, methods and systems, to spatiotemporally control formation of dimeric complexes through thermo-regulated dimerization.

BACKGROUND

Recent advances in synthetic biology are driving the development of biological switches for use in various applications wherein controlled formation of an association, of molecule of interest is desired.

For example, an important capability of biological switches for use in connection, with assays, as well as therapeutic and/or diagnostic applications, is the ability to control binding, and location of molecules such as proteins or other moiety one with another.

Despite development of approaches to control molecular associations, challenges remain for developing high-performance and/or tunable bioswitches to control complex formation with spatiotemporal regulation in a wide range of applications including biomedical and industrial applications.

SUMMARY

Provided herein are modular temperature sensing dimers (herein also dimerization thermoswitches, thermomers, or thermomer dimers) and related monomers constructs, dimeric complexes, vectors, cells, surfaces, devices, as well as related compositions, methods and systems, which allow in several embodiments controlled thermo-regulated formation of molecular complexes.

According to a first aspect, a thermomer monomer is described comprising a temperature sensing region having temperature sensing sequence (SEQ ID NO: 1)
$A_1E_2E_3V_4K_5A_6V_7S_8A_9A_{10}L_{11}S_{12}E_{13}R_{14}I_{15}T_{16}Q_{17}L_{18}A_{19}T_{20}$ $E_{21}L_{22}N_{23}D_{24}K_{25}A_{26}V_{27}R_{28}A_{29}A_{39}E_{31}R_{32}R_{33}V_{34}A_{35}E_{36}V_{37}$ $T_{38}R_{39}A_{40}A_{41}G_{42}E_{43}Q_{44}T_{45}A_{46}Q_{47}A_{48}E_{49}R_{50}E_{51}L_{52}A_{53}D_{54}$ $A_{55}A_{56}Q_{57}T_{58}V_{59}D_{60}D_{61}L_{62}E_{63}E_{64}K_{65}L_{66}D_{67}E_{68}L_{69}Q_{70}D_{71}$ $R_{72}Y_{73}D_{74}S_{75}L_{76}T_{77}L_{78}A_{79}L_{80}E_{81}S_{82}E_{83}R_{84}S_{85}L_{86}R_{87}Q_{88}$ $Q_{89}H_{90}D_{91}V_{92}E_{93}M_{94}A_{95}Q_{96}L_{97}K_{98}E_{99}R_{100}L_{101}A_{102}A_{103}$ $A_{104}E_{105}E_{106}N_{107}T_{108}R_{109}Q_{110}X_{111}X_{112}E_{113}R_{114}Y_{115}$ $Q_{116}E_{117}Q_{118}K_{119}T_{120}V_{121}L_{122}Q_{123}D_{124}A_{125}L_{126}N_{127}$ $A_{128}E_{129}Q_{130}A_{131}Q_{132}H_{132}K_{134}N_{135}T_{136}R_{137}E_{138}D_{139}$ $L_{140}Q_{141}K_{142}R_{143}L_{144}E_{145}Q_{146}I_{147}S_{148}A_{149}E_{150}A_{151}$ $N_{152}A_{153}R_{154}T_{155}E_{156}E_{157}L_{158}K_{159}S_{160}X_{161}X_{162}D_{163}$ $K_{164}V_{165}N_{166}T_{167}L_{168}L_{169}T_{170}R_{171}L_{172}E_{173}S_{174}Q_{175}$ $E_{176}N_{177}A_{178}L_{179}A_{180}S_{181}X_{182}X_{183}Q_{184}Q_{185}H_{186}L_{187}$ $A_{188}T_{189}R_{190}E_{191}T_{192}L_{194}Q_{194}Q_{195}R_{196}L_{197}E_{198}Q_{199}$ $A_{200}I_{201}A_{202}D_{203}T_{204}Q_{205}A_{206}R_{207}A_{208}G_{209}E_{210}I_{211}$ $A_{212}L_{213}E_{214}R_{215}D_{216}R_{217}V_{218}S_{219}S_{220}L_{221}T_{222}A_{223}$ $R_{224}L_{225}E_{226}S_{227}Q_{228}E_{229}K_{230}A_{231}S_{232}S_{233}E_{234}Q_{235}$ $L_{236}V_{237}R_{238}M_{239}G_{240}S_{241}E_{242}I_{243}A_{244}S_{245}L_{246}T_{247}$ $E_{248}R_{249}C_{250}T_{251}Q_{252}L_{253}E_{254}N_{255}Q_{256}R_{257}D_{258}D_{259}$ $A_{260}R_{261}L_{262}E_{263}T_{264}M_{265}G_{266}E_{267}K_{268}E_{269}T_{270}V_{271}$ $A_{272}A_{273}L_{274}R_{275}G_{276}E_{277}A_{278}E_{279}A_{280}L_{281}K_{282}R_{283}$ $Q_{284}N_{285}Q_{286}S_{287}L_{288}M_{289}A_{290}A_{291}$ wherein $X_{111}$ $X_{112}$, $X_{161}$ $X_{162}$ $X_{182}$ and $X_{183}$ are independently a negatively charged amino acid preferably a E and/or D or a positively charged amino acid preferably K and/or R, or any derivative thereof configured to dimerize in a target environment at a target environment temperature Te below a bioswitch temperature Tbs in a temperature dependent manner to form a coiled coil temperature sensing domain.

According to a second aspect, a thermomer dimer is described. The thermomer dimer is formed by a first thermomer monomer of the disclosure having a first temperature sensing region and a second thermomer monomer of the disclosure having a second temperature sensing region.

In the thermomer dimer, the first thermomer monomer and the second thermomer monomer are configured to dimerize in a target environment at a target temperature Te<Tbs with a thermal Hill coefficient above 15, to form a coiled coil temperature sensing domain having comprising the first temperature sensing region and the second temperature sensing region and having a melting temperature Tm=Tbs−0° C. to 5° C.

In the preferred embodiments, at least one pair of corresponding residues forming non-covalent bonds between the first temperature sensing region and the second temperature sensing region, selected from $X_{111}$ of the first thermomer monomer and $X_{112}$, of the second thermomer monomer $X_{161}$ of the first thermomer monomer and $X_{162}$ of the second thermomer monomer and $X_{182}$ of the first thermomer monomer and $X_{183}$ of the second thermomer monomer is formed by oppositely charged amino acids.

In the preferred embodiments, $X_{111}$ and $X_{112}$, of the first thermomer monomer have a same charge and $X_{111}$ and $X_{112}$, of the second thermomer monomer have charge opposite to the same charge of $X_{111}$ and $X_{112}$, of the first thermomer monomer;

$X_{161}$ and $X_{162}$, of the first thermomer monomer have a same charge and $X_{161}$ and $X_{162}$, of the second thermomer monomer have charge opposite to the same charge of $X_{161}$ and $X_{162}$, of the first thermomer monomer; and $X_{182}$ and $X_{183}$, of the first thermomer monomer have a same charge and $X_{182}$ and $X_{183}$, of the second thermomer monomer have charge opposite to the same charge of $X_{182}$ and $X_{183}$ of the first thermomer monomer.

According to a third aspect, a thermomer monomeric construct is described, comprising a thermomer monomer of the present disclosure configured to dimerize in a target environment to form a coiled coil temperature sensing domain at a target environment temperature Te<Tbs, the coiled coil temperature sensing domain having a melting temperature Tm=Tbs−0° C. to 5° C.

In the thermomer monomeric construct, the thermomer monomer has an N-terminus end and a C-terminus and is attached to a linker polypeptide having has an N-terminus end and a C-terminus and/or to a cargo moiety formed by a chemical moiety having a diameter of up to 1 micron.

In particular, in the thermomer monomeric construct, the thermomer monomer is attached to the linker polypeptide through attachment of one of the N-terminus end or a C-terminus of the thermomer monomer with one of the C-terminus end or N-terminus, of the linker polypeptide.

In the alternative, in the thermomer monomeric construct, the thermomer monomer is attached to the cargo moiety through
  direct attachment of one of the N-terminus end or a C-terminus of the thermomer monomer with the cargo moiety, or
  indirect attachment of one of the N-terminus end or a C-terminus of the thermomer monomer to the cargo moiety through attachment of the one of the N-terminus end or C-terminus of the thermomer monomer with one of the C-terminus end or N-terminus, of the linker polypeptide.

According to a fourth aspect, a thermomer dimeric complex is described. The thermomer dimeric complex comprises
  a first thermomer monomeric construct herein described comprising a first thermomer monomer of the present disclosure attached to a first linker polypeptide and/or a first cargo moiety,
and
  a second thermomer monomeric construct herein described, comprising second thermomer monomer of the present disclosure attached to a second linker polypeptide and/or a second cargo moiety, In the thermomer dimeric complex, the first thermomer monomer and the second thermomer monomer are configured to dimerize in a target environment at a target temperature Te<Tbs with a thermal Hill coefficient above 15, to form a coiled coil temperature sensing domain having comprising the first temperature sensing region and the second temperature sensing region and having a melting temperature Tm=Tbs−0° C. to 5° C.

In the thermomer dimeric complex comprising a first cargo moiety and/or second cargo moiety, at least one of the first cargo moiety and the second cargo moiety is configured to have an interface with the target environment subjected to a Stokes' drag force up to 50 pN, preferably up to 20, pN more preferably 10 pN or even more preferably 6-7 pN or lower.

According to a fifth aspect, a thermomer vector is described comprising a thermomer gene expression cassette comprising a polynucleotide encoding for a thermomer monomer or a thermomer monomeric construct herein described comprising the linker polypeptide and/or a cargo moiety in which the chemical moiety comprises a polypeptide. In the thermomer gene expression cassette, the polynucleotide is under control of a promoter and additionally regulatory regions in a configuration allowing expression of the thermomer monomer or thermomer monomeric construct of the present disclosure in a target environment.

According to a sixth aspect, a thermomer cell is described comprising at least one of the thermomer monomer, thermomer dimer, thermomer monomeric construct, thermomer dimeric construct and thermomer vector herein described within a biological cell.

According to a seventh aspect, a thermomer surface is described comprising at least one of the thermomer monomer, thermomer dimer, thermomer monomeric construct, thermomer dimeric construct attached to a surface configured to directly or indirectly attach a polypeptide comprised in the linker polypeptide and/or the cargo moiety.

According to an eighth aspect, a thermomer device is described comprising at least one thermomer surface herein described and configured to allow performance of any one of the methods herein described wherein at least one thermomer monomeric construct and/or thermomer dimeric construct is attached to the thermomer surface.

According to a ninth aspect a method and a system are described to provide a thermomer monomer construct of the present disclosure; the method comprising providing a thermomer monomer of the present disclosure, the thermomer monomer having an N-terminus end and C-terminus, A) providing a thermomer monomer of the instant disclosure;
B) providing at least one of
  a) a linker polypeptide having an N-terminus and a C-terminus; and
  b) a cargo moiety formed by a chemical moiety having a diameter of up to 1 micron;
B) attaching the thermomer monomer moiety to either
  a) the linker polypeptide through attachment of one of the N-terminus end or a C-terminus of the thermomer monomer with one of the C-terminus end or N-terminus, of the linker polypeptide
  or
  b) the cargo moiety through
    i) direct attachment of one of the N-terminus end or a C-terminus of the thermomer monomer with the cargo moiety,
    or
    ii) indirect attachment of one of the N-terminus end or a C-terminus of the thermomer monomer to the cargo moiety through attachment of the one of the N-terminus end or C-terminus of the thermomer monomer with one of the C-terminus end or N-terminus, of the linker polypeptide.
to provide a thermomer monomer construct of the present disclosure The system to provide a thermomer monomer construct of the present disclosure, comprises at least one of a thermomer monomer, a thermomer gene expression cassette, and a thermomer vector of the present disclosure, at least one of a linker polypeptide of the present disclosure or a polynucleotide encoding therefor and a cargo moiety for simultaneous combined or sequential use to perform in the method to provide a thermomer monomer construct of the present disclosure.

In embodiments, wherein the cargo moiety is formed by a polypeptide, the system can also comprise a polynucleotide encoding for the cargo moiety in addition or in the alternative to the cargo moiety as will be understood by a skilled person.

According to a tenth aspect, a method and a system are described to provide a thermomer dimeric complex of the present disclosure. The method comprises providing a first thermomer monomeric construct herein described comprising a first thermomer monomer of the present disclosure attached to a first linker polypeptide and/or a first cargo moiety formed by a chemical moiety having a diameter of up to 1 micron and providing a second thermomer monomeric construct herein described, comprising second thermomer monomer of the present disclosure attached to a second linker polypeptide and/or a second cargo moiety formed by a chemical moiety having a dimeter of up to 1 micron In the method, the first thermomer monomer and the second thermomer monomer are configured to dimerize in a target environment at a target temperature Te<Tbs with a thermal Hill coefficient above 15, to form a coiled coil temperature sensing domain having comprising the first temperature sensing region and the second temperature sensing region and having a melting temperature Tm=Tbs–0° C. to 5° C.

In the method to provide a thermomer dimeric complex at least one of the first cargo moiety and the second cargo moiety has a Stokes' drag force acting on the interface between an aqueous fluid of the target environment and the cargo equal or lower than 6-7 pN.

The method to provide a thermomer dimeric complex of the present disclosure further comprises contacting the first thermomer monomer construct and the second thermomer monomer construct in the target environment at the target temperature Tbs to allow dimerization of the first thermomer monomer and the second thermomer monomer to provide the thermomer dimeric complex.

In some embodiments the method can further comprise, attaching the N-terminus or C-terminus of the linker polypeptide or the cargo moiety of at least one of the first monomeric construct and second monomeric construct to a surface configured to allow the related binding before or after the contacting.

The system to provide a thermomer dimeric complex of the present disclosure, comprises a first thermomer monomeric construct herein described comprising a first thermomer monomer of the present disclosure attached to the first linker polypeptide and/or the first cargo moiety, and a second thermomer monomeric construct herein described, comprising second thermomer monomer of the present disclosure attached to the second linker polypeptide and/or the second cargo moiety, for simultaneous combined or sequential use in the method to provide a thermomer dimeric complex of the present disclosure.

According to an eleventh aspect, a method and a system are described to control location of a first cargo moiety and/or second cargo moiety in a target environment having a target environment temperature Te. In the method and system, the first cargo moiety and optionally the second cargo moiety have a Stokes' drag force acting on the interface between an aqueous fluid of the target environment and the cargo up to 50 pN.

The method to control location of the cargo moiety and optionally the second cargo moiety, comprises administering to the target environment a first thermomer monomeric construct herein described comprising a first thermomer monomer of the present disclosure attached to the first cargo moiety directly or indirectly through a first linker polypeptide, and administering to the target environment a second thermomer monomeric construct herein described comprising a second thermomer monomer of the present disclosure attached to a second linker polypeptide or the second cargo moiety through the second linker polypeptide.

In the thermomer dimeric complex, the first thermomer monomer and the second thermomer monomer are configured to dimerize in a target environment at a target temperature Te<Tbs with a thermal Hill coefficient above 15, to form a coiled coil temperature sensing domain having comprising the first temperature sensing region and the second temperature sensing region and having a melting temperature Tm=Tbs–0° C. to 5° C.

The method further comprises changing the temperature Te to obtain Te<Tbs the changing performed to dimerize the first thermomer monomer and the second thermomer monomer thus obtaining the thermomer dimer complex in the target environment.

In some embodiments, the second thermomer monomeric construct herein described comprises the second thermomer monomer of the present disclosure attached to the second linker polypeptide and the second linker polypeptide is attached to a surface configured to bind the linker polypeptide.

The system to control location of a first cargo moiety and optionally a second cargo moiety in a target environment, comprises the first thermomer monomeric construct herein described comprising a first thermomer monomer of the present disclosure attached to the first cargo moiety directly or through the first linker polypeptide and the second thermomer monomeric construct herein described comprising a second thermomer monomer of the present disclosure attached to the second linker polypeptide or the second cargo moiety through the second linker polypeptide, for simultaneous combined or sequential use in the administering of a method to control location of the first cargo moiety and the second cargo moiety in a target environment herein described.

According to an twelfth aspect, a method and systems to modify a bioswitch temperature $Tbs_0$ of a thermomer dimer of the instant disclosure in a target environment and variants obtained thereby are described.

In the method to modify a bioswitch temperature $Tbs_0$ of a thermomer dimer of the instant disclosure, the thermomer dimer has a melting temperature $Tm_0$ with $Tbs_0 = Tm + 0°$ C. to 5° C.

In the method to modify a bioswitch temperature $Tbs_0$ of a thermomer dimer of the instant disclosure, each thermomer monomer of the thermomer dimer has residues $A_1$ to $A_{291}$ arranged of the respect temperature sensing sequence arranged in consecutive uninterrupted series of heptad repeats a, b, c, d, e, f, or g, with at least two of the heptad repeats having a register in which no amino acid is missing, and up to 49 heptad repeats a register in which up to 5 consecutive amino acid residues are optionally missing.

The method to modify a bioswitch temperature Tbs of the thermomer dimer comprises

- providing a thermomer dimer herein described having a starting bioswitch temperature $Tbs_0$ in the target environment and comprising two thermomer monomer of the disclosure configured to form a dimer in the target environment with a thermal Hill coefficient above 15 at a starting melting temperature $Tm_0$;
- replacing in at least one thermomer monomer of the two thermomer monomer forming the thermomer dimer
  - at least one of a hydrophobic amino acid in position a and a hydrophobic amino acid in position d of at least one heptad repeat in the temperature sensitive amino acid sequence of the at least one monomer with residues configured to increase or decrease hydrophobic packing between corresponding amino acid residues in positions a and/or d of corresponding heptad repeats in monomer proteins of the temperature sensing domain,
  - at least one of a polar or charged amino acid in position b, a polar or charged amino acid in position e, and a polar or charged amino acid in position g of at least one heptad repeat in the temperature sensitive amino acid sequence of the at least one monomer with a hydrophobic residue, and/or
  - at least one of a polar or charged amino acid in position e, and a polar or charged amino acid in a position g of at least one heptad repeat in the temperature sensitive amino acid sequence of the at least one monomer with a residue configured to increase or decrease coulombic repulsion between corresponding amino acid residues in positions a, d, e and/or g of corresponding heptad repeats in monomer proteins of the temperature sensing domain,
- the replacing performed to obtain a variant of the coiled coil temperature sensitive transcription factor with a melting temperature of the temperature sensing domain $Tm_m$ lower or higher than $Tm_0$ in the target environment, the obtained variant having a bioswitch temperature $Tbs_m$ lower or higher than $Tbs_0$ in the target environment.

Additional aspects can comprise, i) a polynucleotide encoding for a thermomer monomer, thermomer dimer, thermomer monomeric constructs and/or a thermomer dimeric complexes, ii) a composition comprising a thermomer monomer, thermomer dimer, thermomer monomeric constructs and/or a thermomer dimeric complexes together with a suitable vehicle, iii) additional methods using a thermomer monomer, thermomer dimer, thermomer monomeric constructs and/or a thermomer dimeric complexes, and iv) additional systems comprising a thermomer monomer, thermomer dimer, thermomer monomeric constructs and/or a thermomer dimeric complexes, as well as additional aspects identifiable by a skilled person.

Thermomer monomers, thermomer dimers, thermomer monomeric construct, thermomer dimeric complexes of the instant disclosure, and related vectors, cells surface, devices, compositions, methods and systems herein described, allow in several embodiments to control spatial and/or temporal location of a cargo moiety in a target environment in a thermoregulated manner.

Thermomer monomers, thermomer dimers, thermomer monomeric construct, thermomer dimeric complexes of the instant disclosure, and related vectors, cells, surface, devices, compositions, methods and systems herein described, allow in several embodiments to thermally control interactions and binding of cargo moieties in a target environment.

Thermomer monomers, thermomer dimers, thermomer monomeric construct, thermomer dimeric complexes of the instant disclosure, and related vectors, cells, surface, devices, compositions, methods and systems herein described, allow in several embodiments to trigger formation and dissociation of dimer complexes in a thermally regulated manner.

Thermomer monomers, thermomer dimers, thermomer monomeric construct, thermomer dimeric complexes of the instant disclosure, and related vectors, cells, surface, devices, compositions, methods and systems herein described, can be used in connection with various applications wherein controlled location, interaction and/or binding of cargo moieties as well as controlled formation and dissociation of related complexes is desired. For example, thermomer monomers, thermomer dimers, thermomer monomeric constructs, thermomer dimeric complexes of the instant disclosure, and related vectors, cells compositions, methods and systems herein described can be used to provide spatially and/or temporally controlled location of therapeutics in medical applications, drug research and manufacturing, biological synthesis of chemicals and proteins such as enzymes or catalysts or polymers, as well diagnostics and/or clinical applications. In another example, thermomer monomers, thermomer dimers, thermomer monomeric constructs, thermomer dimeric complexes of the instant disclosure, and related vectors, cells compositions, methods and systems herein described can be used to control the activity of split proteins and/or protein-inhibitor complexes to regulate protein function in a temperature-dependent fashion.

Additional exemplary applications include uses of the monomers, thermomer dimers, thermomer monomeric construct, thermomer dimeric complexes of the instant disclosure, and related vectors, cells, surface, devices, compositions, methods and systems herein described in several fields including basic biology research, applied biology, bio-engineering, bio-energy, medical research, medical diagnostics, therapeutics, bio-fuels, and in additional fields identifiable by a skilled person upon reading of the present disclosure.

The details of one or more embodiments of the disclosure are set forth in the accompanying drawings and the description below. Other features, objects, and advantages will be apparent from the description and drawings, and from the claims

BRIEF DESCRIPTION OF DRAWINGS

The accompanying drawings, which are incorporated into and constitute a part of this specification, illustrate one or more embodiments of the present disclosure and, together with the detailed description and the examples, serve to explain the principles and implementations of the disclosure.

FIG. 1 illustrates in some embodiments engineering heterodimeric TlpA variants via charge-charge complementation. FIG. 1, Panel a) Illustration of TlpA-based thermomer system. Heterodimeric coiled-coil domains enable reversible association and dissociation of fusion partners as a sharp function of temperature. FIG. 1, Panel b) Diagram of heterodimeric coiled-coil design based on the introduction or modification of electrostatic contacts at the e-to-g' interface between adjacent α-helices. P, H, + and − denote polar, hydrophobic and charged residues, respectively. WT denotes the wild-type protein, while A and B denote engineered mutants. FIG. 1, Panel c) Diagram of predicted electrostatic contacts along the TlpA interface occurring in a nonconventional e-to-d' configuration. FIG. 1, Panel d) Normalized ellipticity of purified TlpA coiled-coil domain variants in isolation or as an equimolar mixture, measured at the 222 nm peak for α-helical spectra as a function of temperature. Data shown normalized from 0 to 1 on a per-sample basis.

Figure 2:
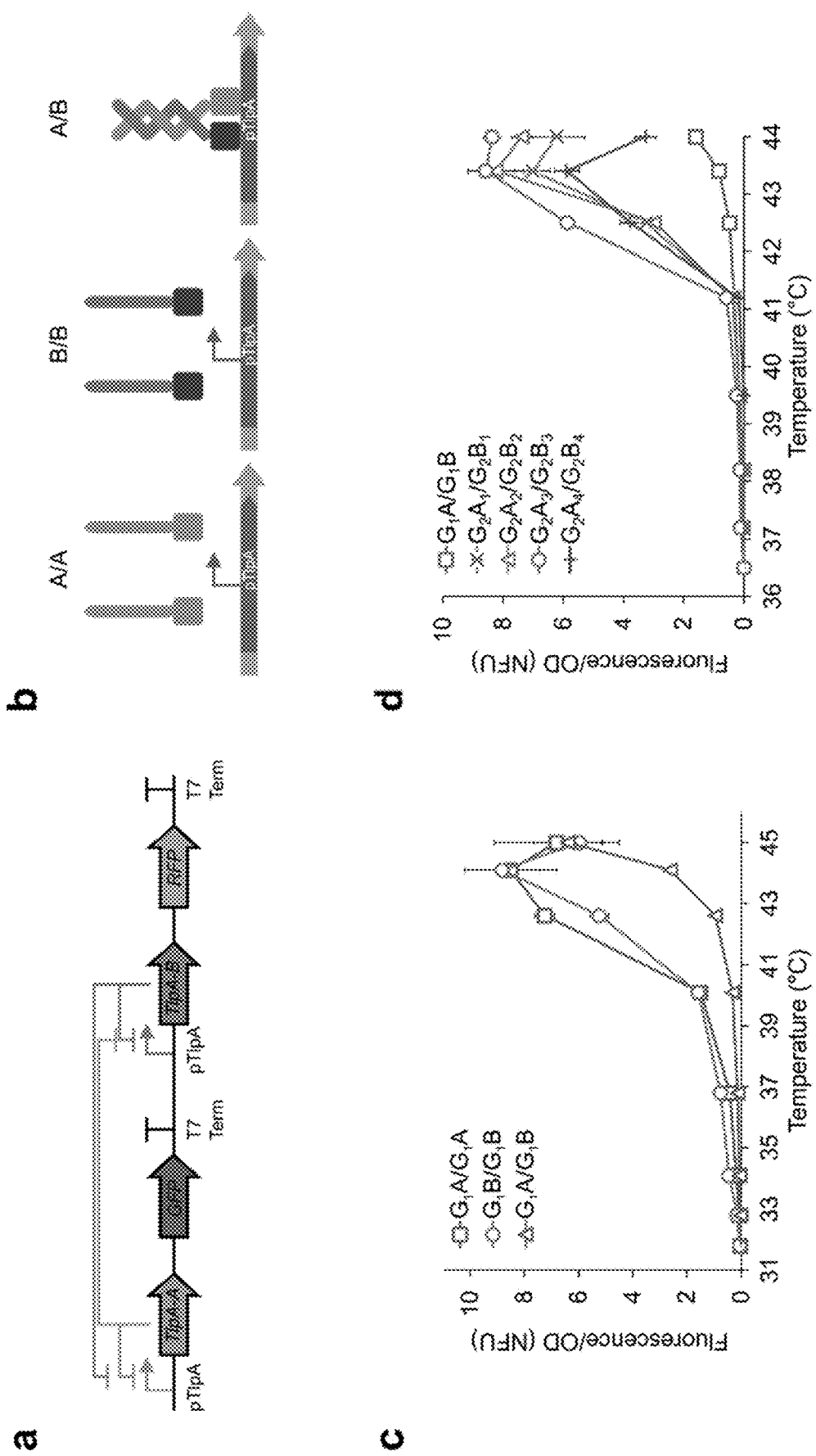

FIG. 2 shows in some embodiments an evaluation of TlpA heterodimerization via reconstitution of promoter repression in bacteria. FIG. 2, Panel a) Diagram of bacterial genetic circuit containing two TlpA genes, each of which can encode one of the engineered variants. Bacteria harboring the $G_1A/G_1A$ and $G_1B/G_1B$ circuits can only produce the homodimeric coils, whereas the $G_1A/G_1B$ circuits can produce either the homodimers or heterodimeric coils. FIG. 2, Panel b) Illustration of operator binding for engineered heterodimeric construct; only cells expressing both partners of the heterodimeric TlpA variant can repress the reporter gene above a certain temperature. FIG. 2, Panel c) OD-normalized fluorescence expression profile of *E. coli* harboring the plasmid constructs shown in a, with the single mutant $G_1A$ and $G_1B$ variants in the A and B positions, as a function of temperature (n=3). Error bars represent ±s.e.m. NFU represents normalized fluorescent units. FIG. 2, Panel d) OD-normalized temperature-dependent fluorescence expression profiles of *E. coli* harboring plasmids bearing the four possible double mutant combinations of the $G_1$ variants and two additional candidate single mutations, all in heterodimeric pairings (n=3). Error bars represent ±s.e.m.

FIG. 3 shows in some embodiments the validation of TlpA heterodimerization by electrophoresis. FIG. 3, Panel a) Left: diagram of genetic construct for simultaneous co-expression of engineered heterodimers of TlpA for biochemical assay. One open reading frame expresses the full length TlpA protein whereas the other ORF produces a truncated version missing its predicted N-terminal DNA-binding domain (ΔNTD). Each position can be occupied by any variant of TlpA, including the wild type protein and engineered mutants. Right: Diagram of the possible SDS-PAGE bands resulting from covalent dimeric crosslinking of the TlpA products expressed from this construct. The example in the left lane corresponds to the wild-type homodimeric TlpA. The example in the right lane corresponds to a pair of heterodimeric TlpA variants. FIG. 3, Panel b) Western blot of $CuCl_2$-catalyzed crosslinking reaction of wild-type TlpA in *E. coli* lysate followed by SDS-PAGE. Crosslinking was performed at 37° C., at 45° C., or at 37° C. to assess reannealing (Re) following a 10-minute incubation at 45° C. Each condition is compared to a non-crosslinked control. The bottom bands on the gel show uncrosslinked monomers. FIG. 3, Panel c) $CuCl_2$ crosslinking, SDS-PAGE, and Western blot of the construct in FIG. 3 Panel a) harboring wild type TlpA (wt), the first generation single mutant heterodimer ($G_1$), or the $G_{2-n}$ double mutant heterodimers. Crosslinking was performed at 37° C. FIG. 3, Panel d) Thermal response of the $G_1$ and $G_{2-3}$ heterodimer constructs analyzed in the absence and presence of $CuCl_2$ at 37° C., 45° C., or with 37° C. reannealing after a 10-minute incubation at 45° C.

FIG. 4 shows the genetic construct of exemplary genetic circuits and the results from the membrane localization assay for TlpA activity in mammalian cells. FIG. 4, Panel a) Genetic construct (top) and schematic (bottom) for temperature-dependent localization of RFP at the plasma membrane. The TlpA39-G2A3 strand is fused to a GAP43 palmitoylation motif, leading to its tethering to the lipid membrane. The partner TlpA39-G2B3 strand is fused to RFP. At low temperature, the heterodimerization of these strands should lead to RFP localization at the membrane. Upon heating, the RFP-fused strand should dissociate from the membrane. FIG. 4, Panel b) Fluorescence images of a representative K562 cell transfected with the construct shown in FIG. 4 Panel a). Robust membrane localization of RFP fluorescence is observed at 25° C. and 37° C. At 40° C., RFP begins to dissociate from the membrane, and by 42° C. fluorescence is distributed throughout the cytoplasm. The globular fluorescent form in the center of the cell represents the nucleus stained in with Hoechst 33342 dye. FIG. 4, Panel c) Genetic construct (top) and experimental schematic (bottom) of a directly palmitoylated RFP control. FIG. 4, Panel d) Fluorescence images of representative K562 cell transfected with the construct shown in FIG. 4, Panel c, displaying robust membrane localization throughout the temperature range tested. FIG. 4, Panel e) Representative fluorescence images of a K562 cell with a lentivirally delivered TlpA-mediated RFP localization construct (shown in FIG. 4, Panel a) and the membrane-staining dye CellBrite Fix 488. FIG. 4, Panel f) Pixel colocalization of RFP with the CellBrite 488 dye as a function of temperature in K562 cells stably expressing directly palmitoylated RFP (shown in FIG. 4, Panel b, n=8), the TlpA-mediated membrane localization construct (shown in FIG. 4, Panel a, n=15), and free cytosolic RFP (n=8). Error bars represent ±s.e.m. FIG. 4, Panel g) Time series of fluorescent images of a representative K562 thermal reporter cell line before heating, after heating to 42° C., and after re-equilibration to 37° C. RFP re-accumulation at the plasma membrane was tracked in 15 minute intervals. Pixel intensity was normalized to the maximal per-image value. FIG. 4, Panel h) Pixel colocalization of the TlpA-RFP signal with CellBrite 488 dye as a function of temperature (dissociation) followed by a time course of incubation at 37° C. reassociation; n=12. Error bars represent ±s.e.m.

FIG. 5 illustrates circular dichroism melting curves of exemplary engineered TlpA variants. Coiled-coil fragments corresponding to residues 69-359 of TlpA were purified from *E. coli* and assayed via CD spectroscopy. Monitoring the ellipticity at 222 nm, corresponding the prototypical peak of the α-helical spectrum, enables tracking the conformation of TlpA as it transitions from the dimeric coiled-coil state to a monomeric random coil configuration.

FIG. 6 shows a graph representing thermal RFP expression profiles of the constructs shown in FIG. 2, Panel b (n=3). Error bars represent ±s.e.m. Where not seen they are smaller than the symbol.

FIG. 7 shows graphs representing thermal GFP (top) and RFP (bottom) expression profiles of construct containing two TlpA variants, TlpA-$G_1A$ and TlpA-$G_1B$, in which the positions of TlpA-$G_1A$ and TlpA-$G_1B$ within the heterodimer co-expression construct in FIG. 2, Panel b were exchanged. The results demonstrate positional independence of the TlpA co-expression construct. The thermal GFP (top) and RFP (bottom) expression profile was determined (n=4). No significant differences were observed in the gene expression profile, thereby excluding position-dependent effects on TlpA behavior within the circuit. Error bars represent ±s.e.m. Where not seen they are smaller than the symbol.

Figure 8:
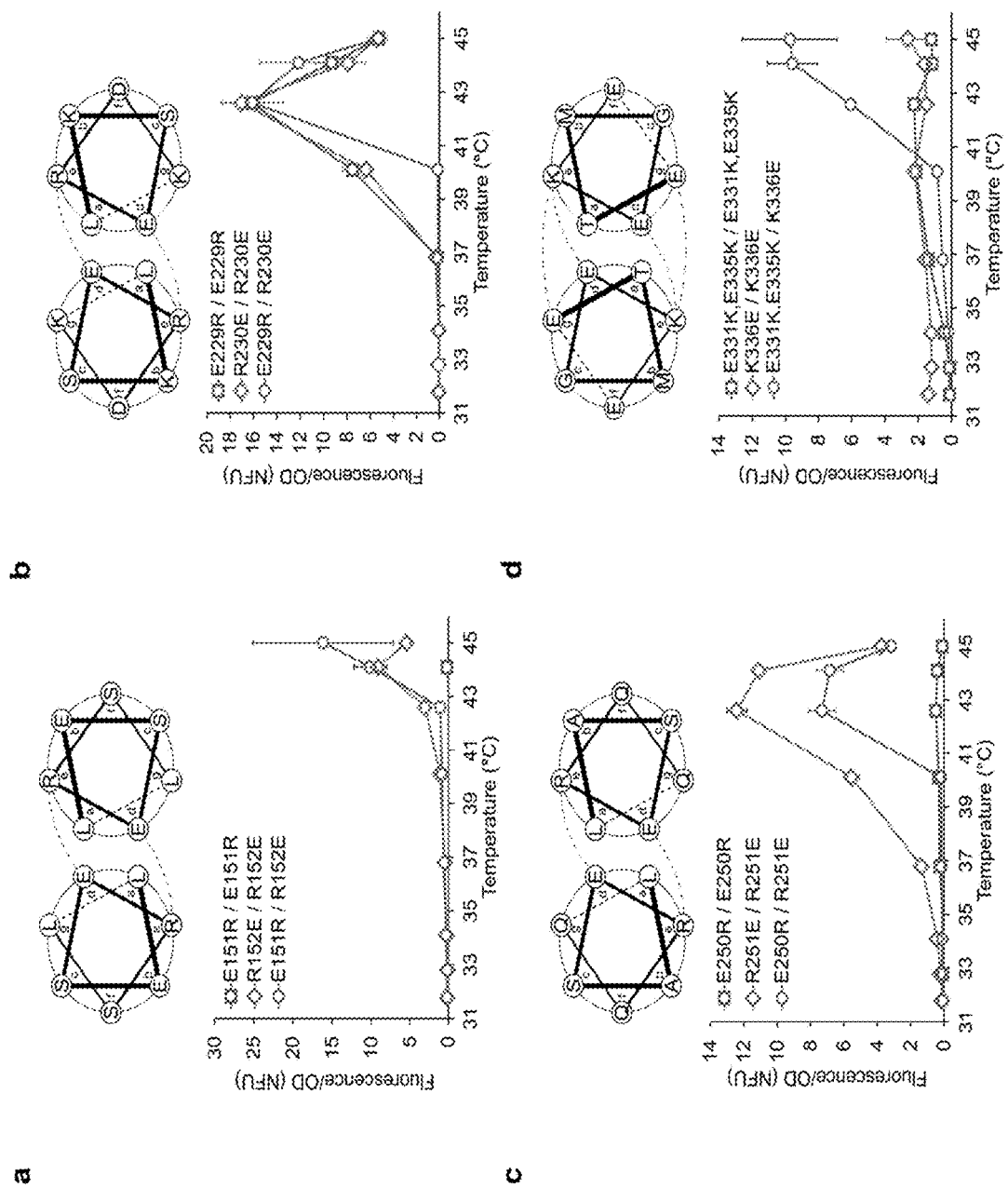

FIG. 8 shows in some embodiments rationally designed mutant panel screened via bacterial thermal gene expression assay. Four positions in the TlpA coiled-coil were selected for mutagenesis based on the predicted similarity of their ionic interaction pattern to the $G_1A/G_1B$ mutant pair according to the heptad repeat register prediction of Koski et al. The following mutations were examined: FIG. 8, Panel a) E151R and R152E FIG. 8, Panel b) E229R and R230E, FIG. 8, Panel c) E250R and R251E, and FIG. 8, Panel d) E331K/E335K and K336E. The predicted interaction pattern of the wild type protein is depicted (top), and the thermal GFP expression profile is reported (bottom). N=3. The E229R/R230E and E250R/R251E pairs were selected for introduction into the TlpA-$G_1A$ and $G_1B$ variants. Error bars represent ±s.e.m. Where not seen they are smaller than the symbol. Mutation positions indicated are relative to the full-length TlpA protein. The thermomer portion starts at "A69".

Figure 9:
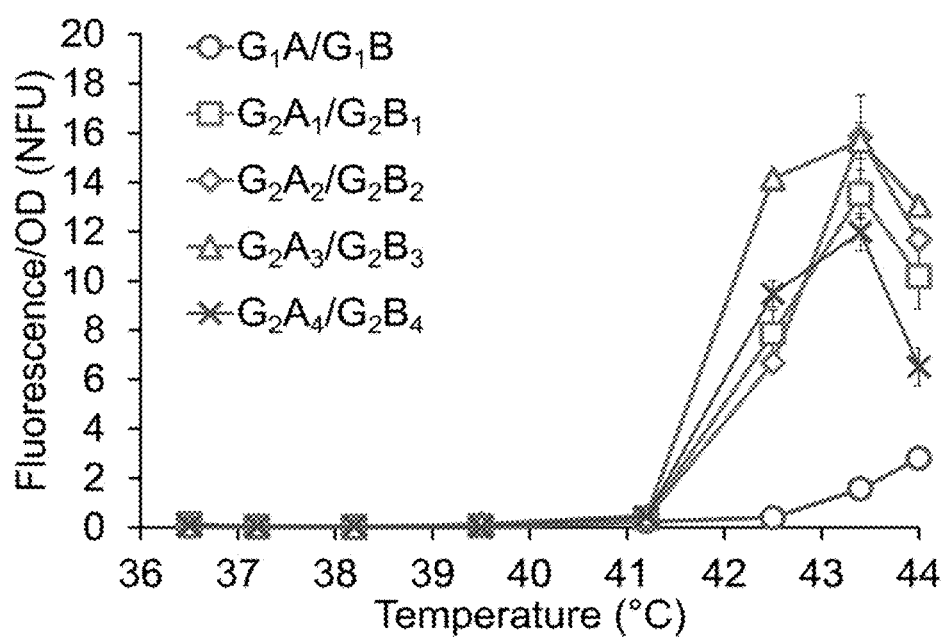

FIG. 9 shows a graph representing thermal RFP expression profiles of the first and second-generation heterodimers shown in FIG. 2, Panel c (n=3). Only the construct containing one copy of each heterodimeric strands are depicted because the $X_nA/X_nB$ homodimeric construct were unable to propagate without accumulating deletion mutations in the TlpA promoters or fluorescent protein open reading frames. Error bars represent ±s.e.m. Where not seen they are smaller than the symbol.

Figure 3:
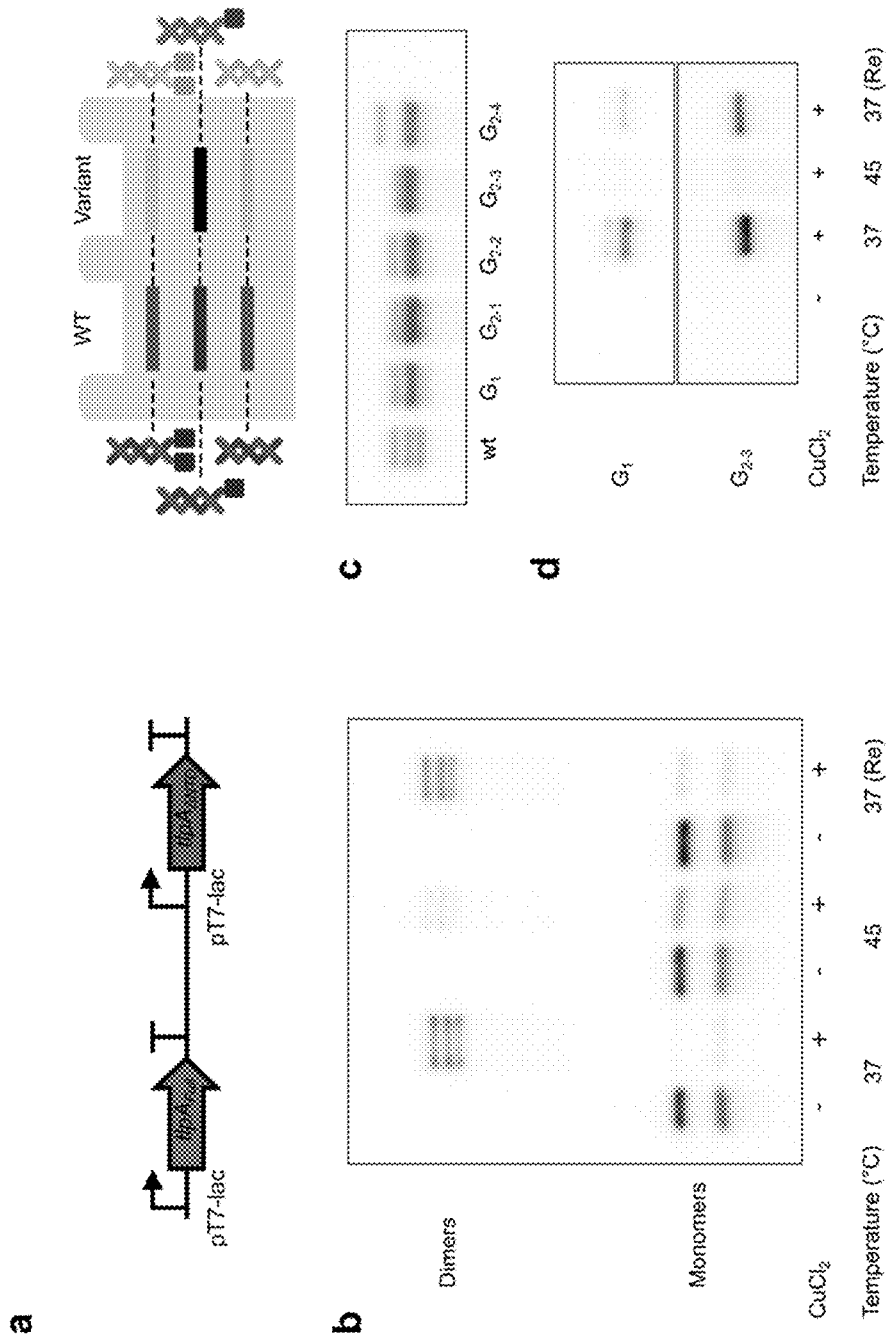
Figure 10:
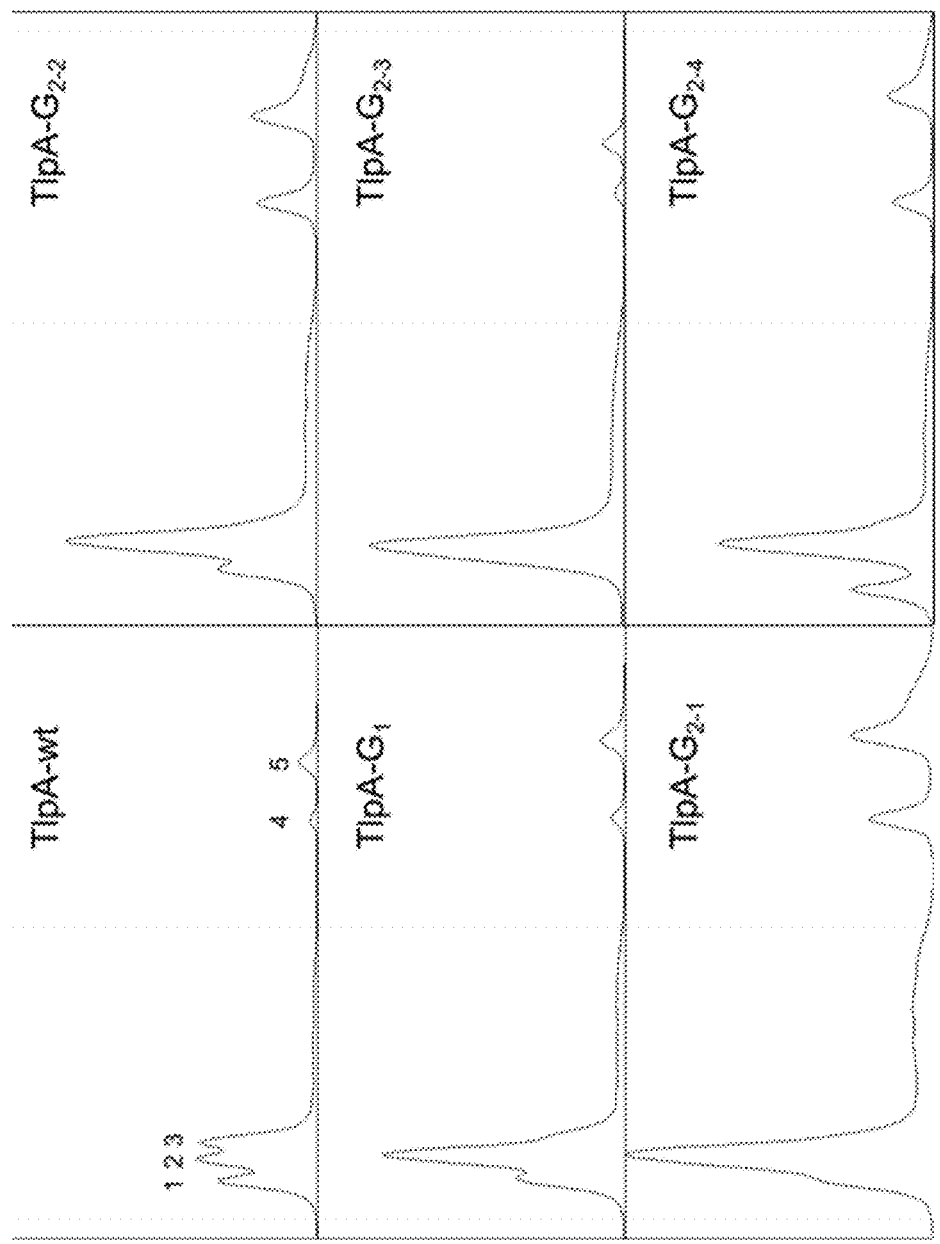

FIG. 10 shows graphs representing Western blot band intensity profiles of co-expressed full and truncated TlpA strands in FIG. 3, Panel c. Note that samples lacking a distinct band corresponding to the truncated homodimer (3), such as TlpA-$G_1$, nevertheless display higher band intensity for the truncated uncrosslinked strand (5) relative to the full-length uncrosslinked species (4), confirming that the lack of a low molecular weight homodimer at position 3 results from reduced homodimer affinity rather than full depletion of the light TlpA strand by heterodimer pairing. This is consistent with cationic and anionic TlpA variants having different homodimerization affinities at 37° C.

Figure 11:
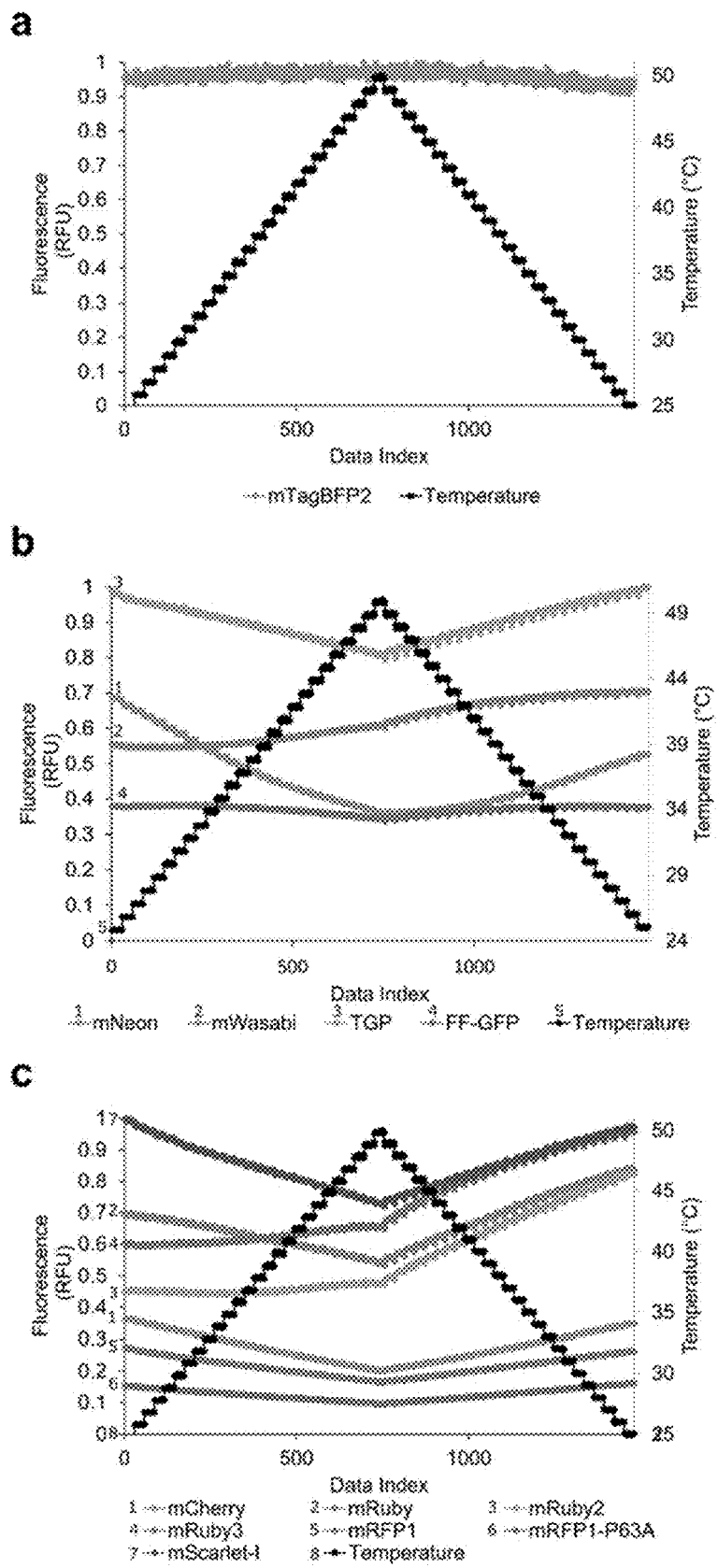

FIG. 11 shows in some embodiments the thermal stability of a panel of blue (FIG. 11, Panel a), green (FIG. 11, Panel b), and red (FIG. 11, Panel c) fluorescent proteins. Proteins were prepared in equimolar concentrations and their fluorescence was measured in an rtPCR thermocycler upon a thermal ramp from 25° C. to 50° C. and subsequent re-annealing to 25° C., with readings taken continuously over 1 minute intervals. Signal intensity is normalized to the maximum for each given experiment. Because different filter sets were used for the three classes of proteins, relative brightness does not correlate between the red, green, and blue channels. While some proteins such as FF-GFP demonstrated more stable signal over the temperature range tested, the overall brightness was maximal in mScarlet-I and TGP. However, TGP demonstrated significant aggregation when expressed as an untagged cytosolic protein in mammalian cells so mScarlet-I was chosen as the reporter for subsequent experiments.

Figure 4:
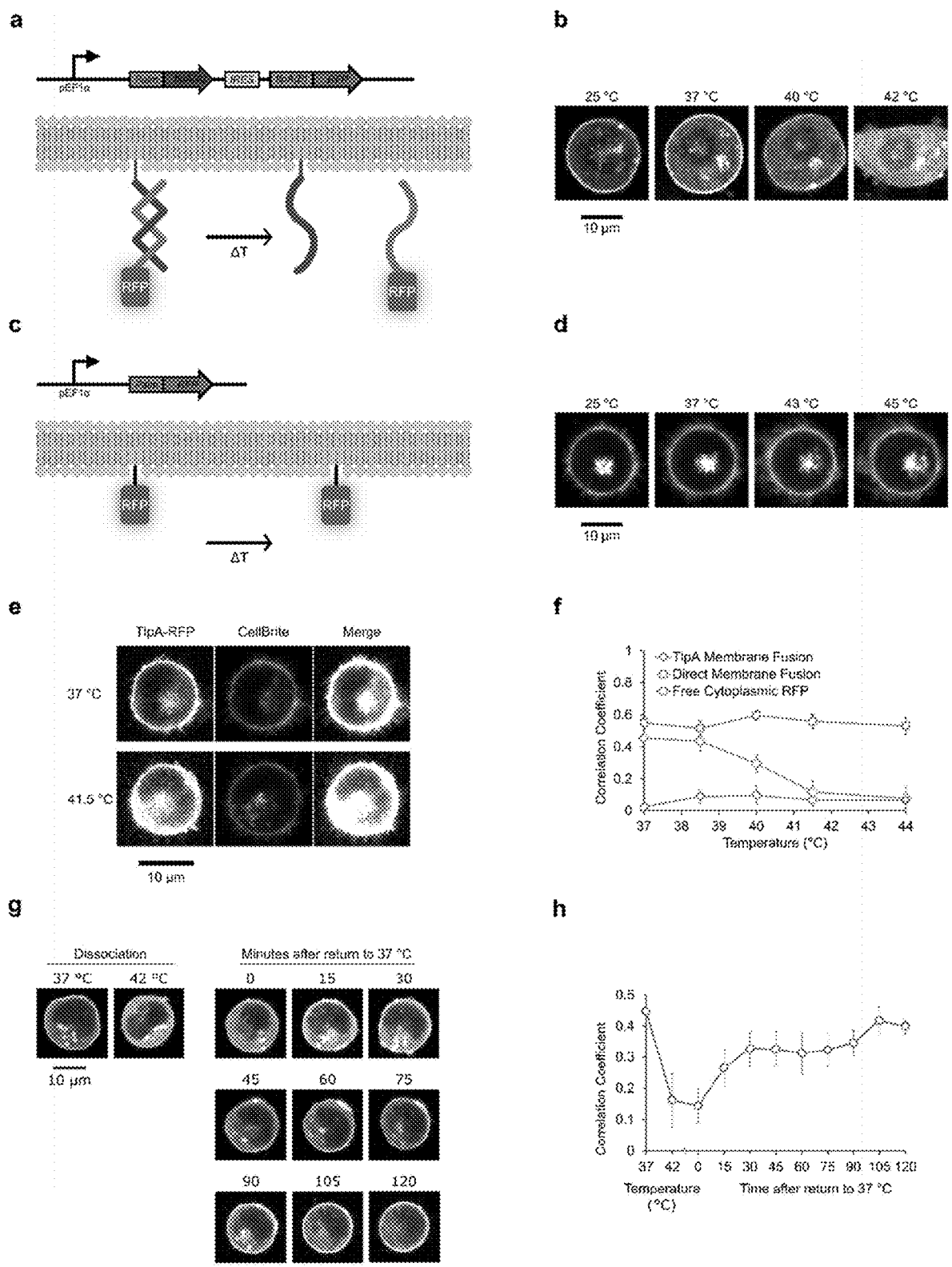
Figure 12:
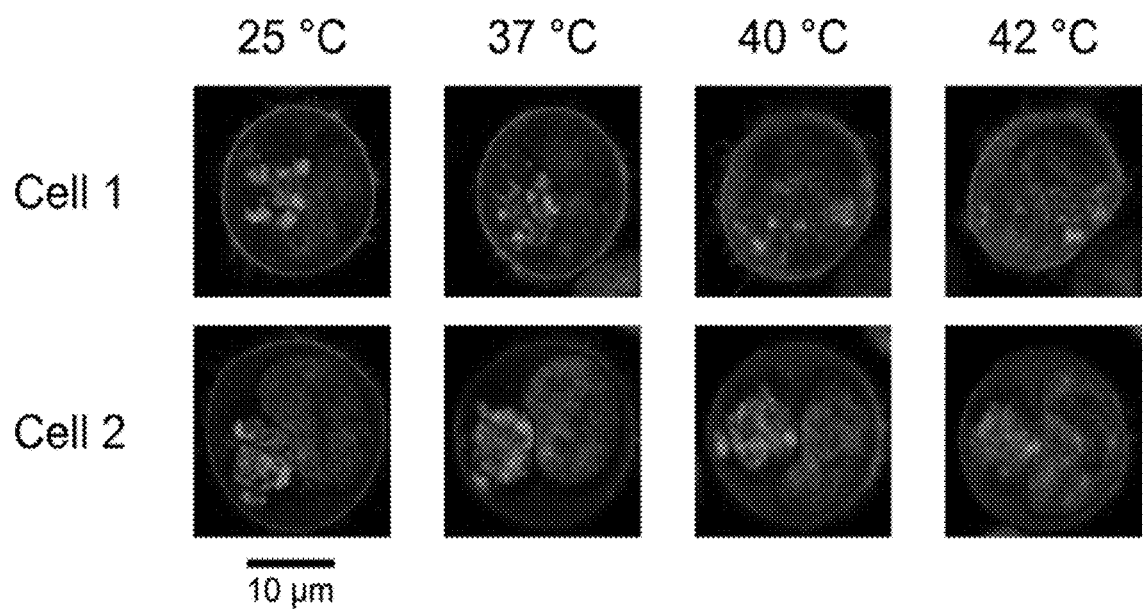

FIG. 12 shows additional replicates for TlpA membrane localization experiment in FIG. 4, Panel b. Pixel intensity was normalized to the maximal per-image value.

Figure 13:
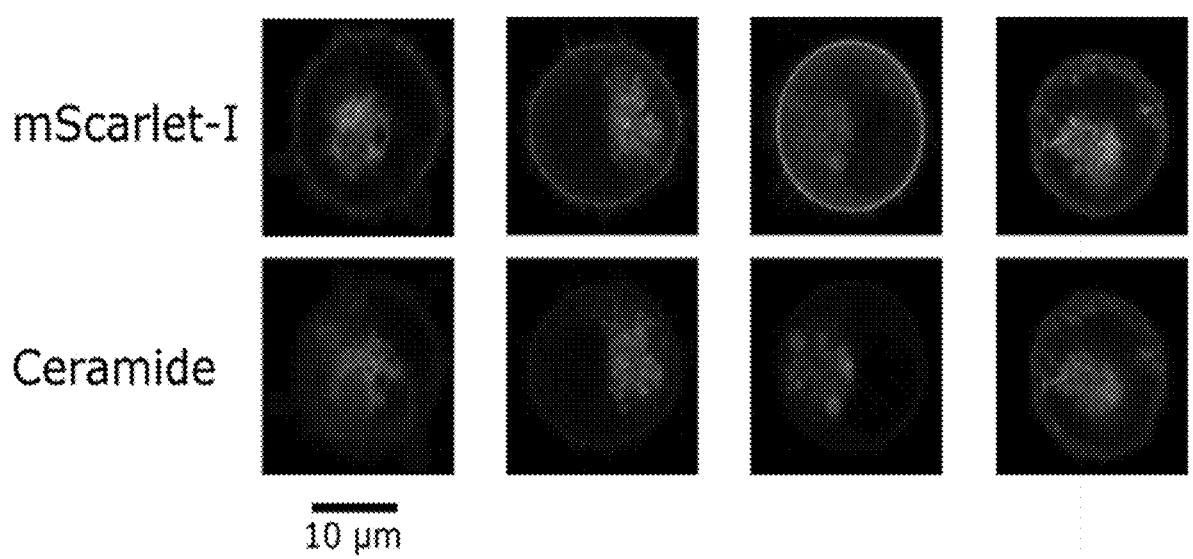

FIG. 13 shows K562 cells transfected with the construct shown in FIG. 4, Panel a were stained with BODIPY-05-Ceramide to label the Golgi transport pathway. Staining morphology was similar to the localization of the mScarlet-I TlpA cargo protein. Four representative cells are shown. Pixel intensity was normalized to the maximal per-image value.

Figure 14:
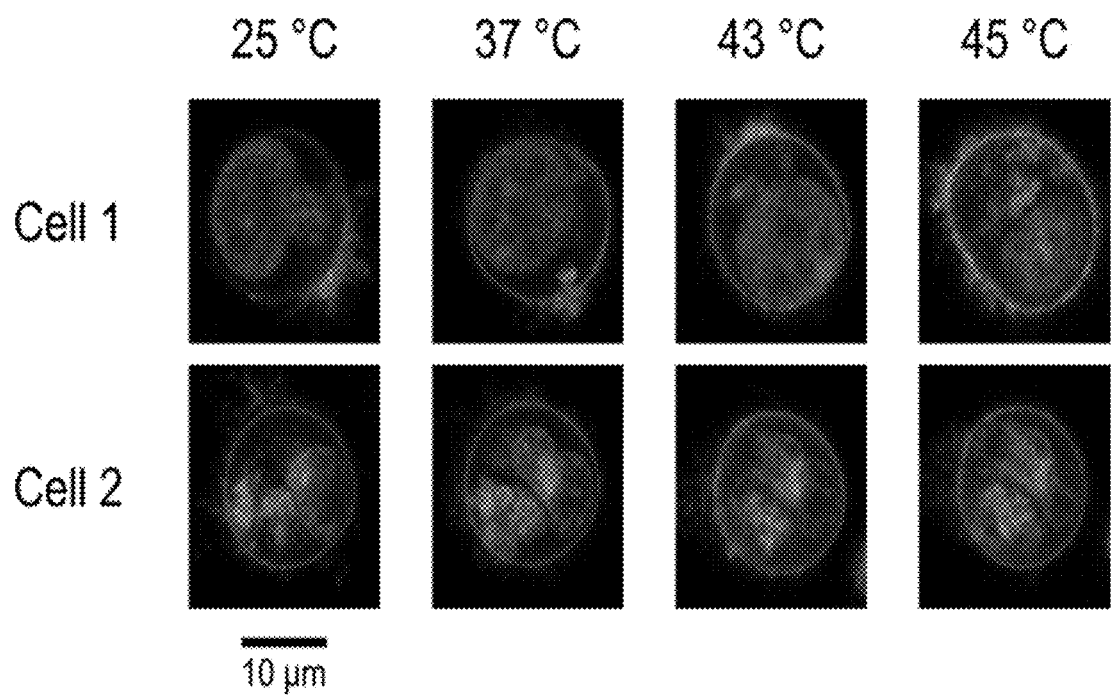

FIG. 14 shows additional replicates of K562 cells transfected with a construct bearing directly palmitoylated mScarlet-I, as in FIG. 4, Panel d. Robust membrane localization was observed up to 45° C. in most cells. Data presented are representative of two separate experiments. Pixel intensity was normalized to the maximal per-image value.

Figure 15:
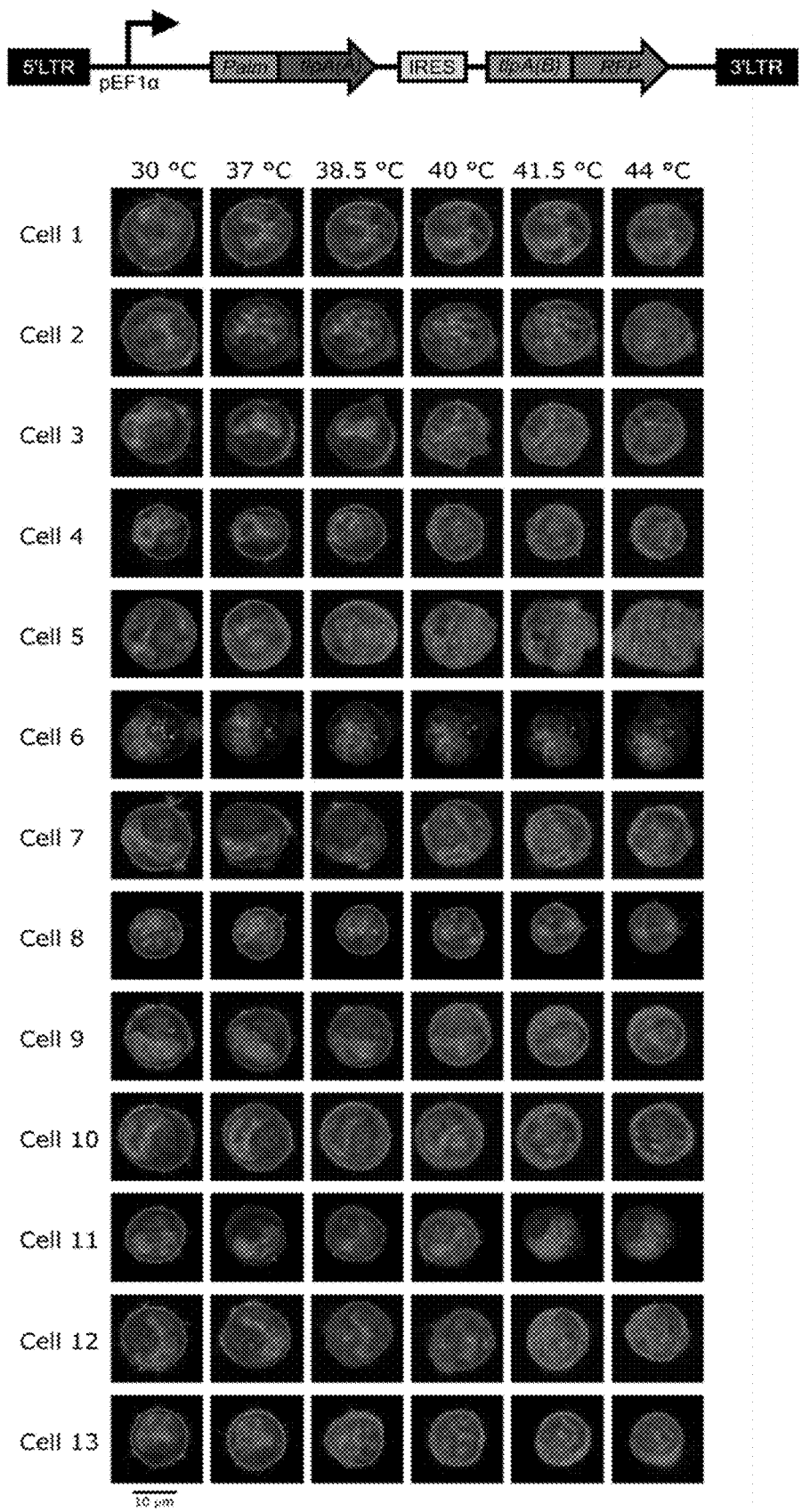

FIG. 15 shows a Lentiviral construct for membrane-localized RFP delivery containing nonhomologous TlpA39-G2A3 (top) and Fluorescence images at different temperatures of K562 cells lentivirally transduced with the nonhomologous TlpA-mediated membrane localization system (bottom). Pixel intensity was normalized to the maximal per-image value.

Figure 16:
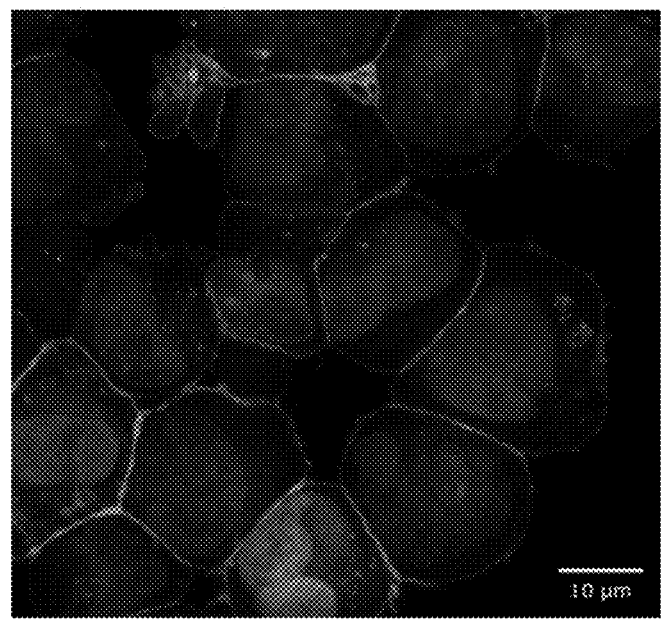

FIG. 16 shows a confocal imaging of K562 cell line transduced with the lentiviral construct depicted in FIG. 15. Cells were pelleted, deposited on a glass slide, sealed with a cover slip, and imaged on an LSM880 with a Plan-Apochromat 63×/1.4 Oil DIC M27 objective with oil immersion. Note that all cells, regardless of local cytoplasmic or membrane brightness, display visible RFP accumulation along the plasma membrane.

Figure 17:
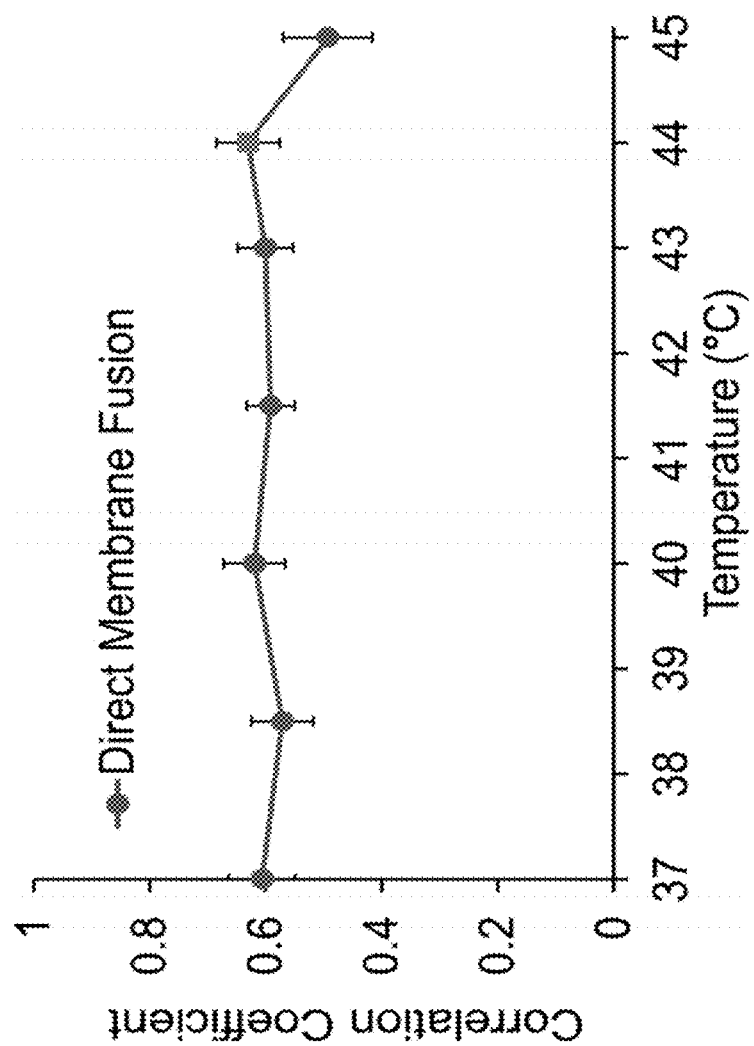

FIG. 17 show a plot representing CellProfiler quantification of the two data sets contributing to the Direct Membrane Fusion curve in FIG. 4, Panel f. The data point acquired separately at 44° C. is indicated as a lighter square. Error bars represent ±s.e.m.

Figure 18:
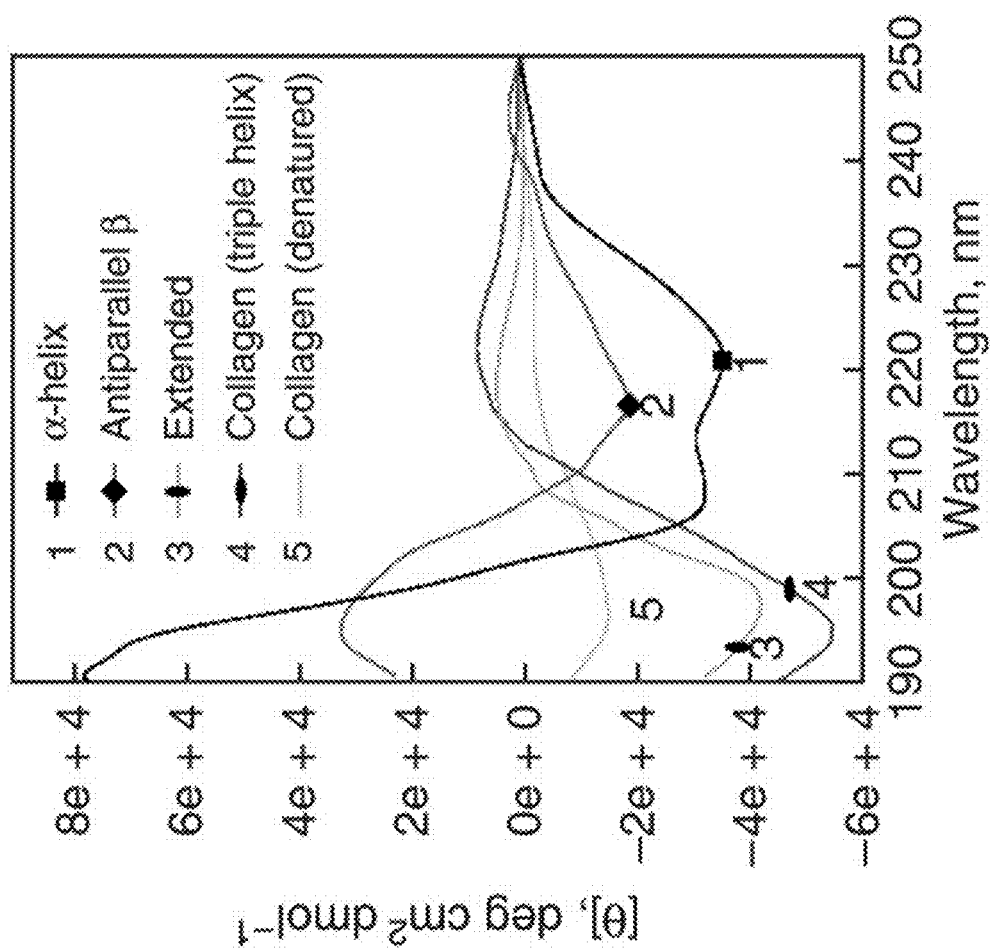

FIG. 18 shows several prototypical protein circular dichroism spectra, including the characteristic alpha-helical spectrum that features local minima at 208 nm+/−3 nm and 222 nm+/−3 nm. Figure from [1].

Figure 19:
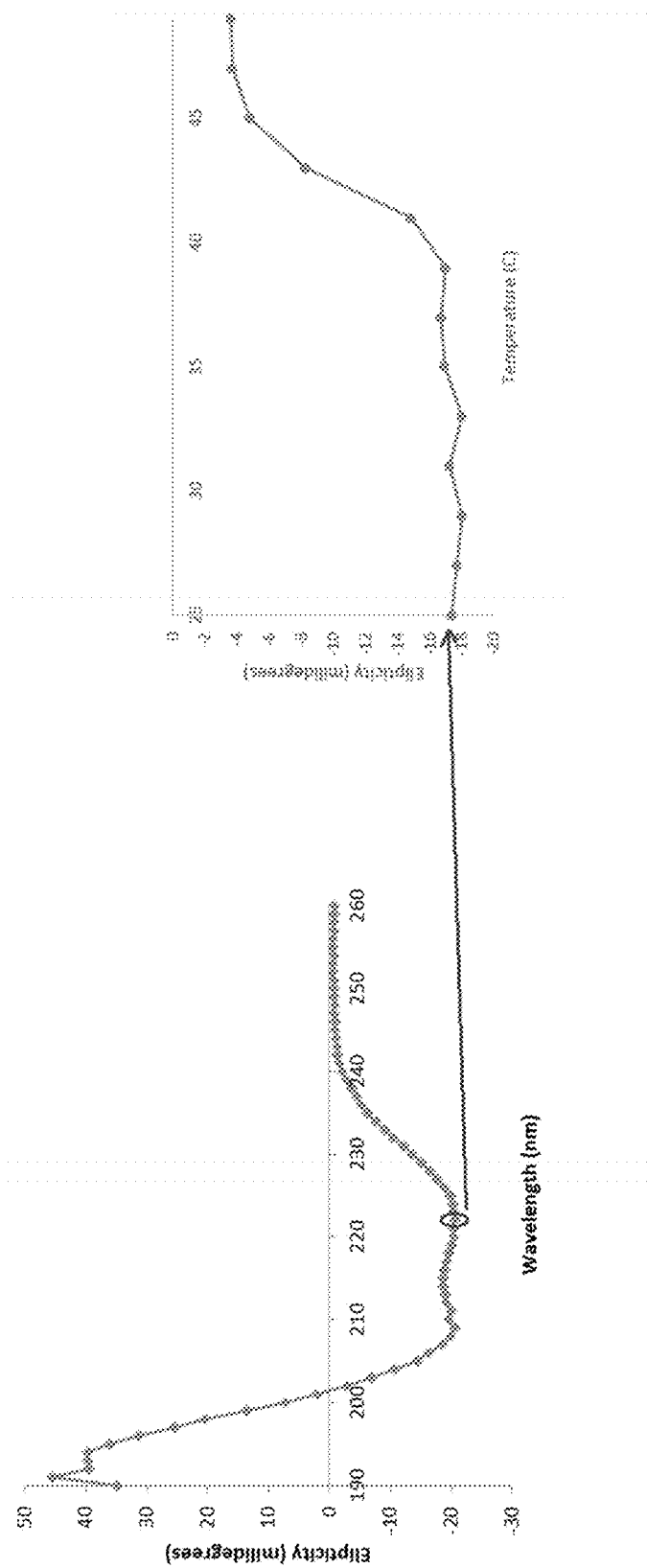

FIG. 19 shows the validation process for thermoswitch evaluation, using the wild type TlpA coiled-coil domain as a prototypical example. First, the circular dichroism spectrum is obtained at a temperature below the expected $T_{bs}$ (in this case at 25° C.). Coiled-coil structure is established by the presence of local minima at 208 nm+/−3 nm and 222 nm+/−3 nm. Subsequently, the ellipticity of the sample at 222 nm is tracked over a temperature course that extends both below and at least 5° C. above the expected $T_{bs}$. An increase of the ellipticity toward zero indicated unfolding of the alpha helical structure, which serves as a proxy for coiled-coil undimerization.

Figure 20:
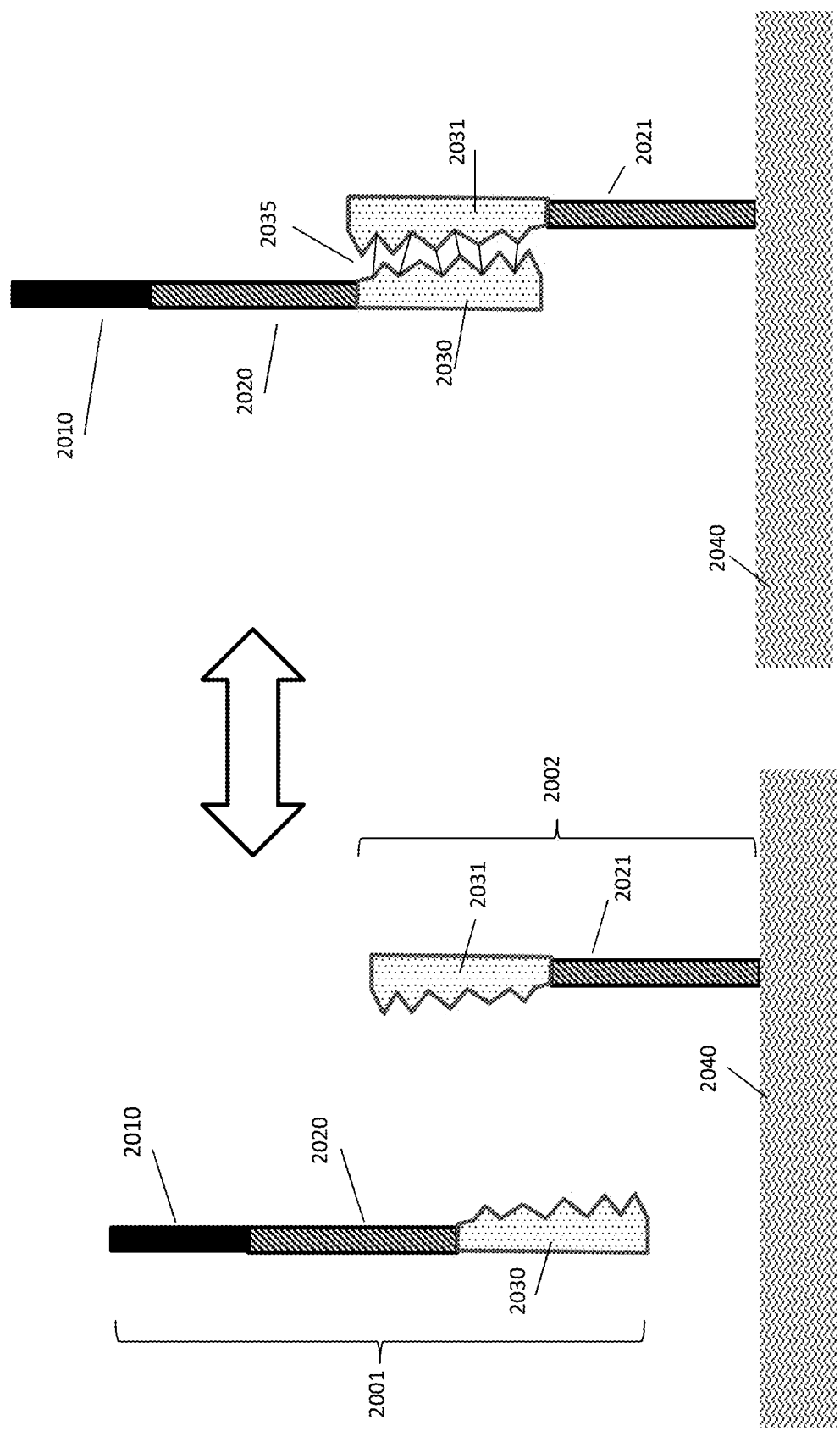
Figure 21:
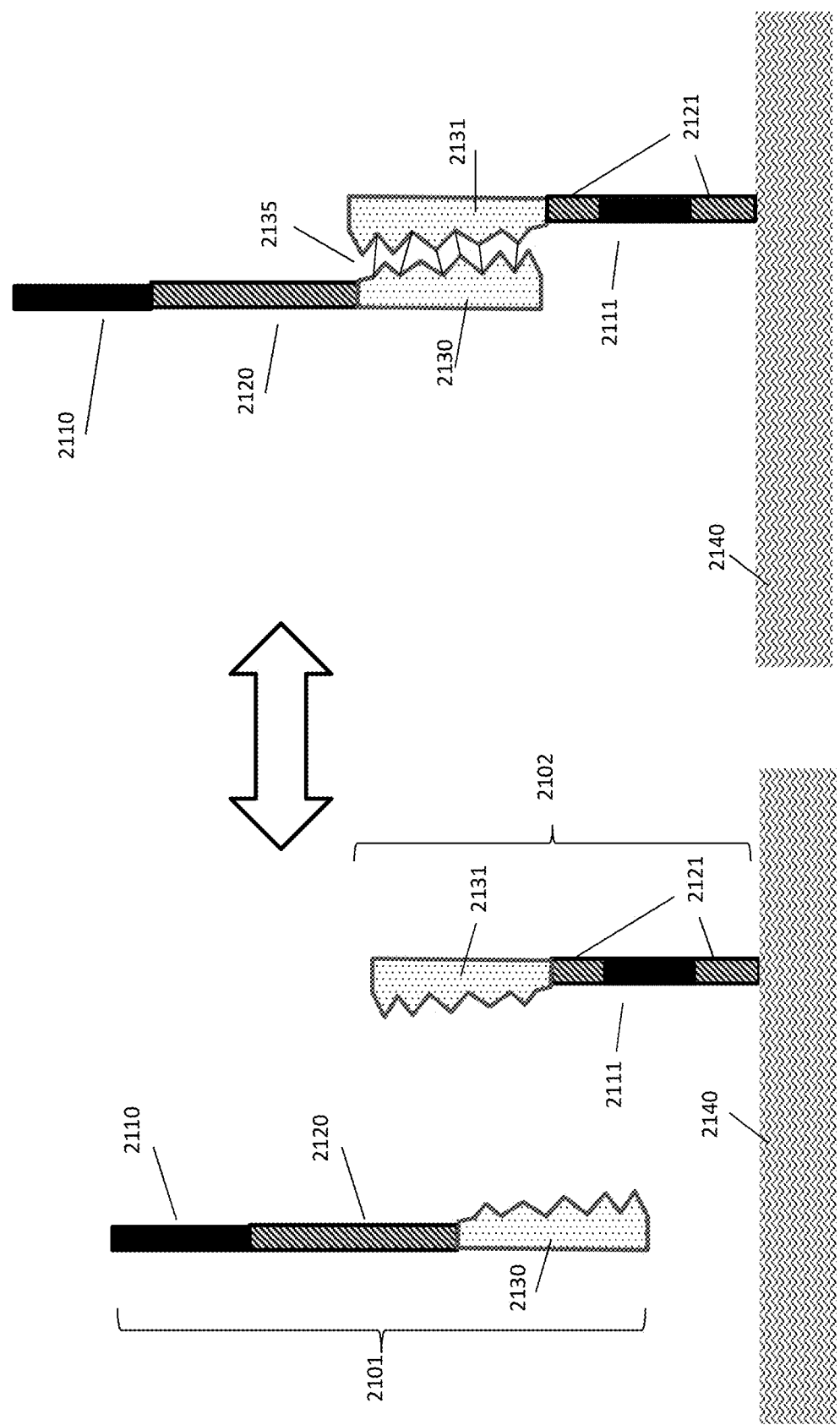

FIGS. 20 to 22 show schematic representation of exemplary surfaces and device according to the present disclosure.

DETAILED DESCRIPTION

Provided herein are modular temperature sensing dimers (herein also dimerization thermoswitches, thermomers, or thermomer dimers) formed by two monomer proteins and related monomers constructs, dimeric complexes, vectors, cells, compositions, methods and systems, which allow in several embodiments controlled thermo-regulated formation of molecular complexes The term "dimer" as used herein indicates a macromolecular complex formed by two polymers and in particular by two proteins.

The term "protein" as used herein indicates a polypeptide with a particular secondary and tertiary structure that can interact with another molecule and in particular, with other biomolecules including other proteins, DNA, RNA, lipids, metabolites, hormones, chemokines, and/or small molecules. The term "polypeptide" as used herein indicates an organic linear, circular, or branched polymer composed of two or more amino acid monomers and/or analogs thereof. The term "polypeptide" includes amino acid polymers of any length including full-length proteins and peptides, as well as analogs and fragments thereof. A polypeptide of three or more amino acids is also called a protein oligomer, peptide, or oligopeptide. In particular, the terms "peptide" and "oligopeptide" usually indicate a polypeptide with less than 100 amino acid monomers. In particular, in a protein, the polypeptide provides the primary structure of the protein, wherein the term "primary structure" of a protein refers to the sequence of amino acids in the polypeptide chain covalently linked to form the polypeptide polymer. A protein "sequence" indicates the order of the amino acids that form the primary structure. Covalent bonds between amino acids within the primary structure can include peptide bonds or disulfide bonds, and additional bonds identifiable by a skilled person. Polypeptides in the sense of the present disclosure are usually composed of a linear chain of alpha-amino acid residues covalently linked by peptide bond or a synthetic covalent linkage. The two ends of the linear polypeptide chain encompassing the terminal residues and the adjacent segment are referred to as the carboxyl terminus (C-terminus) and the amino terminus (N-terminus) based on the nature of the free group on each extremity. Unless otherwise indicated, counting of residues in a polypeptide is performed from the N-terminal end ($NH_2$-group), which is the end where the amino group is not involved in a peptide bond to the C-terminal end (—COOH group) which is the end where a COOH group is not involved in a peptide bond. Proteins and polypeptides can be identified by x-ray crystallography, direct sequencing, immunoprecipitation, and a variety of other methods as understood by a person skilled in the art. Proteins can be provided in vitro or in vivo by several methods identifiable by a skilled person. In some instances where the proteins are synthetic proteins in at least a portion of the polymer two or more amino acid monomers and/or analogs thereof are joined through chemically-mediated condensation of an organic acid (—COOH) and an amine (—$NH_2$) to form an amide bond or a "peptide" bond.

The two ends of the linear polypeptide chain encompassing the terminal amino acid residues and the adjacent segment are referred to as the carboxyl terminus (C-terminus) and the amino terminus (N-terminus) based on the nature of the free group on each extremity. Unless otherwise indicated counting of residues in a polypeptide is performed from the N-terminal end ($NH_2$-group), which is the end where the amino group is not involved in a peptide bond to the C-terminal end (—COOH group) which is the end where a COOH group is not involved in a peptide bond. A C-terminal end of a polypeptide can be comprised within a "tail" of the protein which indicates a segment formed by amino acid at the C-terminus of the protein As used herein the term "amino acid", "amino acid monomer", or "amino acid residue" refers to organic compounds composed of amine and carboxylic acid functional groups, along with a side-chain specific to each amino acid. In particular, alpha- or α-amino acid refers to organic compounds composed of amine (—$NH_2$) and carboxylic acid (—COOH), and a side-chain specific to each amino acid connected to an alpha carbon. Different amino acids have different side chains and have distinctive characteristics, such as charge, polarity, aromaticity, reduction potential, hydrophobicity, and pKa. Amino acids can be covalently linked to form a polymer through peptide bonds by reactions between the amine group of a first amino acid and the carboxylic acid group of a second amino acid. Amino acid in the sense of the disclosure refers to any of the twenty naturally occurring amino acids, non-natural amino acids, and includes both D an L optical isomers.

In a "dimer" in the sense of the disclosure, the two protein monomers bind to one another through covalent and/or non-covalent interactions as will be understood by a skilled person. Examples of non-covalent interactions comprise ionic bonds, Van der Waals interactions, polar interactions, salt bridges, coulombic attraction, coulombic repulsion, hydrophobic interaction, and others identifiable by a skilled person. An example of a non-covalently bound protein dimer is the enzyme reverse transcriptase. Examples of covalent interactions comprise any chemical bond that involves the sharing of electron pairs between such as disulfide bridges.

Dimers in the sense of the disclosure can be homodimers and heterodimers. The term "homodimer" means a dimer consisting of two monomers with identical polymer sequence, and in particular two polypeptide or protein monomers with identical amino acid sequence. Examples of protein homodimers include the enzyme cyclooxygenase (COX), the methionine repressor MetJ, TlpA, the lambda repressor cI, and others identifiable by a skilled person. The term "heterodimer" means a dimer of two monomers with non-identical polymer sequence, and in particular two polypeptide or protein monomers with non-identical amino acid sequence. Examples of protein heterodimers include the enzyme reverse transcriptase and others identifiable by a skilled person.

Accordingly, the term "monomer" in the sense of the disclosure indicates a polypeptide molecule capable of reversibly forming a dimer with another monomer of the same or different sequence. In particular, a monomer in the sense of the disclosure comprises a polypeptide having an N-terminus and a C-terminus, and configured to dimerize through a dimerizing region.

A "thermomer monomers" according to the disclosure, are polypeptide monomers in which the dimerizing region is a temperature sensing region having residues configured to form non-covalent bonds with corresponding residues of another thermomer monomer, to form a temperature sensing domain of dimer protein at a target temperature $Te=Tm\pm10°$ C., wherein Tm is the melting temperature of the dimer protein, the melting temperature "Tm" the temperature, at which the temperature sensing binding domain of the dimer denaturates, as will be understood by a skilled person.

In embodiments herein described, a thermomer monomer in accordance with the present disclosure is a monomer comprising a temperature sensing region having a temperature sensing sequence $A_1E_2E_3V_4K_5A_6V_7S_8A_9A_{10}L_{11}S_{12}E_{13}R_{14}I_{15}T_{16}Q_{17}L_{18}A_{19}T_{20}$ $E_{21}L_{22}N_{23}D_{24}K_{25}A_{26}V_{27}R_{28}A_{29}A_{39}E_{31}R_{32}R_{33}V_{34}A_{35}E_{36}V_{37}$ $T_{38}R_{39}A_{40}A_{41}G_{42}E_{43}Q_{44}T_{45}A_{46}Q_{47}A_{48}E_{49}R_{50}E_{51}L_{52}A_{53}D_{54}$ $A_{55}A_{56}Q_{57}T_{58}V_{59}D_{60}D_{61}L_{62}E_{63}E_{64}K_{65}L_{66}D_{67}E_{68}L_{69}Q_{70}D_{71}$ $R_{72}Y_{73}D_{74}S_{75}L_{76}T_{77}L_{78}A_{79}L_{80}E_{81}S_{82}E_{83}R_{84}S_{85}L_{86}R_{87}Q_{88}$ $Q_{89}H_{90}D_{91}V_{92}E_{93}M_{94}A_{95}Q_{96}L_{97}K_{98}E_{99}R_{100}L_{101}A_{102}A_{103}$ $A_{104}E_{105}E_{106}N_{107}T_{108}R_{109}Q_{110}X_{111}X_{112}E_{113}R_{114}Y_{115}$ $Q_{116}E_{117}Q_{118}K_{119}T_{120}V_{121}L_{122}Q_{123}D_{124}A_{125}L_{126}N_{127}$ -continued $A_{128}E_{129}Q_{130}A_{131}Q_{132}H_{132}K_{134}N_{135}T_{136}R_{137}E_{138}D_{139}$ $L_{140}Q_{141}K_{142}R_{143}L_{144}E_{145}Q_{146}I_{147}S_{148}A_{149}E_{150}A_{151}$ $N_{152}A_{153}R_{154}T_{155}E_{156}E_{157}L_{158}K_{159}S_{160}X_{161}X_{162}D_{163}$ $K_{164}V_{165}N_{166}T_{167}L_{168}L_{169}T_{170}R_{171}L_{172}E_{173}S_{174}Q_{175}$ $E_{176}N_{177}A_{178}L_{179}A_{180}S_{181}X_{182}X_{183}Q_{184}Q_{185}H_{186}L_{187}$ $A_{188}T_{189}R_{190}E_{191}T_{192}L_{194}Q_{194}Q_{195}R_{196}L_{197}E_{198}Q_{199}$ $A_{200}I_{201}A_{202}D_{203}T_{204}Q_{205}A_{206}R_{207}A_{208}G_{209}E_{210}I_{211}$ $A_{212}L_{213}E_{214}R_{215}D_{216}R_{217}V_{218}S_{219}S_{220}L_{221}T_{222}A_{223}$ $R_{224}L_{225}E_{226}S_{227}Q_{228}E_{229}K_{230}A_{231}S_{232}S_{233}E_{234}Q_{235}$ $L_{236}V_{237}R_{238}M_{239}G_{240}S_{241}E_{242}I_{243}A_{244}S_{245}L_{246}T_{247}$ $E_{248}R_{249}C_{250}T_{251}Q_{252}L_{253}E_{254}N_{255}Q_{256}R_{257}D_{258}D_{259}$ $A_{260}R_{261}L_{262}E_{263}T_{264}M_{265}G_{266}E_{267}K_{268}E_{269}T_{270}V_{271}$ $A_{272}A_{273}L_{274}R_{275}G_{276}E_{277}A_{278}E_{279}A_{280}L_{281}K_{282}R_{283}$ $Q_{284}N_{285}Q_{286}S_{287}L_{288}M_{289}A_{290}A_{291}$ wherein $X_{111}$ $X_{112}$, $X_{161}$ $X_{162}$ $X_{182}$ and $X_{183}$ are independently a negatively charged amino acid preferably a E and/or D or a positively charged amino acid preferably K and/or R, or a derivative thereof comprising neutral substitution of at least one residue of the temperature sensing region.

The term "charged" as used herein means a molecule, and in particular an amino acid that has an ionically charged side chain at the pH of a target environment, e.g. at physiological pH of a cellular or intracellular cellular environment, as understood by a skilled person.

In particular, charged amino acid in the sense of the disclosure can be selected taking into account the fact that in an amino acid the α-carboxylic acid group of amino acids is a weak acid, meaning that it releases a proton at moderate pH values. In other words, carboxylic acid groups (—$CO_2H$) can be deprotonated to become negative carboxylates (—$CO_2$—). The negatively charged carboxylate ion predominates at pH values greater than the pKa of the carboxylic acid group. Also, in a cellular or intracellular cellular environment in a complementary fashion, the α-amine of amino acids is a weak base, meaning that it accepts a proton at moderate pH values. In other words, α-amino groups ($NH_2$—) can be protonated to become positive α-ammonium groups (+$NH_3$—). The positively charged α-ammonium group predominates at pH values less than the pKa of the α-ammonium group.

Therefore, a positively charged amino acid in the sense of the disclosure has a side chain positively charged at the pH defined by a target environment where the thermomer monomer is configured to operate.

A negatively charged amino acid in the sense of the disclosure, is an amino acid having a side chain positively charged at the pH defined by a target environment where the thermomer monomer is configured to operate.

The wording “target environment” as used herein indicates any a combination of structures and fluids where the thermomer monomers, dimers, construct and complexes of the disclosure are configured to operate. Typically, the target environment includes a combination of structures and fluid (herein also media) with a dielectric constant around 80. In particular, exemplary environment can have a dielectric constant ranging from 40 to 150, 50 to 80, 30 to 60, and higher than 15.

Exemplary target environments comprise cell free reactions mixture, cells, tissues, organs in vitro in vivo or ex vivo, collections of microorganisms in vitro as well as cells grown in an in vitro culture, including, primary mammalian, cells, immortalized cell lines, tumor cells, stem cells, and the like. Additional exemplary target environment include tissues and organs in an ex vivo culture and tissue, organs, or organ systems in a subject, for example, lungs, brain, kidney, liver, heart, the central nervous system, the peripheral nervous system, the gastrointestinal system, the circulatory system, the immune system, the skeletal system, the sensory system, within a body of an individual and additional environments identifiable by a skilled person. The term “individual” or “subject” or “patient” as used herein in the context of the present disclosure includes a single plant, fungus or animal and in particular higher plants or animals and in particular vertebrates such as mammals and more particularly human beings.

Exemplary pH values of exemplary target environments herein described comprise pH 7.2 (cytoplasm of most cells), 6.8-7.2 (cytoplasm of mammalian skeletal muscle), 5 (lysosomes), and 7.4 (standard PBS buffer).

Charges of natural amino acids can be determined by a skilled person upon identification of the target environment. For example, at pH=7.4 (e.g. in cellular or intracellular cellular environment), among the twenty common natural amino acids, five have a side chain which can be charged. At pH=7.4, two are negatively charged: aspartic acid (Asp, D) and glutamic acid (Glu, E) (acidic side chains), and three are positive charged: lysine (Lys, K), arginine (Arg, R) and histidine (His, H) (basic side chains).

Charged of non-natural amino acid such as noncanonical amino acids with sidechains that bear charges at their environmental pH can also be determined by a skilled person based on the related side chain. Exemplary charged noncanonical amino acids include α-aminoadipic acid (Aad) and γ-carboxyglutamic acid (Gla). Other non-canonical amino acids can contain positive charges harbored in moieties known to a skilled person to harbor positive charges such as a primary amine or guanidino group, or can contain negative charges harbored in moieties known to a skilled person to harbor negative charges such as carboxylate groups as will be understood by a skilled person.

Positively charged and negatively charged amino acids in the sense of the disclosure are therefore configured to have electrical interactions under pH conditions at which both species bear a charge (such as 7.2 in the cytoplasm of most cells), and under dielectric constants that permit coulombic interactions (such as 76 in the cytoplasm of most cells), and at distances between the charged moieties that permit significant force transmission between the charged moieties (such as <4 Angstroms in a dielectric constant of 76, as in the cytoplasm of most cells) >as will be understood by a skilled person.

The term “coulombic interactions” or “electrostatic interactions” as used herein, refers to interactions between static electrically charged particles, an in particular between amino acids, wherein amino acids can be coulombically attracting or coulombically repelling, according to Coulomb’s law where $\varepsilon_0$ is the vacuum permittivity, $\varepsilon_r$ is the dielectric constant of the medium, and $q_1$ and $q_2$ are the respective charges on the participating atoms.

$$F = \frac{1}{4\pi\varepsilon_0\varepsilon_r}\frac{q_1 q_2}{r^2}. \quad \text{(Eq. 1)}$$

Electrostatic interactions comprise ionic interactions, hydrogen bonding, halogen bonding, Van der Waals forces, dipole-dipole, dipole-induced dipole, hydrophobic effects, and others as understood by a skilled person.

In particular, a thermomer monomer in accordance with the present disclosure the temperature sensing region is configured to dimerize in a target environment at a target temperature Te<Tbs in a temperature dependent manner to form a coiled coil temperature sensing domain. Preferably in accordance with the present disclosure the temperature sensing region is configured to dimerize in a target environment at a target temperature Te=Tbs−from 2° C. to 10° C.

The term "domain" as related to the protein indicates any continuous part of a protein sequence from single amino acid up to the full protein associated to an identifiable structure within the protein. An "identifiable structure" in the sense of the disclosure indicates a spatial arrangement of the primary structure or portions thereof which can be detected by techniques such as crystallography, hydrophobicity analysis or additional techniques known by a skilled person. In many instances, a protein domain comprises one or more secondary structures of the protein, which together form a tertiary or quaternary structure of a protein.

The "secondary structure" of a protein refers to local sub-structures with a repeating geometry identifiable within crystal structure of the protein, circular dichroism or by additional techniques identifiable by a skilled person. In some instances, a secondary structure of a protein can be identified by the patterns of hydrogen bonds between backbone amino and carboxyl groups. Secondary structures can also be defined based on a regular, repeating, geometry, being constrained to approximate values of the dihedral angles ψ and φ of the amino acids in the secondary structure unit on the Ramachandran plot. Two main types of secondary structure are the alpha helix and the beta strand or beta sheets as will be identifiable by a skilled person. Both the alpha helix and the beta sheet represent a way of establishing non-covalent hydrogen bonds between constituents of the peptide backbone, thus forming secondary structural features. Secondary structure formation can be promoted by formation of hydrogen bonds between backbone atoms. Amino acids that can minimize formation of a secondary structure by destabilizing the structure of the hydrogen bonding interactions are referred to as secondary structure breakers. Amino acids that can promote formation of a secondary structure by stabilizing formation of hydrogen bonding interactions are referred to as structure makers.

The term "tertiary structure" refers to the three-dimensional structure of a protein, stabilized by non-covalent interactions among non-adjacent segments of the protein and optionally by one or more additional compounds or ions interacting through covalent or non-covalent interactions with one or more segments of the proteins. Exemplary non-covalent interactions stabilizing the three dimensional structure of the proteins comprise non-specific hydrophobic interactions, burial of hydrophobic residues from water, specific tertiary interactions, such as salt bridges, hydrogen bonds, the tight packing of side chains, chelation and disulfide bonds and additional interactions identifiable by a skilled person. Exemplary covalent interactions among compounds or ions and segments of the protein comprise N-linked glycosylation, cytochrome C haem attachment and additional interaction identifiable by a skilled person.

The term "quaternary structure" when referred to a complex refers to the three-dimensional structure of a protein complex, also called a multimer, stabilized by non-transitory interactions between the two or more proteins forming the complex. Accordingly, the quaternary structure can be stabilized by some of the same types of non-covalent and covalent interactions as the tertiary structure as will be understood by a skilled person. Multimers made up of identical subunits are referred to with a prefix of "homo-" (e.g. a homotetramer) and those made up of different subunits are referred to with a prefix of "hetero-", for example, a heterotetramer, such as the two alpha and two beta chains of hemoglobin. "Non-transitory interactions" as used herein indicates interactions between proteins or related segments that are detectable by laboratory techniques such as immunoprecipitation, crosslinking and Forster Resonance Energy Transfer (FRET) measurements, crystallography, Nuclear Magnetic Resonance (NMR) and additional techniques identifiable by a skilled person.

Detection of three-dimensional secondary, tertiary, or quaternary protein structure can be performed using techniques such as x-ray crystallography, NMR spectroscopy, dual polarization interferometry among others known to a skilled person. Using such techniques, the position of structural features comprising alpha-helices, beta strands, turns, beta bridges, bends, loops, coils, coiled coils, and others identifiable by a skilled person within the N-terminal to C-terminal primary sequence of a protein can be detected.

In particular, detection of repeated motifs in a protein domain in the sense of the disclosure can be performed using structure prediction servers COILS[2], Paircoil2[3], LOGICOIL[4] and JPred[5]. Structure of polypeptides and proteins can also be obtained from publicly available sources such as Protein Data Bank [6] and others known to a skilled person.

The term "temperature-sensing domain" refers to a protein or a portion thereof having a sequence configured to provide structural lability in response to temperature changes. This structural lability results in a change in the behavior of the switch between the "below threshold" and "above threshold" temperatures, where behavior means the output of the system controlled by the switch. In one embodiment, the output is a mRNA transcript whose production is blocked by binding of the switch to DNA at low temperature and enabled by unbinding of the switch from the DNA at high temperature.

A coiled coil temperature sensing domain in the sense of the disclosure indicates a temperature sensing domain comprising temperature sensing supercoiled motif of alpha-helical secondary structures. In particular, the term "coiled coil" indicates a structural motif in a protein in which two to seven alpha-helices are coiled together like the strands of a rope and interact with coiled coil structural motifs in one or more other proteins. Dimers and trimers are the most common types.

Coiled coils usually contain a repeated pattern, "hxxhcxc" (SEQ ID NO: 2), of hydrophobic (h) and charged or polar (c) amino-acid residues, referred to as a heptad repeat. The positions in the heptad repeat can be labeled "abcdefg", according to a register where "a" and "d" are generally hydrophobic positions, often being occupied by isoleucine, leucine, or valine.

The term "register" as used herein in relation to a heptad repeat indicates the sequence of the positions a, b, c, d, e, f, g within the heptad repeat in an alpha-helical coiled coil. In particular a register indicates a series of consecutive positions among the possible consecutive a, b, c, d, e, f and g positions starting at any one of positions a, b, c, d, e, f, or g and can be interrupted by variation of the sequence such as deletion or insertions. A heptad coil register can be assigned based on consensus between previous literature [7] and structure prediction servers including COILS[2], Paircoil2 [3], LOGICOIL[4], and Jpred[5]. Folding a sequence with this repeating pattern into an alpha-helical secondary structure causes the generally hydrophobic "a" and "d" residues to be presented as a stripe that coils around the alpha helix, forming an amphipathic structure as will be understood by a skilled person.

In a coiled coil temperature sensing domain, alpha helices of the coiled coil motif form a tertiary or quaternary structure in a water-filled environment such as the cytoplasm, and in particular the hydrophobic strands are wrapped against each other and are sandwiched between the hydrophilic amino acids. The alpha-helices can be parallel or anti-parallel, and can adopt either a left-handed or right-handed coiled coil. Coiled coils can be depicted using a 'helical wheel' diagram, in which the coiled coils are viewed down the axis of the alpha-helices from N-terminus to C-terminus such as the exemplary structure schematically illustrated in FIG. 16 of U.S. application Ser. No. 15,384,254 filed on Dec. 19, 2016 and published with publication number US2017/0928425 with reference to the coiled coil domain of TlpA, which shows a series of helical wheel representations of the homodimeric coiled-coil, with each monomer coil made up of heptad repeats.

In embodiment herein described, dimerization involves a dynamic process of forming a thermomer dimer of two thermomer monomers involving interactions between corresponding residues of the two thermomer monomers in their respective temperature sensing regions forming the temperature sensing domain of the thermomer dimers herein described.

The term "corresponding residues" as used herein indicates residues capable of interacting within a protein complex and typically forming through covalent or non-covalent binding or links.

The terms "covalent bond", "covalent binding" or "covalent link" as used herein indicate an interaction by which two moieties are associated by formation of a covalent chemical bond. Exemplary covalent bonds comprise s disulfide bond, and amide bond of amino acid side chains of a peptide or protein.

The terms "non-covalent bond", "non-covalent binding" or "non-covalent link" as used herein indicate to an interaction by which two moieties are associated by a non-covalent attractive force. Non-covalent interactions comprise hydrophobic interactions such as pi-pi interaction of aromatic groups, or van der Waals interaction of hydrophobic groups of amino acid side chain, electrostatic interactions such as polar interactions, coulombic attraction of opposite charge groups, coulombic repulsion of same charge group and others identifiable by a skilled person.

In embodiment herein described, dimerization of thermomer monomers involves a dynamic process of forming a coiled coil temperature sensing domain of a thermomer dimer involving non-covalent interactions between corresponding residues in positions a to g of heptad repeats in the temperature sensing region of each monomer protein as will be understood by a skilled person.

In particular, in dimerization of thermomer monomers herein described corresponding hydrophobic residues at positions a and d interact with each other and form the hydrophobic core or interface of the coiled coils, and are mainly responsible for the formation and stability of the coiled-coil. Electrostatic attractions at between corresponding residues in positions d-e and g-e can provide additional stability to the system by encouraging the salt bridge formation between the two coils.

Formation of these interchain salt bridges can also shield the non-polar core from solvent, further stabilizing the coiled-coils. Positions e and g of the heptad repeat flank the hydrophobic interface of the coiled-coil and can contribute to the hydrophobicity of the core by folding over the interface to interact with the hydrophobic residues through their side chain methylene groups, thereby shielding the core from water. Examples of proteins including coiled coil temperature domain include dimers such as lac repressor, TlpA protein, KfrA and others identifiable by a skilled person and other proteins not involved in regulation of gene expression, such as myosin, tropomyosin, and others as will be identified by a skilled person.

Structure prediction servers such as COILS[2], Paircoil2 [3] and LOGICOIL[4] and Jpred among other as will be understood by a skilled person can be further used for analysis of coiled coil domains. Graphical depictions of coiled coils can be produced using software such as Draw-Coil 1.0[8].

Examples of structural analysis results of thermomers derived from the TlpA coiled-coil domain using these programs are shown in FIG. 8, where the coiled-coil regions and heptad registers are predicted via consensus between COILS, Paircoil2, and LOGICOIL, and the resulting spatial arrangement of amino acids including the resulting predicted charge-charge interactions are predicted using DrawCoil 1.0. In particular, in the exemplary illustration of FIG. 8 The predicted alpha-helical heptad repeat (labeled a-b-c-d-e-f-g) is shown, connected by progressively thinner straight lines shown in an N-terminal to C-terminal direction. A straight dashed line is shown between the last residue of a heptad and the first residue of a next heptad in a portion of the heptad repeat. Single-letter amino acid symbols shown circled at each position in a heptad. The sequence of amino acids in an N-terminal to C-terminal direction are shown at each position of a heptad, with the first heptad in the portion of the heptad repeat shown on the line of each large circle representing an alpha-helix, and the amino acids of consecutive heptads are shown further out from the large circle. Curved dashed lines represent predicted ionic interactions. The coil register was assigned based on the COILS server in the www.ch.embnet.org/cgi-bin/COILS_form_parser webpage. The images were produced using DrawCoil 1.0[8].

Thermomer monomers according to the disclosure and related configuration are based on the temperature sensing domain of the temperature sensing transcription factor TlpA Temperature sensitive transcription factors" "thermal transcriptional bioswitches" or "transcriptional bioswitches" in the sense of the disclosure herein also indicated as "transcriptional bioswitches" are transcription factors that have a DNA-bound state or conformation in which the transcription factor is specifically bound to a corresponding DNA regulatory sequence through a DNA binding domain, and a DNA unbound state or conformation in which the transcription factor is not bound to a corresponding DNA regulatory sequence in particular.

A temperature sensitive transcription factor comprises a DNA binding domain and a temperature-sensing domain. In temperature sensing transcription factor, the factor can convert from a DNA-bound state to a DNA-unbound state with reference to corresponding DNA regulatory sequence at a bioswitch temperature Tbs through binding and dissociation of the temperature sensing domain of the transcription factor at the bioswitch temperature Tbs.

The thermomers of the present disclosure, are based on the surprising finding that the temperature sensing domain or the temperature sensing transcription factor TlpA maintain an ability to dimerize and disassociate in a temperature-controlled fashion at a bioswitch temperature Tbs even in absence of a related DNA binding.

Accordingly, thermomer monomers comprising a temperature sensing region from TlpA and in particular the temperature sensing region of SEQ ID NO: 1, can dimerize and disassociate in a temperature controlled fashion at a bioswitch temperature Tbs thus forming thermomer dimer having the ability to act as bioswitches a bioswitch temperature Tbs as will be understood by a skilled person.

In exemplary embodiments, the bioswitch temperature is, 39° C. to 42° C. range preferably 40° C. Accordingly, the target environment temperature can be from 25° C. to 40° C. preferably 36° C. to 38° C. and preferably Te is 37° C.

In particular, in a temperature sensing domain of a thermomer dimer of the disclosure, the coiled coil temperature sensing region of a first thermomer monomer and the coiled coil temperature sensing region of a second thermomer monomer are joined by non-covalent bounds of corresponding residues comprising $X_{111}$ of the first thermomer monomer and $X_{112}$, of the second thermomer monomer $X_{162}$ of the first thermomer monomer and $X_{161}$ of the second thermomer monomer and $X_{183}$ of the first thermomer monomer and $X_{182}$ of the second thermomer monomer as well as, other corresponding residues having non-covalent bonds that can serve to induce interactions between the first thermomer monomer and the second thermomer monomer.

These corresponding residues and related interactions can be predicted using coiled-coil heptad register prediction software (e.g. COILS) and visualization software (e.g. DrawCoil 1.0) as discussed elsewhere in the document, and their functionality can be validated via circular dichroism spectroscopy as exemplified in FIG. 19, and as will be understood by a skilled person upon reading of the present disclosure (see also Examples section).

In in coiled coil temperature sensing domain of thermomer dimers herein described, the dimerization or de-dimerization of two monomers exhibits a cooperative behavior, also referred to as "cooperativity". Cooperativity occurs in molecular structures containing multiple binding sites. In general, cooperativity describes the changes in conformation or binding energy that occur when a binding site of one of these structures is activated or deactivated effecting the other binding sites in the same molecule. It can also be described as the increasing (positive cooperativity) or decreasing (negative cooperativity) affinity for binding of the other sites affected by the original binding site. Cooperativity can occur in enzymes, receptors, DNA and many molecules that are made of identical or near identical subunits. An example of positive cooperativity can be seen on the binding of oxygen to hemoglobin to form oxyhemoglobin. Another example is the unwinding of DNA in which sections of DNA first unwind followed by the process of unwinding another group of adjacent nucleotides. Similar processes also apply to other types of chain molecules, such as the folding and unfolding of alpha-helices in coiled-coils of the temperature-sensing domain.

In embodiments herein described, the cooperativity of a temperature-sensing domain can be quantified by a single parameter referred to as "Hill coefficient". The Hill coefficient is a measure for the cooperative of the temperature-sensing domain de-dimerization transition. High Hill coefficients go together with sharp de-dimerization transitions while low Hill coefficients indicate a gradual transition from the folded dimer to unfolded two monomer conformation. The Hill coefficient can be mathematically calculated from fitting a circular dichroism (CD) melting curves as follow:

$$f(T) = \frac{aT^b}{T_m^b + T^b} \quad \text{Eq. 2}$$

where $T_m$ is the melting temperature of a temperature-sensing domain of a thermomer dimer, a the amplitude, T the temperature in units of Celsius or and b the Hill coefficient.

The melting temperature "Tm" of a temperature sensing binding domain is the temperature, at which the temperature sensing binding domain desaturates. The change in size or structure that accompanies the protein denaturation can be identified using DLS techniques, CD techniques and other techniques identifiable by a skilled person. Factors affecting the Tm of a temperature sensing domain comprise the primary sequence of amino acids and environment conditions, e.g. pH and salt concentration, as well as post translational modifications, e.g. glycosylation, and formation of complex with other molecules (proteins or DNA) or other factors that can affect the stability of the protein structure and hence the melting temperature as will be understood by a skilled person.

As a person skilled in the art would understand, CD and other spectroscopic measurements that measure changes in absorption and fluorescence collected as a function of temperature can determine the thermodynamics of protein unfolding and binding interaction. For example, measuring CD as a function of temperature can be used to determine the effects of mutations on protein stability, as well as the binding constants of interacting proteins and protein-ligand complexes.

In some embodiments, a CD melting curve can be recorded using spectroscopic technique for following the de-dimerization and dimerization of temperature-sensing domains as a function of temperature, as will be understood by a person skilled in the art.

Coiled coil temperature temperature-sensing domains in the sense of the current disclosure contain a two-stranded α-helical coiled-coil structure that have sharp uncoiling transitions with a Hill coefficient above 15. In some embodiments, the two monomer proteins of the coiled coil temperature sensing domain are further configured to bind to one another in the target environment with a thermal Hill coefficient from 15 to 40 to form the dimer in a temperature dependent manner. For example, the coiled-coil domain of thermomer dimers herein described can have a Hill coefficient of from about 15 to 25.

For example, a sharp transition of thermomer dimerization between coiled coil domains of each monomer features cooperative binding, as indicated by the Hill coefficient. The Hill coefficient can be identified by fitting a circular dichroism melting curve dataset of any thermomer to the thermal Hill equation, with signal normalized from 0 to 1 on the Y-axis and temperature in units of ° C. on the x axis. As a representative example, the thermal Hill coefficient of the $G_1A/G_1B$ thermomer in FIG. 1d is computed to be 17.85 using the "Specific binding with Hill Slope" curve fit function in the GraphPad Prism software package. Identification of proteins having similar cooperative dimer binding can be done using techniques including circular dichroism (CD) spectroscopy and calculating Hill coefficient from fitting a circular dichroism (CD) melting curve, as previously described.

In coiled coil temperature sensing dimers, the Tm of the temperature sensing domain also controls the temperature of the target environment at which the temperature sensitive monomers specifically bind to one another forming a dimer, herein also bioswitch temperature or Tbs), determined by the melting temperature Tm of the temperature sensitive binding domain.

In particular, in temperature sensing coiled-coil interaction domain essentially consisting of supercoiled alpha-helical structure, cooperative unfolding of the coil results in a loss of the ability to correctly position the two halves of the DNA binding domain found at the N-termini of each protein chain.

In particular, in coiled coil temperature sensing domain, the Tm of the temperature sensing domain defines the bioswitch temperature of the temperature sensitive dimer (Tbs) herein also indicated as threshold temperature, the Tbs being a temperature of the target environment at which the temperature sensitive monomers bind to form a dimer, with Tbs=Tm+0° C. to 5° C. In particular, Tbs=Tm+0° C. to 5° C. in a target environment with a net concentration of monomer proteins from 2 to 20 uM.

In some embodiments, the melting temperature Tm of a coiled coil temperature sensing domain herein described can be Tm=from 20 to 80° C. In some embodiments, the melting temperature Tm of the coiled coil temperature sensing domain herein described can be Tm=from 25 to 60° C. In some embodiments the melting temperature Tm of the coiled coil temperature sensing domain herein described can be Tm=from 30 to 50° C. In some embodiments, the melting temperature Tm of the coiled coil temperature sensing domain herein described can be Tm=from 32 to 46° C.

In some embodiments, the Tbs can be Tbs=Tm+2.5 to 5° C., wherein the temperature sensitive dimer is encoded in the target environment by a polynucleotide in a number from 100 to 1000 copies per cell. In some embodiments, the Tbs can be Tbs=Tm+1 to 3.5° C., wherein the temperature sensitive dimer is encoded in the target environment by a polynucleotide in a number from 10 to 100 copies per cell. In some embodiments, the Tbs can be Tbs=Tm+0 to 1.5° C., wherein the temperature sensitive dimer is encoded in the target environment by a polynucleotide in a number below 10 copies per cell.

In some embodiments, association of adjacent thermomer cargoes may increase the Tbs above the value set by independent thermoswitches. Affinity between cargo 1 and cargo 2 may stabilize the overall structure, as will be understood by a skilled person, resulting in a shift of $T_{bs}$ by up to 10° C.

Accordingly, a skilled person upon reading of the present disclosure will understand that thermomer monomer of the instant disclosure encompass not only polypeptide of SEQ ID NO: 1 but also by any derivative thereof.

, The term "derivative" as used herein in connection with the temperature sensitive region indicates a polypeptide having a same length of the temperature sensitive region and comprising a neutral substitution of at least one of the amino acid residues of the temperature sensing region.

The term "neutral substitution" as used herein indicates amino acid replacement in a polypeptide that changes a given amino acid to a different amino acid resulting in maintenance of the structural properties of the polypeptide. Accordingly, one or more neutral substitutions in temperature sensitive region of thermomer monomer herein described result in a polypeptide having same structural properties of the temperature sensing region of SEQ ID NO: 1 as will be understood by a skilled person.

Accordingly, in a thermomer monomer with SEQ ID NO: 1 neutral substitution of one or more residues of the temperature sensing region are amino acid substitutions that do not perturb the structural stability of the thermomers (e.g. their affinity for each other, and the $T_m$ of the resulting dimer). A substitution can be defined as "neutral" relative to the original thermomer if the circular dichroism spectrum of the substitution product (in complex with the same partner thermomer as the partner of the original thermomer, and at the same concentration as the original thermomer) is superimposable upon the circular dichroism spectrum of the original thermomer with its original partner, to within a margin of error of 5% for any given data point, when normalized from the minimal value to the maximal value, setting the bounds at 0 and 1 respectively. Additionally, the neutral substitution, under the same conditions, do display a melting curve at 222 nm that is superimposable upon the circular dichroism spectrum of the original thermomer with its original partner, to within a margin of error of 5% for any given data point, when normalized from the minimal value to the maximal value, setting the bounds at 0 and 1 respectively.

In view of their ability to associate and disassociate in a temperature dependent manner, thermomer monomers of the present disclosure and related thermomer dimers can be used as modular dimerization thermoswitches, in which the bioswitch temperature of the coiled coil temperature sensing dimers affects the related thermoswitch properties in a target environment wherein the thermomer conversion from monomer state to heterodimer state can be used to control spatiotemporal locations of cargo moieties as will be understood by a skilled person upon reading of the present disclosure.

In particular, in application where thermomer monomers and related thermomer dimers of the instant disclosure are used as dimerization thermoswitches, the coiled coil temperature sensing domain of the thermomer dimers are configured so that the coiled coil temperature sensing dimers exhibit an ON or OFF state at a particular temperature range of interest while still retaining a sharp thermal transition resulting in a large change in activity. For example, thermomer dimers of the disclosure can have a >100-fold difference between an on and off state, and a 10-fold switching over a temperature range less than 5° C. in some exemplary embodiments, fold switching lower that 10-fold switching, and in particular to a 4-fold switching, or even lower such as a 2-fold switching. (see FIG. 4f, the correlation coefficient over a ~5° C. range drops from ~0.5 to ~0.1) as will be understood by a skilled person.

In a preferred embodiment, the first thermomer monomer and the second thermomer monomer have X111=R, X112=E, X161=E, X162=R, X182=E, X183=R and the thermomer monomer comprise the sequence of wild type TlpA.

In preferred embodiments, thermomers of the present disclosure are also based on the surprising finding that engineering in the temperature sensing region of a first thermomer monomer and a second thermomer monomer forming a thermomer dimer herein descried, of at least one of the following pair of corresponding residues $X_{111}$ of the first thermomer monomer and $X_{112}$ of the second thermomer monomer $X_{161}$ of the first thermomer monomer and $X_{162}$ of the second thermomer monomer and $X_{182}$ of the first thermomer monomer and $X_{183}$ of the second thermomer monomer to have the at least one pair formed by oppositely charged amino acids will result in thermomer monomer that preferably heterodimerize in a target environment.

In the preferred embodiments, $X_{111}$ and $X_{112}$, of the first thermomer monomer have a same charge and $X_{111}$ and $X_{112}$, of the second thermomer monomer have charge opposite to the same charge of $X_{111}$ and $X_{112}$, of the first thermomer monomer;

$X_{161}$ and $X_{162}$, of the first thermomer monomer have a same charge and $X_{161}$ and $X_{162}$, of the second thermomer monomer have charge opposite to the same charge of $X_{161}$ and $X_{162}$, of the first thermomer monomer; and $X_{182}$ and $X_{183}$, of the first thermomer monomer have a same charge and $X_{182}$ and $X_{183}$, of the second thermomer monomer have charge opposite to the same charge of $X_{182}$ and $X_{183}$ of the first thermomer monomer.

Exemplary oppositely charged residues used in the thermomer monomers and dimers herein described comprise glutamic acid (E, negative) and arginine (R, positive), and glutamic acid (E, negative) and lysine (K, positive). Additional possible oppositely charged residue interactions may consist of aspartic acid (D, negative) and arginine (R, positive), and aspartic acid (D, negative) and lysine (K, positive) as well as additional combinations identifiable by a skilled person.

Accordingly, in thermomers of the present disclosure, inclusion of the above corresponding residues in a thermomer monomer with SEQ ID NO: 1, the thermomer bioswitches of the present disclosure are heterodimeric.

Heterodimer formation occurs when the affinity of two different thermomers for each other exceeds the affinity of two copies of the same thermomer for each other. In cases where the thermomers are produced in separate enclosures (e.g. cells) and the homodimer interaction energy exceeds the ambient energy at the temperature of storage, the homodimers may be mixed at an equimolar ratio, heated to above their $T_m$ and cooled back to their ambient storage temperature to escape from their kinetically trapped conformation and relax to their thermodynamically favored conformation.

Heterodimer formation can be detected by obtaining the circular dichroism spectrum and melting curve at 222 nm, as exemplified for the wild type TlpA coiled-coil in FIG. 19. The inability of a solution containing only thermomer A or only thermomer B to demonstrate the characteristic alpha-helical CD spectrum, combined with the ability of an equimolar solution of thermomer A and thermomer B to demonstrate the characteristic alpha-helical CD spectrum, enables detection of obligate heterodimerization. The rise of the circular dichroism signal (ellipticity) to approach zero in a sigmoidal fashion with a thermal Hill coefficient >15 indicates the preservation of thermomer switching functionality. In cases where an isolated solution of thermomer A and/or an isolated solution of thermomer B demonstrate a characteristic alpha-helical CD spectrum, preferential heterodimerization can be detected by a shift of the $T_m$ of the melting curve at 222 nm toward higher temperature in an equimolar mixture of thermomer A and thermomer B relative to the isolated solutions of only thermomer A or thermomer B, as exemplified for the E180R and R179E variants in FIG. 5.

In a preferred embodiment, an heterodimeric thermomer dimers comprise, the thermomer dimer wherein the first thermomer monomer is (R179), in which X111=E, X112=E, X161=E, X162=R X182=E, and X183=R and the second thermomer monomer is (E180R) in which X111=R X112=R X161=E X162=R X182=E X183=R In another preferred embodiment, an heterodimeric thermomer dimers comprises, the thermomer dimer wherein the first thermomer monomer is (E229R) in which X111=R, X112=E, X161=R, X162=R, X182=E, X183=R and in the second thermomer monomer is (R230E) in which X111=R, X112=E, X161=E, X162=E, X182=E, X183=R, In another preferred embodiment, an heterodimeric thermomer dimers comprises, the thermomer dimer wherein the first thermomer monomer is (E250R) in which X111=R, X112=E, X161=E, X162=R, X182=R, X183=R, and in the second thermomer monomer is (R251E) in which X111=R, X112=E, X161=E X162=R, X182=E X183=E.

In another preferred embodiment, an heterodimeric thermomer dimers comprises, the thermomer dimer wherein the first thermomer monomer is (E180R, E229R) in which X111=R, X112=R, X161=R, X162=R, X182=E, X183=R, G2A1 and the second thermomer monomer is (R179E, R230E) in which X111=E, X112=E, X161=E, X162=E, X182=E, X183=R, G2B1.

In another preferred embodiment, an heterodimeric thermomer dimers comprises, the thermomer dimer wherein the first thermomer monomer is (E180R, R230E) X111=R, X112=R, X161=E, X162=E, X182=E, X183=R, G2A2 and the second thermomer monomer is (R179E) E229R) in which X111=E, X112=E, X161=R, X162=R, X182=E, X183=R, G2B2

In another preferred embodiment, a heterodimeric thermomer dimers comprises, the thermomer dimer wherein the first thermomer monomer is (E180R, E250R), X111=R, X112=R, X161=E, X162=R, X182=R, X183=R, G2A3 and in the second thermomer monomer is (R179E, R251E) in which X111=E, X112=E, X161=E, X162=R, X182=E, X183=E, G2B3

In another preferred embodiment, an heterodimeric thermomer dimers comprises, the thermomer dimer wherein the first thermomer monomer is (E180R, R251E), in which X111=R, X112=R, X161=E, X162=R, X182=E, X183=E, G2A4 and in the second thermomer monomer is (R179E), E250R) in which X111=E, X112=E, X161=R, X162=R, X182=R, X183=R, G2B4.

In another preferred embodiment, an heterodimeric thermomer dimers comprises, the thermomer dimer wherein the first thermomer monomer is (E229R, E250R) in which X111=R, X112=E, X161=R, X162=R, X182=R, X183=R G2A5 and in the second thermomer monomer is (R230E, R251E) in which X111=R, X112=E, X161=E, X162=E, X182=E, X183=E, G2B5.

In another preferred embodiment, a heterodimeric thermomer dimers comprises, the thermomer dimer wherein the first thermomer monomer is (E229R, R251E), in which X111=R, X112=E, X161=R, X162=R, X182=E, X183=E, G2A6 and in the second thermomer monomer is (R230E, E250R) in which X111=R, X112=E, X161=E, X162=E, X182=R, X183=R, G2B6

In particular in applications where thermomer monomers and related thermomer dimers of the instant disclosure are used as dimerization thermoswitches, the unexpected modularity of the thermomer monomers and dimers allow to build thermomer constructs where the thermomer monomers are linked to cargo moieties and to use the thermomer dimers herein described are used as thermoswitches to control spatiotemporal location of the cargo moiety as well as formation and dissociation of dimer complexes comprising the cargo moieties in a thermally regulated manner.

In particular it has been surprisingly found that the temperature sensing region of a TlpA monomer retain an ability to dimerize in a temperature controlled manner also in a construct if the TlpA temperature sensing region is linked to the construct through a linker polypeptide attached at the N-terminus or the C-terminus of the TlpA temperature sensing region.

The term "linker polypeptide" as used herein indicates a short peptide sequences that occur between protein domains. A linker polypeptide in accordance with the disclosure can have a length that can be selected in view of the target environment and the construct where the thermomer monomer of the instant disclosure is to be included and the experimental design.

The term "attach" or "attached" as used herein, refers to connecting or uniting by a bond, link, force, or tie in order to keep two or more components together, which encompasses either direct or indirect attachment. For example, "direct attachment" refers to a first molecule directly bound to a second molecule or material, while "indirect attachment" in refers to one or more intermediate molecules being disposed between the first molecule and the second molecule or material. Attachment between two referenced molecules therefore comprises connecting or uniting the two referenced molecules by covalent bonds, or non-covalent bonds between the two molecules introduced and by chemical modification of the molecules (such as with a maleimide-cysteine conjugation) or by creation of a precursor of the two molecules which will provide the two molecules attached one to the other (e.g. by creating a fusion gene comprising polynucleotides encoding for two polypeptide to be attached.)

In thermomer monomer herein described, attachment of a linker polypeptide can occur at the N-terminus the C-terminus of the thermomer monomer which in embodiments herein described the N-terminus and the C-terminus are typically range independently from 5 to 12 amino acids long as will be understood by a skilled person. In particular, one of the N-terminus or the C-terminus can attach to one of the C-terminus and N-terminus of a linker polypeptide to for a stable construct in the target environment as will be understood by a skilled person.

In embodiments here described, a linker polypeptide allows attachment of a thermomer monomer of the disclosure to a cargo and/or a surface configured to bind a polypeptide. In some embodiments, the linker polypeptide can be part of the cargo as will be understood by a skilled person upon reading of the present disclosure.

The term "cargo" refers to any chemical moiety having a diameter up to 1 micron configured to be attached to a polypeptide either directly or through a linker described herein. Exemplary cargo moiety can have a diameter of 100-200 nm or lower than 100-nm as will be understood by a skilled person upon reading of the present disclosure. Accordingly, the term "cargo" as used herein indicates any group of atoms linked to one another to form a compound molecule substance or material that can be attached to a polypeptide or any portions thereof.

Cargo moieties in the sense of the disclosure typically have an identifiable chemical or physical property associated thereto In particular, chemical moieties forming cargo according to the disclosure can have chemical properties such as chemical reactivity (e.g. a gold nanoparticle to form a S—Au bond with a thiol group (—SH)) and physical properties such as, radioactivity (e.g. radioactive isotope moiety), fluorescence (e.g. fluorophore moiety, chemiluminescence (e.g. a chemiluminescent dye moiety), light absorption (a chromophore moiety), catalytic activity (e.g. enzymatic activity), binding activity (e.g. scFvs or Fabs), signaling activity (e.g. adaptor protein domains such as SH2 and SH3), or combinations thereof (e.g. antibodies, nanobodies, natural cell surface receptors, chimeric cell surface receptors, and similar) or a Stokes' drag force for a cargo moiety in including a bead as used in the present application.

In some embodiments, the cargo can have a molecular weight of less than 500 kD. Typical cargoes and associated molecular weights include proteins (5-100 kD), large proteins and protein complexes (100-500 kD), small molecules (0.05-1.5 kDa), and peptides (1-5 kDa). Oligonucleotides of <100 kD, and additional cargos identifiable by a skilled person.

Exemplary cargo moieties in the sense of the disclosure polypeptides, polynucleotides nanomaterial such as beads In some embodiments, the cargo can be attached to the thermomer through a covalent bond such as a peptide bond or a non-covalent bond.

In some embodiments, the cargo can be a protein, polynucleotide or macromolecular complex such as a bead, that is covalently fused to the thermoswitch by chemical modification (such as with a maleimide-cysteine conjugation)

In some embodiments, herein described, a thermomer monomer of the disclosure is covalently attached to a suitable cargo moiety directly or through a linker polypeptide to provide a thermomer monomeric construct herein described In embodiments, wherein a cargo is comprised in a thermomer monomeric construct, selection of the correct linker can be aided by approximating the cargo as a sphere of hydrodynamic radius R based on known structural information regarding the cargo, drawing the two spheres so as to touch each other tangentially, and drawing straight lines toward from the expected attachment sites on the cargo to the same point in space (which represents the attachment site on the coiled coil). The length of the resulting lines indicates the minimal required length of the linkers, and can be converted into number of amino acids by the relationship 1 aa=3.5 Angstroms. Typically, a linker polypeptide for a thermomer monomeric construct herein described can be shorter than 50 amino acids and most often shorter than 30 amino acids In some embodiments, a linker polypeptide in thermomer monomeric construct can be a flexible linker polypeptide, and therefore polypeptide predicted to be unstructured using software known to someone skilled in the art, such as Jpred, or selected from published lists of such linker sequences. linkers can be categorized as short (such as the representative example GGSGGS (SEQ ID NO: 3) used to fuse the palmitoylation domain to one strand of an exemplar thermoswitch ($G_2A_3$ of the disclosure), or long (such as the representative example GGGGSGGGGSGGGG-SGGGGSGGGGS (SEQ ID NO: 34) used to fuse the RFP to the other strand of an exemplary thermoswitch ($G_2B_3$ in FIG. 4a) of the disclosure). Linkers are often composed of flexible residues like glycine and serine so that the adjacent protein domains are free to move relative to one another. In particular, in engineered microcompartment protein of the disclosure linkers are typically peptide of 2 to 5 residues in combination with a protease cleavage site, a target protein, and/or a tag as will be understood by a skilled person upon reading of the present disclosure.

Exemplary linkers further include GGGGS (SEQ ID NO: 4), GSGSG (SEQ ID NO: 5), GGGG (SEQ ID NO: 6), GGG (SEQ ID NO: 7), GG (SEQ ID NO 8), GS (SEQ ID NO: 9), GSGS(SEQ ID NO: 10), GGGS(SEQ ID NO: 11), GGS (SEQ ID NO: 12), GTS (SEQ ID NO: 13) GGSGGS (SEQ ID NO 14), GGG (SEQ ID NO: 15), GGGGGG (SEQ ID NO: 16), GGGGGGGGG (SEQ ID NO: 17), GGGG-GGGGGGGG (SEQ ID NO:18), GGGGGGGGGGGGGGG (SEQ ID NO: 19), GGS(SEQ ID NO: 20), GGSGGS(SEQ ID NO: 21), GGSGGSGGS (SEQ ID NO 22), GG-SGGSGGSGGS (SEQ ID NO: 23), GGSGGSGG-SGGSGGS (SEQ ID NO: 24), GSG (SEQ ID NO: 25), GSGGSG (SEQ ID NO: 26), GSGGSGGSG (SEQ ID NO: 27), GSGGSGGSGGSG (SEQ ID NO: 28), GS-GGSGGSGGSGGSG (SEQ ID NO:29), GGGGS(SEQ ID NO: 30), GGGGSGGGGS (SEQ ID NO: 31), GGGGS-GGGGSGGGGS (SEQ ID NO: 32), GGGGSGG-GGSGGGGSGGGGS (SEQ ID NO: 33), GGGGSG-GGGSGGGGSGGGGSGGGGS (SEQ ID NO:34) and additional polypeptide linkers identifiable by a skilled person.

In some embodiments, a linker polypeptide in thermomer monomeric construct can be a rigid linker polypeptide, and therefore can comprise amino acids predicted to assemble into rigid sequences (most often alpha helices). Examples of rigid linkers include one or more (typically <10) repeats of the motif EAAAK (SEQ ID NO: 35), which fold into alpha helices.

In some of the embodiments wherein a linker polypeptide is used to provide thermomer monomeric construct of the disclosure, the combination of cargo and a linker enables the correct spacing of the coiled-coil terminus. The spacing of the coiled-coil terminus can be estimated from the crystal structure of any coiled-coil. For example, for the coiled-coil Tropomyosin, the N-terminus to N-terminus distance is 6.5 Angstroms. The size of the cargos and the location of the linker fusion can be selected to maintain such distance.

In other exemplary embodiments, for example for certain cargo moieties wherein the chemical moiety is formed by a protein, the cargo can be directly attached to the thermomers, without an intervening linker sequence. This can occur when the cargo itself contains a flexible region that can serve as the linker. For example, in the case where the palmitoylation motif is fused to the N-terminus of a thermomer in the context of the full-length TlpA protein, residues SQSTVVTEPVAELPVEV (SEQ ID NO 36): which are predicted via Jpred to be unstructured are presumed to comprise the linker between the folded domain and the thermomer.

Accordingly, in a thermomer monomeric construct the cargo moiety can be attached to one of the N-terminus end or a C-terminus of the thermomer monomer. In the alternative in a thermomer monomeric construct the cargo moiety can be attached to one of the N-terminus end or a C-terminus, of the linker polypeptide and the thermomer monomer is attached to the other one of the N-terminus end and C-terminus of the linker polypeptide.

The thermomer herein described can be attached to a cargo comprising transcription factor domains. The cargo coupled or linked to one monomer of a thermomer in the sense of the present disclosure can comprise a transactivation domain of a transcription factor or a functional fragment thereof, while the cargo coupled or linked to the other monomer of the thermomer can comprise a DNA binding domain of a transcription factor or a functional fragment thereof.

The thermomer herein described can also be attached to a cargo comprising molecules that mediate signaling, e.g., the intracellular signaling domain(s) through proliferation pathways, e.g., the P13K or AKT pathway. Accordingly, in some embodiments the cargo can be a protein kinase.

The thermomer herein described can also be attached to a cargo comprising molecules that regulate protein translocation to a membrane of a cell. Accordingly, in some embodiments, the thermomers can be coupled or fused to a membrane anchoring domain such as a molecule that is localized to the plasma membrane such as a myristoyl group, or a myristoylation site, or a transmembrane domain.

The thermomer herein described can also be attached to a cargo comprising molecules that regulate protein translocation to and from the nucleus of a cell. Accordingly, in some embodiments, the thermomers can be coupled or fused to nuclear localization signaling sequence for nuclear import or nuclear export signaling sequence for export to form a transport complex that is passed through the nuclear pore complex.

The thermomer herein described can also be attached to a cargo comprising gene editing systems that can regulate gene editing by modifying the nucleic acids of a target gene and/or for modulating the expression of a target gene. The gene editing systems typically comprise a DNA binding domain and a DND modifying domain. For example, in some embodiments, one of two monomers of a thermomer can be coupled or fused to a DNA binding domain while the other monomer can be coupled or fused to a DNA modifying domain.

A "DNA-modifying domain" of the present invention is a molecule or domain of a molecule that is capable of causing a change to the covalent structure of a DNA molecule. In some aspects, the change to the covalent structure of a DNA molecule is a cleavage (a breakage, of the covalent backbone of a DNA molecule). The association of the two monomers will cause the association of the DNA-binding domain and the DNA-modifying domain thereby enabling the gene editing functionality. Exemplary gene editing systems include TALEN gene editing system, CRISPR/Cas gene editing system, Zinc Finger nuclease gene editing system, meganuclease gene editing system, and others identifiable to a person skilled in the art.

Exemplary cargo moieties in the sense of the disclosure further comprise Chimeric antigen receptors, Engineered GPCRs such as TanGo, Engineered enzymes such as Cellobiohydrolase, Cellulase, Lignase, Immunological receptors such as Toll-Like receptors, Antibodies and fragments thereof, Viruses and exosomes, and protein Gas vesicles Additional cargo molecules that can be coupled or fused to thermomers herein described can be found in Table 5 of WO 2016/098078 incorporated herein by reference in its entirety and further cargo moieties identifiable by a skilled person Additional preferred cargos comprise the cargo moiety is selected from a chimeric Antigen Receptor, Cas9, split Cas9, dCas9, split dCas9, anti-CRISPR, Cpf1, split Cpf1, dCpf1, split dCpf1, TALENs and split TALENs, and Chimeric GPCR (e.g. TanGo, DREADDs).

In some embodiments herein described, a thermomer monomeric construct can be provided by selecting suitable thermomer monomer in view of the cargo, the target environment and the target temperature Tbs where the thermomer monomeric construct is to be operated. to be attached to a cargo moiety, optionally through a linker polypeptide In those embodiments, a first thermomer monomer can be provided configured to dimerize with a second thermomer monomer in the target environment at a target temperature Tbs with a thermal Hill coefficient above 15, to form a thermomer dimer of the present disclosure having a melting temperature Tm=Tbs−0° C. to 5° C.

In methods to provide a thermomer monomeric construct of the present disclosure the methods comprising attaching the cargo moiety to the thermomer monomer directly or through a linker polypeptide as will be understood by a skilled person.

In some embodiments, the attaching can be performed by translational conjugation via generation of a fusion protein gene, Untargeted chemical conjugation e.g. via (maleimide, iodoacetamide, 2-thiopyridine, 3-arylpropiolonitrile) binding to one or more cysteine residues, (NHS, isocyanate, isothiocyanate, or benzoyl fluoride) conjugation to one or more lysine residues, (diazonium salts, PTAD, or mannich reaction) to one or more tyrosine residues, N-terminal serine or threonine conjugation via $NaIO_4$, N-terminal cysteine conjugation via iodoacetamides, N-terminal conjugation via pyridoxal phosphate (PLP), Native chemical ligation.

In some embodiments, the attaching can also be performed by targeted chemical conjugation via click reaction to an introduced noncanonical amino acid at any position that demonstrates evidence of being a neutral substitution as herein described, In some embodiments, the attaching can also be performed by any other conjugation method described in [9], by Introduction of specific sequences for chemical reaction such as FlAsH and ReAsH and/or by Fusion of a biotinylation sequence for modification via BirA.

In some embodiments, the attaching can also be performed by Translational fusion to antibodies or other dimerization/oligomerization domains and/or Fusion to Spy-Tag or SpyCatcher (or related systems such as SnoopTag-SnoopCatcher and SpyLigase or SnoopLigase) for covalent bond formation In some embodiments providing, the attaching can be performed by providing a thermomer gene expression cassette comprising a polynucleotide encoding for a thermomer monomer herein described under control of a promoter and additionally regulatory regions in a configuration allowing expression of the monomer of the present disclosure in a target environment.

In those embodiment, where construct comprises a linker polypeptide and/or a cargo moiety is formed by or comprising a protein, the polynucleotide encoding for a thermomer monomer herein described can be a fusion gene comprising the thermomer monomer, the cargo and/or the linker polypeptide in a configuration allowing expression of a polypeptide forming the thermomer monomeric construct as will be understood by a skilled person The term "gene cassette" as used herein indicated a mobile genetic element that contains at least one gene and a recombination site. Accordingly, a gene cassette can contain a single gene or multiple genes possibly organized in an operon structure A gene cassette can be transferred from one DNA sequence (usually on a vector) to another by 'cutting' the fragment out using restriction enzymes or transposase, cripr, viral and/or recombinase enzymes and other nucleases and 'pasting' it back into the new context or other molecular biology and cloning techniques (e.g. per, CRISPR, TALENs, ZFN). Gene cassettes can move around within an organism's genome or be transferred to another organism in the environment via horizontal gene transfer.

A "gene expression cassette" is a gene cassette comprising regulatory sequence to be expressed by a transfected cell. Following transformation, the expression cassette directs the cell's machinery to make RNA and proteins. Some expression cassettes are designed for modular cloning of protein-encoding sequences so that the same cassette can easily be altered to make different proteins. An expression cassette is composed of one or more genes and the sequences controlling their expression. An expression cassette typically comprises at least three components: a promoter sequence, an open reading frame, and a 3' untranslated region that, in eukaryotes, usually contains a polyadenylation site. An expression cassette can be formed by manipulable fragment of DNA carrying, and capable of expressing, one or more genes of interest optionally located between one or more sets of restriction sites Gene expression cassettes as used herein typically comprise further regulatory sequences additional to the prompter to regulated the expression of the gene or genes within the open reading frame herein also indicated as coding region of the cassette.

The term "regulatory sequence" or "regulatory regions" as described herein indicate a segment of a nucleic acid molecule which is capable of increasing or decreasing transcription or translation of a gene within an organism either in vitro or in vivo. In particular, coding regions of the GV genes herein described comprise one or more protein coding regions which when transcribed and translated produce a polypeptide. Regulatory regions of a gene herein described comprise promoters, transcription factor binding sites, operators, activator binding sites, repressor binding sites, enhancers, protein-protein binding domains, RNA binding domains, DNA binding domains, silencers, insulators and additional regulatory regions that can alter gene expression in response to developmental and/or external stimuli as will be recognized by a person skilled in the art.

The term "operative connection" as used herein indicate an arrangement of elements in a combination enabling production of an appropriate effect. With respect to genes and regulatory sequences an operative connection indicates a configuration of the genes with respect to the regulatory sequence allowing the regulatory sequences to directly or indirectly increase or decrease transcription or translation of the genes.

Accordingly, in some embodiments, a thermomer monomeric construct can comprise thermomer monomer attached to its cargo in the form of a fusion protein with or without an intervening linker. The term "fusion protein" as used herein refers to proteins expressed through the joined two or more genes or gene fragments which originally code for separate proteins. Translation of the joined two or more genes results in a single fusion protein with retained functional properties derived from each of the original proteins.

In embodiments wherein providing and/or attaching thermomer monomers of the present disclosure are performed through gene expression cassettes, the cassettes can be comprised in a thermomer vector comprising a thermomer gene expression cassette comprising a polynucleotide encoding for a thermomer monomer herein described under control of a promoter and additionally regulatory regions in a configuration allowing expression of the monomer of the present disclosure in a target environment.

The term "vector" indicates a molecule configured to be used as a vehicle to artificially carry foreign genetic material into a cell, where it can be replicated and/or expressed. An expression vector is configured to carry and express the material in a cell under appropriate conditions. In some embodiments, a suitable vector can comprise a recombinant plasmid, a recombinant non-viral vector, or a recombinant viral vector. Vectors described herein can comprise suitable promoters, enhancers, post-transcriptional and post-translational elements for expression in mammalian that are identifiable by those skilled in the art. Vectors suitable for transduction of mammalian cells, are known to those skilled in the art.

Vectors for establishing heterodimer performance can consist of one or more TlpA DNA binding domain-thermomer open reading frames along with a TlpA promoter controlling expression of one or more fluorescent proteins, as depicted in FIG. 2a. Additional vectors for establishing heterodimer performance can consist of one thermomer fused to a cargo and another thermomer lacking a cargo, as depicted in FIG. 3a. Additional vectors can consist of two thermomers carrying different cargos, as depicted in FIG. 4a. Vectors can also contain a single thermomer variant optionally carrying cargo.

In some embodiments, the vector can be a selected from lentiviral vectors, AAV vectors, Sleeping Beauty, and PiggyBac.

In embodiments herein described thermomer monomeric constructs can administered to the target environment for a time and under condition to form a thermomer dimeric complex. In particular, in those embodiments which a first thermomer monomeric construct herein described is provided comprising a first thermomer monomer of the present disclosure attached to a first linker polypeptide and/or a first cargo moiety and a second thermomer monomeric construct herein described is provided, comprising second thermomer monomer of the present disclosure attached to a second linker polypeptide and/or a second cargo In particular, the first thermomer monomer and the second thermomer monomer can be selected that are configured to dimerize in a target environment at a target temperature Tbs with a thermal Hill coefficient above 15, to form a thermomer dimer of the present disclosure having a melting temperature Tm=Tbs–0° C. to 5° C.

In embodiments of the present disclosure the temperature of the target environment Te can be modified in accordance with the experimental design. In particular, the temperature of the target environment Te can be changed to have Te=Tbs to dimerize and/or have Te<Tbs to disassociate the complex in the target environment. Lowering the $T_e$ can be accomplished using a peltier cooler, refrigerator, or placing the medium in contact with a colder medium. Raising the $T_e$ can be accomplished via microwaving, exposing to other forms of radiation that can be absorbed by the environment including solar, radiofrequency, and ultrasonic, or by placing the medium in contact with a warmer medium.

In thermomer dimeric complexes of the present disclosure at least one of the first cargo moiety and the second cargo moiety is formed by a chemical moiety configured to have an interface with the target environment subjected to a Stokes' drag force up to 50 pN, preferably equal or lower than 6-7 pN.

The wording "stokes' drag force" as used herein indicate the drag force F on a sphere of radius R moving through a fluid of viscosity μ at speed v is given by:

$$Fd=6\pi\mu Rv \qquad [\text{Eq. 3}]$$

wherein Fd is the frictional force known as Stokes' drag acting on the interface between the fluid and the spherical object; μ is the dynamic viscosity; R is the radius of the spherical object; and v is the flow velocity relative to the spherical object.

In particular, the cargos are selected to ensure that the coiled-coil structure of the thermomer will not be pulled apart due to the Stokes' drag as the molecule moves through its surroundings. The force applied to the coiled coil can be estimated from the Stokes' drag of its cargo as will be understood by a person skilled in the art. In some embodiments, the combined stoke's drag of the cargo coupled or fused to one monomer and the cargo coupled or fused to the other monomer cannot exceed up to 50 pN preferably 6-7 pN.

Accordingly, in an exemplary embodiment the first cargo moiety is a bead which produces 1000 pN of, and the second thermomer constructs comprises no second cargo moiety.

In another exemplary, embodiment the first cargo moiety is a bead which produces 1000 pN a do the second cargo moiety can be a small protein that produces 1 pN of force with a maximum force pulling in opposite direction being 1 pN.

Accordingly, in some embodiments, no more than ono more than one cargo (or the combination of the N-terminal and C-terminal cargo) can induce an SDF up to 50 pN and preferably induce a stoke's draft force of 6-7 pN or lower.

In some embodiments, the target environment is a cell and the cell comprises at least one of the thermomer monomer, thermomer dimer, thermomer monomeric construct, and thermomer dimeric construct and thermomer vector herein described.

In some embodiments, deposition of thermal energy to activate thermomer dimers is guided spatially by magnetic resonance imaging (MRI). Additionally, MRI can be used to monitor the temperature of the target region and adjust the energy source to achieve the desired local temperature (FIG. 9b of U.S. application Ser. No. 15/384,254 filed on Dec. 19, 20176 and published with publication number US2017/0928425 incorporated herein by reference in its entirety).

In an exemplary embodiment, a fluorescent protein is covalently fused to one polypeptide of the thermomer while a plasma membrane-localization signal is covalently fused to the other strand of the thermomer, resulting in a fluorescent indicator that is localized to the plasma membrane at low temperature and released to diffuse freely in the cell at high temperature.

In another exemplary embodiment, one strand of the thermomer can be covalently fused to an enzyme while the other strand can be covalently fused to an inhibitor, resulting in the activation of that enzyme upon an increase in temperature.

In another exemplary embodiment, one strand of the thermomer can be fused to an arbitrary molecular binding domain (defined as a domain that can bind to a biological or non-biological macromolecule such as DNA, RNA, or a protein) while another strand can be fused to another arbitrary molecular binding domain, resulting in a temperature-dependent bridging system that holds two molecules in close proximity at low temperature and releases them to diffuse freely at high temperature. This embodiment can be used in the creation of new temperature-sensitive transcriptional transactivators or repressors which can bind to a specific DNA sequence only when two halves of the DNA binding domain are brought in close proximity. A naturally occurring example of a repressor that can only bind to a specific DNA sequence only when two halves of the DNA binding domain are brought in close proximity is TlpA. Another potential use of this embodiment is the covalent fusion of an intact DNA binding domain to one polypeptide strand of the thermomer and a transactivation domain (such as VP16) or repression domain (such as KRAB) on the other strand of the thermomer, which would be recognizable to someone skilled in the art as a "two hybrid system" with temperature-mediated control imparted by the thermomers.

In an exemplary embodiments, thermomer dimers herein described, a fluorescent protein is covalent fused to one of the two bioswitch polypeptides in a heterodimeric coiled-coil bioswitch. The other polypeptide in the heterodimer is covalently fused to a peptide region that undergoes enzymatic palmitoylation using endogenous cellular machinery, resulting in its insertion into the cell membrane via hydrophobic interaction. The resulting bioswitch confines the fluorescent protein to the vicinity of the plasma membrane at low temperature, and releases it to diffuse throughout the cell at high temperature.

In some embodiments, each monomer of the protein of the coiled coil temperature sensing dimer can be fused to another protein, protein domain, or protein motif, either directly or via a linker sequence. The term "motif" as related to the protein indicates any continuous part of a protein sequence, regardless of whether or not it folds into a defined tertiary structure, that can be robustly associated with a function. Motifs are typically short (<50 amino acids). A representative motif is the GAP43 palmitoylation sequence MLCCMRRTKQVEKNDEDQKI which is recognized by endogenous mammalian cellular machinery and covalently fused to a lipid macromolecule. The thermoswitchable protein system (which is comprised of two or more proteins, domains, and/or motifs fused via the N-terminus or the C-terminus to the coiled-coil bioswitch) is regulated in response to temperature. This regulation is made apparent by the change in activity of one or more domains fused to the bioswitch (such as a change in the rate of catalysis of an enzyme protein or domain fused to the bioswitch), or by the change in intracellular localization of one or more of the domains fused to the bioswitch (such as the change in the apparent membrane localization of a fluorescent protein fused to the bioswitch).

Additional exemplary embodiments comprise temperature-dependent reconstitution catalytically active Cas9, catalytically inactive Cas9 (dCas9), analogous variants of other Cas proteins. Other potential examples include temperature-dependent reconstitution of split enzymes. Other examples include temperature-dependent activation by temperature-inducible release of an inhibitor from an enzyme. Other examples include temperature-dependent reconstitution of split signaling molecules such as chimeric antigen receptors.

In some embodiments, in a thermomer dimeric complex herein described, the first cargo moiety is Split CAR (N-terminal half) and the second cargo moiety is Split CAR (C-terminal half)

In some embodiments, in a thermomer dimeric complex herein described, the first cargo moiety is Cas9 and the second cargo moiety is anti-CRISPR.

In some embodiments, in a thermomer dimeric complex herein described, the first cargo moiety is Split Cas9 (N-terminal half) and the second cargo moiety is Split Cas9 (C-terminal half).

In some embodiments, in a thermomer dimeric complex herein described, the first cargo moiety is Cpf1 and the second cargo moiety is anti-CRISPR In some embodiments, in a thermomer dimeric complex herein described, the first cargo moiety is Split Cpf1 (N-terminal half) and the second cargo moiety is Split Cpf1 (C-terminal half)

In some embodiments, in a thermomer dimeric complex herein described, the first cargo moiety is Split dCpf1 (N-terminal half) and the second cargo moiety is Split Cpf1 (C-terminal half).

In some embodiments, in a thermomer dimeric complex herein described, the first cargo moiety is Split TALEN (N-terminal half) and the second cargo moiety is +Split TALEN (C-terminal half)

In some embodiments, in a thermomer dimeric complex herein described, the first cargo moiety is Gal4 DBD and the second cargo moiety is VP16.

In some embodiments, in a thermomer dimeric complex herein described, the first cargo moiety is Gal4 DBD and the second cargo moiety is VP64.

Thermomer monomers, thermomer monomeric constructs and/or thermomer dimeric complexes can be attached to a surface and/or be part of a device as will be understood by a skilled person.

A suitable surface encompasses any surface configured to bind a polypeptide as will be understood by a skilled person upon reading of the present disclosure. Such as surface can be functionalized with chemical handles to facilitate reactions with biological or and/or organic molecules including direct conjugation to the thermomer or its cargo, or via a bridging moiety that serves to chemically link the functionalized surface to the thermomer or its cargo. Additionally, the thermomer may be attached to the surface noncovalently, such as by fusing the thermomer to streptavidin and coating the surface with biotin. Additionally, the thermomer may be attached to the surface nonspecifically, such as via adsorption.

A further description of thermomer surfaces and thermomer devices in accordance with the disclosure is provided herein in connection with the schematic illustration of FIGS. 20 to 22.

FIG. 20 shows an example of a thermomer monomeric construct. A load bearing construct 2001 can be composed of a cargo moiety 2010, a thermomer monomer 2030, and a linker polypeptide 2020 linking the cargo 2010 to the thermomer monomer 2030. A corresponding attachment construct 2002 is composed at least of a linker polypeptide 2021 and a thermomer monomer 2031 that can couple 2035 (or de-couple), under the proper thermal conditions, with the thermomer monomer 2030 of the load bearing construct 2001. In some embodiments the attachment construct 2002 is attached to a surface 2040, for example by its linker 2021.

FIG. 21 shows another example of a thermomer monomeric construct. A load bearing construct 2101 can be composed of a cargo moiety 2010, a thermomer monomer 2130, and a linker polypeptide 2120 linking the cargo 2110 to the thermomer monomer 2130. A corresponding attachment construct 2102 is composed at least one linker polypeptide 2121 and a thermomer monomer 2131 that can couple 2135 (or de-couple), under the proper thermal conditions, with the thermomer monomer 2130 of the load bearing construct 2101. In this embodiment, the attachment construct also includes its own cargo moiety 2111. In some embodiments the attachment construct 2102 is attached to a surface 2140, for example by one of its linkers 2121.

FIG. 22 shows an example device that utilizes thermomer monomeric constructs in accordance with this disclosure. The device can be a microfluidic chip 2210 with an input 2220 and an output 2230 to a chamber 2240. The device can be a SlipChip device where there is a cleave 2250 separating the layers of the device. A magnification 2260 of the chamber 2240 shows attachment constructs 2280 attached to a surface 2270 of the chamber 2240. Load bearing constructs 2290 can either be loaded in the chamber 2240 and pre-attached to the attachment construction 2280 to be released under the proper thermal conditions, or can be attached to the attachment constructs 2280 during operation of the device, attaching only under proper thermal conditions.

In some embodiments, the bioswitch temperature of the coiled coil temperature sensing dimers herein described can be increased or decreased through modification of the amino acid sequences of the temperature sensing domain to obtain temperature sensitive dimers that can operate at controlled temperatures.

In particular, coiled coil temperature sensing dimers operating at controlled temperature can be created by modifying the thermomer to result in modulation of the temperature response profile to higher or lower temperatures, as well as in changing the profile from a cooperative, switch-like induction to a linear "analog" transition.

In some of those embodiments, a coiled coil temperature sensing dimers can be mutated and "tuned" in the sense of the disclosure, to increase or decrease their bioswitch temperature Tbs and activate at different transition temperatures. In particular, in some embodiments, the coiled coil temperature sensing dimers can be tuned to activate at new temperatures while retaining sharp, robust switching performance.

In particular, temperature sensing domain of the coiled coil temperature sensing dimers obtainable with methods herein described can be configured so that the coiled coil temperature sensing dimers can be tuned to exhibit an ON or OFF state at a particular temperature range while still retaining a sharp thermal transition resulting in a large change in activity. For example, modification of the thermomer can be performed to obtain a >100-fold difference between an on and off state, and a 10-fold switching over a temperature range less than 5° C.

A modification of the a coiled coil temperature sensing dimer herein described can be performed to obtain a dimer with a Tbs bioswitch temperature that selected for specific application such as tunable thresholds within a biomedically relevant range of 32° C. to 46° C. Accordingly, one or more coiled coil temperature sensing dimers can be provided starting from coiled coil temperature sensing dimers for use within a cell can be provided that are orthogonal to endogenous cellular machinery and compatible with other thermos-responsive components and a Tbs compatible with the cell physiological temperature to allow multiplexed thermal logic.

In some embodiments, tuning of the thermal response curve is achieved by modulating the affinity of the two coiled coil strands for each other. In those embodiments modification of a bioswitch temperature Tbs of a coiled coil temperature sensing dimer can be performed by providing a coiled coil temperature sensing dimer herein described having a starting bioswitch temperature $Tbs_0$ in the target environment and two monomer proteins configured to form a coiled coil temperature sensing dimer in the target environment with a starting melting temperature $Tm_0$; and replacing in at least one monomer protein of the two monomer proteins forming the t one or more residues in positions a, b, d, e and g of a heptad repeat in the temperature sensing amino acid sequence of the provided coiled coil temperature sensing dimer.

In particular in some embodiments the replacing can be performed by replacing at least one of a hydrophobic amino acid in a position a and/or d of an heptad repeat of the temperature sensitive amino acid sequence of the temperature sensing domain with residues configured to increase or decrease hydrophobic packing between corresponding amino acid residues in positions a and/or d of the two monomer forming temperature sensing domain.

The term "hydrophobic packing" as used herein relates to the aggregating together of nonpolar molecules, and in particular, amino acids, to reduce the surface area exposed to water and minimize their disruptive effect. The efficiency of hydrophobic packing can be quantified by measuring the partition coefficients of non-polar molecules between water and non-polar solvents. The partition coefficients can be transformed to free energy of transfer which includes enthalpic and entropic components:

$$\Delta G = \Delta H - T\Delta S \qquad \text{Eq. 4}$$

where G is the Gibbs free energy of protein folding, H is the total enthalpy of a system, T is temperature, and S is entropy. These components can be experimentally determined using techniques such as calorimetry, circular dichroism or NMR, where an increase in $\Delta G$ indicates a decrease in efficiency of hydrophobic packing Hydrophobicity refers to the property of thermodynamically unfavorable interaction with water. In contrast, hydrophilicity refers to the property of thermodynamically favorable interaction with water.

Thus, hydrophobic effect represents the tendency of water to exclude non-polar molecules. The effect originates from the disruption of hydrogen bonds between water molecules. Hydrophobic molecules tend to be nonpolar and, thus, prefer other neutral molecules and nonpolar solvents. Because water molecules are polar, hydrophobic molecules do not dissolve well among them. Hydrophobic molecules in water often cluster together.

There are different hydrophobicity scales (or alternatively, hydropathy indices) of amino acid residues, based on measurement of the level of disruption of hydrogen bonds between water molecules, such as that of Kyte and Doolittle [10] as shown in FIG. 24 of U.S. application Ser. No. 15/384,254 filed on Dec. 19, 2016 and published as US 2017/0298425 incorporated herein by referenced in its entirety.

Exemplary hydrophobic amino acids include alanine, valine, leucine, isoleucine, proline, phenylalanine, tryptophan, cysteine and methionine.

Hydrophobicity scales or hydropathy indices are values that can be used to define relative hydrophobicity or conversely relative polarity (hydrophilicity) of amino acid residues, wherein, the more positive the value, the more hydrophobic the amino acid, and conversely the more negative the value, the more polar the amino acid.

Techniques of measuring amino acid hydrophobicity or polarity comprise wet lab methods such as partitioning between two immiscible phases or reverse phase liquid chromatographic methods, or computer-based methods such as calculation of solvent accessible surface area.

In some embodiments the replacing can be performed by replacing at least one polar or charged amino acid in position b e, and/or g of at least one heptad repeat of the temperature sensing domain amino acid sequence, with a hydrophobic residue, In some embodiments the replacing can be performed by replacing at least one polar or charged amino acid in positions e and/or g of at least one heptad repeat of the temperature sensing domain amino acid sequence with a residue configured to increase or decrease coulombic repulsion between corresponding residues in positions a, d, e and/or g of at least one heptad repeat of the temperature sensing domain amino acid sequence of the two monomers forming the temperature sensing domain.

In some embodiments the replacing can be performed by replacing one or more amino acid residues in anyone of positions a, b, d, e and/or g of at least one heptad repeat of the temperature sensing domain amino acid sequence as indicated above in combination one with the other.

In embodiments of the method to modify the amino acid sequences of the temperature sensing domain of coiled coil temperature sensing dimers herein described, the replacing is performed to obtain a variant of the coiled coil temperature sensing dimer with a melting temperature of the temperature sensing domain $Tm_m$ lower or higher than $Tm_0$ in the target environment, the obtained variant having a bioswitch temperature $Tbs_m$ lower or higher than $Tbs_0$ in the target environment.

In particular, some of those embodiments coiled coil temperature sensing dimers of the disclosure can be engineered to lower the bioswitch temperature Tbs of a starting coiled coil temperature sensing dimer, by replacing
- a polar amino acid in a position b of at least one heptad repeat of the temperature sensing domain amino acid sequence with a hydrophobic amino acid,
- a hydrophobic amino acid in a position d at least one heptad repeat of the temperature sensing domain amino acid sequence with a polar amino acid,
- a charged amino acid in a position e at least one heptad repeat of the temperature sensing domain amino acid sequence with a charged amino acid having a pKa different from the original by equal or higher than 0.5 or
- at least one of a hydrophobic amino acid in a position a, a hydrophobic amino acid in a position d, a charged amino acid in a position e and a charged amino acid in a position g in at least one heptad repeat of the temperature sensing domain amino acid sequence with amino acid residues such that pairs formed by corresponding residues in positions a, d, e, and g on the two monomer protein interact with a coulombic force F≥1 pN, wherein $$F = k_e \frac{q_1 q_2}{r^2} \quad \text{Eq. (4)}$$

where $k_e$ is Coulomb's constant ($k_e$=8.99×$10^9$ N $m^2$ $C^{-2}$), $q_1$ and $q_2$ are the signed magnitudes of the charges on each amino acid residue of the pair of residues, and the scalar r is the distance between the charges Accordingly, an amino acid substitution that changes the coulombic force (in pN) between two amino acids residues by changing from positive to negative or vice-versa, or increases the coulombic force in either direction, can change the structure of a polypeptide or protein, or protein-protein interactions, and related functional characteristics of the polypeptide or protein.

Exemplary variants of coiled coil temperature sensing dimers herein described having a lower bioswitch temperature with respect to a starting coiled coil temperature sensitive dimer, and obtainable methods herein described comprise TlpA39 coiled coil temperature sensing homodimer in which each monomer has sequence MRPATYEPE QIIEAGLALQAEGRNITGFALRNQVGGGNPTRLRQI WDEYQASQSTVVTE PVAELPVEVAEEVKAVSAALSE RITQLATELNDKAVRAAERRVAEVTRAAGEQTAQAE RELADAAQTVDDLEEKLVELQDRYDSLTLALESER-SLRQQHDVEMAQLKERLAAAEEN TRQREERYQE-QKTVLQDALNAEQAQHKNTREDLQKRLEQISVEAN-ARTEELKSERDKV NTFLTRLESQENALASERQQHLA-TRETLQQRLEQAIADTQARAGEIALERDRVSSLTARL ESQEKASSEQLVRMGSEIASLTERCTQLENQRDDAR-LETMGEKETVAALRGEAEALKRQ NQSLMAALSG-NKQTGGQNA (SEQ ID NO: 37) and TlpA36 oiled coil temperature sensing homodimer in which each monomer has sequence

```
                                                 (SEQ ID NO: 38)
MRPATYEPEQIIEAGLALQAEGRNITGFALRNQVGGGNPTRLRQIWDEYQA

SQSTVVTELVAELPVEVAEEVKAVSAALSERITQLATELNDKAVRAAERRV

AEVTRAAGEQTAQAERELADAAQTVDDLEEKLVELQDRYDSLTLALESERS

LRQQHDVEMAQLKERLAAAEENTRQREERYQEQRTVLQDALNAEQAQHINT

REDQQKRLEQISAEANARTEELKSERDKVNTLLTRLESQENALASERQQHL

ATRETLQQRLEQAIADTQARAGEIALERDRVSSLTARLESQEKASSEQLVR

MGSEIASLTERCTQLENQRDDARLETMGEKETVAALRGEAEALKRQNQSLM

AALSGNKQTGGQNA
```

In some embodiments coiled coil temperature sensing dimers herein described can be engineered to increase the bioswitch temperature Tbs of a starting coiled coil temperature sensing dimers, by replacing

- at least one of a hydrophobic amino acid in a position a and the hydrophobic amino acid in a position d of at least one heptad repeat of the temperature sensing amino acid sequence, with a polar amino acid or a charged amino acid, and/or
- at least one of a hydrophobic amino acid in a position a, a hydrophobic amino acid in a position d, a charged amino acid in a position e and a charged amino acid in a position g of at least one heptad repeat of the temperature sensing amino acid sequence with amino acid residues such that pairs formed by corresponding residues in positions a, d, e, and g on the two monomers interact with a coulombic force F≤1 pN calculated according to Equation 3.

Exemplary variants of coiled coil temperature sensing dimers herein described having a higher bioswitch temperature with respect to a starting coiled coil temperature sensing dimers, and obtainable methods herein described comprise dimers comprising a coiled coil temperature sensing domain of sequence SEQ ID NO: 1 possibly with a 0% to 20% variation and including at least one of the replacement herein described in one or more of the amino acid residues in positions a, b, d e and g of at least one heptad repeat in the sequence that increases the bioswitch temperature Tbs of the coiled coil transcriptional bioswitch dimers.

The structure of the resulting variant and structure of related temperature sensitive amino acid sequence, of temperature sensing domain herein described can be performed to detect can be arranged in heptad repeats each with a register that begins with either a, b, c, d, e, f or g to verify maintenance of the variant's ability to form coiled coil dimerization domains Accordingly, an uninterrupted series of heptad repeats without modification of any one of the a to g positions beginning at position a has a heptad repeat register of $[a, b, c, d, e, f, g]_n$; beginning at position b has a heptad repeat register of $[b, c, d, e, f, g, a]_n$; beginning at position c has a heptad repeat register of $[c, d, e, f, g, a, b]_n$; beginning at position d has a heptad repeat register of $[d, e, f, g, a, b, c]_n$; beginning at position e has a heptad repeat register of [e, f, g, a, b, c, d]$_n$; beginning at position f has a heptad repeat register of [f, g, a, b, c, d, e,]$_n$; and beginning at position g has a heptad repeat register of [g, a, b, c, d, e, f]$_n$.

Detection of heptad repeats within a coiled coil amino acid sequence can be performed using structure prediction servers COILS[2], Paircoil2[3], LOGICOIL[4], among others identifiable by a skilled person. In particular, COILS[2] detects predicted heptad repeats within an amino acid sequence and provides a probability score for each amino acid relative to the position a, b, c, d, e, f, or g within the heptad.

In a thermomer variant herein described heptad repeats in a register can have up to 5 consecutive amino acid residues missing in view of possible deletion or insertion in the sequence within a 0% to 20% percent variation range.

The term "percent variation" or "percentage variation" as used herein means the difference between two amino acid residue sequences, expressed as a percentage, wherein the difference between two amino acid sequences is measured by a process that comprises the steps of aligning the two amino acid sequences, then detecting one or more differences between the aligned sequences, and calculating the total number of differences divided by the total number of aligned amino acids in each amino acid sequence, including gaps with the result expressed as a percentage. The term "alignment" as used herein means aligning the positions of structural features of statistically significant structural similarity between two amino acid sequences, where "statistically significant structural similarity" means greater than 95% probability that two structural features are structurally homologous, for example, alpha-helix. The term "difference" indicates mismatches in the position of structural features in the position of structural features in the two amino acid sequences, whereby each amino acid that comprises part of a mismatched structural feature is counted as one difference between the two aligned amino acid sequences. Mismatches between aligned sequences can comprise an insertion, a deletion, and/or a replacement of one or more structural features in one amino acid sequence compared to the other aligned amino acid sequence as would be understood by a skilled person. Several publicly available online servers can be used to detect protein structure alignment and calculate percent variation, such as FATCAT [11], SuperPose [12], iPBA [13], MAPSCI [14], and others known to a person skilled in the art.

In some embodiments, variation in the temperature sensing amino acid sequence SEQ ID NO: 1 can result in having a total of 2 to 49 consecutive uninterrupted heptad repeats in the temperature sensing amino acid sequence within the 0% to 20% variation range, In some embodiments, variation in the temperature sensing amino acid sequence SEQ ID NO: 1 can result in having a total of 10 to 30 consecutive uninterrupted heptad repeats in the temperature sensing amino acid sequence within the 0% to 20% variation range In some embodiments, variation in the temperature sensing amino acid sequence SEQ ID NO: 1 can result in having heptad repeats interrupted by one or more insertions distributed unevenly throughout the system.

In some embodiments, a Minimum and Maximum number of amino acids residues can be inserted in the coiled coil temperature sensitive amino acid sequence, wherein—Minimum=1. Maximum=maximum number of amino acids–(minimum number of heptad repeats*7) to provide the temperature sensitive amino acid sequence with breaks that can be distributed unevenly throughout the coil, with long stretches of heptads and short puncta of heptads. Accordingly in some embodiments the number of uninterrupted heptad repeats in the coiled coil temperature sensitive amino acid sequence can be 2 to 30, in some embodiments the number of uninterrupted heptad repeats in the coiled coil temperature sensitive amino acid sequence can be 5-20 based on the consensus coiled coil prediction for TlpA.

Additional embodiments can comprise a thermomer cell is described comprising at least one of the thermomer monomer, thermomer dimer, thermomer monomeric construct, thermomer dimeric construct and thermomer vector herein described within a biological cell.

A "biological cell or "cell" as used herein indicates the basic structural, functional, and biological unit of all known organism. Cells consist of cytoplasm enclosed within a membrane, which contains many biomolecules such as proteins and nucleic acids had has dimensions typically between 1 and 100 micrometers. Exemplary cells comprise eukaryotic cells, prokaryotic cells identifiable by a skilled person.

Exemplary cells in the sense of the disclosure comprise a plurality of bacterial cells such as *E. coli, Salmonella, Bacteroides, Lactobacillus*. The cells can be natural cells or they can be genetically modified cells that have been engineered for enhanced disease homing, proliferation, and additional properties identifiable by a skilled person.

Exemplary cells in the sense of the disclosure can comprise a plurality of eukaryotic cells. In some embodiments, the eukaryotic cells are unicellular organisms. Exemplary unicellular eukaryotes comprise protozoa, such as ciliates such as *Paramecia, Stentors* and *Vorticella*, amoebas such as *Physarum* and *Entamoeba*, unicellular algae such as euglenophyta, chlorophyte, diatoms, dinoflagellates, unicellular fungi such as yeasts such as *Saccharomyces* and *Candida* species.

Exemplary cells in the sense of the disclosure comprise cells in or isolated from multicellular eukaryotic species. Multicellular eukaryotic species comprise mammalian species such as animals, plants, and multicellular fungi. In some embodiments, multicellular eukaryotes comprise species such as *Homo sapiens* and *Mus musculus*, for example, among others. In some embodiments, cells comprise stem cells, progenitor cells, induced pluripotent stem cells, and others identifiable by a skilled person. In some embodiments, cells comprise genetically engineered mammalian stem cells, for or example, genetically engineered stem cells that have been designed to secrete therapeutic substance after introduction into a host, such as a human.

Exemplary cells comprise further comprises plants and animal cells such as a human cell, an immune cell, a neural cells, Stem cells, T-cells, Neuron cell and additional cell identifiable by a skilled person.

As mentioned above, thermomer monomers, linker polypeptides, cargo moieties, thermomer dimer, thermomer monomeric constructs, thermomer dimeric complex, and related polypeptides, polynucleotidic constructs, vectors, cells and compositions herein described can be provided as a part of systems to perform any of the above mentioned methods. The systems can be provided in the form of kits of parts. In a kit of parts, one or more thermomer monomers, linker polypeptides, cargo moieties, thermomer dimer, thermomer monomeric constructs, thermomer dimeric complex, and related polypeptides, polynucleotidic constructs, vectors, and cells as well as other reagents to perform the methods herein described are comprised in the kit independently. thermomer monomers, linker polypeptides, cargo moieties, thermomer dimer, thermomer monomeric constructs, thermomer dimeric complex, and related polypeptides, polynucleotidic constructs, vectors, and cells and other reagents can be included in one or more compositions, and each thermomer monomers, linker polypeptides, cargo moieties, thermomer dimer, thermomer monomeric constructs, thermomer dimeric complex, and related polypeptides, polynucleotidic constructs, vectors, cells and reagents is in a composition together with a suitable vehicle.

Additional components can include labeled polynucleotides, labeled antibodies, labels, microfluidic chip, reference standards, and additional components identifiable by a skilled person upon reading of the present disclosure.

The terms "label" and "labeled molecule" as used herein refer to a molecule capable of detection, including but not limited to radioactive isotopes, fluorophores, chemiluminescent dyes, chromophores, enzymes, enzymes substrates, enzyme cofactors, enzyme inhibitors, dyes, metal ions, nanoparticles, metal sols, ligands (such as biotin, avidin, streptavidin or haptens) and the like. The term "fluorophore" refers to a substance or a portion thereof which is capable of exhibiting fluorescence in a detectable image. As a consequence, the wording "labeling signal" as used herein indicates the signal emitted from the label that allows detection of the label, including but not limited to radioactivity, fluorescence, chemoluminescence, production of a compound in outcome of an enzymatic reaction and the like.

In embodiments herein described, the components of the kit can be provided, with suitable instructions and other necessary reagents, in order to perform the methods here disclosed. The kit will normally contain the compositions in separate containers. Instructions, for example written or audio instructions, on paper or electronic support such as tapes, CD-ROMs, flash drives, or by indication of a Uniform Resource Locator (URL), which contains a pdf copy of the instructions for carrying out the assay, will usually be included in the kit. The kit can also contain, depending on the particular method used, other packaged reagents and materials (i.e. wash buffers and the like).

Further details concerning the thermal bioswitches, and related thermal genetic circuits, therapeutic cells, systems and methods of the present disclosure will become more apparent hereinafter from the following detailed disclosure of examples by way of illustration only with reference to an experimental section.

EXAMPLES

The thermal bioswitches and related systems and methods herein disclosed are further illustrated in the following examples, which are provided by way of illustration and are not intended to be limiting.

In particular, the following examples illustrate exemplary methods and protocols for preparing sets of polynucleotides and polypeptides, testing and characterizing these sets of polynucleotides and polypeptides, building genetic circuits, and testing genetic circuits in vivo and in vitro. A person skilled in the art will appreciate the applicability and the necessary modifications to adapt the features described in detail in the present section, to additional tunable thermal bioswitches, genetic circuits and therapeutic cells and related methods and systems according to embodiments of the present disclosure.

Plasmid Construction and Molecular Biology. All plasmids were designed using SnapGene (GSL Biotech) and assembled via KLD mutagenesis or Gibson Assembly using enzymes from New England Biolabs. All plasmids and sequences will be deposited to Addgene. After assembly, constructs were transformed into NEB Turbo and NEB Stable E. coli (New England Biolabs) for growth and plasmid preparation. Constructs containing long homologous regions such, including all plasmids containing two TlpA ORFs, were propagated using NEB Stable. Thermal gene expression assays were performed in NEB Stable E. coli. Bacterial reporters of gene expression referred to in the text as GFP and RFP are mWasabi[15] and mCherry[16], respectively. The mammalian fusion protein fluorophore referred to in the text and figures as RFP is mScarlet-I[17]. TlpA, mCherry and mWasabi were obtained from our previous work[18]. mScarlet-I was obtained from Addgene (pmScarlet-i_C1, plasmid #85044). Coiled-coil structure prediction and helical wheel diagram annotation was performed using the software DrawCoil 1.0[8]. In the creation of dual-expression GFP/RFP thermal reporter plasmids such as that described in FIG. 1e, an additional terminator was placed upstream of each pTlpA promoter to suppress crosstalk from the weak upstream transcription previously observed from this element[18]. nhTlpA was designed using a homemade script to minimize codon homology while retaining protein sequence identity. Subsequently, 11 nucleotides were altered manually to minimize short repeats that prevented custom gene synthesis. The nhTlpA$_{39}$ gBlock was synthesized by Integrated DNA Technologies.

Bacterial Thermal Regulation Assay. Determination of temperature-dependent gene expression was performed as described previously[18]. Briefly, saturated precultures were diluted to $OD_{600}$=0.1 and propagated at 30° C. until reaching $OD_{600}$=0.3 as measured via Nanodrop 2000c (Thermo Scientific), at which point 25 uL aliquots were dispensed into PCR tubes with transparent caps (Bio-Rad) and incubated for 12 hours in a thermal gradient using a Bio-Rad C1000 Touch thermocycler. After thermal stimulus, fluorescence was measured using a Stratagene MX3005p qPCR (Agilent), after which cultures were diluted 4×, transferred into microplates (Costar black/clear bottom), and measured for $OD_{600}$ using a Molecular Devices SpectraMax M5 plate reader. The background-corrected F/OD is reported as described previously [18].

Protein Expression and Purification for CD Spectroscopy. pET26b-based expression constructs were transformed into BL21-DE3 E. coli and grown on kanamycin-selective plates. Saturated overnight cultures were diluted 1 mL into 400 mL expression cultures and induced with a final IPTG (Sigma Aldrich) concentration of 1 mM at $OD_{600}$=0.6. After 24 hours of expression at 25° C., cultures were harvested by centrifugation using a JLA-16.250 rotor (Beckman Coulter) at 6,000 rpm and 4° C. for 8 minutes. Pellets were lysed using the detergent Solulyse in Tris Buffer (Genlantis) and debris was pelleted by centrifugation at 35,343 rcf in a JS-24.38 rotor (Beckman Coulter). Polyhistidine-tagged proteins were purified on an AKTA purifier (GE Healthcare) using 1 mL cOmplete columns (Roche) and buffer exchanged into 1×PBS (Corning) using Zeba spin desalting columns. Concentration was determined using the Pierce 660 nm Protein Assay (Thermo Fisher Scientific) and proteins were stored at 4° C. until use. Proteins were subsequently analyzed within 24 hours of purification.

Circular Dichroism Spectroscopy. CD melting curves were taken using an Aviv Circular Dichroism Spectrophotometer (Model 60DS) at 222 nm with 0.1 minute equilibration time and 5 second averaging time. Purified proteins were diluted to 3 µM in 1×PBS and measured in a 1 mm quartz cuvette.

Temperature-dependent protein fluorescence measurement. Fluorescent proteins were purified as described above and diluted to 1 µM for analysis. 25 µL samples were placed in N=3 replicates in PCR strips with optically transparent caps (Bio Rad) into a Stratagene MX3005p qPCR (Agilent) for intensity measurements. Filter sets used for red, green, and blue proteins were ROX, FAM, and ATTO, respectively. Sample fluorescence was measured continuously as temperature was ramped from 25° C. to 50° C. in 1° C. increments and with 1 minute of equilibration time at each increment.

Mass-based validation of heterodimerization. Dual TlpA expression constructs were transformed into BL21-DE3 cells (NEB) and grown as 1 mL precultures in 2×YT/ampicillin for 20-24 hours at 30° C. in an Infors Multitron with shaking at 250 rpm. 10 µL saturated cultures were diluted into 4 mL 2×YT/ampicillin and returned to 30° C. At $OD_{600}$—0.6 to 0.7, cultures were induced with 4 µL of 1 M IPTG (Sigma Aldrich) and returned to 30° C. for 12 hours, at which point they were transferred into 2 mL centrifuge tubes (USA Scientific) and pelleted in a Beckman Microfuge 20 at maximum speed for 1 minute. Supernatant was carefully and completely aspirated with a pipette, and the pellet was weighed and frozen at −20° C. for at least 20 minutes. After thawing, Solulyse in Tris Buffer (Genlantis) was added at 10 µL per 1 mg. Pellets were gently resuspended via pipetting and shaken in an Eppendorf ThermoMixer at room temperature (800 rpm for 20 minutes). Subsequently the tubes were spun at 13,000 rcf for 10 minutes and the lysate was diluted 5-fold in Solulyse in Tris Buffer. A pilot Western blot was performed and total TlpA band intensity was quantified for each variant, after which loading amounts for all variants were normalized to that of the wild type via dilution in Solulyse. For crosslinking, 1 µL of 50 mM $CuCl_2$ (Sigma Aldrich) was added to 10 µL lysate in an Eppendorf microcentrifuge tube. The lysate and $CuCl_2$ solution were pre-heated separately for 5 minutes prior to co-incubation. Subsequently, the lysate and crosslinker mixture was shaken at 800 rpm for 10 minutes in an Eppendorf ThermoMixer at the desired temperature. After 10 minutes of $CuCl_2$-catalyzed crosslinking, the reaction was quenched with 11 µL Laemmli buffer (Bio Rad). For uncrosslinked samples, 10 uL Laemmli buffer was added to the lysate at the appropriate temperature. SDS-PAGE was performed using 7.5% pre-cast polyacrylamide gels (Bio Rad) run at 75 V for 140 minutes. Western blotting was performed using the Trans-blot Turbo apparatus and nitrocellulose membrane kit (Bio Rad). Transfer was performed at 25 V for 7 minutes. Membranes were blocked with 5% w/v Blotto milk (Santa Cruz Biotechnology) in 0.05% TBS-Tween for 1 hour at room temperature. Primary staining was performed using the mouse anti-HA sc-7392 antibody (Santa Cruz Biotech) overnight at 4° C. Blots were then washed three times for 15 minutes at 4° C. with 0.05% TBS-Tween and stained for 4 hours with goat anti-mouse IgG-HRP sc-2005 (Santa Cruz Biotech) at room temperature. After three 15-minute washes, HRP visualization was performed using Supersignal West Pico PLUS reagent (Thermo Fisher Scientific). Imaging was performed in a Bio-Rad ChemiDoc MP gel imager.

Mammalian cell culture. K562 cells (gift of D. Baltimore) were cultured in RPMI 1640 media (Thermo Fisher Scientific) with 1×Penicillin/Streptomycin (Corning). Transient transfection was performed using Lonza 4D nucleofection with SF Cell Line buffer and the pre-programmed K562 protocol. Lentivirus was prepared using a third-generation viral vector and helper plasmids (gifts of D. Baltimore). Virus was packaged in HEK293T cells grown in 10 cm dishes after 2 days of transfection and concentrated via the Lenti-X reagent (Takara Bio). Infection was performed by resuspending viral pellets in 250 uL RPMI and spinfecting 1E6 K562 cells in 1 mL RPMI with 10 µL virus at 800×g, 30° C., for 90 minutes. Experiments were performed at least five passages after infection.

Live cell microscopy. Delta-T dishes (Bioptechs) were coated with 400 µL 0.1 mg/mL Poly-D Lysine (Sigma Aldrich) for 30 minutes. Meanwhile, 1E6 K562 cells were pelleted at 300 rcf for 5 minutes and resuspended in staining solution (1×PBS or HBSS with 2.5 µg/mL Hoechst 33342, Thermo Fisher Scientific). For Golgi staining, the solution (in HBSS) also contained BODIPY FL C5-Ceramide complexed to BSA (Thermo Fisher Scientific, 50 nM final concentration). Cells were stained at room temperature for 10 minutes before being pelleted and resuspended in 1 mL RPMI 1640. For co-localization experiments, the staining solution (in HBSS) also contained CellBrite Fix 488 at 1×concentration as described in the product manual, and staining was performed at 37° C. for 10 minutes. After at least 20 minutes of coating, PDL was aspirated from the Delta-T dishes, which were then rinsed once with 1×PBS and dried. Cells were then transferred to the Delta-T dishes, which where adhesively affixed to the swinging plates of an Allegra X-12 centrifuge with SX4750 rotor (Beckman Coulter) and centrifugated at 30° C. for 15 minutes at 300 rcf. Imaging was performed at the California Institute of Technology confocal microscopy facility using an LSM880 (Zeiss) with Airyscan. Cells with sufficient overall brightness to discern membrane contrast were imaged; the membrane localization of dimmer cells could not be discerned in our thermal imaging configuration but was observable under higher magnification on a conventional glass slide (FIG. 16). Delta-T dishes were mounted onto the thermal stage interfaced with a Bioptechs Delta T4 Culture Dish Controller and imaged using a 1080-378 C-Achroplan 40×/0.80 W objective. Airyscan processing was performed in 2D mode using default settings.

Image analysis. Image analysis was performed using the Zeiss Zen Black software for pre-processing and CellProfiler[19] for correlation quantification. Images were manually cropped to include only a single cell per ROI, with approximately 408×408 pixel FOVs. For cells with poor attachment to the plate, resulting in position offsets between the red, blue, and green channels, frame alignment between the red and green channels was performed in Zen Black. All available transformations were sampled and the best-aligned transformation on a per-cell basis was used. Blue channel alignment was performed in CellProfiler on a per-cell basis for images with obvious displacement of the nucleus using the Mutual Information module, correlating the blue channel image with the inverted red channel image. Exported images were then loaded in CellProfiler and analyzed using a custom pipeline. Briefly, cell boundaries were determined from red channel using Hoescht 33342-stained nuclei as primary seed objects. Colocalization was calculated for the ROI defined between the outer cell membrane and the nucleus. The nucleus was excluded because it acts as a diffusion barrier to TlpA-RFP but not to free mScarlet-I. For the free mScarlet-I cell line in FIG. 4, panel f, a modified pipeline using the CellBrite Fix 488 stain for cell boundary determination was used to improve the detection of cell edges. For the Direct Membrane Fusion data set in FIG. 4, panel f, the 44° C. point was acquired in a separate experiment using the same cell line and is consistent with the 43° C. and 45° C. data points of the original data set (FIG. 17).

Example 1: Redesign of Wild Type TlpA into a Pair of Heterodimeric Coiled-Coil Species (First-Generation Variants)

Most applications of inducible dimerization systems require the interacting modules to be heterodimeric to enforce selective binding between two desired molecular partners [20]. To redesign the wild type TlpA into a pair of heterodimeric coiled-coil species (FIG. 1a), Applicant used rational mutagenesis guided by bioinformatic prediction of the TlpA dimerization domain structure.

Coiled-coil domains typically consist of repetitive seven-amino acid residue sequences known as heptad repeats[21]. Applicant used a published annotation of the TlpA sequence [7], cross-referenced against a computational annotation from the COILS[2] prediction server, to establish the register of heptad repeats within the TlpA primary sequence. Charge-complementary pairs of residues [22] predicted either at conventional g-to-e' contacts or at alternative g-to-d' interfaces were then introduced to disfavor homodimerization and favor heterodimerization (FIG. 1, panels b-c). The latter architecture occurs when large ionic sidechains at the core peripherally expose their charged termini, as has been described for the Fos-Jun coiled coil interaction[23].

Figure 5:
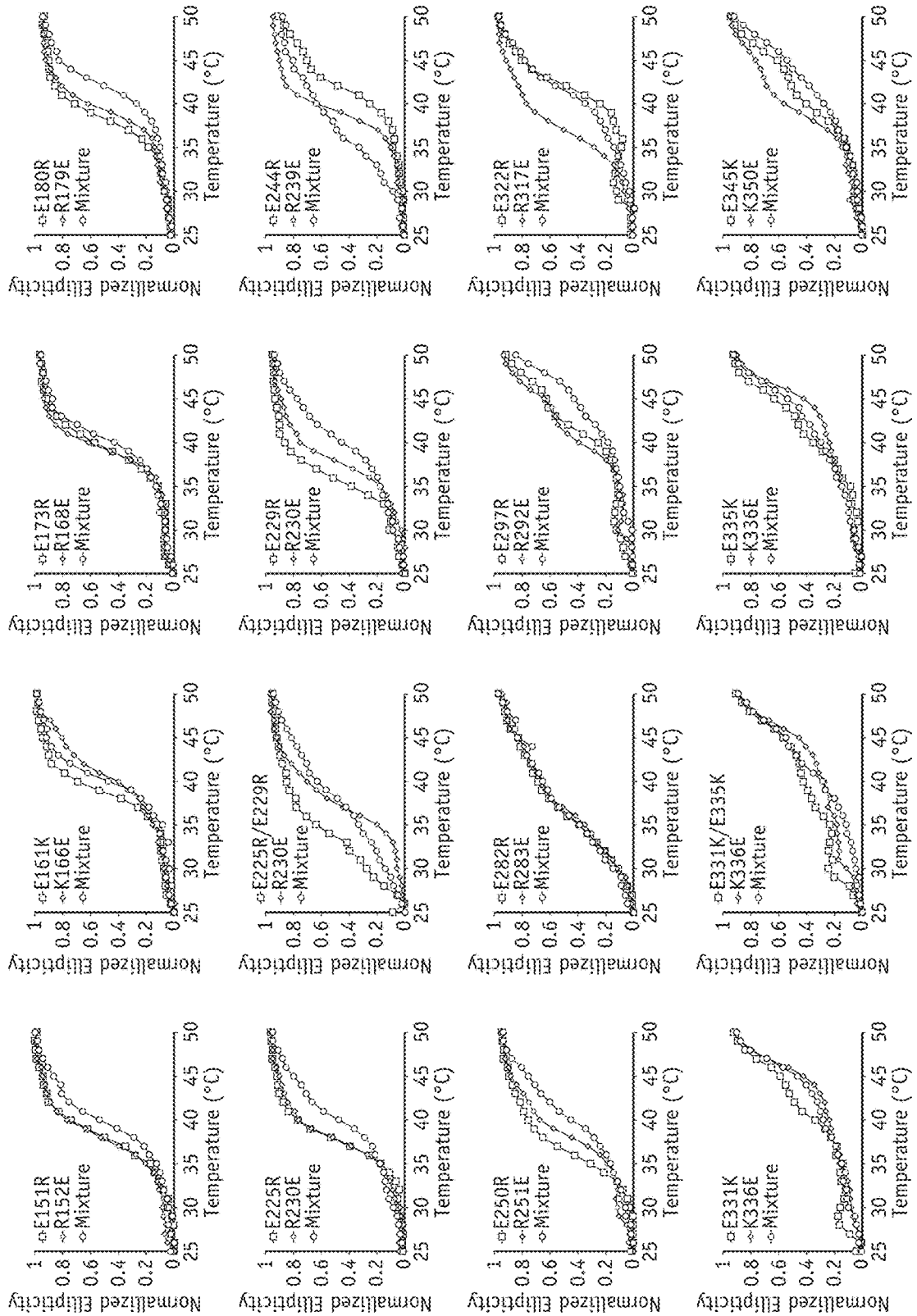

To maintain the highly switch-like thermal dissociation behavior of TlpA, Applicant reasoned that the least perturbative positions for mutagenesis would be at existing interfacial ionic interaction sites in the wild-type protein, which are present due to the C2 symmetry of the parallel coiled-coil structure. All such positions were mutated one by one, replacing cationic residues with glutamate and anionic side chains with arginine or lysine. The resulting coiled-coil domains were expressed in *E. coli*, the proteins purified via affinity chromatography, and their helical content assayed over a relevant thermal range using circular dichroism spectroscopy (FIG. 5).

From this initial screen a pair of charge-complemented mutants was obtained, dubbed TlpA-$G_1A$ (E180R) and TlpA-$G_1B$ (R179E), that demonstrated a sharp, sigmoidal thermal response profile with a notable upshift in the temperature threshold for an equimolar mixture of the mutant pair relative to pure solutions of either species (FIG. 1, panel d).

Example 2: Validation of In Cellulo Functionality of the TlpA-$G_1A$ and $G_1B$ Mutants To validate the in cellulo functionality of the TlpA-$G_1A$ and $G_1B$ mutants, the ability of TlpA was utilized to modulate the expression of a fluorescent reporter gene in *E. coli*[18].

A temperature-inducible circuit was constructed containing two separate copies of the TlpA gene, with TlpA operators upstream of a green fluorescent protein (GFP) and a red fluorescent protein (RFP). To compare the repression efficiency of the $G_1A/G_1A$ and $G_1B/G_1B$ homodimers to that of the $G_1A/G_1B$ heterodimer, circuit variants was generated containing two copies of TlpA-$G_1A$, two copies of TlpA-$G_1B$, or one copy of each TlpA variant (FIG. 2, panels a-b).

Figure 6:
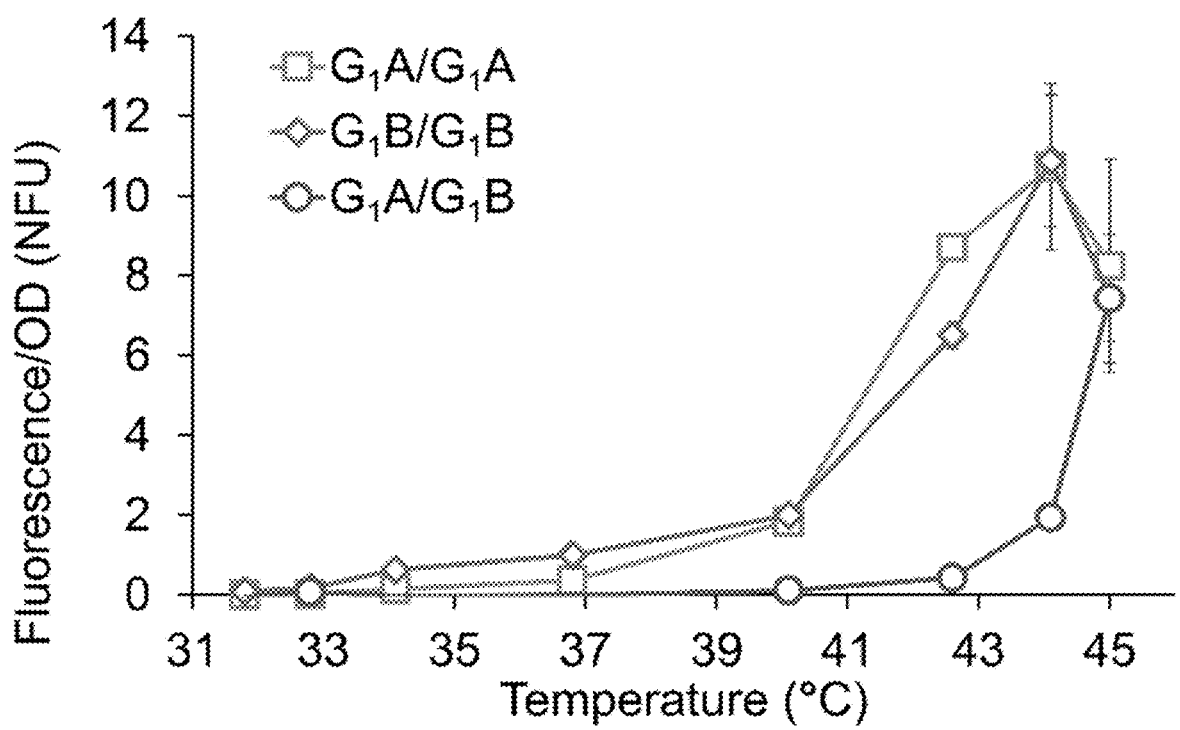

The thermal gene expression profiles of GFP showed all three circuits to produce a highly switch-like cooperative activation. However, the two homodimeric constructs had a clear downshift in their transition temperature compared to the heterodimeric construct containing both TlpA variants (FIG. 2, panel c), confirming a stabilized heterotypic association between the two coiled-coil strands. The RFP output displayed similar activation profiles (FIG. 6). Swapping the positions of the two TlpA copies within the vector did not significantly influence the expression profile, controlling for inadvertent stoichiometric effects (FIG. 7).

Example 3: Design of Second-Generation Variants and Validation their Functionality In Cellulo While the first-generation variants shown in Examples 1-2 demonstrated the ability to engineer a heterodimerization preference, it was noted that the $G_1A/G_1A$ and $G_1B/G_1B$ circuit constructs still had a transition setpoint above 37° C., indicating that these mutants retained the ability to homodimerize under typical mammalian homeostatic conditions.

Therefore, thermal GFP expression assay was used to evaluate a subset of additional rational mutant pairs selected from the original panel (FIG. 8). The two best-performing pairs of substitutions from this subset was selected to combine with TlpA $G_1A$ and TlpA $G_1B$ in all possible permutations. This resulted in the second-generation coiled-coil pairs dubbed TlpA $G_{2-1}$-$G_{2-4}$, each comprising a $G_2A_n$ and a $G_2B_n$ monomer (Table 1). Table 1 lists the second-generation TlpA mutants utilized in this example.

TABLE 1

| Second-generation TlpA mutants | |
|---|---|
| Mutant | Mutations |
| $G_2A_1$ | E180R + E229R |
| $G_2B_1$ | R179E + R230E |
| $G_2A_2$ | E180R + R230E |
| $G_2B_2$ | R179E + E229R |
| $G_2A_3$ | E180R + E250R |
| $G_2B_3$ | R179E + R251E |
| $G_2A_4$ | E180R + R251E |
| $G_2B_4$ | R179E + E250R |

In the bacterial bioswitch assay, all the heterodimeric circuits combining $G_2A_n$ with its complementary $G_2B_n$ displayed switch-like activation of reporter fluorescence (FIG. 2, panel d, FIG. 9). In contrast, the homodimeric constructs containing two copies of $G_2A_n$ or $G_2B_n$ were unable to propagate in a stable manner, consistently displaying deletions in the TlpA promoter or the fluorescent reporter gene, even when grown at 30° C. in recombination-deficient *E. coli*. These results suggest that the second-generation variants are unable to form homodimeric interactions at the concentrations defined by the circuits, resulting in constitutive expression from the TlpA promoter and an untenable metabolic burden to the host cell[24, 25].

Example 4: Validation of TlpA Heterodimerization by Electrophoresis

To confirm the dimerization preference of the engineered coiled-coils, a biochemical assay was designed based on covalent crosslinking and size-based gel separation.

TlpA dimers can be crosslinked via $CuCl_2$-catalyzed oxidation of the protein's single cysteine residue[26]. To distinguish hetero- from homodimerization, one of the two TlpA sequences was truncated by removing its DNA binding domain, thereby altering its electrophoretic mobility on a polyacrylamide gel without perturbing its ability to dimerize (FIG. 3, panel a). HA tags were added at the C-termini of both proteins to facilitate specific detection via Western blotting. the resulting pairs of truncated and full-length TlpA variants were expressed in *E. coli*. To validate this assay, Applicant expressed a pair of wild-type TlpA coils and crosslinked them at 37° C., or after a thermal elevation to 45° C., or after return to 37° C. Three bands corresponding to the expected mixture of the two types of homodimers and one type of heterodimer were visible after crosslinking at 37° C., while crosslinking at the higher temperature resulted in a preponderance of monomers, which could be re-annealed by bringing the temperature back down to 37° C. (FIG. 3, panel b).

Substituting the wild type coiled-coils with the first-generation heterodimerizing mutants resulted in preferential accumulation of the TlpA heterodimer at 37° C. (FIG. 3, panel c). Constructs containing the second-generation variants demonstrated further reduction in the intensity of the homodimer bands in favor of the intermediate molecular weight heterodimer, with TlpA $G_{2-3}$ demonstrating the strongest heterodimeric enrichment. (FIG. 3, panel c, FIG. 10). The first- and second-generation heterodimers both showed reversible dissociation at 45° C. (FIG. 3, panel d). On the basis of these results, the TlpA $G_{2-3}$ pair was chosen as the "thermomer" construct for further experiments.

Example 5: Demonstration of Temperature-Dependent Membrane Localization of TlpA Variants in Mammalian Cells After validating the temperature-dependent association of the engineered heterodimeric TlpA thermomers, Applicant set out to demonstrate their ability to be fused with other proteins and confer controlled protein-protein association in mammalian cells.

A construct was designed wherein one TlpA-$G_{2-3}$ strand was N-terminally fused with the palmitoylation sequence of GAP43, thereby compartmentalizing it to the plasma membrane. The complementary TlpA-$G_{2-3}$ strand was fused at the C-terminus to mScarlet-I (FIG. 4, panel a), an RFP chosen for its robust fluorescence at elevated temperature (FIG. 11). To make this system compatible with mammalian homeostatic conditions, the TlpA-$G_{2-3}$ heterodimerizing mutations were combined with three previously described amino acid substitutions that lower the coiled-coil dissociation temperature to approximately 39° C.[18].

Using live cell confocal microscopy of transiently transfected K562 cells, at physiological temperature strong localization of fluorescence to the plasma membrane (FIG. 4, panel b and FIG. 12) and also to the Golgi apparatus (FIG. 13) was observed. Increasing the cells' temperature using resistive heating above a threshold of 40° C. resulted in the redistribution of membrane fluorescence into the cytosol. As a control for non-specific thermal dissociation, cells in which the RFP was directly palmitoylated showed no redistribution of membrane fluorescence within this temperature range (FIG. 4, panels c-d, and FIG. 14). This confirms that RFP dissociation from the membrane is driven by a TlpA-mediated binding transition rather than disruption of membrane integrity.

To enable the use of the thermomer system with viral gene delivery and genomic integration, Applicant generated a nonhomologous variant of the TlpA $G_2A_3$ strand (nhTlpA $G_2A_3$) in which all degenerate codons were mutagenized to synonymous triplets with minimal identity to the original sequence. This mutagenesis helps avoid template switching-mediated recombination during viral delivery of high-homology constructs[27]. The resulting open reading frame had 57.48% sequence identity to the parent sequence, with no more than 5 consecutive homologous nucleotides. Lentiviral delivery of a construct containing palmitoylated nhTlpA $G_2A_3$ and mScarlet-fused TlpA $G_2B_3$ resulted in robust temperature-induced dissociation of fluorescence from the plasma membrane (FIG. 15), similar to the results of transient transfection.

This virally-engineered K562 cell line was used to quantify the co-localization of RFP fluorescence intensity with signal from the plasma membrane, as delineated by CellBrite Fix 488 staining (FIG. 4, panel e). Cells with thermomer-mediated RFP targeting to the membrane demonstrated co-localization with the dye at physiological temperature, followed by loss of pixel correlation above 40° C. (FIG. 4, f). In contrast, control cells with directly palmitoylated RFP demonstrate robust co-localization with the membrane stain throughout the temperature range tested, while free cytoplasmic RFP showed no correlation with the CellBrite dye (FIG. 4, panel f).

The TlpA reporter cell line was also used to evaluate the reversibility of TlpA-mediated membrane localization after heating. Membrane localization was released by a 5-minute incubation at 42° C. Upon cooling back to 37° C., TlpA re-partitioned to the plasma membrane, indicating reversibility, albeit with slower kinetics than observed for dissociation (FIG. 4, panels g-h).

Example 6: Exemplary Thermomer Monomers, and Thermomer Monomeric Constructs

Exemplary monomers and monomeric structure are listed in Table 2 below, wherein the cargo moiety is indicated with brackets, the linker is indicated with underlined fonts and the thermomer monomer is indicated with italic fonts

TABLE 2

| Features | Sequence | SEQ ID NO |
|---|---|---|
| Sequence: TlpA<br>Description: Wild type TlpA Homodimer<br>Referenced in FIGS.: N/A<br>Key features: D135V A217V L236F<br>Key features: The bolded A is a D in the GenBank listing for TlpA (Accession # NC_003277). This variant (with A) is what was received by the Shapiro lab when it first obtained the TlpA gene | [MRPATYEPEQIIEAGLALQAEGRNITGFALRNQVGGG<br>NPTRERQIWDEYQASQSTVVTEPVAELPVEV]AEEVKA<br>VSAALSERITQLATELNDKAVRAAERRVAEVTRAAGEQTAQ<br>AERELADAAQTVDDLEEKLDELQDRYDSLTLALESERSLR<br>QQHDVEMAQLKERLAAAEENTRQREERYQEQKTVLQDAL<br>NAEQAQHKNTREDLQKRLEQISAEANARTEELKSERDKVN<br>TLLTRLESQENALASERQQHLATRETLQQRLEQAIADTQAR<br>AGEIALERDRVSSLTARLESQEKASSEQLVRMGSEIASLTER<br>CTQLENQRDDARLETMGEKETVAALRGEAEALKRQNQSL<br>MAALSGNKQTGGQNA | 39 |
| Sequence: TlpA39<br>Description: Homodimer TlpA variant with Tbs = 39 (described in previous application) | [MRPATYEPEQIIEAGLALQAEGRNITGFALRNQVGGG<br>NPTRLRQIWDEYQASQSTVVTEPVAELPVEV]AEEVKA<br>VSAALSERITQLATELNDKAVRAAERRVAEVTRAAGEQTAQ<br>AERELADAAQTVDDLEEKLVELQDRYDSLTLALESERSLR | 40 |

TABLE 2-continued

| Features | Sequence | SEQ ID NO |
|---|---|---|
| Referenced in FIGS.: N/A<br>Key features: D135V A217V L236F | QQHDVEMAQLKERLAAAEENTRQREERYQEQKTVLQDAL<br>NAEQAQHKNTREDLQKRLEQISVEANARTEELKSERDKVN<br>TFLTRLESQENALASERQQHLATRETLQQRLEQAIADTQA<br>RAGEIALERDRVSSLTARLESQEKASSEQLVRMGSEIASLTE<br>RCTQLENQRDDARLETMGEKETVAALRGEAEALKRQNQS<br>LMAALSGNKQTGGQNA | |
| Sequence: TlpA $G_1A$<br>Description: Full length TlpA with $G_1A$ heterodimerizing mutation<br>Referenced in FIGS.: FIG. 2C, FIG. 2D<br>Key Features: E180R | [MRPATYEPEQIIEAGLALQAEGRNITGFALRNQVGGG<br>NPTRLRQIWDEYQASQSTVVTEPVAELPVEV]AEEVKA<br>VSAALSERITQLATELNDKAVRAAERRVAEVTRAAGEQTAQ<br>AERELADAAQTVDDLEEKLDELQDRYDSLTLALESERSLR<br>QQHDVEMAQLKERLAAAEENTRQRRERYQEQKTVLQDAL<br>NAEQAQHKNTREDLQKRLEQISAEANARTEELKSERDKVN<br>TLLTRLESQENALASERQQHLATRETLQQRLEQAIADTQAR<br>AGEIALERDRVSSLTARLESQEKASSEQLVRMGSEIASLTER<br>CTQLENQRDDARLETMGEKETVAALRGEAEALKRQNQSL<br>MAALSGNKQTGGQNA | 41 |
| Sequence: TlpA $G_1B$<br>Description: Full length TlpA with $G_1B$ heterodimerizing mutation<br>Referenced in FIGS.: FIG. 2C, FIG. 2D<br>Key Features: R179E | [MRPATYEPEQIIEAGLALQAEGRNITGFALRNQVGGG<br>NPTRLRQIWDEYQASQSTVVTEPVAELPVEV]AEEVKA<br>VSAALSERITQLATELNDKAVRAAERRVAEVTRAAGEQTAQ<br>AERELADAAQTVDDLEEKLDELQDRYDSLTLALESERSLR<br>QQHDVEMAQLKERLAAAEENTRQEEERYQEQKTVLQDAL<br>NAEQAQHKNTREDLQKRLEQISAEANARTEELKSERDKVN<br>TLLTRLESQENALASERQQHLATRETLQQRLEQAIADTQAR<br>AGEIALERDRVSSLTARLESQEKASSEQLVRMGSEIASLTER<br>CTQLENQRDDARLETMGEKETVAALRGEAEALKRQNQSL<br>MAALSGNKQTGGQNA | 42 |
| Sequence: TlpA $G_2A_1$<br>Description: Full length TlpA with $G_2A_1$ heterodimerizing mutations<br>Referenced in FIGS.: FIG. 2D<br>Key Features: E180R, E229R | [MRPATYEPEQIIEAGLALQAEGRNITGFALRNQVGGG<br>NPTRLRQIWDEYQASQSTVVTEPVAELPVEV]AEEVKA<br>VSAALSERITQLATELNDKAVRAAERRVAEVTRAAGEQTAQ<br>AERELADAAQTVDDLEEKLDELQDRYDSLTLALESERSLR<br>QQHDVEMAQLKERLAAAEENTRQRRERYQEQKTVLQDAL<br>NAEQAQHKNTREDLQKRLEQISAEANARTEELKSRRDKVN<br>TLLTRLESQENALASERQQHLATRETLQQRLEQAIADTQAR<br>AGEIALERDRVSSLTARLESQEKASSEQLVRMGSEIASLTER<br>CTQLENQRDDARLETMGEKETVAALRGEAEALKRQNQSL<br>MAALSGNKQTGGQNA | 43 |
| Sequence: TlpA $G_2B_1$<br>Description: Full length TlpA with G2B1 heterodimerizing mutations<br>Referenced in FIGS.: FIG. 2D<br>Key features: R179E, R230E | [MRPATYEPEQIIEAGLALQAEGRNITGFALRNQVGGG<br>NPTRLRQIWDEYQASQSTVVTEPVAELPVEV]AEEVKA<br>VSAALSERITQLATELNDKAVRAAERRVAEVTRAAGEQTAQ<br>AERELADAAQTVDDLEEKLDELQDRYDSLTLALESERSLR<br>QQHDVEMAQLKERLAAAEENTRQEEERYQEQKTVLQDAL<br>NAEQAQHKNTREDLQKRLEQISAEANARTEELKSEEDKVN<br>TLLTRLESQENALASERQQHLATRETLQQRLEQAIADTQAR<br>AGEIALERDRVSSLTARLESQEKASSEQLVRMGSEIASLTER<br>CTQLENQRDDARLETMGEKETVAALRGEAEALKRQNQSL<br>MAALSGNKQTGGQNA | 44 |
| Sequence: TlpA $G_2A_2$<br>Description: Full length TlpA with $G_2A_2$ heterodimerizing mutations<br>Referenced in FIGS.: FIG. 2D<br>Key features: E180R, R230E | [MRPATYEPEQIIEAGLALQAEGRNITGFALRNQVGGG<br>NPTRLRQIWDEYQASQSTVVTEPVAELPVEV]AEEVKA<br>VSAALSERITQLATELNDKAVRAAERRVAEVTRAAGEQTAQ<br>AERELADAAQTVDDLEEKLDELQDRYDSLTLALESERSLR<br>QQHDVEMAQLKERLAAAEENTRQRRERYQEQKTVLQDAL<br>NAEQAQHKNTREDLQKRLEQISAEANARTEELKSEEDKVN<br>TLLTRLESQENALASERQQHLATRETLQQRLEQAIADTQAR<br>AGEIALERDRVSSLTARLESQEKASSEQLVRMGSEIASLTER<br>CTQLENQRDDARLETMGEKETVAALRGEAEALKRQNQSL<br>MAALSGNKQTGGQNA | 45 |
| Sequence: TlpA $G_2B_2$<br>Description: Full length TlpA with $G_2B_2$ heterodimerizing mutations<br>Referenced in FIGS.: FIG. 2D<br>Key features: R179E, E229R | [MRPATYEPEQIIEAGLALQAEGRNITGFALRNQVGGG<br>NPTRLRQIWDEYQASQSTVVTEPVAELPVEV]AEEVKA<br>VSAALSERITQLATELNDKAVRAAERRVAEVTRAAGEQTAQ<br>AERELADAAQTVDDLEEKLDELQDRYDSLTLALESERSLR<br>QQHDVEMAQLKERLAAAEENTRQEEERYQEQKTVLQDAL<br>NAEQAQHKNTREDLQKRLEQISAEANARTEELKSRRDKVN<br>TLLTRLESQENALASERQQHLATRETLQQRLEQAIADTQAR<br>AGEIALERDRVSSLTARLESQEKASSEQLVRMGSEIASLTER<br>CTQLENQRDDARLETMGEKETVAALRGEAEALKRQNQSL<br>MAALSGNKQTGGQNA | 46 |
| Sequence: TlpA $G_2A_3$<br>Description: Full length TlpA with $G_2A_3$ heterodimerizing mutations | [MRPATYEPEQIIEAGLALQAEGRNITGFALRNQVGGG<br>NPTRLRQIWDEYQASQSTVVTEPVAELPVEV]AEEVKA<br>VSAALSERITQLATELNDKAVRAAERRVAEVTRAAGEQTAQ | 47 |

TABLE 2-continued

| Features | Sequence | SEQ ID NO |
|---|---|---|
| Referenced in FIGS.: FIG. 2D<br>Key features: E180R, E250R | AERELADAAQTVDDLEEKLDELQDRYDSLTLALESERSLR<br>QQHDVEMAQLKERLAAAEENTRQRRERYQEQKTVLQDAL<br>NAEQAQHKNTREDLQKRLEQISAEANARTEELKSERDKVN<br>TLLTRLESQENALASRRQQHLATRETLQQRLEQAIADTQAR<br>AGEIALERDRVSSLTARLESQEKASSEQLVRMGSEIASLTER<br>CTQLENQRDDARLETMGEKETVAALRGEAEALKRQNQSL<br>MAALSGNKQTGGQNA | |
| Sequence: TlpA G₂B₃<br>Description: Full length TlpA with G₂B₃ heterodimerizing mutations<br>Referenced in FIGS.: FIG. 2D<br>Key features: R179E, R251E | [MRPATYEPEQIIEAGLALQAEGRNITGFALRNQVGGG<br>NPTRLRQIWDEYQASQSTVVTEPVAELPVEV]AEEVKA<br>VSAALSERITQLATELNDKAVRAAERRVAEVTRAAGEQTAQ<br>AERELADAAQTVDDLEEKLDELQDRYDSLTLALESERSLR<br>QQHDVEMAQLKERLAAAEENTRQEERYQEQKTVLQDAL<br>NAEQAQHKNTREDLQKRLEQISAEANARTEELKSERDKVN<br>TLLTRLESQENALASEEQQHLATRETLQQRLEQAIADTQAR<br>AGEIALERDRVSSLTARLESQEKASSEQLVRMGSEIASLTER<br>CTQLENQRDDARLETMGEKETVAALRGEAEALKRQNQSL<br>MAALSGNKQTGGQNA | 48 |
| Sequence: TlpA G₂A₄<br>Description: Full length TlpA with G₂A₄ heterodimerizing mutations<br>Referenced in FIGS.: FIG. 2D<br>Key features: E180R, R251E | [MRPATYEPEQIIEAGLALQAEGRNITGFALRNQVGGG<br>NPTRLRQIWDEYQASQSTVVTEPVAELPVEV]AEEVKA<br>VSAALSERITQLATELNDKAVRAAERRVAEVTRAAGEQTAQ<br>AERELADAAQTVDDLEEKLDELQDRYDSLTLALESERSLR<br>QQHDVEMAQLKERLAAAEENTRQRRERYQEQKTVLQDAL<br>NAEQAQHKNTREDLQKRLEQISAEANARTEELKSEEDKVN<br>TLLTRLESQENALASEEQQHLATRETLQQRLEQAIADTQAR<br>AGEIALERDRVSSLTARLESQEKASSEQLVRMGSEIASLTER<br>CTQLENQRDDARLETMGEKETVAALRGEAEALKRQNQSL<br>MAALSGNKQTGGQNA | 49 |
| Sequence: TlpA G₂B₄<br>Description: Full length TlpA with G₂B₄ heterodimerizing mutations<br>Referenced in FIGS.: FIG. 2D<br>Key features: R179E, E250R | [MRPATYEPEQIIEAGLALQAEGRNITGFALRNQVGGG<br>NPTRLRQIWDEYQASQSTVVTEPVAELPVEV]AEEVKA<br>VSAALSERITQLATELNDKAVRAAERRVAEVTRAAGEQTAQ<br>AERELADAAQTVDDLEEKLDELQDRYDSLTLALESERSLR<br>QQHDVEMAQLKERLAAAEENTRQEERYQEQKTVLQDAL<br>NAEQAQHKNTREDLQKRLEQISAEANARTEELKSERDKVN<br>TLLTRLESQENALASRRQQHLATRETLQQRLEQAIADTQAR<br>AGEIALERDRVSSLTARLESQEKASSEQLVRMGSEIASLTER<br>CTQLENQRDDARLETMGEKETVAALRGEAEALKRQNQSL<br>MAALSGNKQTGGQNA | 50 |
| Sequence: TlpA G₂A₅<br>Description: Full length TlpA with G₂A₅ heterodimerizing mutations<br>Referenced in FIGS.: N/A (variant was made and demonstrated to be functional, but not included in publication for reasons unrelated to functionality).<br>Key features: R230E, R251E | [MRPATYEPEQIIEAGLALQAEGRNITGFALRNQVGGG<br>NPTRLRQIWDEYQASQSTVVTEPVAELPVEV]AEEVKA<br>VSAALSERITQLATELNDKAVRAAERRVAEVTRAAGEQTAQ<br>AERELADAAQTVDDLEEKLDELQDRYDSLTLALESERSLR<br>QQHDVEMAQLKERLAAAEENTRQREERYQEQKTVLQDAL<br>NAEQAQHKNTREDLQKRLEQISAEANARTEELKSEEDKVN<br>TLLTRLESQENALASEEQQHLATRETLQQRLEQAIADTQAR<br>AGEIALERDRVSSLTARLESQEKASSEQLVRMGSEIASLTER<br>CTQLENQRDDARLETMGEKETVAALRGEAEALKRQNQSL<br>MAALSGNKQTGGQNA | 51 |
| Sequence: TlpA G₂A₆<br>Description: Full length TlpA with G₂A₆ heterodimerizing mutations<br>Referenced in FIGS.: N/A (variant was made and demonstrated to be functional, but not included in publication for reasons unrelated to functionality).<br>Key features: E229R, E250R | [MRPATYEPEQIIEAGLALQAEGRNITGFALRNQVGGG<br>NPTRLRQIWDEYQASQSTVVTEPVAELPVEV]AEEVKA<br>VSAALSERITQLATELNDKAVRAAERRVAEVTRAAGEQTAQ<br>AERELADAAQTVDDLEEKLDELQDRYDSLTLALESERSLR<br>QQHDVEMAQLKERLAAAEENTRQREERYQEQKTVLQDAL<br>NAEQAQHKNTREDLQKRLEQISAEANARTEELKSRRDKVN<br>TLLTRLESQENALASRRQQHLATRETLQQRLEQAIADTQAR<br>AGEIALERDRVSSLTARLESQEKASSEQLVRMGSEIASLTER<br>CTQLENQRDDARLETMGEKETVAALRGEAEALKRQNQSL<br>MAALSGNKQTGGQNA | 52 |
| Sequence: TlpA G₂B₅<br>Description: Full length TlpA with G₂B₅ heterodimerizing mutations<br>Referenced in FIGS.: N/A (variant was made and demonstrated to be functional, but not included in publication for reasons unrelated to functionality).<br>Key features: E229R, R251E | [MRPATYEPEQIIEAGLALQAEGRNITGFALRNQVGGG<br>NPTRLRQIWDEYQASQSTVVTEPVAELPVEV]AEEVKA<br>VSAALSERITQLATELNDKAVRAAERRVAEVTRAAGEQTAQ<br>AERELADAAQTVDDLEEKLDELQDRYDSLTLALESERSLR<br>QQHDVEMAQLKERLAAAEENTRQREERYQEQKTVLQDAL<br>NAEQAQHKNTREDLQKRLEQISAEANARTEELKSRDKVN<br>TLLTRLESQENALASEEQQHLATRETLQQRLEQAIADTQAR<br>AGEIALERDRVSSLTARLESQEKASSEQLVRMGSEIASLTER<br>CTQLENQRDDARLETMGEKETVAALRGEAEALKRQNQSL<br>MAALSGNKQTGGQNA | 53 |

TABLE 2-continued

| Features | Sequence | SEQ ID NO |
|---|---|---|
| Sequence: TlpA G₂B₆<br>Description: Full length TlpA with G₂B₆ heterodimerizing mutations<br>Referenced in FIGS.: N/A (variant was made and demonstrated to be functional but not included in publication for reasons unrelated to functionality).<br>Key features: R230E, E250R | [MRPATYEPEQIIEAGLALQAEGRNITGFALRNQVGGG NPTRLRQIWDEYQASQSTVVTEPVAELPVEV]AEEVKA VSAALSERITQLATELNDKAVRAAERRVAEVTRAAGEQTAQ AERELADAAQTVDDLEEKLDELQDRYDSLTLALESERSLR QQHDVEMAQLKERLAAAEENTRQREERYQEQKTVLQDAL NAEQAQHKNTREDLQKRLEQISAEANARTEELKSEEDKVN TLLTRLESQENALASRRQQHLATRETLQQRLEQAIADTQAR AGEIALERDRVSSLTARLESQEKASSEQLVRMGSEIASLTER CTQLENQRDDARLETMGEKETVAALRGEAEAALKRQNQSL MAALSGNKQTGGQNA | 54 |
| Sequence: TlpA_CC E151R<br>Description: Coiled-coil domain of TlpA (with initiating methionine) with candidate heterodimerizing mutation E151R.<br>Sequence contains C-terminal Leucine-Glycine (from XhoI restriction site used for cloning) and a hexahistidine tag used for purification. Note: Mutation position in referenced to the original position within full-length TlpA rather than the position within the coiled-coil domain fragment.<br>Referenced in FIGS.: FIG. 5<br>Key features: E151R | MAEEVKAVSAALSERITQLATELNDKAVRAAERRVAEVTRA AGEQTAQAERELADAAQTVDDLEEKLDELQDRYDSLTLAL ESERRSLRQQHDVEMAQLKERLAAAEENTRQREERYQEQK TVLQDALNAEQAQHKNTREDLQKRLEQISAEANARTEELK SERDKVNTLLTRLESQENALASERQQHLATRETLQQRLEQ AIADTQARAGEIALERDRVSSLTARLESQEKASSEQLVRMG SEIASLTERCTQLENQRDDARLETMGEKETVAALRGEAEA LKRQNQSLMAALGHHHHHH | 55 |
| Sequence: TlpA_CC R152E<br>Description: Coiled-coil domain of TlpA (with initiating methionine) with candidate heterodimerizing mutation R152E.<br>Sequence contains C-terminal Leucine-Glycine (from XhoI restriction site used for cloning) and a hexahistidine tag used for purification. Note: Mutation position in referenced to the original position within full-length TlpA rather than the position within the coiled-coil domain fragment.<br>Referenced in FIGS.: FIG. 5 (S1)<br>Key features: R152E | MAEEVKAVSAALSERITQLATELNDKAVRAAERRVAEVTRA AGEQTAQAERELADAAQTVDDLEEKLDELQDRYDSLTLAL ESEESLRQQHDVEMAQLKERLAAAEENTRQREERYQEQK TVLQDALNAEQAQHKNTREDLQKRLEQISAEANARTEELK SERDKVNTLLTRLESQENALASERQQHLATRETLQQRLEQ AIADTQARAGEIALERDRVSSLTARLESQEKASSEQLVRMG SEIASLTERCTQLENQRDDARLETMGEKETVAALRGEAEA LKRQNQSLMAALGHHHHHH | 56 |
| Sequence: TlpA_CC R168E<br>Description: Coiled-coil domain of TlpA (with initiating methionine) with candidate heterodimerizing mutation R168E.<br>Sequence contains C-terminal Leucine-Glycine (from XhoI restriction site used for cloning) and a hexahistidine tag used for purification. Note: Mutation position in referenced to the original position within full-length TlpA rather than the position within the coiled-coil domain fragment.<br>Referenced in FIGS.: FIG. 5 (S1)<br>Key features: R168E | MAEEVKAVSAALSERITQLATELNDKAVRAAERRVAEVTRA AGEQTAQAERELADAAQTVDDLEEKLDELQDRYDSLTLAL ESERSLRQQHDVEMAQLKEELAAAEENTRQREERYQEQK TVLQDALNAEQAQHKNTREDLQKRLEQISAEANARTEELK SERDKVNTLLTRLESQENALASERQQHLATRETLQQRLEQ AIADTQARAGEIALERDRVSSLTARLESQEKASSEQLVRMG SEIASLTERCTQLENQRDDARLETMGEKETVAALRGEAEA LKRQNQSLMAALGHHHHHH | 57 |
| Sequence: TlpA_CC E173R<br>Description: Coiled-coil domain of TlpA (with initiating methionine) with candidate heterodimerizing mutation E173R.<br>Sequence contains C-terminal Leucine-Glycine (from XhoI restriction site used for cloning) and a hexahistidine tag used for purification. Note: Mutation position in referenced to the original position within full-length TlpA rather than the position within the coiled-coil domain fragment.<br>Referenced in FIGS.: FIG. 5 (S1)<br>Key features: E173R | MAEEVKAVSAALSERITQLATELNDKAVRAAERRVAEVTRA AGEQTAQAERELADAAQTVDDLEEKLDELQDRYDSLTLAL ESERSLRQQHDVEMAQLKERLAAARENTRQREERYQEQK TVLQDALNAEQAQHKNTREDLQKRLEQISAEANARTEELK SERDKVNTLLTRLESQENALASERQQHLATRETLQQRLEQ AIADTQARAGEIALERDRVSSLTARLESQEKASSEQLVRMG SEIASLTERCTQLENQRDDARLETMGEKETVAALRGEAEA LKRQNQSLMAALGHHHHHH | 58 |
| Sequence: TlpA_CC R179E (G₁B)<br>Description: Coiled-coil domain of TlpA (with initiating methionine) with candidate heterodimerizing mutation R179E.<br>Sequence contains C-terminal Leucine-Glycine (from XhoI restriction site used for cloning) and a hexahistidine tag used for purification. Note: Mutation position in referenced to the original position within | MAEEVKAVSAALSERITQLATELNDKAVRAAERRVAEVTRA AGEQTAQAERELADAAQTVDDLEEKLDELQDRYDSLTLAL ESERSLRQQHDVEMAQLKERLAAAEENTRQEEERYQEQK TVLQDALNAEQAQHKNTREDLQKRLEQISAEANARTEELK SERDKVNTLLTRLESQENALASERQQHLATRETLQQRLEQ AIADTQARAGEIALERDRVSSLTARLESQEKASSEQLVRMG SEIASLTERCTQLENQRDDARLETMGEKETVAALRGEAEA LKRQNQSLMAALGHHHHHH | 59 |

TABLE 2-continued

| Features | Sequence | SEQ ID NO |
|---|---|---|
| full-length TlpA rather than the position within the coiled-coil domain fragment. Referenced in FIGS.: FIG. 5 (S1) Key features: R179E | | |
| Sequence: TlpA_CC E180R (G$_i$A) Description: Coiled-coil domain of TlpA (with initiating methionine) with candidate heterodimerizing mutation E180R. Sequence contains C-terminal Leucine-Glycine (from XhoI restriction site used for cloning) and a hexahistidine tag used for purification. Note: Mutation position in referenced to the original position within full-length TlpA rather than the position within the coiled-coil domain fragment. Referenced in FIGS.: FIG. 5 (S1) Key features: E180R | MAEEVKAVSAALSERITQLATELNDKAVRAAERRVAEVTRA AGEQTAQAERELADAAQTVDDLEEKLDELQDRYDSLTLAL ESERSLRQQHDVEMAQLKERLAAAEENTRQRRERYQEQK TVLQDALNAEQAQHKNTREDLQKRLEQISAEANARTEELK SERDKVNTLLTRLESQENALASERQQHLATRETLQQRLEQ AIADTQARAGEIALERDRVSSLTARLESQEKASSEQLVRMG SEIASLTERCTQLENQRDDARLETMGEKETVAALRGEAEA LKRQNQSLMAALGHHHHHH | 60 |
| Sequence: TlpA_CC E225R Description: Coiled-coil domain of TlpA (with initiating methionine) with candidate heterodimerizing mutation E225R. Sequence contains C-terminal Leucine-Glycine (from XhoI restriction site used for cloning) and a hexahistidine tag used for purification. Note: Mutation position in referenced to the original position within full-length TlpA rather than the position within the coiled-coil domain fragment. Referenced in FIGS.: FIG. 5 (S1) Key features: E225R | MAEEVKAVSAALSERITQLATELNDKAVRAAERRVAEVTRA AGEQTAQAERELADAAQTVDDLEEKLDELQDRYDSLTLAL ESERSLRQQHDVEMAQLKERLAAAEENTRQREERYQEQK TVLQDALNAEQAQHKNTREDLQKRLEQISAEANARTERLK SERDKVNTLLTRLESQENALASERQQHLATRETLQQRLEQ AIADTQARAGEIALERDRVSSLTARLESQEKASSEQLVRMG SEIASLTERCTQLENQRDDARLETMGEKETVAALRGEAEA LKRQNQSLMAALGHHHHHH | 61 |
| Sequence: TlpA_CC R230E Description: Coiled-coil domain of TlpA (with initiating methionine) with candidate heterodimerizing mutation R230E. Sequence contains C-terminal Leucine-Glycine (from XhoI restriction site used for cloning) and a hexahistidine tag used for purification. Note: Mutation position in referenced to the original position within full-length TlpA rather than the position within the coiled-coil domain fragment. Referenced in FIGS.: FIG. 5 Key features: R230E | MAEEVKAVSAALSERITQLATELNDKAVRAAERRVAEVTRA AGEQTAQAERELADAAQTVDDLEEKLDELQDRYDSLTLAL ESERSLRQQHDVEMAQLKERLAAAEENTRQREERYQEQK TVLQDALNAEQAQHKNTREDLQKRLEQISAEANARTEELK SEEDKVNTLLTRLESQENALASERQQHLATRETLQQRLEQ AIADTQARAGEIALERDRVSSLTARLESQEKASSEQLVRMG SEIASLTERCTQLENQRDDARLETMGEKETVAALRGEAEA LKRQNQSLMAALGHHHHHH | 62 |
| Sequence: TlpA_CC E229R Description: Coiled-coil domain of TlpA (with initiating methionine) with candidate heterodimerizing mutation E229R. Sequence contains C-terminal Leucine-Glycine (from XhoI restriction site used for cloning) and a hexahistidine tag used for purification. Note: Mutation position in referenced to the original position within full-length TlpA rather than the position within the coiled-coil domain fragment. Referenced in FIGS.: FIG. 5 (S1) Key features: E229R | MAEEVKAVSAALSERITQLATELNDKAVRAAERRVAEVTRA AGEQTAQAERELADAAQTVDDLEEKLDELQDRYDSLTLAL ESERSLRQQHDVEMAQLKERLAAAEENTRQREERYQEQK TVLQDALNAEQAQHKNTREDLQKRLEQISAEANARTEELK SRRDKVNTLLTRLESQENALASERQQHLATRETLQQRLEQ AIADTQARAGEIALERDRVSSLTARLESQEKASSEQLVRMG SEIASLTERCTQLENQRDDARLETMGEKETVAALRGEAEA LKRQNQSLMAALGHHHHHH | 63 |
| Sequence: TlpA_CC E250R Description: Coiled-coil domain of TlpA (with initiating methionine) with candidate heterodimerizing mutation E250R. Sequence contains C-terminal Leucine-Glycine (from XhoI restriction site used for cloning) and a hexahistidine tag used for purification. Note: Mutation position in referenced to the original position within full-length TlpA rather than the position within the coiled-coil domain fragment. Referenced in FIGS.: FIG. 5 (S1) Key features: E250R | MAEEVKAVSAALSERITQLATELNDKAVRAAERRVAEVTRA AGEQTAQAERELADAAQTVDDLEEKLDELQDRYDSLTLAL ESERSLRQQHDVEMAQLKERLAAAEENTRQREERYQEQK TVLQDALNAEQAQHKNTREDLQKRLEQISAEANARTEELK SERDKVNTLLTRLESQENALASRRQQHLATRETLQQRLEQ AIADTQARAGEIALERDRVSSLTARLESQEKASSEQLVRMG SEIASLTERCTQLENQRDDARLETMGEKETVAALRGEAEA LKRQNQSLMAALGHHHHHH | 64 |

TABLE 2-continued

| Features | Sequence | SEQ ID NO |
|---|---|---|
| Sequence: TlpA_CC R251E<br>Description: Coiled-coil domain of TlpA (with initiating methionine) with candidate heterodimerizing mutation R251E. Sequence contains C-terminal Leucine-Glycine (from XhoI restriction site used for cloning) and a hexahistidine tag used for purification. Note: Mutation position in referenced to the original position within full-length TlpA rather than the position within the coiled-coil domain fragment.<br>Referenced in FIGS.: FIG. 5 (S1)<br>Key features: R251E | MAEEVKAVSAALSERITQLATELNDKAVRAAERRVAEVTRA<br>AGEQTAQAERELADAAQTVDDLEEKLDELQDRYDSLTLAL<br>ESERSLRQQHDVEMAQLKERLAAAEENTRQREERYQEQK<br>TVLQDALNAEQAQHKNTREDLQKRLEQISAEANARTEELK<br>SERDKVNTLLTRLESQENALASEEQQHLATRETLQQRLEQ<br>AIADTQARAGEIALERDRVSSLTARLESQEKASSEQLVRMG<br>SEIASLTERCTQLENQRDDARLETMGEKETVAALRGEAEA<br>LKRQNQSLMAALGHHHHHH | 65 |
| Sequence: Palm-TlpA$_{39}$-G$_2$A$_3$<br>Description: TlpA$_{39}$ with the G$_2$A$_3$ heterodimerizing mutations fused to an N-terminal palmitoylation sequence MLCCMRRTKQVEKNDEDQKI using a short flexible linker GGSGGS.<br>Note that the initiating methionine of TlpA is omitted (e.g. TlpA begins with RPATY instead of MRPATY).<br>Referenced in FIGS.: FIG. 4a, FIG. 4b, FIG. 4e, FIG. 4f, FIG. 4g, FIG. 4h<br>Key features:<br>TlpA$_{39}$ mutations D135V, A217V, L236F<br>Heterodimerizing mutations E180R, E250 | [MLCCMRRTKQVEKNDEDQKIGGSGGSRPATYEPEQII<br>EAGLALQAEGRNITGFALRNQVGGGNPTRLRQIWDEY<br>QASQSTVVTEPVAELPVEV]AEEVKAVSAALSERITQLAT<br>ELNDKAVRAAERRVAEVTRAAGEQTAQAERELADAAQTV<br>DDLEEKLVELQDRYDSLTLALESERSLRQQHDVEMAQLK<br>ERLAAAEENTRQRRERYQEQKTVLQDALNAEQAQHKNTR<br>EDLQKRLEQISREANARTEELKSERDKVNRLESQENA<br>LASRRQQHLATRETLQQRLEQAIADTQARAGEIALERDRVS<br>SLTARLESQEKASSEQLVRMGSEIASLTERCTQLENQRDDA<br>RLETMGEKETVAALRGEAEALKRQNQSLMAALSGNKQTG<br>GQNA | 66 |
| Sequence: TlpA$_{39}$-G$_2$B$_3$-mScarletI<br>Description: TlpA$_{39}$ with the G$_2$B$_3$ heterodimerizing fused to a C-terminal mScarlet-I fluorescent protein using a long flexible linker.<br>Referenced in FIGS.: FIG. 4a, FIG. 4b, FIG. 4e, FIG. 4f, FIG. 4g, FIG. 4h<br>Key features:<br>TlpA$_{39}$ mutations D135V, A217V, L236F<br>Heterodimerizing mutations R179E, R251E | MRPATYEPEQIIEAGLALQAEGRNITGFALRN<br>QVGGGNPTRLRQIWDEYQASQSTVVTEPVAE<br>LPVEVAEEVKAVSAALSERITQLATELNDKAVRAAERRVA<br>EVTRAAGEQTAQAERELADAAQTVDDLEEKLVELQDRYD<br>SLTLALESERSLRQQHDVEMAQLKERLAAAEENTRQEEER<br>YQEQKTVLQDALNAEQAQHKNTREDLQKRLEQISVEANA<br>RTEELKSERDKVNTLTRLESQENALASEEQQHLATRETL<br>QQRLEQAIADTQARAGEIALERDRVSSLTARLESQEKASSE<br>QLVRMGSEIASLTERCTQLENQRDDARLETMGEKETVAAL<br>RGEAEALKRQNQSLMAALSGNKQTGGQNAGGGGSGGGGSGGGGS<br>GGGSGGGS[MVSKGEAVIKEFMRFKVHMEGSMNGHEFEIEGEGE<br>GRPYEGTQTAKLKVTKGGPLPFSWDILSPQFMYGSRAF<br>IKHPADIPDYYKQSFPEGFKWERVMNFEDGGAVTVTQ<br>DTSLEDGTLIYKVKLRGTNFPPDGPVMQKKTMGWEAS<br>TERLYPEDGVLKGDIKMALRLKDGGRYLADFKTTYKA<br>KKPVQMPGAYNVDRKLDITSHNEDYTVVEQYERSEGR<br>HSTGGMDELYK] | 67 |

Additional monomers are listed in Table 3 below wherein

TABLE 3

| Features | Sequence | SEQ ID NO |
|---|---|---|
| Sequence: TlpA_CC E161K<br>Description: Coiled-coil domain of TlpA (with initiating methionine) with candidate heterodimerizing mutation E161K. Sequence contains C-terminal Leucine-Glycine (from XhoI restriction site used for cloning) and a hexahistidine tag used for purification. Note: Mutation position in referenced to the original position within full-length TlpA rather than the position within the coiled-coil domain fragment.<br>Referenced in FIGS.: FIG. 5<br>Key features: E161K | MAEEVKAVSAALSERITQLATELNDKAVRAAERRVAEV<br>TRAAGEQTAQAERELADAAQTVDDLEEKLDELQDRY<br>DSLTLALESERSLRQQHDVKMAQLKERLAAAEENTRQ<br>REERYQEQKTVLQDALNAEQAQHKNTREDLQKRLEQI<br>SAEANARTEELKSERDKVNTLLTRLESQENALASERQQ<br>HLATRETLQQRLEQAIADTQARAGEIALERDRVSSLTA<br>RLESQEKASSEQLVRMGSEIASLTERCTQLENQRDDAR<br>LETMGEKETVAALRGEAEALKRQNQSLMAALGHHHH<br>HH | 68 |
| Sequence: TlpA_CC K166E<br>Description: Coiled-coil domain of TlpA (with initiating methionine) with candidate heterodimerizing mutation K166E. Sequence contains C-terminal Leucine-Glycine (from XhoI restriction site used for cloning) and a | MAEEVKAVSAALSERITQLATELNDKAVRAAERRVAEV<br>TRAAGEQTAQAERELADAAQTVDDLEEKLDELQDRY<br>DSLTLALESERSLRQQHDVEMAQLEERLAAAEENTRQ<br>REERYQEQKTVLQDALNAEQAQHKNTREDLQKRLEQ<br>ISAEANARTEELKSERDKVNTLLTRLESQENALASERQ<br>QHLATRETLQQRLEQAIADTQARAGEIALERDRVSSLT | 69 |

TABLE 3-continued

| Features | Sequence | SEQ ID NO |
|---|---|---|
| hexahistidine tag used for purification. Note: Mutation position in referenced to the original position within full-length TlpA rather than the position within the coiled-coil domain fragment. Referenced in FIGS.: FIG. 5 (S1) Key features: K166E | ARLESQEKASSEQLVRMGSEIASLTERCTQLENQRDD ARLETMGEKETVAALRGEAEALKRQNQSLMAALGHH HHHH | |
| Sequence: TlpA_CC E225R/E229R Description: Coiled-coil domain of TlpA (with initiating methionine) with candidate heterodimerizing mutations E225R and E229R. Sequence contains C-terminal Leucine-Glycine (from XhoI restriction site used for cloning) and a hexahistidine tag used for purification. Note: Mutation position in referenced to the original position within full-length TlpA rather than the position within the coiled-coil domain fragment. Referenced in FIGS.: FIG. 5 (S1) Key features: E225R, E229R | MAEEVKAVSAALSERITQLATELNDKAVRAAERRVAEV TRAAGEQTAQAERELADAAQTVDDLEEKLDELQDRY DSLTLALESERSLRQQHDVEMAQLKERLAAAEENTRQ REERYQEQKTVLQDALNAEQAQHKNTREDLQKRLEQ ISAEANARTERLKSRRDKVNTLLTRLESQENALASERQ QHLATRETLQQRLEQAIADTQARAGEIALERDRVSSLT ARLESQEKASSEQLVRMGSEIASLTERCTQLENQRDD ARLETMGEKETVAALRGEAEALKRQNQSLMAALGHH HHHH | 70 |
| Sequence: TlpA_CC R239E Description: Coiled-coil domain of TlpA (with initiating methionine) with candidate heterodimerizing mutation R239E. Sequence contains C-terminal Leucine-Glycine (from XhoI restriction site used for cloning) and a hexahistidine tag used for purification. Note: Mutation position in referenced to the original position within full-length TlpA rather than the position within the coiled-coil domain fragment. Referenced in FIGS.: FIG. 5 (S1) Key features: R239E | MAEEVKAVSAALSERITQLATELNDKAVRAAERRVAEV TRAAGEQTAQAERELADAAQTVDDLEEKLDELQDRY DSLTLALESERSLRQQHDVEMAQLKERLAAAEENTRQ REERYQEQKTVLQDALNAEQAQHKNTREDLQKRLEQ ISAEANARTEELKSERDKVNTLLTELESQENALASERQ QHLATRETLQQRLEQAIADTQARAGEIALERDRVSSLT ARLESQEKASSEQLVRMGSEIASLTERCTQLENQRDD ARLETMGEKETVAALRGEAEALKRQNQSLMAALGHH HHHH | 71 |
| Sequence: TlpA_CC E244R Description: Coiled-coil domain of TlpA (with initiating methionine) with candidate heterodimerizing mutation E244R. Sequence contains C-terminal Leucine-Glycine (from XhoI restriction site used for cloning) and a hexahistidine tag used for purification. Note: Mutation position in referenced to the original position within full-length TlpA rather than the position within the coiled-coil domain fragment. Referenced in FIGS.: FIG. 5 (S1) Key features: E244R | MAEEVKAVSAALSERITQLATELNDKAVRAAERRVAEV TRAAGEQTAQAERELADAAQTVDDLEEKLDELQDRY DSLTLALESERSLRQQHDVEMAQLKERLAAAEENTRQ REERYQEQKTVLQDALNAEQAQHKNTREDLQKRLEQ ISAEANARTEELKSERDKVNTLLTRLESQRNALASERQ QHLATRETLQQRLEQAIADTQARAGEIALERDRVSSLT ARLESQEKASSEQLVRMGSEIASLTERCTQLENQRDD ARLETMGEKETVAALRGEAEALKRQNQSLMAALGHH HHHH | 72 |
| Sequence: TlpA_CC E282R Description: Coiled-coil domain of TlpA (with initiating methionine) with candidate heterodimerizing mutation E282R. Sequence contains C-terminal Leucine-Glycine (from XhoI restriction site used for cloning) and a hexahistidine tag used for purification. Note: Mutation position in referenced to the original position within full-length TlpA rather than the position within the coiled-coil domain fragment. Referenced in FIGS.: FIG. 5 (S1) Key features: E282R | MAEEVKAVSAALSERITQLATELNDKAVRAAERRVAEV TRAAGEQTAQAERELADAAQTVDDLEEKLDELQDRY DSLTLALESERSLRQQHDVEMAQLKERLAAAEENTRQ REERYQEQKTVLQDALNAEQAQHKNTREDLQKRLEQ ISAEANARTEELKSERDKVNTLLTRLESQENALASERQ QHLATRETLQQRLEQAIADTQARAGEIALRRDRVSSLT ARLESQEKASSEQLVRMGSEIASLTERCTQLENQRDD ARLETMGEKETVAALRGEAEALKRQNQSLMAALGHH HHHH | 73 |
| Sequence: TlpA_CC R283E Description: Coiled-coil domain of TlpA (with initiating methionine) with candidate heterodimerizing mutation R283E. Sequence contains C-terminal Leucine-Glycine (from XhoI restriction site used for cloning) and a hexahistidine tag used for purification. Note: Mutation position in referenced to the original position within full-length TlpA rather than the position within the coiled-coil domain fragment. Referenced in FIGS.: FIG. 5 (S1) Key features: R283E | MAEEVKAVSAALSERITQLATELNDKAVRAAERRVAEV TRAAGEQTAQAERELADAAQTVDDLEEKLDELQDRY DSLTLALESERSLRQQHDVEMAQLKERLAAAEENTRQ REERYQEQKTVLQDALNAEQAQHKNTREDLQKRLEQ ISAEANARTEELKSERDKVNTLLTRLESQENALASERQ QHLATRETLQQRLEQAIADTQARAGEIALEEDRVSSLT ARLESQEKASSEQLVRMGSEIASLTERCTQLENQRDD ARLETMGEKETVAALRGEAEALKRQNQSLMAALGHH HHHH | 74 |
| Sequence: TlpA_CC R292E Description: Coiled-coil domain of TlpA (with initiating methionine) with candidate heterodimerizing mutation R292E. Sequence | MAEEVKAVSAALSERITQLATELNDKAVRAAERRVAEV TRAAGEQTAQAERELADAAQTVDDLEEKLDELQDRY DSLTLALESERSLRQQHDVEMAQLKERLAAAEENTRQ REERYQEQKTVLQDALNAEQAQHKNTREDLQKRLEQ | 75 |

TABLE 3-continued

| Features | Sequence | SEQ ID NO |
|---|---|---|
| contains C-terminal Leucine-Glycine (from XhoI restriction site used for cloning) and a hexahistidine tag used for purification. Note: Mutation position in referenced to the original position within full-length TlpA rather than the position within the coiled-coil domain fragment. Referenced in FIGS.: FIG. 5 (S1) Key features: R292E | ISAEANARTEELKSERDKVNTLLTRLESQENALASERQ QHLATRETLQQRLEQAIADTQARAGEIALERDRVSSLT AELESQEKASSEQLVRMGSEIASLTERCTQLENQRDD ARLETMGEKETVAALRGEAEALKRQNQSLMAALGHH HHHH | |
| Sequence: TlpA_CC E297R Description: Coiled-coil domain of TlpA (with initiating methionine) with candidate heterodimerizing mutation E297R. Sequence contains C-terminal Leucine-Glycine (from XhoI restriction site used for cloning) and a hexahistidine tag used for purification. Note: Mutation position in referenced to the original position within full-length TlpA rather than the position within the coiled-coil domain fragment. Referenced in FIGS.: FIG. 5 (S1) Key features: E297R | MAEEVKAVSAALSERITQLATELNDKAVRAAERRVAEV TRAAGEQTAQAERELADAAQTVDDLEEKLDELQDRY DSLTLALESERSLRQQHDVEMAQLKERLAAAEENTRQ REERYQEQKTVLQDALNAEQAQHKNTREDLQKRLEQ ISAEANARTEELKSERDKVNTLLTRLESQENALASERQ QHLATRETLQQRLEQAIADTQARAGEIALERDRVSSLT ARLESQRKASSEQLVRMGSEIASLTERCTQLENQRDD ARLETMGEKETVAALRGEAEALKRQNQSLMAALGHH HHHH | 76 |
| Sequence: TlpA_CC R317E Description: Coiled-coil domain of TlpA (with initiating methionine) with candidate heterodimerizing mutation R317E. Sequence contains C-terminal Leucine-Glycine (from XhoI restriction site used for cloning) and a hexahistidine tag used for purification. Note: Mutation position in referenced to the original position within full-length TlpA rather than the position within the coiled-coil domain fragment. Referenced in FIGS.: FIG. 5 (S1) Key features: R317E | MAEEVKAVSAALSERITQLATELNDKAVRAAERRVAEV TRAAGEQTAQAERELADAAQTVDDLEEKLDELQDRY DSLTLALESERSLRQQHDVEMAQLKERLAAAEENTRQ REERYQEQKTVLQDALNAEQAQHKNTREDLQKRLEQ ISAEANARTEELKSERDKVNTLLTRLESQENALASERQ QHLATRETLQQRLEQAIADTQARAGEIALERDRVSSLT ARLESQEKASSEQLVRMGSEIASLTEECTQLENQRDD ARLETMGEKETVAALRGEAEALKRQNQSLMAALGHH HHHH | 77 |
| Sequence: TlpA_CC E322R Description: Coiled-coil domain of TlpA (with initiating methionine) with candidate heterodimerizing mutation E322R. Sequence contains C-terminal Leucine-Glycine (from XhoI restriction site used for cloning) and a hexahistidine tag used for purification. Note: Mutation position in referenced to the original position within full-length TlpA rather than the position within the coiled-coil domain fragment. Referenced in FIGS.: FIG. 5 (S1) Key features: E322R | MAEEVKAVSAALSERITQLATELNDKAVRAAERRVAEV TRAAGEQTAQAERELADAAQTVDDLEEKLDELQDRY DSLTLALESERSLRQQHDVEMAQLKERLAAAEENTRQ REERYQEQKTVLQDALNAEQAQHKNTREDLQKRLEQ ISAEANARTEELKSERDKVNTLLTRLESQENALASERQ QHLATRETLQQRLEQAIADTQARAGEIALERDRVSSLT ARLESQEKASSEQLVRMGSEIASLTERCTQLRNQRDD ARLETMGEKETVAALRGEAEALKRQNQSLMAALGHH HHHH | 78 |
| Sequence: TlpA_CC E331K Description: Coiled-coil domain of TlpA (with initiating methionine) with candidate heterodimerizing mutation E331K. Sequence contains C-terminal Leucine-Glycine (from XhoI restriction site used for cloning) and a hexahistidine tag used for purification. Note: Mutation position in referenced to the original position within full-length TlpA rather than the position within the coiled-coil domain fragment. Referenced in FIGS.: FIG. 5 (S1) Key features: E331K | MAEEVKAVSAALSERITQLATELNDKAVRAAERRVAEV TRAAGEQTAQAERELADAAQTVDDLEEKLDELQDRY DSLTLALESERSLRQQHDVEMAQLKERLAAAEENTRQ REERYQEQKTVLQDALNAEQAQHKNTREDLQKRLEQ ISAEANARTEELKSERDKVNTLLTRLESQENALASERQ QHLATRETLQQRLEQAIADTQARAGEIALERDRVSSLT ARLESQEKASSEQLVRMGSEIASLTERCTQLENQRDD ARLKTMGEKETVAALRGEAEALKRQNQSLMAALGHH HHHH | 79 |
| Sequence: TlpA_CC E335K Description: Coiled-coil domain of TlpA (with initiating methionine) with candidate heterodimerizing mutation E335K. Sequence contains C-terminal Leucine-Glycine (from XhoI restriction site used for cloning) and a hexahistidine tag used for purification. Note: Mutation position in referenced to the original position within full-length TlpA rather than the position within the coiled-coil domain fragment. Referenced in FIGS.: FIG. 5 (S1) Key features: E335K | MAEEVKAVSAALSERITQLATELNDKAVRAAERRVAEV TRAAGEQTAQAERELADAAQTVDDLEEKLDELQDRY DSLTLALESERSLRQQHDVEMAQLKERLAAAEENTRQ REERYQEQKTVLQDALNAEQAQHKNTREDLQKRLEQ ISAEANARTEELKSERDKVNTLLTRLESQENALASERQ QHLATRETLQQRLEQAIADTQARAGEIALERDRVSSLT ARLESQEKASSEQLVRMGSEIASLTERCTQLENQRDD ARLETMGKKETVAALRGEAEALKRQNQSLMAALGHH HHHH | 80 |

TABLE 3-continued

| Features | Sequence | SEQ ID NO |
|---|---|---|
| Sequence: TlpA_CC K336E<br>Description: Coiled-coil domain of TlpA (with initiating methionine) with candidate heterodimerizing mutation K336E. Sequence contains C-terminal Leucine-Glycine (from XhoI restriction site used for cloning) and a hexahistidine tag used for purification. Note: Mutation position in referenced to the original position within full-length TlpA rather than the position within the coiled-coil domain fragment.<br>Referenced in FIGS.: FIG. 5 (S1)<br>Key features: K336E | MAEEVKAVSAALSERITQLATELNDKAVRAAERRVAEV<br>TRAAGEQTAQAERELADAAQTVDDLEEKLDELQDRY<br>DSLTLALESERSLRQQHDVEMAQLKERLAAAEENTRQ<br>REERYQEQKTVLQDALNAEQAQHKNTREDLQKRLEQ<br>ISAEANARTEELKSERDKVNTLLTRLESQENALASERQ<br>QHLATRETLQQRLEQAIADTQARAGEIALERDRVSSLT<br>ARLESQEKASSEQLVRMGSEIASLTERCTQLENQRDD<br>ARLETMGEEETVAALRGEAEALKRQNQSLMAALGHH<br>HHHH | 81 |
| Sequence: TlpA_CC E331K/E335K<br>Description: Coiled-coil domain of TlpA (with initiating methionine) with candidate heterodimerizing mutations E331K and E335K. Sequence contains C-terminal Leucine-Glycine (from XhoI restriction site used for cloning) and a hexahistidine tag used for purification. Note: Mutation position in referenced to the original position within full-length TlpA rather than the position within the coiled-coil domain fragment.<br>Referenced in FIGS.: FIG. 5 (S1)<br>Key features: E331K, E335K | MAEEVKAVSAALSERITQLATELNDKAVRAAERRVAEV<br>TRAAGEQTAQAERELADAAQTVDDLEEKLDELQDRY<br>DSLTLALESERSLRQQHDVEMAQLKERLAAAEENTRQ<br>REERYQEQKTVLQDALNAEQAQHKNTREDLQKRLEQ<br>ISAEANARTEELKSERDKVNTLLTRLESQENALASERQ<br>QHLATRETLQQRLEQAIADTQARAGEIALERDRVSSLT<br>ARLESQEKASSEQLVRMGSEIASLTERCTQLENQRDD<br>ARLKTMGKKETVAALRGEAEALKRQNQSLMAALGHH<br>HHHH | 82 |
| Sequence: TlpA_CC E345K<br>Description: Coiled-coil domain of TlpA (with initiating methionine) with candidate heterodimerizing mutations E345K. Sequence contains C-terminal Leucine-Glycine (from XhoI restriction site used for cloning) and a hexahistidine tag used for purification. Note: Mutation position in referenced to the original position within full-length TlpA rather than the position within the coiled-coil domain fragment.<br>Referenced in FIGS.: FIG. 5 (S1)<br>Key features: E345K | MAEEVKAVSAALSERITQLATELNDKAVRAAERRVAEV<br>TRAAGEQTAQAERELADAAQTVDDLEEKLDELQDRY<br>DSLTLALESERSLRQQHDVEMAQLKERLAAAEENTRQ<br>REERYQEQKTVLQDALNAEQAQHKNTREDLQKRLEQ<br>ISAEANARTEELKSERDKVNTLLTRLESQENALASERQ<br>QHLATRETLQQRLEQAIADTQARAGEIALERDRVSSLT<br>ARLESQEKASSEQLVRMGSEIASLTERCTQLENQRDD<br>ARLETMGEKETVAALRGKAEALKRQNQSLMAALGHH<br>HHHH | 83 |
| Sequence: TlpA_CC K350E<br>Description: Coiled-coil domain of TlpA (with initiating methionine) with candidate heterodimerizing mutations K350E. Sequence contains C-terminal Leucine-Glycine (from XhoI restriction site used for cloning) and a hexahistidine tag used for purification. Note: Mutation position in referenced to the original position within full-length TlpA rather than the position within the coiled-coil domain fragment.<br>Referenced in FIGS.: FIG. 5 (S1)<br>Key features: K350E | MAEEVKAVSAALSERITQLATELNDKAVRAAERRVAEV<br>TRAAGEQTAQAERELADAAQTVDDLEEKLDELQDRY<br>DSLTLALESERSLRQQHDVEMAQLKERLAAAEENTRQ<br>REERYQEQKTVLQDALNAEQAQHKNTREDLQKRLEQ<br>ISAEANARTEELKSERDKVNTLLTRLESQENALASERQ<br>QHLATRETLQQRLEQAIADTQARAGEIALERDRVSSLT<br>ARLESQEKASSEQLVRMGSEIASLTERCTQLENQRDD<br>ARLETMGEKETVAALRGEAEALERQNQSLMAALGHH<br>HHHH | 84 |

From a comparison with the results shown in FIG. 5, the monomer of Table 3 appear not to demonstrate a thermoswitching behavior.

Applicant however expect this apparent negative result to be due to aggregation resulting from a combination of the specific monomer and protocols used to produce the Circular Dichroism spectra shown in FIG. 5 which required production of each monomer in in a separate bacterium (e.g. bacterial culture).

This protocol presents a solubility challenge to the thermomers of SEQ ID NO: 1 as will be understood by a skilled person, in view of the positions of charged residues in the thermomers.

In particular, the charged residues are within a string of hydrophobic corresponding residues in each thermomer monomer of the thermomer dimer attaching one with the other through non-covalent bonds to provide interlinked the quaternary structure of the coiled coil temperature sensitive domain.

Accordingly, separate production of thermomer monomers followed by assembly can result in aggregation of the monomers, depending on the specific experimental settings, as will be understood by a skilled person.

Applicant expects that different protocols such as co expression in a same bacteria will overcome this issue and show functionality of the monomers of Table 3 as heterodimers in view of their structure and results related to the monomers of Table 2.

Applicant also indicates that when thermomer monomers of the disclosure are provided through in cell or cell free expression, protocols avoiding separate expression of the monomers should be used in providing the thermomer dimer here described, as well as in screening neutral substitutions, as well as variants as will be understood by a skilled person.

Example 7: Performance Criteria to Evaluate Derivatives and Variants of the Disclosure The following steps can be performed to evaluate the structural properties of a derivative or variant of a thermomer monomer and dimers according to the present disclosure.

First, a coiled-coil construct is tested for alpha helical content. If the construct contains predicted heterodimerizing mutations, then an equimolar combination of each strand is prepared. Furthermore, if the construct contains predicted heterodimerizing mutations and the two polypeptides were expressed in separate cells (allowing the potential formation of homodimers due to the absence of the other polypeptide), the mixture is heated to $T_{bs}+10°$ C. and then cooled to at least $T_{bs}-10°$ C. to facilitate strand exchange and generation of the most stable (e.g. heterodimeric) product.

If a construct is derived from TlpA or one of its claimed variants (e.g. TlpA or variant containing a limited number of temperature-shifting, heterodimerizing, or neutral mutations generated via directed evolution or rational mutagenesis), then alpha helical content is interpreted as being indicative of dimerization because when coiled-coils disassemble they do not maintain an alpha helical secondary structure (they transition into random coil). Evaluation of secondary structure is performed via circular dichroism spectroscopy at a temperature at least 10° C. below the predicted $T_{bs}$. The presence of a peak at both 208 nm+/−3 nm and 222 nm+/−3 nm (note: I'm estimating the error here but 3 nm seems reasonable) indicates alpha helical secondary structure.

Representative examples of circular dichroism spectra is shown in FIG. 18 (image from DOI: 10.1038/nprot.2006.202)

Next, the same sample is incubated at a temperature range from at least $T_{bs}-5°$ C. to $T_{bs}+5°$ C. (with a greater range being desirable). The circular dichroism at 222 nm is tracked throughout this range and the resulting data is fit to the Hill equation. If the Hill coefficient is >15, then the switch is deemed a functional thermomer. An illustration of this process is shown below (sample=wild type TlpA). Note that above $T_{bs}$, the value at 222 nm approaches 0, as is the case for "Extended" (unstructured) proteins in the chart shown in FIG. 19.

Note that in some cases, candidate coiled-coils will fails to adopt an alpha helical CD spectrum. In such cases, the temperature scan does not need to be performed. In other cases, we have observed that candidate coiled-coils adopt an alpha helical CD spectrum but have a non-switch-like (e.g. low Hill-coefficient) thermal transition. Either failure disqualifies the candidate from being a thermomer. This was the primary test that we used to establish the functionality of thermomers. More rigorous tests can be performed as described by inserting the thermomers into a thermal gene regulation vector as exemplified in FIG. 2a and testing the resulting gene expression profile as demonstrated in FIG. 2c and FIG. 2d, or as described by inserting the thermomers into a SDS-PAGE visualization construct as exemplified in FIG. 3a and testing the resulting banding pattern as demonstrated in FIG. 3c and FIG. 3d, but this process is the bare minimum and should be both necessary and sufficient.

In summary, described herein are thermomer monomer, thermomer dimers, thermomer monomeric constructs, thermomer dimeric complexes, and related gene expression cassette vectors, cells, surfaces devices, compositions methods and systems, that provide a thermobioswitch suitable to control location and/or binding of cargo moiety of interest in a temperature regulated manner.

The examples set forth above are provided to give those of ordinary skill in the art a complete disclosure and description of how to make and use the embodiments of the materials, compositions, systems and methods of the disclosure, and are not intended to limit the scope of what the inventors regard as their disclosure. Those skilled in the art will recognize how to adapt the features of the exemplified methods and arrangements to additional genetic circuit, related nodes, molecular components, sets of polynucleotides, polypeptides and/or metabolites, in according to various embodiments and scope of the claims.

All patents and publications mentioned in the specification are indicative of the levels of skill of those skilled in the art to which the disclosure pertains.

The entire disclosure of each document cited (including patents, patent applications, journal articles, abstracts, laboratory manuals, books, or other disclosures) in the Background, Summary, Detailed Description, and Examples is hereby incorporated herein by reference. All references cited in this disclosure are incorporated by reference to the same extent as if each reference had been incorporated by reference in its entirety individually. However, if any inconsistency arises between a cited reference and the present disclosure, the present disclosure takes precedence. Further, the computer readable form of the sequence listing of the ASCII text file P2503-US-Sequence-Listing_ST25 is incorporated herein by reference in its entirety.

The terms and expressions which have been employed herein are used as terms of description and not of limitation, and there is no intention in the use of such terms and expressions of excluding any equivalents of the features shown and described or portions thereof, but it is recognized that various modifications are possible within the scope of the disclosure claimed. Thus, it should be understood that although the disclosure has been specifically disclosed by embodiments, exemplary embodiments and optional features, modification and variation of the concepts herein disclosed can be resorted to by those skilled in the art, and that such modifications and variations are considered to be within the scope of this disclosure as defined by the appended claims.

It is also to be understood that the terminology used herein is for the purpose of describing particular embodiments only, and is not intended to be limiting. As used in this specification and the appended claims, the singular forms "a," "an," and "the" include plural referents unless the content clearly dictates otherwise. The term "plurality" includes two or more referents unless the content clearly dictates otherwise. Unless defined otherwise, all technical and scientific terms used herein have the same meaning as commonly understood by one of ordinary skill in the art to which the disclosure pertains.

When a Markush group or other grouping is used herein, all individual members of the group and all combinations and possible subcombinations of the group are intended to be individually included in the disclosure. Every combination of components or materials described or exemplified herein can be used to practice the disclosure, unless otherwise stated. One of ordinary skill in the art will appreciate that methods, device elements, and materials other than those specifically exemplified may be employed in the practice of the disclosure without resort to undue experimentation. All art-known functional equivalents, of any such methods, device elements, and materials are intended to be included in this disclosure. Whenever a range is given in the specification, for example, a temperature range, a frequency range, a time range, or a composition range, all intermediate ranges and all subranges, as well as, all individual values included in the ranges given are intended to be included in the disclosure. Any one or more individual members of a range or group disclosed herein may be excluded from a claim of this disclosure. The disclosure illustratively described herein suitably may be practiced in the absence of any element or elements, limitation or limitations which is not specifically disclosed herein.

A number of embodiments of the disclosure have been described. The specific embodiments provided herein are examples of useful embodiments of the invention and it will be apparent to one skilled in the art that the disclosure can be carried out using a large number of variations of the devices, device components, methods steps set forth in the present description. As will be obvious to one of skill in the art, methods and devices useful for the present methods may include a large number of optional composition and processing elements and steps.

In particular, it will be understood that various modifications may be made without departing from the spirit and scope of the present disclosure. Accordingly, other embodiments are within the scope of the following claims.

REFERENCES

1. Greenfield, N.J., *Using circular dichroism collected as a function of temperature to determine the thermodynamics of protein unfolding and binding interactions.* Nat Protoc, 2006. 1(6): p. 2527-35.
2. Lupas, A., M. Van Dyke, and J. Stock, *Predicting coiled coils from protein sequences.* Science, 1991. 252(5009): p. 1162-4.
3. McDonnell, A. V., et al., *Paircoil2: improved prediction of coiled coils from sequence.* Bioinformatics, 2006. 22(3): p. 356-8.
4. Vincent, T. L., P. J. Green, and D. N. Woolfson, *LOGI-COIL—multi-state prediction of coiled-coil oligomeric state.* Bioinformatics, 2013. 29(1): p. 69-76.
5. Drozdetskiy, A., et al., *JPred4: a protein secondary structure prediction server.* Nucleic Acids Res, 2015. 43(W1): p. W389-94.
6. Berman, H. M., et al., *The protein data bank.* Acta Crystallographica Section D: Biological Crystallography, 2002. 58(6): p. 899-907.
7. Koski, P., et al., *A new alpha-helical coiled coil protein encoded by the Salmonella typhimurium virulence plasmid.* J Biol Chem, 1992. 267(17): p. 12258-65.
8. Grigoryan, G. and A. E. Keating, *Structural specificity in coiled-coil interactions.* Curr Opin Struct Biol, 2008. 18(4): p. 477-83.
9. Available from: https://en.wikipedia.org/wiki/Bioconjugation
10. Kyte, J. and R. F. Doolittle, *A simple method for displaying the hydropathic character of a protein.* Journal of molecular biology, 1982. 157(1): p. 105-132.
11. Ye, Y. and A. Godzik, *Flexible structure alignment by chaining aligned fragment pairs allowing twists.* Bioinformatics, 2003. 19(suppl 2): p. ii246-ii255.
12. Maiti, R., et al., *SuperPose: a simple server for sophisticated structural superposition.* Nucleic acids research, 2004. 32(suppl 2): p. W590-W594.
13. Gelly, J.-C., et al., *iPBA: a tool for protein structure comparison using sequence alignment strategies.* Nucleic acids research, 2011. 39(suppl 2): p. W18-W23.
14. Ilinkin, I., J. Ye, and R. Janardan, *Multiple structure alignment and consensus identification for proteins.* BMC bioinformatics, 2010. 11(1): p. 1.
15. Ai, H. W., et al., *Hue-shifted monomeric variants of Clavularia cyan fluorescent protein: identification of the molecular determinants of color and applications in fluorescence imaging.* BMC Biol, 2008. 6: p. 13.
16. Shaner, N.C., et al., *Improved monomeric red, orange and yellow fluorescent proteins derived from Discosoma sp. red fluorescent protein.* Nat Biotechnol, 2004. 22(12): p. 1567-72.
17. Mastop, M., et al., *Characterization of a spectrally diverse set of fluorescent proteins as FRET acceptors for mTurquoise2.* Sci Rep, 2017. 7(1): p. 11999.
18. Piraner, D. I., et al., *Tunable thermal bioswitches for in vivo control of microbial therapeutics.* Nat Chem Biol, 2017. 13(1): p. 75-80.
19. Carpenter, A. E., et al., *CellProfiler: image analysis software for identifying and quantifying cell phenotypes.* Genome Biol, 2006. 7(10): p. R100.
20. Stanton, B. Z., E. J. Chory, and G. R. Crabtree, *Chemically induced proximity in biology and medicine.* Science, 2018. 359(6380).
21. Mason, J. M. and K. M. Arndt, *Coiled coil domains: stability, specificity, and biological implications.* Chembiochem, 2004. 5(2): p. 170-6.
22. Tripet, B., et al., *Engineering a de novo-designed coiled-coil heterodimerization domain off the rapid detection, purification and characterization of recombinantly expressed peptides and proteins.* Protein Eng, 1996. 9(11): p. 1029-42.
23. Azuma, Y., et al., *Controlling leucine-zipper partner recognition in cells through modification of a-g interactions.* Chem Commun (Camb), 2014. 50(48): p. 6364-7.
24. Kawe, M., U. Horn, and A. Pluckthun, *Facile promoter deletion in Escherichia coli in response to leaky expression of very robust and benign proteins from common expression vectors.* Microb Cell Fact, 2009. 8: p. 8.
25. Silva, F., J. A. Queiroz, and F. C. Domingues, *Evaluating metabolic stress and plasmid stability in plasmid DNA production by Escherichia coli.* Biotechnol Adv, 2012. 30(3): p. 691-708.
26. Hurme, R., et al., *Intermediate filament-like network formed in vitro by a bacterial coiled coil protein.* J Biol Chem, 1994. 269(14): p. 10675-82.
27. Delviks, K. A. and V. K. Pathak, *Effect of Distance between Homologous Sequences and 3′ Homology on the Frequency of Retroviral Reverse Transcriptase Template Switching.* Journal of Virology, 1999. 73(10): p. 7923-7932.

The invention claimed is:

1. A thermomer monomer comprising aft a modified amino acid sequence of TlpA from *Salmonella typhimurium* comprising a modified form of SEQ ID NO: 39 wherein position A341 is substituted with an aspartate and further comprising one of the following amino acid substitution mutations:
   (a) E180 is substituted with R;
   (b) R179 is substituted with E;
   (c) E180 is substituted with R and E229 is substituted with R;
   (d) R179 is substituted with E and R230 is substituted with E;
   (e) E180 is substituted with R and R230 is substituted with E;
   (f) R179 is substituted with E and E229 is substituted with R;
   (g) E180 is substituted with R and E250 is substituted with R;
   (h) 8179 is substituted with E and R251 is substituted with E;
   (i) E180 is substituted with R and R251 is substituted with E;
   (j) R179 is substituted with E and E250 is substituted with R;
   (k) E229 is substituted with R;
   (l) R230 is substituted with E;
   (m) E250 is substituted with R; or
   (n) R251 is substituted with E.

2. The thermomer monomer of claim 1, wherein
   (c) E180 is substituted with R and E229 is substituted with R;
   (d) R179 is substituted with E and R230 is substituted with E;
   (e) E180 is substituted with R and R230 is substituted with E;
   (f) R179 is substituted with E and E229 is substituted with R;
   (g) E180 is substituted with R and E250 is substituted with R;
   (h) R179 is substituted with E and R251 is substituted with E;
   (i) E180 is substituted with R and R251 is substituted with E; or
   (j) R179 is substituted with E and E250 is substituted with R.

3. The thermomer monomer of claim 1, having an amino acid sequence selected from the group consisting of: SEQ ID NOS: 41-54, wherein the selected amino acid sequence further comprises an A341D substitution.

4. The thermomer monomer of claim 1, having an amino acid sequence of SEQ ID NO: 47, wherein the amino acid sequence further comprises an A341D substitution.

5. A thermomer dimer, comprising the thermomer monomer of claim 1.

6. The thermomer dimer of claim 5, wherein the thermomer dimer is a heterodimer.

7. The thermomer dimer of claim 6, wherein
   (c) E180 is substituted with R and E229 is substituted with R;
   (d) R179 is substituted with E and R230 is substituted with E;
   (e) E180 is substituted with R and R230 is substituted with E;
   (f) R179 is substituted with E and E229 is substituted with R;
   (g) E180 is substituted with R and E250 is substituted with R;
   (h) R179 is substituted with E and R251 is substituted with E;
   (i) E180 is substituted with R and R251 is substituted with E; or
   (j) R179 is substituted with E and E250 is substituted with R.

8. The thermomer dimer of claim 6, comprising a first thermomer monomer having an amino acid sequence selected from the group consisting of: SEQ ID NOS: 43-50, wherein the selected amino acid sequence further comprises an A341D substitution.

9. The thermomer dimer of claim 8, comprising a first thermomer monomer having an amino acid sequence of SEQ ID NO: 47, wherein the amino acid sequence further comprises an A341D substitution.

10. The thermomer dimer of claim 9, comprising a second thermomer monomer having an amino acid sequence of SEQ ID NO: 48, wherein the amino acid sequence further comprises an A341D substitution.

* * * * *

SEQUENCE LISTING

<160> NUMBER OF SEQ ID NOS: 84

<210> SEQ ID NO 1
<211> LENGTH: 291
<212> TYPE: PRT

```
<213> ORGANISM: Artificial Sequence
<220> FEATURE:
<223> OTHER INFORMATION: synthetic polypeptide
<220> FEATURE:
<221> NAME/KEY: misc_feature
<222> LOCATION: (111)..(112)
<223> OTHER INFORMATION: Xaa can be any naturally occurring amino acid
<220> FEATURE:
<221> NAME/KEY: misc_feature
<222> LOCATION: (161)..(162)
<223> OTHER INFORMATION: Xaa can be any naturally occurring amino acid
<220> FEATURE:
<221> NAME/KEY: misc_feature
<222> LOCATION: (182)..(183)
<223> OTHER INFORMATION: Xaa can be any naturally occurring amino acid

<400> SEQUENCE: 1

Ala Glu Glu Val Lys Ala Val Ser Ala Ala Leu Ser Glu Arg Ile Thr
 1               5                  10                  15

Gln Leu Ala Thr Glu Leu Asn Asp Lys Ala Val Arg Ala Ala Glu Arg
            20                  25                  30

Arg Val Ala Glu Val Thr Arg Ala Ala Gly Glu Gln Thr Ala Gln Ala
        35                  40                  45

Glu Arg Glu Leu Ala Asp Ala Ala Gln Thr Val Asp Asp Leu Glu Glu
    50                  55                  60

Lys Leu Asp Glu Leu Gln Asp Arg Tyr Asp Ser Leu Thr Leu Ala Leu
65                  70                  75                  80

Glu Ser Glu Arg Ser Leu Arg Gln Gln His Asp Val Glu Met Ala Gln
                85                  90                  95

Leu Lys Glu Arg Leu Ala Ala Ala Glu Glu Asn Thr Arg Gln Xaa Xaa
            100                 105                 110

Glu Arg Tyr Gln Glu Gln Lys Thr Val Leu Gln Asp Ala Leu Asn Ala
        115                 120                 125

Glu Gln Ala Gln His Lys Asn Thr Arg Glu Asp Leu Gln Lys Arg Leu
    130                 135                 140

Glu Gln Ile Ser Ala Glu Ala Asn Ala Arg Thr Glu Glu Leu Lys Ser
145                 150                 155                 160

Xaa Xaa Asp Lys Val Asn Thr Leu Leu Thr Arg Leu Glu Ser Gln Glu
                165                 170                 175

Asn Ala Leu Ala Ser Xaa Xaa Gln Gln His Leu Ala Thr Arg Glu Thr
            180                 185                 190

Leu Gln Gln Arg Leu Glu Gln Ala Ile Ala Asp Thr Gln Ala Arg Ala
        195                 200                 205

Gly Glu Ile Ala Leu Glu Arg Asp Arg Val Ser Ser Leu Thr Ala Arg
    210                 215                 220

Leu Glu Ser Gln Glu Lys Ala Ser Ser Glu Gln Leu Val Arg Met Gly
225                 230                 235                 240

Ser Glu Ile Ala Ser Leu Thr Glu Arg Cys Thr Gln Leu Glu Asn Gln
                245                 250                 255

Arg Asp Asp Ala Arg Leu Glu Thr Met Gly Glu Lys Glu Thr Val Ala
            260                 265                 270

Ala Leu Arg Gly Glu Ala Glu Ala Leu Lys Arg Gln Asn Gln Ser Leu
        275                 280                 285

Met Ala Ala
    290

<210> SEQ ID NO 2
<211> LENGTH: 7
<212> TYPE: PRT
```

```
<213> ORGANISM: Artificial Sequence
<220> FEATURE:
<223> OTHER INFORMATION: synthetic polypeptide
<220> FEATURE:
<221> NAME/KEY: misc_feature
<222> LOCATION: (2)..(3)
<223> OTHER INFORMATION: Xaa can be any naturally occurring amino acid
<220> FEATURE:
<221> NAME/KEY: misc_feature
<222> LOCATION: (6)..(6)
<223> OTHER INFORMATION: Xaa can be any naturally occurring amino acid

<400> SEQUENCE: 2

His Xaa Xaa His Cys Xaa Cys
1               5

<210> SEQ ID NO 3
<211> LENGTH: 6
<212> TYPE: PRT
<213> ORGANISM: Artificial Sequence
<220> FEATURE:
<223> OTHER INFORMATION: synthetic polypeptide

<400> SEQUENCE: 3

Gly Gly Ser Gly Gly Ser
1               5

<210> SEQ ID NO 4
<211> LENGTH: 5
<212> TYPE: PRT
<213> ORGANISM: Artificial Sequence
<220> FEATURE:
<223> OTHER INFORMATION: synthetic polypeptide

<400> SEQUENCE: 4

Gly Gly Gly Gly Ser
1               5

<210> SEQ ID NO 5
<211> LENGTH: 5
<212> TYPE: PRT
<213> ORGANISM: Artificial Sequence
<220> FEATURE:
<223> OTHER INFORMATION: synthetic polypeptide

<400> SEQUENCE: 5

Gly Ser Gly Ser Gly
1               5

<210> SEQ ID NO 6
<211> LENGTH: 4
<212> TYPE: PRT
<213> ORGANISM: Artificial Sequence
<220> FEATURE:
<223> OTHER INFORMATION: synthetic polypeptide

<400> SEQUENCE: 6

Gly Gly Gly Gly
1

<210> SEQ ID NO 7
<211> LENGTH: 3
<212> TYPE: PRT
<213> ORGANISM: Artificial Sequence
<220> FEATURE:
<223> OTHER INFORMATION: synthetic polypeptide

<400> SEQUENCE: 7
```

```
Gly Gly Gly
1

<210> SEQ ID NO 8
<211> LENGTH: 2
<212> TYPE: PRT
<213> ORGANISM: Artificial Sequence
<220> FEATURE:
<223> OTHER INFORMATION: synthetic polypeptide

<400> SEQUENCE: 8

Gly Gly
1

<210> SEQ ID NO 9
<211> LENGTH: 2
<212> TYPE: PRT
<213> ORGANISM: Artificial Sequence
<220> FEATURE:
<223> OTHER INFORMATION: synthetic polypeptide

<400> SEQUENCE: 9

Gly Ser
1

<210> SEQ ID NO 10
<211> LENGTH: 4
<212> TYPE: PRT
<213> ORGANISM: Artificial Sequence
<220> FEATURE:
<223> OTHER INFORMATION: synthetic polypeptide

<400> SEQUENCE: 10

Gly Ser Gly Ser
1

<210> SEQ ID NO 11
<211> LENGTH: 4
<212> TYPE: PRT
<213> ORGANISM: Artificial Sequence
<220> FEATURE:
<223> OTHER INFORMATION: synthetic polypeptide

<400> SEQUENCE: 11

Gly Gly Gly Ser
1

<210> SEQ ID NO 12
<211> LENGTH: 3
<212> TYPE: PRT
<213> ORGANISM: Artificial Sequence
<220> FEATURE:
<223> OTHER INFORMATION: synthetic polypeptide

<400> SEQUENCE: 12

Gly Gly Ser
1

<210> SEQ ID NO 13
<211> LENGTH: 3
<212> TYPE: PRT
<213> ORGANISM: Artificial Sequence
<220> FEATURE:
<223> OTHER INFORMATION: synthetic polypeptide

<400> SEQUENCE: 13

Gly Thr Ser
```

```
<210> SEQ ID NO 14
<211> LENGTH: 6
<212> TYPE: PRT
<213> ORGANISM: Artificial Sequence
<220> FEATURE:
<223> OTHER INFORMATION: synthetic polypeptide

<400> SEQUENCE: 14

Gly Gly Ser Gly Gly Ser
1               5

<210> SEQ ID NO 15
<211> LENGTH: 3
<212> TYPE: PRT
<213> ORGANISM: Artificial Sequence
<220> FEATURE:
<223> OTHER INFORMATION: synthetic polypeptide

<400> SEQUENCE: 15

Gly Gly Gly
1

<210> SEQ ID NO 16
<211> LENGTH: 6
<212> TYPE: PRT
<213> ORGANISM: Artificial Sequence
<220> FEATURE:
<223> OTHER INFORMATION: synthetic polypeptide

<400> SEQUENCE: 16

Gly Gly Gly Gly Gly Gly
1               5

<210> SEQ ID NO 17
<211> LENGTH: 9
<212> TYPE: PRT
<213> ORGANISM: Artificial Sequence
<220> FEATURE:
<223> OTHER INFORMATION: synthetic polypeptide

<400> SEQUENCE: 17

Gly Gly Gly Gly Gly Gly Gly Gly Gly
1               5

<210> SEQ ID NO 18
<211> LENGTH: 12
<212> TYPE: PRT
<213> ORGANISM: Artificial Sequence
<220> FEATURE:
<223> OTHER INFORMATION: synthetic polypeptide

<400> SEQUENCE: 18

Gly Gly Gly Gly Gly Gly Gly Gly Gly Gly Gly Gly
1               5                   10

<210> SEQ ID NO 19
<211> LENGTH: 15
<212> TYPE: PRT
<213> ORGANISM: Artificial Sequence
<220> FEATURE:
<223> OTHER INFORMATION: synthetic polypeptide

<400> SEQUENCE: 19

Gly Gly Gly Gly Gly Gly Gly Gly Gly Gly Gly Gly Gly Gly Gly
1               5                   10                  15
```

```
<210> SEQ ID NO 20
<211> LENGTH: 3
<212> TYPE: PRT
<213> ORGANISM: Artificial Sequence
<220> FEATURE:
<223> OTHER INFORMATION: synthetic polypeptide

<400> SEQUENCE: 20

Gly Gly Ser
1

<210> SEQ ID NO 21
<211> LENGTH: 6
<212> TYPE: PRT
<213> ORGANISM: Artificial Sequence
<220> FEATURE:
<223> OTHER INFORMATION: synthetic polypeptide

<400> SEQUENCE: 21

Gly Gly Ser Gly Gly Ser
1               5

<210> SEQ ID NO 22
<211> LENGTH: 9
<212> TYPE: PRT
<213> ORGANISM: Artificial Sequence
<220> FEATURE:
<223> OTHER INFORMATION: synthetic polypeptide

<400> SEQUENCE: 22

Gly Gly Ser Gly Gly Ser Gly Gly Ser
1               5

<210> SEQ ID NO 23
<211> LENGTH: 12
<212> TYPE: PRT
<213> ORGANISM: Artificial Sequence
<220> FEATURE:
<223> OTHER INFORMATION: synthetic polypeptide

<400> SEQUENCE: 23

Gly Gly Ser Gly Gly Ser Gly Gly Ser Gly Gly Ser
1               5                   10

<210> SEQ ID NO 24
<211> LENGTH: 15
<212> TYPE: PRT
<213> ORGANISM: Artificial Sequence
<220> FEATURE:
<223> OTHER INFORMATION: synthetic polypeptide

<400> SEQUENCE: 24

Gly Gly Ser Gly Gly Ser Gly Gly Ser Gly Gly Ser Gly Gly Ser
1               5                   10                  15

<210> SEQ ID NO 25
<211> LENGTH: 3
<212> TYPE: PRT
<213> ORGANISM: Artificial Sequence
<220> FEATURE:
<223> OTHER INFORMATION: synthetic polypeptide

<400> SEQUENCE: 25

Gly Ser Gly
1
```

<210> SEQ ID NO 26
<211> LENGTH: 6
<212> TYPE: PRT
<213> ORGANISM: Artificial Sequence
<220> FEATURE:
<223> OTHER INFORMATION: synthetic polypeptide

<400> SEQUENCE: 26

Gly Ser Gly Gly Ser Gly
1               5

<210> SEQ ID NO 27
<211> LENGTH: 9
<212> TYPE: PRT
<213> ORGANISM: Artificial Sequence
<220> FEATURE:
<223> OTHER INFORMATION: synthetic polypeptide

<400> SEQUENCE: 27

Gly Ser Gly Gly Ser Gly Gly Ser Gly
1               5

<210> SEQ ID NO 28
<211> LENGTH: 12
<212> TYPE: PRT
<213> ORGANISM: Artificial Sequence
<220> FEATURE:
<223> OTHER INFORMATION: synthetic polypeptide

<400> SEQUENCE: 28

Gly Ser Gly Gly Ser Gly Gly Ser Gly Gly Ser Gly
1               5                   10

<210> SEQ ID NO 29
<211> LENGTH: 15
<212> TYPE: PRT
<213> ORGANISM: Artificial Sequence
<220> FEATURE:
<223> OTHER INFORMATION: synthetic polypeptide

<400> SEQUENCE: 29

Gly Ser Gly Gly Ser Gly Gly Ser Gly Gly Ser Gly Gly Ser Gly
1               5                   10                  15

<210> SEQ ID NO 30
<211> LENGTH: 5
<212> TYPE: PRT
<213> ORGANISM: Artificial Sequence
<220> FEATURE:
<223> OTHER INFORMATION: synthetic polypeptide

<400> SEQUENCE: 30

Gly Gly Gly Gly Ser
1               5

<210> SEQ ID NO 31
<211> LENGTH: 10
<212> TYPE: PRT
<213> ORGANISM: Artificial Sequence
<220> FEATURE:
<223> OTHER INFORMATION: synthetic polypeptide

<400> SEQUENCE: 31

Gly Gly Gly Gly Ser Gly Gly Gly Gly Ser
1               5                   10

-continued

<210> SEQ ID NO 32
<211> LENGTH: 15
<212> TYPE: PRT
<213> ORGANISM: Artificial Sequence
<220> FEATURE:
<223> OTHER INFORMATION: synthetic polypeptide

<400> SEQUENCE: 32

Gly Gly Gly Gly Ser Gly Gly Gly Ser Gly Gly Gly Gly Ser
1               5                  10                  15

<210> SEQ ID NO 33
<211> LENGTH: 20
<212> TYPE: PRT
<213> ORGANISM: Artificial Sequence
<220> FEATURE:
<223> OTHER INFORMATION: synthetic polypeptide

<400> SEQUENCE: 33

Gly Gly Gly Gly Ser Gly Gly Gly Gly Ser Gly Gly Gly Gly Ser Gly
1               5                   10                  15

Gly Gly Gly Ser
            20

<210> SEQ ID NO 34
<211> LENGTH: 25
<212> TYPE: PRT
<213> ORGANISM: Artificial Sequence
<220> FEATURE:
<223> OTHER INFORMATION: synthetic polypeptide

<400> SEQUENCE: 34

Gly Gly Gly Gly Ser Gly Gly Gly Gly Ser Gly Gly Gly Gly Ser Gly
1               5                   10                  15

Gly Gly Gly Ser Gly Gly Gly Gly Ser
            20                  25

<210> SEQ ID NO 35
<211> LENGTH: 5
<212> TYPE: PRT
<213> ORGANISM: Artificial Sequence
<220> FEATURE:
<223> OTHER INFORMATION: synthetic polypeptide

<400> SEQUENCE: 35

Glu Ala Ala Ala Lys
1               5

<210> SEQ ID NO 36
<211> LENGTH: 17
<212> TYPE: PRT
<213> ORGANISM: Artificial Sequence
<220> FEATURE:
<223> OTHER INFORMATION: synthetic polypeptide

<400> SEQUENCE: 36

Ser Gln Ser Thr Val Val Thr Glu Pro Val Ala Glu Leu Pro Val Glu
1               5                   10                  15

Val

<210> SEQ ID NO 37
<211> LENGTH: 371
<212> TYPE: PRT
<213> ORGANISM: Artificial Sequence
<220> FEATURE:
<223> OTHER INFORMATION: synthetic polypeptide

<400> SEQUENCE: 37

```
Met Arg Pro Ala Thr Tyr Glu Pro Glu Gln Ile Ile Glu Ala Gly Leu
1               5                   10                  15

Ala Leu Gln Ala Glu Gly Arg Asn Ile Thr Gly Phe Ala Leu Arg Asn
            20                  25                  30

Gln Val Gly Gly Asn Pro Thr Arg Leu Arg Gln Ile Trp Asp Glu
        35                  40                  45

Tyr Gln Ala Ser Gln Ser Thr Val Val Thr Glu Pro Val Ala Glu Leu
    50                  55                  60

Pro Val Glu Val Ala Glu Val Lys Ala Val Ser Ala Ala Leu Ser
65                  70                  75                  80

Glu Arg Ile Thr Gln Leu Ala Thr Glu Leu Asn Asp Lys Ala Val Arg
                85                  90                  95

Ala Ala Glu Arg Arg Val Ala Glu Val Thr Arg Ala Ala Gly Glu Gln
            100                 105                 110

Thr Ala Gln Ala Glu Arg Glu Leu Ala Asp Ala Ala Gln Thr Val Asp
        115                 120                 125

Asp Leu Glu Glu Lys Leu Val Glu Leu Gln Asp Arg Tyr Asp Ser Leu
130                 135                 140

Thr Leu Ala Leu Glu Ser Glu Arg Ser Leu Arg Gln Gln His Asp Val
145                 150                 155                 160

Glu Met Ala Gln Leu Lys Glu Arg Leu Ala Ala Glu Glu Asn Thr
                165                 170                 175

Arg Gln Arg Glu Glu Arg Tyr Gln Glu Gln Lys Thr Val Leu Gln Asp
            180                 185                 190

Ala Leu Asn Ala Glu Gln Ala Gln His Lys Asn Thr Arg Glu Asp Leu
        195                 200                 205

Gln Lys Arg Leu Glu Gln Ile Ser Val Glu Ala Asn Ala Arg Thr Glu
210                 215                 220

Glu Leu Lys Ser Glu Arg Asp Lys Val Asn Thr Phe Leu Thr Arg Leu
225                 230                 235                 240

Glu Ser Gln Glu Asn Ala Leu Ala Ser Glu Arg Gln Gln His Leu Ala
                245                 250                 255

Thr Arg Glu Thr Leu Gln Gln Arg Leu Glu Gln Ala Ile Ala Asp Thr
            260                 265                 270

Gln Ala Arg Ala Gly Glu Ile Ala Leu Glu Arg Asp Arg Val Ser Ser
        275                 280                 285

Leu Thr Ala Arg Leu Glu Ser Gln Glu Lys Ala Ser Ser Glu Gln Leu
290                 295                 300

Val Arg Met Gly Ser Glu Ile Ala Ser Leu Thr Glu Arg Cys Thr Gln
305                 310                 315                 320

Leu Glu Asn Gln Arg Asp Asp Ala Arg Leu Glu Thr Met Gly Glu Lys
                325                 330                 335

Glu Thr Val Ala Ala Leu Arg Gly Glu Ala Glu Ala Leu Lys Arg Gln
            340                 345                 350

Asn Gln Ser Leu Met Ala Ala Leu Ser Gly Asn Lys Gln Thr Gly Gly
        355                 360                 365

Gln Asn Ala
    370
```

<210> SEQ ID NO 38
<211> LENGTH: 371
<212> TYPE: PRT

<213> ORGANISM: Artificial Sequence
<220> FEATURE:
<223> OTHER INFORMATION: synthetic polypeptide

<400> SEQUENCE: 38

Met Arg Pro Ala Thr Tyr Glu Pro Glu Gln Ile Ile Glu Ala Gly Leu
1               5                   10                  15

Ala Leu Gln Ala Glu Gly Arg Asn Ile Thr Gly Phe Ala Leu Arg Asn
            20                  25                  30

Gln Val Gly Gly Asn Pro Thr Arg Leu Arg Gln Ile Trp Asp Glu
        35                  40                  45

Tyr Gln Ala Ser Gln Ser Thr Val Val Thr Glu Leu Val Ala Glu Leu
    50                  55                  60

Pro Val Glu Val Ala Glu Val Lys Ala Val Ser Ala Ala Leu Ser
65                  70                  75                  80

Glu Arg Ile Thr Gln Leu Ala Thr Glu Leu Asn Asp Lys Ala Val Arg
                85                  90                  95

Ala Ala Glu Arg Arg Val Ala Glu Val Thr Arg Ala Ala Gly Glu Gln
            100                 105                 110

Thr Ala Gln Ala Glu Arg Glu Leu Ala Asp Ala Ala Gln Thr Val Asp
        115                 120                 125

Asp Leu Glu Glu Lys Leu Val Glu Leu Gln Asp Arg Tyr Asp Ser Leu
    130                 135                 140

Thr Leu Ala Leu Glu Ser Glu Arg Ser Leu Arg Gln Gln His Asp Val
145                 150                 155                 160

Glu Met Ala Gln Leu Lys Glu Arg Leu Ala Ala Ala Glu Glu Asn Thr
                165                 170                 175

Arg Gln Arg Glu Glu Arg Tyr Gln Glu Gln Arg Thr Val Leu Gln Asp
            180                 185                 190

Ala Leu Asn Ala Glu Gln Ala Gln His Ile Asn Thr Arg Glu Asp Gln
        195                 200                 205

Gln Lys Arg Leu Glu Gln Ile Ser Ala Glu Ala Asn Ala Arg Thr Glu
    210                 215                 220

Glu Leu Lys Ser Glu Arg Asp Lys Val Asn Thr Leu Leu Thr Arg Leu
225                 230                 235                 240

Glu Ser Gln Glu Asn Ala Leu Ala Ser Glu Arg Gln Gln His Leu Ala
                245                 250                 255

Thr Arg Glu Thr Leu Gln Gln Arg Leu Glu Gln Ala Ile Ala Asp Thr
            260                 265                 270

Gln Ala Arg Ala Gly Glu Ile Ala Leu Glu Arg Asp Arg Val Ser Ser
        275                 280                 285

Leu Thr Ala Arg Leu Glu Ser Gln Glu Lys Ala Ser Ser Glu Gln Leu
    290                 295                 300

Val Arg Met Gly Ser Glu Ile Ala Ser Leu Thr Glu Arg Cys Thr Gln
305                 310                 315                 320

Leu Glu Asn Gln Arg Asp Asp Ala Arg Leu Thr Met Gly Glu Lys
                325                 330                 335

Glu Thr Val Ala Ala Leu Arg Gly Glu Ala Glu Ala Leu Lys Arg Gln
            340                 345                 350

Asn Gln Ser Leu Met Ala Ala Leu Ser Gly Asn Lys Gln Thr Gly Gly
        355                 360                 365

Gln Asn Ala
    370

```
<210> SEQ ID NO 39
<211> LENGTH: 371
<212> TYPE: PRT
<213> ORGANISM: Artificial Sequence
<220> FEATURE:
<223> OTHER INFORMATION: synthetic polypeptide

<400> SEQUENCE: 39
```

Met Arg Pro Ala Thr Tyr Glu Pro Glu Gln Ile Ile Glu Ala Gly Leu
1               5                   10                  15

Ala Leu Gln Ala Glu Gly Arg Asn Ile Thr Gly Phe Ala Leu Arg Asn
            20                  25                  30

Gln Val Gly Gly Gly Asn Pro Thr Arg Leu Arg Gln Ile Trp Asp Glu
        35                  40                  45

Tyr Gln Ala Ser Gln Ser Thr Val Val Thr Glu Pro Val Ala Glu Leu
    50                  55                  60

Pro Val Glu Val Ala Glu Glu Val Lys Ala Val Ser Ala Ala Leu Ser
65                  70                  75                  80

Glu Arg Ile Thr Gln Leu Ala Thr Glu Leu Asn Asp Lys Ala Val Arg
                85                  90                  95

Ala Ala Glu Arg Arg Val Ala Glu Val Thr Arg Ala Ala Gly Glu Gln
            100                 105                 110

Thr Ala Gln Ala Glu Arg Glu Leu Ala Asp Ala Ala Gln Thr Val Asp
        115                 120                 125

Asp Leu Glu Glu Lys Leu Asp Glu Leu Gln Asp Arg Tyr Asp Ser Leu
    130                 135                 140

Thr Leu Ala Leu Glu Ser Glu Arg Ser Leu Arg Gln Gln His Asp Val
145                 150                 155                 160

Glu Met Ala Gln Leu Lys Glu Arg Leu Ala Ala Ala Glu Glu Asn Thr
                165                 170                 175

Arg Gln Arg Glu Glu Arg Tyr Gln Glu Gln Lys Thr Val Leu Gln Asp
            180                 185                 190

Ala Leu Asn Ala Glu Gln Ala Gln His Lys Asn Thr Arg Glu Asp Leu
        195                 200                 205

Gln Lys Arg Leu Glu Gln Ile Ser Ala Glu Ala Asn Ala Arg Thr Glu
    210                 215                 220

Glu Leu Lys Ser Glu Arg Asp Lys Val Asn Thr Leu Thr Arg Leu
225                 230                 235                 240

Glu Ser Gln Glu Asn Ala Leu Ala Ser Glu Arg Gln Gln His Leu Ala
                245                 250                 255

Thr Arg Glu Thr Leu Gln Gln Arg Leu Glu Gln Ala Ile Ala Asp Thr
            260                 265                 270

Gln Ala Arg Ala Gly Glu Ile Ala Leu Glu Arg Asp Arg Val Ser Ser
        275                 280                 285

Leu Thr Ala Arg Leu Glu Ser Gln Glu Lys Ala Ser Ser Glu Gln Leu
    290                 295                 300

Val Arg Met Gly Ser Glu Ile Ala Ser Leu Thr Glu Arg Cys Thr Gln
305                 310                 315                 320

Leu Glu Asn Gln Arg Asp Asp Ala Arg Leu Glu Thr Met Gly Glu Lys
                325                 330                 335

Glu Thr Val Ala Ala Leu Arg Gly Glu Ala Ala Leu Lys Arg Gln
            340                 345                 350

Asn Gln Ser Leu Met Ala Ala Leu Ser Gly Asn Lys Gln Thr Gly Gly
        355                 360                 365

Gln Asn Ala

370

<210> SEQ ID NO 40
<211> LENGTH: 371
<212> TYPE: PRT
<213> ORGANISM: Artificial Sequence
<220> FEATURE:
<223> OTHER INFORMATION: synthetic polypeptide

<400> SEQUENCE: 40

```
Met Arg Pro Ala Thr Tyr Glu Pro Glu Gln Ile Ile Glu Ala Gly Leu
1               5                   10                  15

Ala Leu Gln Ala Glu Gly Arg Asn Ile Thr Gly Phe Ala Leu Arg Asn
            20                  25                  30

Gln Val Gly Gly Gly Asn Pro Thr Arg Leu Arg Gln Ile Trp Asp Glu
        35                  40                  45

Tyr Gln Ala Ser Gln Ser Thr Val Val Thr Glu Pro Val Ala Glu Leu
    50                  55                  60

Pro Val Glu Val Ala Glu Val Lys Ala Val Ser Ala Ala Leu Ser
65                  70                  75                  80

Glu Arg Ile Thr Gln Leu Ala Thr Glu Leu Asn Asp Lys Ala Val Arg
                85                  90                  95

Ala Ala Glu Arg Arg Val Ala Glu Val Thr Arg Ala Ala Gly Glu Gln
            100                 105                 110

Thr Ala Gln Ala Glu Arg Glu Leu Ala Asp Ala Ala Gln Thr Val Asp
        115                 120                 125

Asp Leu Glu Glu Lys Leu Val Glu Leu Gln Asp Arg Tyr Asp Ser Leu
    130                 135                 140

Thr Leu Ala Leu Glu Ser Glu Arg Ser Leu Arg Gln Gln His Asp Val
145                 150                 155                 160

Glu Met Ala Gln Leu Lys Glu Arg Leu Ala Ala Glu Glu Asn Thr
                165                 170                 175

Arg Gln Arg Glu Glu Arg Tyr Gln Glu Gln Lys Thr Val Leu Gln Asp
            180                 185                 190

Ala Leu Asn Ala Glu Gln Ala Gln His Lys Asn Thr Arg Glu Asp Leu
        195                 200                 205

Gln Lys Arg Leu Glu Gln Ile Ser Val Glu Ala Asn Ala Arg Thr Glu
    210                 215                 220

Glu Leu Lys Ser Glu Arg Asp Lys Val Asn Thr Phe Leu Thr Arg Leu
225                 230                 235                 240

Glu Ser Gln Glu Asn Ala Leu Ala Ser Glu Arg Gln Gln His Leu Ala
                245                 250                 255

Thr Arg Glu Thr Leu Gln Gln Arg Leu Glu Gln Ala Ile Ala Asp Thr
            260                 265                 270

Gln Ala Arg Ala Gly Glu Ile Ala Leu Glu Arg Asp Arg Val Ser Ser
        275                 280                 285

Leu Thr Ala Arg Leu Glu Ser Gln Glu Lys Ala Ser Ser Glu Gln Leu
    290                 295                 300

Val Arg Met Gly Ser Glu Ile Ala Ser Leu Thr Glu Arg Cys Thr Gln
305                 310                 315                 320

Leu Glu Asn Gln Arg Asp Asp Ala Arg Leu Glu Thr Met Gly Glu Lys
                325                 330                 335

Glu Thr Val Ala Ala Leu Arg Gly Glu Ala Glu Ala Leu Lys Arg Gln
            340                 345                 350

Asn Gln Ser Leu Met Ala Ala Leu Ser Gly Asn Lys Gln Thr Gly Gly
```

Gln Asn Ala
    370

<210> SEQ ID NO 41
<211> LENGTH: 371
<212> TYPE: PRT
<213> ORGANISM: Artificial Sequence
<220> FEATURE:
<223> OTHER INFORMATION: synthetic polypeptide

<400> SEQUENCE: 41

Met Arg Pro Ala Thr Tyr Glu Pro Glu Gln Ile Ile Glu Ala Gly Leu
1               5                   10                  15

Ala Leu Gln Ala Glu Gly Arg Asn Ile Thr Gly Phe Ala Leu Arg Asn
            20                  25                  30

Gln Val Gly Gly Gly Asn Pro Thr Arg Leu Arg Gln Ile Trp Asp Glu
        35                  40                  45

Tyr Gln Ala Ser Gln Ser Thr Val Val Thr Glu Pro Val Ala Glu Leu
    50                  55                  60

Pro Val Glu Val Ala Glu Val Lys Ala Val Ser Ala Ala Leu Ser
65                  70                  75                  80

Glu Arg Ile Thr Gln Leu Ala Thr Glu Leu Asn Asp Lys Ala Val Arg
                85                  90                  95

Ala Ala Glu Arg Arg Val Ala Glu Val Thr Arg Ala Ala Gly Glu Gln
            100                 105                 110

Thr Ala Gln Ala Glu Arg Glu Leu Ala Asp Ala Ala Gln Thr Val Asp
        115                 120                 125

Asp Leu Glu Glu Lys Leu Asp Glu Leu Gln Asp Arg Tyr Asp Ser Leu
    130                 135                 140

Thr Leu Ala Leu Glu Ser Glu Arg Ser Leu Arg Gln Gln His Asp Val
145                 150                 155                 160

Glu Met Ala Gln Leu Lys Glu Arg Leu Ala Ala Ala Glu Glu Asn Thr
                165                 170                 175

Arg Gln Arg Arg Glu Arg Tyr Gln Glu Gln Lys Thr Val Leu Gln Asp
            180                 185                 190

Ala Leu Asn Ala Glu Gln Ala Gln His Lys Asn Thr Arg Glu Asp Leu
        195                 200                 205

Gln Lys Arg Leu Glu Gln Ile Ser Ala Glu Ala Asn Ala Arg Thr Glu
    210                 215                 220

Glu Leu Lys Ser Glu Arg Asp Lys Val Asn Thr Leu Thr Arg Leu
225                 230                 235                 240

Glu Ser Gln Glu Asn Ala Leu Ala Ser Glu Arg Gln Gln His Leu Ala
                245                 250                 255

Thr Arg Glu Thr Leu Gln Gln Arg Leu Glu Gln Ala Ile Ala Asp Thr
            260                 265                 270

Gln Ala Arg Ala Gly Glu Ile Ala Leu Glu Arg Asp Arg Val Ser Ser
        275                 280                 285

Leu Thr Ala Arg Leu Glu Ser Gln Glu Lys Ala Ser Ser Glu Gln Leu
    290                 295                 300

Val Arg Met Gly Ser Glu Ile Ala Ser Leu Thr Glu Arg Cys Thr Gln
305                 310                 315                 320

Leu Glu Asn Gln Arg Asp Asp Ala Arg Leu Glu Thr Met Gly Glu Lys
                325                 330                 335

Glu Thr Val Ala Ala Leu Arg Gly Glu Ala Glu Ala Leu Lys Arg Gln

```
                    340                 345                 350
Asn Gln Ser Leu Met Ala Ala Leu Ser Gly Asn Lys Gln Thr Gly Gly
            355                 360                 365

Gln Asn Ala
    370

<210> SEQ ID NO 42
<211> LENGTH: 371
<212> TYPE: PRT
<213> ORGANISM: Artificial Sequence
<220> FEATURE:
<223> OTHER INFORMATION: synthetic polypeptide

<400> SEQUENCE: 42

Met Arg Pro Ala Thr Tyr Glu Pro Glu Gln Ile Ile Glu Ala Gly Leu
1               5                   10                  15

Ala Leu Gln Ala Glu Gly Arg Asn Ile Thr Gly Phe Ala Leu Arg Asn
            20                  25                  30

Gln Val Gly Gly Gly Asn Pro Thr Arg Leu Arg Gln Ile Trp Asp Glu
        35                  40                  45

Tyr Gln Ala Ser Gln Ser Thr Val Val Thr Glu Pro Val Ala Glu Leu
    50                  55                  60

Pro Val Glu Val Ala Glu Val Lys Ala Val Ser Ala Ala Leu Ser
65                  70                  75                  80

Glu Arg Ile Thr Gln Leu Ala Thr Glu Leu Asn Asp Lys Ala Val Arg
                85                  90                  95

Ala Ala Glu Arg Arg Val Ala Glu Val Thr Arg Ala Ala Gly Glu Gln
            100                 105                 110

Thr Ala Gln Ala Glu Arg Glu Leu Ala Asp Ala Ala Gln Thr Val Asp
        115                 120                 125

Asp Leu Glu Glu Lys Leu Asp Glu Leu Gln Asp Arg Tyr Asp Ser Leu
    130                 135                 140

Thr Leu Ala Leu Glu Ser Glu Arg Ser Leu Arg Gln Gln His Asp Val
145                 150                 155                 160

Glu Met Ala Gln Leu Lys Glu Arg Leu Ala Ala Ala Glu Glu Asn Thr
                165                 170                 175

Arg Gln Glu Glu Glu Arg Tyr Gln Glu Gln Lys Thr Val Leu Gln Asp
            180                 185                 190

Ala Leu Asn Ala Glu Gln Ala Gln His Lys Asn Thr Arg Glu Asp Leu
        195                 200                 205

Gln Lys Arg Leu Glu Gln Ile Ser Ala Glu Ala Asn Ala Arg Thr Glu
    210                 215                 220

Glu Leu Lys Ser Glu Arg Asp Lys Val Asn Thr Leu Leu Thr Arg Leu
225                 230                 235                 240

Glu Ser Gln Glu Asn Ala Leu Ala Ser Glu Arg Gln His Leu Ala
                245                 250                 255

Thr Arg Glu Thr Leu Gln Arg Leu Glu Gln Ala Ile Ala Asp Thr
            260                 265                 270

Gln Ala Arg Ala Gly Glu Ile Ala Leu Glu Arg Asp Arg Val Ser Ser
        275                 280                 285

Leu Thr Ala Arg Leu Glu Ser Gln Glu Lys Ala Ser Ser Glu Gln Leu
    290                 295                 300

Val Arg Met Gly Ser Glu Ile Ala Ser Leu Thr Glu Arg Cys Thr Gln
305                 310                 315                 320

Leu Glu Asn Gln Arg Asp Asp Ala Arg Leu Glu Thr Met Gly Glu Lys
```

```
                    325                 330                 335
Glu Thr Val Ala Ala Leu Arg Gly Glu Ala Glu Ala Leu Lys Arg Gln
                340                 345                 350

Asn Gln Ser Leu Met Ala Ala Leu Ser Gly Asn Lys Gln Thr Gly Gly
            355                 360                 365

Gln Asn Ala
    370

<210> SEQ ID NO 43
<211> LENGTH: 371
<212> TYPE: PRT
<213> ORGANISM: Artificial Sequence
<220> FEATURE:
<223> OTHER INFORMATION: synthetic polypeptide

<400> SEQUENCE: 43

Met Arg Pro Ala Thr Tyr Glu Pro Glu Gln Ile Ile Glu Ala Gly Leu
1               5                   10                  15

Ala Leu Gln Ala Glu Gly Arg Asn Ile Thr Gly Phe Ala Leu Arg Asn
                20                  25                  30

Gln Val Gly Gly Gly Asn Pro Thr Arg Leu Arg Gln Ile Trp Asp Glu
            35                  40                  45

Tyr Gln Ala Ser Gln Ser Thr Val Val Thr Glu Pro Val Ala Glu Leu
    50                  55                  60

Pro Val Glu Val Ala Glu Val Lys Ala Val Ser Ala Ala Leu Ser
65                  70                  75                  80

Glu Arg Ile Thr Gln Leu Ala Thr Glu Leu Asn Asp Lys Ala Val Arg
                85                  90                  95

Ala Ala Glu Arg Arg Val Ala Glu Val Thr Arg Ala Ala Gly Glu Gln
            100                 105                 110

Thr Ala Gln Ala Glu Arg Glu Leu Ala Asp Ala Ala Gln Thr Val Asp
        115                 120                 125

Asp Leu Glu Glu Lys Leu Asp Glu Leu Gln Asp Arg Tyr Asp Ser Leu
    130                 135                 140

Thr Leu Ala Leu Glu Ser Glu Arg Ser Leu Arg Gln Gln His Asp Val
145                 150                 155                 160

Glu Met Ala Gln Leu Lys Glu Arg Leu Ala Ala Ala Glu Glu Asn Thr
                165                 170                 175

Arg Gln Arg Arg Glu Arg Tyr Gln Glu Gln Lys Thr Val Leu Gln Asp
            180                 185                 190

Ala Leu Asn Ala Glu Gln Ala Gln His Lys Asn Thr Arg Glu Asp Leu
        195                 200                 205

Gln Lys Arg Leu Glu Gln Ile Ser Ala Glu Ala Asn Ala Arg Thr Glu
    210                 215                 220

Glu Leu Lys Ser Arg Arg Asp Lys Val Asn Thr Leu Leu Thr Arg Leu
225                 230                 235                 240

Glu Ser Gln Glu Asn Ala Leu Ala Ser Glu Arg Gln Gln His Leu Ala
                245                 250                 255

Thr Arg Glu Thr Leu Gln Gln Arg Leu Glu Gln Ala Ile Ala Asp Thr
            260                 265                 270

Gln Ala Arg Ala Gly Glu Ile Ala Leu Glu Arg Asp Arg Val Ser Ser
        275                 280                 285

Leu Thr Ala Arg Leu Glu Ser Gln Glu Lys Ala Ser Ser Glu Gln Leu
    290                 295                 300

Val Arg Met Gly Ser Glu Ile Ala Ser Leu Thr Glu Arg Cys Thr Gln
```

305 310 315 320

Leu Glu Asn Gln Arg Asp Asp Ala Arg Leu Glu Thr Met Gly Glu Lys
            325                 330                 335

Glu Thr Val Ala Ala Leu Arg Gly Glu Ala Glu Ala Leu Lys Arg Gln
            340                 345                 350

Asn Gln Ser Leu Met Ala Ala Leu Ser Gly Asn Lys Gln Thr Gly Gly
            355                 360                 365

Gln Asn Ala
    370

<210> SEQ ID NO 44
<211> LENGTH: 371
<212> TYPE: PRT
<213> ORGANISM: Artificial Sequence
<220> FEATURE:
<223> OTHER INFORMATION: synthetic polypeptide

<400> SEQUENCE: 44

Met Arg Pro Ala Thr Tyr Glu Pro Glu Gln Ile Ile Glu Ala Gly Leu
1               5                   10                  15

Ala Leu Gln Ala Glu Gly Arg Asn Ile Thr Gly Phe Ala Leu Arg Asn
            20                  25                  30

Gln Val Gly Gly Gly Asn Pro Thr Arg Leu Arg Gln Ile Trp Asp Glu
        35                  40                  45

Tyr Gln Ala Ser Gln Ser Thr Val Val Thr Glu Pro Val Ala Glu Leu
    50                  55                  60

Pro Val Glu Val Ala Glu Val Lys Ala Val Ser Ala Ala Leu Ser
65                  70                  75                  80

Glu Arg Ile Thr Gln Leu Ala Thr Glu Leu Asn Asp Lys Ala Val Arg
                85                  90                  95

Ala Ala Glu Arg Arg Val Ala Glu Val Thr Arg Ala Ala Gly Glu Gln
            100                 105                 110

Thr Ala Gln Ala Glu Arg Glu Leu Ala Asp Ala Ala Gln Thr Val Asp
            115                 120                 125

Asp Leu Glu Glu Lys Leu Asp Glu Leu Gln Asp Arg Tyr Asp Ser Leu
130                 135                 140

Thr Leu Ala Leu Glu Ser Glu Arg Ser Leu Arg Gln Gln His Asp Val
145                 150                 155                 160

Glu Met Ala Gln Leu Lys Glu Arg Leu Ala Ala Glu Glu Asn Thr
                165                 170                 175

Arg Gln Glu Glu Arg Tyr Gln Glu Gln Lys Thr Val Leu Gln Asp
            180                 185                 190

Ala Leu Asn Ala Glu Gln Ala Gln His Lys Asn Thr Arg Glu Asp Leu
            195                 200                 205

Gln Lys Arg Leu Glu Gln Ile Ser Ala Glu Ala Asn Ala Arg Thr Glu
        210                 215                 220

Glu Leu Lys Ser Glu Glu Asp Lys Val Asn Thr Leu Leu Thr Arg Leu
225                 230                 235                 240

Glu Ser Gln Glu Asn Ala Leu Ala Ser Glu Arg Gln Gln His Leu Ala
                245                 250                 255

Thr Arg Glu Thr Leu Gln Gln Arg Leu Glu Gln Ala Ile Ala Asp Thr
            260                 265                 270

Gln Ala Arg Ala Gly Glu Ile Ala Leu Glu Arg Asp Arg Val Ser Ser
            275                 280                 285

Leu Thr Ala Arg Leu Glu Ser Gln Glu Lys Ala Ser Ser Glu Gln Leu

```
                290                 295                 300
Val Arg Met Gly Ser Glu Ile Ala Ser Leu Thr Glu Arg Cys Thr Gln
305                 310                 315                 320

Leu Glu Asn Gln Arg Asp Asp Ala Arg Leu Glu Thr Met Gly Glu Lys
                325                 330                 335

Glu Thr Val Ala Ala Leu Arg Gly Glu Ala Glu Ala Leu Lys Arg Gln
                340                 345                 350

Asn Gln Ser Leu Met Ala Ala Leu Ser Gly Asn Lys Gln Thr Gly Gly
            355                 360                 365

Gln Asn Ala
    370

<210> SEQ ID NO 45
<211> LENGTH: 371
<212> TYPE: PRT
<213> ORGANISM: Artificial Sequence
<220> FEATURE:
<223> OTHER INFORMATION: synthetic polypeptide

<400> SEQUENCE: 45

Met Arg Pro Ala Thr Tyr Glu Pro Glu Gln Ile Ile Glu Ala Gly Leu
1               5                   10                  15

Ala Leu Gln Ala Glu Gly Arg Asn Ile Thr Gly Phe Ala Leu Arg Asn
                20                  25                  30

Gln Val Gly Gly Asn Pro Thr Arg Leu Arg Gln Ile Trp Asp Glu
                35                  40                  45

Tyr Gln Ala Ser Gln Ser Thr Val Val Thr Glu Pro Val Ala Glu Leu
    50                  55                  60

Pro Val Glu Val Ala Glu Val Lys Ala Val Ser Ala Ala Leu Ser
65                  70                  75                  80

Glu Arg Ile Thr Gln Leu Ala Thr Glu Leu Asn Asp Lys Ala Val Arg
                85                  90                  95

Ala Ala Glu Arg Arg Val Ala Glu Val Thr Arg Ala Ala Gly Glu Gln
                100                 105                 110

Thr Ala Gln Ala Glu Arg Glu Leu Ala Asp Ala Ala Gln Thr Val Asp
                115                 120                 125

Asp Leu Glu Glu Lys Leu Asp Glu Leu Gln Asp Arg Tyr Asp Ser Leu
    130                 135                 140

Thr Leu Ala Leu Glu Ser Glu Arg Ser Leu Arg Gln Gln His Asp Val
145                 150                 155                 160

Glu Met Ala Gln Leu Lys Glu Arg Leu Ala Ala Ala Glu Glu Asn Thr
                165                 170                 175

Arg Gln Arg Arg Glu Arg Tyr Gln Glu Gln Lys Thr Val Leu Gln Asp
                180                 185                 190

Ala Leu Asn Ala Glu Gln Ala Gln His Lys Asn Thr Arg Glu Asp Leu
            195                 200                 205

Gln Lys Arg Leu Glu Gln Ile Ser Ala Glu Ala Asn Ala Arg Thr Glu
    210                 215                 220

Glu Leu Lys Ser Glu Glu Asp Lys Val Asn Thr Leu Leu Thr Arg Leu
225                 230                 235                 240

Glu Ser Gln Glu Asn Ala Leu Ala Ser Glu Arg Gln Gln His Leu Ala
                245                 250                 255

Thr Arg Glu Thr Leu Gln Gln Arg Leu Glu Gln Ala Ile Ala Asp Thr
                260                 265                 270

Gln Ala Arg Ala Gly Glu Ile Ala Leu Glu Arg Asp Arg Val Ser Ser
```

```
                275                 280                 285
Leu Thr Ala Arg Leu Glu Ser Gln Glu Lys Ala Ser Ser Glu Gln Leu
    290                 295                 300

Val Arg Met Gly Ser Glu Ile Ala Ser Leu Thr Glu Arg Cys Thr Gln
305                 310                 315                 320

Leu Glu Asn Gln Arg Asp Asp Ala Arg Leu Glu Thr Met Gly Glu Lys
                325                 330                 335

Glu Thr Val Ala Ala Leu Arg Gly Glu Ala Glu Ala Leu Lys Arg Gln
            340                 345                 350

Asn Gln Ser Leu Met Ala Ala Leu Ser Gly Asn Lys Gln Thr Gly Gly
                355                 360                 365

Gln Asn Ala
    370

<210> SEQ ID NO 46
<211> LENGTH: 371
<212> TYPE: PRT
<213> ORGANISM: Artificial Sequence
<220> FEATURE:
<223> OTHER INFORMATION: synthetic polypeptide

<400> SEQUENCE: 46

Met Arg Pro Ala Thr Tyr Glu Pro Glu Gln Ile Ile Glu Ala Gly Leu
1               5                   10                  15

Ala Leu Gln Ala Glu Gly Arg Asn Ile Thr Gly Phe Ala Leu Arg Asn
                20                  25                  30

Gln Val Gly Gly Gly Asn Pro Thr Arg Leu Arg Gln Ile Trp Asp Glu
            35                  40                  45

Tyr Gln Ala Ser Gln Ser Thr Val Val Thr Glu Pro Val Ala Glu Leu
    50                  55                  60

Pro Val Glu Val Ala Glu Val Lys Ala Val Ser Ala Ala Leu Ser
65                  70                  75                  80

Glu Arg Ile Thr Gln Leu Ala Thr Glu Leu Asn Asp Lys Ala Val Arg
                85                  90                  95

Ala Ala Glu Arg Arg Val Ala Glu Val Thr Arg Ala Ala Gly Glu Gln
            100                 105                 110

Thr Ala Gln Ala Glu Arg Glu Leu Ala Asp Ala Ala Gln Thr Val Asp
    115                 120                 125

Asp Leu Glu Glu Lys Leu Asp Glu Leu Gln Asp Arg Tyr Asp Ser Leu
130                 135                 140

Thr Leu Ala Leu Glu Ser Glu Arg Ser Leu Arg Gln Gln His Asp Val
145                 150                 155                 160

Glu Met Ala Gln Leu Lys Glu Arg Leu Ala Ala Ala Glu Glu Asn Thr
                165                 170                 175

Arg Gln Glu Glu Glu Arg Tyr Gln Glu Gln Lys Thr Val Leu Gln Asp
            180                 185                 190

Ala Leu Asn Ala Glu Gln Ala Gln His Lys Thr Arg Glu Asp Leu
    195                 200                 205

Gln Lys Arg Leu Glu Gln Ile Ser Ala Glu Ala Asn Ala Arg Thr Glu
210                 215                 220

Glu Leu Lys Ser Arg Arg Asp Lys Val Asn Thr Leu Leu Thr Arg Leu
225                 230                 235                 240

Glu Ser Gln Glu Asn Ala Leu Ala Ser Glu Arg Gln Gln His Leu Ala
                245                 250                 255

Thr Arg Glu Thr Leu Gln Gln Arg Leu Glu Gln Ala Ile Ala Asp Thr
```

```
              260                 265                 270
Gln Ala Arg Ala Gly Glu Ile Ala Leu Glu Arg Asp Arg Val Ser Ser
            275                 280                 285

Leu Thr Ala Arg Leu Glu Ser Gln Glu Lys Ala Ser Ser Glu Gln Leu
        290                 295                 300

Val Arg Met Gly Ser Glu Ile Ala Ser Leu Thr Glu Arg Cys Thr Gln
305                 310                 315                 320

Leu Glu Asn Gln Arg Asp Asp Ala Arg Leu Glu Thr Met Gly Glu Lys
                325                 330                 335

Glu Thr Val Ala Ala Leu Arg Gly Glu Ala Glu Ala Leu Lys Arg Gln
            340                 345                 350

Asn Gln Ser Leu Met Ala Ala Leu Ser Gly Asn Lys Gln Thr Gly Gly
        355                 360                 365

Gln Asn Ala
    370

<210> SEQ ID NO 47
<211> LENGTH: 371
<212> TYPE: PRT
<213> ORGANISM: Artificial Sequence
<220> FEATURE:
<223> OTHER INFORMATION: synthetic polypeptide

<400> SEQUENCE: 47

Met Arg Pro Ala Thr Tyr Glu Pro Glu Gln Ile Ile Glu Ala Gly Leu
1               5                   10                  15

Ala Leu Gln Ala Glu Gly Arg Asn Ile Thr Gly Phe Ala Leu Arg Asn
            20                  25                  30

Gln Val Gly Gly Gly Asn Pro Thr Arg Leu Arg Gln Ile Trp Asp Glu
        35                  40                  45

Tyr Gln Ala Ser Gln Ser Thr Val Val Thr Glu Pro Val Ala Glu Leu
    50                  55                  60

Pro Val Glu Val Ala Glu Val Lys Ala Val Ser Ala Ala Leu Ser
65                  70                  75                  80

Glu Arg Ile Thr Gln Leu Ala Thr Glu Leu Asn Asp Lys Ala Val Arg
                85                  90                  95

Ala Ala Glu Arg Arg Val Ala Glu Val Thr Arg Ala Ala Gly Glu Gln
            100                 105                 110

Thr Ala Gln Ala Glu Arg Glu Leu Ala Asp Ala Ala Gln Thr Val Asp
        115                 120                 125

Asp Leu Glu Glu Lys Leu Asp Glu Leu Gln Asp Arg Tyr Asp Ser Leu
    130                 135                 140

Thr Leu Ala Leu Glu Ser Glu Arg Ser Leu Arg Gln Gln His Asp Val
145                 150                 155                 160

Glu Met Ala Gln Leu Lys Glu Arg Leu Ala Ala Ala Glu Glu Asn Thr
                165                 170                 175

Arg Gln Arg Arg Glu Arg Tyr Gln Glu Gln Lys Thr Val Leu Gln Asp
            180                 185                 190

Ala Leu Asn Ala Glu Gln Ala Gln His Lys Asn Thr Arg Glu Asp Leu
        195                 200                 205

Gln Lys Arg Leu Glu Gln Ile Ser Ala Glu Ala Asn Ala Arg Thr Glu
    210                 215                 220

Glu Leu Lys Ser Glu Arg Asp Lys Val Asn Thr Leu Leu Thr Arg Leu
225                 230                 235                 240

Glu Ser Gln Glu Asn Ala Leu Ala Ser Arg Arg Gln Gln His Leu Ala
```

```
                        245                 250                 255
Thr Arg Glu Thr Leu Gln Gln Arg Leu Glu Gln Ala Ile Ala Asp Thr
                260                 265                 270

Gln Ala Arg Ala Gly Glu Ile Ala Leu Glu Arg Asp Arg Val Ser Ser
            275                 280                 285

Leu Thr Ala Arg Leu Glu Ser Gln Glu Lys Ala Ser Ser Glu Gln Leu
    290                 295                 300

Val Arg Met Gly Ser Glu Ile Ala Ser Leu Thr Glu Arg Cys Thr Gln
305                 310                 315                 320

Leu Glu Asn Gln Arg Asp Asp Ala Arg Leu Glu Thr Met Gly Glu Lys
                325                 330                 335

Glu Thr Val Ala Ala Leu Arg Gly Glu Ala Glu Ala Leu Lys Arg Gln
            340                 345                 350

Asn Gln Ser Leu Met Ala Ala Leu Ser Gly Asn Lys Gln Thr Gly Gly
        355                 360                 365

Gln Asn Ala
    370

<210> SEQ ID NO 48
<211> LENGTH: 371
<212> TYPE: PRT
<213> ORGANISM: Artificial Sequence
<220> FEATURE:
<223> OTHER INFORMATION: synthetic polypeptide

<400> SEQUENCE: 48

Met Arg Pro Ala Thr Tyr Glu Pro Glu Gln Ile Ile Glu Ala Gly Leu
1               5                   10                  15

Ala Leu Gln Ala Glu Gly Arg Asn Ile Thr Gly Phe Ala Leu Arg Asn
            20                  25                  30

Gln Val Gly Gly Gly Asn Pro Thr Arg Leu Arg Gln Ile Trp Asp Glu
        35                  40                  45

Tyr Gln Ala Ser Gln Ser Thr Val Val Thr Glu Pro Val Ala Glu Leu
    50                  55                  60

Pro Val Glu Val Ala Glu Glu Val Lys Ala Val Ser Ala Ala Leu Ser
65                  70                  75                  80

Glu Arg Ile Thr Gln Leu Ala Thr Glu Leu Asn Asp Lys Ala Val Arg
                85                  90                  95

Ala Ala Glu Arg Arg Val Ala Glu Val Thr Arg Ala Ala Gly Glu Gln
            100                 105                 110

Thr Ala Gln Ala Glu Arg Glu Leu Ala Asp Ala Ala Gln Thr Val Asp
        115                 120                 125

Asp Leu Glu Glu Lys Leu Asp Glu Leu Gln Asp Arg Tyr Asp Ser Leu
    130                 135                 140

Thr Leu Ala Leu Glu Ser Glu Arg Ser Leu Arg Gln Gln His Asp Val
145                 150                 155                 160

Glu Met Ala Gln Leu Lys Glu Arg Leu Ala Ala Glu Glu Asn Thr
                165                 170                 175

Arg Gln Glu Glu Glu Arg Tyr Gln Glu Gln Lys Thr Val Leu Gln Asp
            180                 185                 190

Ala Leu Asn Ala Glu Gln Ala His Lys Asn Thr Arg Glu Asp Leu
        195                 200                 205

Gln Lys Arg Leu Glu Gln Ile Ser Ala Glu Ala Asn Ala Arg Thr Glu
    210                 215                 220

Glu Leu Lys Ser Glu Arg Asp Lys Val Asn Thr Leu Leu Thr Arg Leu
```

```
                225                 230                 235                 240
Glu Ser Gln Glu Asn Ala Leu Ala Ser Glu Glu Gln Gln His Leu Ala
                245                 250                 255

Thr Arg Glu Thr Leu Gln Gln Arg Leu Glu Gln Ala Ile Ala Asp Thr
                260                 265                 270

Gln Ala Arg Ala Gly Glu Ile Ala Leu Glu Arg Asp Arg Val Ser Ser
                275                 280                 285

Leu Thr Ala Arg Leu Glu Ser Gln Glu Lys Ala Ser Ser Glu Gln Leu
                290                 295                 300

Val Arg Met Gly Ser Glu Ile Ala Ser Leu Thr Glu Arg Cys Thr Gln
305                 310                 315                 320

Leu Glu Asn Gln Arg Asp Asp Ala Arg Leu Glu Thr Met Gly Glu Lys
                325                 330                 335

Glu Thr Val Ala Ala Leu Arg Gly Glu Ala Glu Ala Leu Lys Arg Gln
                340                 345                 350

Asn Gln Ser Leu Met Ala Ala Leu Ser Gly Asn Lys Gln Thr Gly Gly
                355                 360                 365

Gln Asn Ala
    370

<210> SEQ ID NO 49
<211> LENGTH: 371
<212> TYPE: PRT
<213> ORGANISM: Artificial Sequence
<220> FEATURE:
<223> OTHER INFORMATION: synthetic polypeptide

<400> SEQUENCE: 49

Met Arg Pro Ala Thr Tyr Glu Pro Glu Gln Ile Ile Glu Ala Gly Leu
1               5                   10                  15

Ala Leu Gln Ala Glu Gly Arg Asn Ile Thr Gly Phe Ala Leu Arg Asn
                20                  25                  30

Gln Val Gly Gly Gly Asn Pro Thr Arg Leu Arg Gln Ile Trp Asp Glu
                35                  40                  45

Tyr Gln Ala Ser Gln Ser Thr Val Val Thr Glu Pro Val Ala Glu Leu
    50                  55                  60

Pro Val Glu Val Ala Glu Val Lys Ala Val Ser Ala Ala Leu Ser
65                  70                  75                  80

Glu Arg Ile Thr Gln Leu Ala Thr Glu Leu Asn Asp Lys Ala Val Arg
                85                  90                  95

Ala Ala Glu Arg Arg Val Ala Glu Val Thr Arg Ala Ala Gly Glu Gln
                100                 105                 110

Thr Ala Gln Ala Glu Arg Glu Leu Ala Asp Ala Ala Gln Thr Val Asp
                115                 120                 125

Asp Leu Glu Glu Lys Leu Asp Glu Leu Gln Asp Arg Tyr Asp Ser Leu
    130                 135                 140

Thr Leu Ala Leu Glu Ser Glu Arg Ser Leu Arg Gln Gln His Asp Val
145                 150                 155                 160

Glu Met Ala Gln Leu Lys Glu Arg Leu Ala Ala Ala Glu Glu Asn Thr
                165                 170                 175

Arg Gln Arg Arg Glu Arg Tyr Gln Glu Gln Lys Thr Val Leu Gln Asp
                180                 185                 190

Ala Leu Asn Ala Glu Gln Ala Gln His Lys Asn Thr Arg Glu Asp Leu
    195                 200                 205

Gln Lys Arg Leu Glu Gln Ile Ser Ala Glu Ala Asn Ala Arg Thr Glu
```

```
                    210                 215                 220
Glu Leu Lys Ser Glu Arg Asp Lys Val Asn Thr Leu Thr Arg Leu
225                 230                 235                 240

Glu Ser Gln Glu Asn Ala Leu Ala Ser Glu Gln Gln His Leu Ala
                245                 250                 255

Thr Arg Glu Thr Leu Gln Gln Arg Leu Glu Gln Ala Ile Ala Asp Thr
            260                 265                 270

Gln Ala Arg Ala Gly Glu Ile Ala Leu Glu Arg Asp Arg Val Ser Ser
                275                 280                 285

Leu Thr Ala Arg Leu Glu Ser Gln Glu Lys Ala Ser Ser Glu Gln Leu
290                 295                 300

Val Arg Met Gly Ser Glu Ile Ala Ser Leu Thr Glu Arg Cys Thr Gln
305                 310                 315                 320

Leu Glu Asn Gln Arg Asp Asp Ala Arg Leu Glu Thr Met Gly Glu Lys
                325                 330                 335

Glu Thr Val Ala Ala Leu Arg Gly Glu Ala Glu Ala Leu Lys Arg Gln
                340                 345                 350

Asn Gln Ser Leu Met Ala Ala Leu Ser Gly Asn Lys Gln Thr Gly Gly
                355                 360                 365

Gln Asn Ala
    370

<210> SEQ ID NO 50
<211> LENGTH: 371
<212> TYPE: PRT
<213> ORGANISM: Artificial Sequence
<220> FEATURE:
<223> OTHER INFORMATION: synthetic polypeptide

<400> SEQUENCE: 50

Met Arg Pro Ala Thr Tyr Glu Pro Glu Gln Ile Ile Glu Ala Gly Leu
1               5                   10                  15

Ala Leu Gln Ala Glu Gly Arg Asn Ile Thr Gly Phe Ala Leu Arg Asn
                20                  25                  30

Gln Val Gly Gly Gly Asn Pro Thr Arg Leu Arg Gln Ile Trp Asp Glu
            35                  40                  45

Tyr Gln Ala Ser Gln Ser Thr Val Val Thr Glu Pro Val Ala Glu Leu
        50                  55                  60

Pro Val Glu Val Ala Glu Glu Val Lys Ala Val Ser Ala Ala Leu Ser
65                  70                  75                  80

Glu Arg Ile Thr Gln Leu Ala Thr Glu Leu Asn Asp Lys Ala Val Arg
                85                  90                  95

Ala Ala Glu Arg Arg Val Ala Glu Val Thr Arg Ala Ala Gly Glu Gln
                100                 105                 110

Thr Ala Gln Ala Glu Arg Glu Leu Ala Asp Ala Ala Gln Thr Val Asp
            115                 120                 125

Asp Leu Glu Glu Lys Leu Asp Glu Leu Gln Asp Arg Tyr Asp Ser Leu
        130                 135                 140

Thr Leu Ala Leu Glu Ser Glu Arg Ser Leu Arg Gln Gln His Asp Val
145                 150                 155                 160

Glu Met Ala Gln Leu Lys Glu Arg Leu Ala Ala Glu Glu Asn Thr
                165                 170                 175

Arg Gln Glu Glu Glu Arg Tyr Gln Glu Gln Lys Thr Val Leu Gln Asp
                180                 185                 190

Ala Leu Asn Ala Glu Gln Ala Gln His Lys Asn Thr Arg Glu Asp Leu
```

```
            195                 200                 205
Gln Lys Arg Leu Glu Gln Ile Ser Ala Glu Ala Asn Ala Arg Thr Glu
    210                 215                 220

Glu Leu Lys Ser Glu Arg Asp Lys Val Asn Thr Leu Leu Thr Arg Leu
225                 230                 235                 240

Glu Ser Gln Glu Asn Ala Leu Ala Ser Arg Gln Gln His Leu Ala
                245                 250                 255

Thr Arg Glu Thr Leu Gln Gln Arg Leu Glu Gln Ala Ile Ala Asp Thr
            260                 265                 270

Gln Ala Arg Ala Gly Glu Ile Ala Leu Glu Arg Asp Arg Val Ser Ser
        275                 280                 285

Leu Thr Ala Arg Leu Glu Ser Gln Glu Lys Ala Ser Ser Glu Gln Leu
    290                 295                 300

Val Arg Met Gly Ser Glu Ile Ala Ser Leu Thr Glu Arg Cys Thr Gln
305                 310                 315                 320

Leu Glu Asn Gln Arg Asp Asp Ala Arg Leu Glu Thr Met Gly Glu Lys
                325                 330                 335

Glu Thr Val Ala Ala Leu Arg Gly Glu Ala Glu Ala Leu Lys Arg Gln
            340                 345                 350

Asn Gln Ser Leu Met Ala Ala Leu Ser Gly Asn Lys Gln Thr Gly Gly
        355                 360                 365

Gln Asn Ala
    370

<210> SEQ ID NO 51
<211> LENGTH: 371
<212> TYPE: PRT
<213> ORGANISM: Artificial Sequence
<220> FEATURE:
<223> OTHER INFORMATION: synthetic polypeptide

<400> SEQUENCE: 51

Met Arg Pro Ala Thr Tyr Glu Pro Glu Gln Ile Ile Glu Ala Gly Leu
1               5                   10                  15

Ala Leu Gln Ala Glu Gly Arg Asn Ile Thr Gly Phe Ala Leu Arg Asn
            20                  25                  30

Gln Val Gly Gly Gly Asn Pro Thr Arg Leu Arg Gln Ile Trp Asp Glu
        35                  40                  45

Tyr Gln Ala Ser Gln Ser Thr Val Val Thr Glu Pro Val Ala Glu Leu
    50                  55                  60

Pro Val Glu Val Ala Glu Val Lys Ala Val Ser Ala Ala Leu Ser
65                  70                  75                  80

Glu Arg Ile Thr Gln Leu Ala Thr Glu Leu Asn Asp Lys Ala Val Arg
                85                  90                  95

Ala Ala Glu Arg Arg Val Ala Glu Val Thr Arg Ala Ala Gly Glu Gln
            100                 105                 110

Thr Ala Gln Ala Glu Arg Glu Leu Ala Asp Ala Gln Thr Val Asp
        115                 120                 125

Asp Leu Glu Glu Lys Leu Asp Glu Leu Gln Asp Arg Tyr Asp Ser Leu
    130                 135                 140

Thr Leu Ala Leu Glu Ser Glu Arg Ser Leu Arg Gln Gln His Asp Val
145                 150                 155                 160

Glu Met Ala Gln Leu Lys Glu Arg Leu Ala Ala Ala Glu Glu Asn Thr
                165                 170                 175

Arg Gln Arg Glu Glu Arg Tyr Gln Glu Gln Lys Thr Val Leu Gln Asp
```

```
            180                 185                 190
Ala Leu Asn Ala Glu Gln Ala Gln His Lys Asn Thr Arg Glu Asp Leu
        195                 200                 205

Gln Lys Arg Leu Glu Gln Ile Ser Ala Glu Ala Asn Ala Arg Thr Glu
    210                 215                 220

Glu Leu Lys Ser Glu Glu Asp Lys Val Asn Thr Leu Leu Thr Arg Leu
225                 230                 235                 240

Glu Ser Gln Glu Asn Ala Leu Ala Ser Glu Gln Gln His Leu Ala
                245                 250                 255

Thr Arg Glu Thr Leu Gln Gln Arg Leu Glu Gln Ala Ile Ala Asp Thr
            260                 265                 270

Gln Ala Arg Ala Gly Glu Ile Ala Leu Glu Arg Asp Arg Val Ser Ser
        275                 280                 285

Leu Thr Ala Arg Leu Glu Ser Gln Glu Lys Ala Ser Ser Glu Gln Leu
        290                 295                 300

Val Arg Met Gly Ser Glu Ile Ala Ser Leu Thr Glu Arg Cys Thr Gln
305                 310                 315                 320

Leu Glu Asn Gln Arg Asp Asp Ala Arg Leu Glu Thr Met Gly Glu Lys
                325                 330                 335

Glu Thr Val Ala Ala Leu Arg Gly Glu Ala Glu Ala Leu Lys Arg Gln
            340                 345                 350

Asn Gln Ser Leu Met Ala Ala Leu Ser Gly Lys Gln Thr Gly Gly
        355                 360                 365

Gln Asn Ala
    370

<210> SEQ ID NO 52
<211> LENGTH: 371
<212> TYPE: PRT
<213> ORGANISM: Artificial Sequence
<220> FEATURE:
<223> OTHER INFORMATION: synthetic polypeptide

<400> SEQUENCE: 52

Met Arg Pro Ala Thr Tyr Glu Pro Glu Gln Ile Ile Glu Ala Gly Leu
1               5                   10                  15

Ala Leu Gln Ala Glu Gly Arg Asn Ile Thr Gly Phe Ala Leu Arg Asn
            20                  25                  30

Gln Val Gly Gly Gly Asn Pro Thr Arg Leu Arg Gln Ile Trp Asp Glu
        35                  40                  45

Tyr Gln Ala Ser Gln Ser Thr Val Val Thr Glu Pro Val Ala Glu Leu
    50                  55                  60

Pro Val Glu Val Ala Glu Glu Val Lys Ala Val Ser Ala Ala Leu Ser
65                  70                  75                  80

Glu Arg Ile Thr Gln Leu Ala Thr Glu Leu Asn Asp Lys Ala Val Arg
                85                  90                  95

Ala Ala Glu Arg Arg Val Ala Glu Val Thr Arg Ala Ala Gly Glu Gln
            100                 105                 110

Thr Ala Gln Ala Glu Arg Glu Leu Ala Asp Ala Ala Gln Thr Val Asp
        115                 120                 125

Asp Leu Glu Glu Lys Leu Asp Glu Leu Gln Asp Arg Tyr Asp Ser Leu
    130                 135                 140

Thr Leu Ala Leu Glu Ser Glu Arg Ser Leu Arg Gln Gln His Asp Val
145                 150                 155                 160

Glu Met Ala Gln Leu Lys Glu Arg Leu Ala Ala Ala Glu Glu Asn Thr
```

```
                    165                 170                 175
Arg Gln Arg Glu Glu Arg Tyr Gln Glu Gln Lys Thr Val Leu Gln Asp
            180                 185                 190

Ala Leu Asn Ala Glu Gln Ala Gln His Lys Asn Thr Arg Glu Asp Leu
        195                 200                 205

Gln Lys Arg Leu Glu Gln Ile Ser Ala Glu Ala Asn Ala Arg Thr Glu
    210                 215                 220

Glu Leu Lys Ser Arg Arg Asp Lys Val Asn Thr Leu Leu Thr Arg Leu
225                 230                 235                 240

Glu Ser Gln Glu Asn Ala Leu Ala Ser Arg Arg Gln Gln His Leu Ala
                245                 250                 255

Thr Arg Glu Thr Leu Gln Gln Arg Leu Glu Gln Ala Ile Ala Asp Thr
            260                 265                 270

Gln Ala Arg Ala Gly Glu Ile Ala Leu Glu Arg Asp Arg Val Ser Ser
        275                 280                 285

Leu Thr Ala Arg Leu Glu Ser Gln Glu Lys Ala Ser Ser Glu Gln Leu
    290                 295                 300

Val Arg Met Gly Ser Glu Ile Ala Ser Leu Thr Glu Arg Cys Thr Gln
305                 310                 315                 320

Leu Glu Asn Gln Arg Asp Asp Ala Arg Leu Glu Thr Met Gly Glu Lys
                325                 330                 335

Glu Thr Val Ala Ala Leu Arg Gly Glu Ala Glu Ala Leu Lys Arg Gln
            340                 345                 350

Asn Gln Ser Leu Met Ala Ala Leu Ser Gly Asn Lys Gln Thr Gly Gly
        355                 360                 365

Gln Asn Ala
    370

<210> SEQ ID NO 53
<211> LENGTH: 371
<212> TYPE: PRT
<213> ORGANISM: Artificial Sequence
<220> FEATURE:
<223> OTHER INFORMATION: synthetic polypeptide

<400> SEQUENCE: 53

Met Arg Pro Ala Thr Tyr Glu Pro Glu Gln Ile Ile Glu Ala Gly Leu
1               5                  10                  15

Ala Leu Gln Ala Glu Gly Arg Asn Ile Thr Gly Phe Ala Leu Arg Asn
            20                  25                  30

Gln Val Gly Gly Gly Asn Pro Thr Arg Leu Arg Gln Ile Trp Asp Glu
        35                  40                  45

Tyr Gln Ala Ser Gln Ser Thr Val Val Thr Glu Pro Val Ala Glu Leu
    50                  55                  60

Pro Val Glu Val Ala Glu Val Lys Ala Val Ser Ala Ala Leu Ser
65                  70                  75                  80

Glu Arg Ile Thr Gln Leu Ala Thr Glu Leu Asn Asp Lys Ala Val Arg
                85                  90                  95

Ala Ala Glu Arg Arg Val Ala Glu Val Thr Arg Ala Ala Gly Glu Gln
            100                 105                 110

Thr Ala Gln Ala Glu Arg Glu Leu Ala Asp Ala Gln Thr Val Asp
        115                 120                 125

Asp Leu Glu Glu Lys Leu Asp Glu Leu Gln Asp Arg Tyr Asp Ser Leu
    130                 135                 140

Thr Leu Ala Leu Glu Ser Glu Arg Ser Leu Arg Gln Gln His Asp Val
```

```
145                 150                 155                 160
Glu Met Ala Gln Leu Lys Glu Arg Leu Ala Ala Glu Glu Asn Thr
                165                 170                 175
Arg Gln Arg Glu Glu Arg Tyr Gln Glu Gln Lys Thr Val Leu Gln Asp
                180                 185                 190
Ala Leu Asn Ala Glu Gln Ala Gln His Lys Asn Thr Arg Glu Asp Leu
                195                 200                 205
Gln Lys Arg Leu Glu Gln Ile Ser Ala Glu Ala Asn Ala Arg Thr Glu
        210                 215                 220
Glu Leu Lys Ser Arg Arg Asp Lys Val Asn Thr Leu Leu Thr Arg Leu
225                 230                 235                 240
Glu Ser Gln Glu Asn Ala Leu Ala Ser Glu Gln Gln His Leu Ala
                245                 250                 255
Thr Arg Glu Thr Leu Gln Gln Arg Leu Glu Gln Ala Ile Ala Asp Thr
                260                 265                 270
Gln Ala Arg Ala Gly Glu Ile Ala Leu Glu Arg Asp Arg Val Ser Ser
            275                 280                 285
Leu Thr Ala Arg Leu Glu Ser Gln Glu Lys Ala Ser Ser Glu Gln Leu
        290                 295                 300
Val Arg Met Gly Ser Glu Ile Ala Ser Leu Thr Glu Arg Cys Thr Gln
305                 310                 315                 320
Leu Glu Asn Gln Arg Asp Asp Ala Arg Leu Glu Thr Met Gly Glu Lys
                325                 330                 335
Glu Thr Val Ala Ala Leu Arg Gly Glu Ala Glu Ala Leu Lys Arg Gln
                340                 345                 350
Asn Gln Ser Leu Met Ala Ala Leu Ser Gly Asn Lys Gln Thr Gly Gly
            355                 360                 365
Gln Asn Ala
    370

<210> SEQ ID NO 54
<211> LENGTH: 371
<212> TYPE: PRT
<213> ORGANISM: Artificial Sequence
<220> FEATURE:
<223> OTHER INFORMATION: synthetic polypeptide

<400> SEQUENCE: 54

Met Arg Pro Ala Thr Tyr Glu Pro Glu Gln Ile Ile Glu Ala Gly Leu
1               5                   10                  15
Ala Leu Gln Ala Glu Gly Arg Asn Ile Thr Gly Phe Ala Leu Arg Asn
                20                  25                  30
Gln Val Gly Gly Gly Asn Pro Thr Arg Leu Arg Gln Ile Trp Asp Glu
            35                  40                  45
Tyr Gln Ala Ser Gln Ser Thr Val Val Thr Glu Pro Val Ala Glu Leu
    50                  55                  60
Pro Val Glu Val Ala Glu Val Lys Ala Val Ser Ala Ala Leu Ser
65                  70                  75                  80
Glu Arg Ile Thr Gln Leu Ala Thr Glu Leu Asn Asp Lys Ala Val Arg
                85                  90                  95
Ala Ala Glu Arg Arg Val Ala Glu Thr Arg Ala Ala Gly Glu Gln
                100                 105                 110
Thr Ala Gln Ala Glu Arg Glu Leu Ala Asp Ala Ala Gln Thr Val Asp
            115                 120                 125
Asp Leu Glu Glu Lys Leu Asp Glu Leu Gln Asp Arg Tyr Asp Ser Leu
```

-continued

```
            130                 135                 140
Thr Leu Ala Leu Glu Ser Glu Arg Ser Leu Arg Gln Gln His Asp Val
145                 150                 155                 160

Glu Met Ala Gln Leu Lys Glu Arg Leu Ala Ala Glu Glu Asn Thr
                165                 170                 175

Arg Gln Arg Glu Glu Arg Tyr Gln Glu Gln Lys Thr Val Leu Gln Asp
                180                 185                 190

Ala Leu Asn Ala Glu Gln Ala Gln His Lys Asn Thr Arg Glu Asp Leu
                195                 200                 205

Gln Lys Arg Leu Glu Gln Ile Ser Ala Glu Ala Asn Ala Arg Thr Glu
210                 215                 220

Glu Leu Lys Ser Glu Glu Asp Lys Val Asn Thr Leu Leu Thr Arg Leu
225                 230                 235                 240

Glu Ser Gln Glu Asn Ala Leu Ala Ser Arg Arg Gln Gln His Leu Ala
                245                 250                 255

Thr Arg Glu Thr Leu Gln Gln Arg Leu Glu Gln Ala Ile Ala Asp Thr
                260                 265                 270

Gln Ala Arg Ala Gly Glu Ile Ala Leu Glu Arg Asp Arg Val Ser Ser
                275                 280                 285

Leu Thr Ala Arg Leu Glu Ser Gln Glu Lys Ala Ser Ser Glu Gln Leu
290                 295                 300

Val Arg Met Gly Ser Glu Ile Ala Ser Leu Thr Glu Arg Cys Thr Gln
305                 310                 315                 320

Leu Glu Asn Gln Arg Asp Asp Ala Arg Leu Glu Thr Met Gly Glu Lys
                325                 330                 335

Glu Thr Val Ala Ala Leu Arg Gly Glu Ala Glu Ala Leu Lys Arg Gln
                340                 345                 350

Asn Gln Ser Leu Met Ala Ala Leu Ser Gly Asn Lys Gln Thr Gly Gly
                355                 360                 365

Gln Asn Ala
    370

<210> SEQ ID NO 55
<211> LENGTH: 300
<212> TYPE: PRT
<213> ORGANISM: Artificial Sequence
<220> FEATURE:
<223> OTHER INFORMATION: synthetic polypeptide

<400> SEQUENCE: 55

Met Ala Glu Glu Val Lys Ala Val Ser Ala Leu Ser Glu Arg Ile
1               5                   10                  15

Thr Gln Leu Ala Thr Glu Leu Asn Asp Lys Ala Val Arg Ala Ala Glu
                20                  25                  30

Arg Arg Val Ala Glu Val Thr Arg Ala Ala Gly Glu Gln Thr Ala Gln
                35                  40                  45

Ala Glu Arg Glu Leu Ala Asp Ala Gln Thr Val Asp Asp Leu Glu
            50                  55                  60

Glu Lys Leu Asp Glu Leu Gln Asp Arg Tyr Asp Ser Leu Thr Leu Ala
65                  70                  75                  80

Leu Glu Ser Arg Arg Ser Leu Arg Gln Gln His Asp Val Glu Met Ala
                85                  90                  95

Gln Leu Lys Glu Arg Leu Ala Ala Ala Glu Glu Asn Thr Arg Gln Arg
                100                 105                 110

Glu Glu Arg Tyr Gln Glu Gln Lys Thr Val Leu Gln Asp Ala Leu Asn
```

```
            115                 120                 125
Ala Glu Gln Ala Gln His Lys Asn Thr Arg Glu Asp Leu Gln Lys Arg
    130                 135                 140

Leu Glu Gln Ile Ser Ala Glu Ala Asn Ala Arg Thr Glu Glu Leu Lys
145                 150                 155                 160

Ser Glu Arg Asp Lys Val Asn Thr Leu Leu Thr Arg Leu Glu Ser Gln
                165                 170                 175

Glu Asn Ala Leu Ala Ser Glu Arg Gln Gln His Leu Ala Thr Arg Glu
            180                 185                 190

Thr Leu Gln Gln Arg Leu Glu Gln Ala Ile Ala Asp Thr Gln Ala Arg
        195                 200                 205

Ala Gly Glu Ile Ala Leu Glu Arg Asp Arg Val Ser Ser Leu Thr Ala
    210                 215                 220

Arg Leu Glu Ser Gln Glu Lys Ala Ser Ser Glu Gln Leu Val Arg Met
225                 230                 235                 240

Gly Ser Glu Ile Ala Ser Leu Thr Glu Arg Cys Thr Gln Leu Glu Asn
                245                 250                 255

Gln Arg Asp Asp Ala Arg Leu Glu Thr Met Gly Glu Lys Glu Thr Val
            260                 265                 270

Ala Ala Leu Arg Gly Glu Ala Glu Ala Leu Lys Arg Gln Asn Gln Ser
        275                 280                 285

Leu Met Ala Ala Leu Gly His His His His His
    290                 295                 300

<210> SEQ ID NO 56
<211> LENGTH: 300
<212> TYPE: PRT
<213> ORGANISM: Artificial Sequence
<220> FEATURE:
<223> OTHER INFORMATION: synthetic polypeptide

<400> SEQUENCE: 56

Met Ala Glu Glu Val Lys Ala Val Ser Ala Ala Leu Ser Glu Arg Ile
1               5                   10                  15

Thr Gln Leu Ala Thr Glu Leu Asn Asp Lys Ala Val Arg Ala Ala Glu
            20                  25                  30

Arg Arg Val Ala Glu Val Thr Arg Ala Ala Gly Glu Gln Thr Ala Gln
        35                  40                  45

Ala Glu Arg Glu Leu Ala Asp Ala Ala Gln Thr Val Asp Asp Leu Glu
    50                  55                  60

Glu Lys Leu Asp Glu Leu Gln Asp Arg Tyr Asp Ser Leu Thr Leu Ala
65                  70                  75                  80

Leu Glu Ser Glu Glu Ser Leu Arg Gln Gln His Asp Val Glu Met Ala
                85                  90                  95

Gln Leu Lys Glu Arg Leu Ala Ala Ala Glu Glu Asn Thr Arg Gln Arg
            100                 105                 110

Glu Glu Arg Tyr Gln Gln Lys Thr Val Leu Gln Asp Ala Leu Asn
        115                 120                 125

Ala Glu Gln Ala Gln His Lys Asn Thr Arg Glu Asp Leu Gln Lys Arg
    130                 135                 140

Leu Glu Gln Ile Ser Ala Glu Ala Asn Ala Arg Thr Glu Glu Leu Lys
145                 150                 155                 160

Ser Glu Arg Asp Lys Val Asn Thr Leu Leu Thr Arg Leu Glu Ser Gln
                165                 170                 175

Glu Asn Ala Leu Ala Ser Glu Arg Gln Gln His Leu Ala Thr Arg Glu
```

```
                180                 185                 190
Thr Leu Gln Gln Arg Leu Glu Gln Ala Ile Ala Asp Thr Gln Ala Arg
        195                 200                 205
Ala Gly Glu Ile Ala Leu Glu Arg Asp Arg Val Ser Ser Leu Thr Ala
        210                 215                 220
Arg Leu Glu Ser Gln Glu Lys Ala Ser Ser Glu Gln Leu Val Arg Met
225                 230                 235                 240
Gly Ser Glu Ile Ala Ser Leu Thr Glu Arg Cys Thr Gln Leu Glu Asn
                245                 250                 255
Gln Arg Asp Asp Ala Arg Leu Glu Thr Met Gly Glu Lys Glu Thr Val
            260                 265                 270
Ala Ala Leu Arg Gly Glu Ala Glu Ala Leu Lys Arg Gln Asn Gln Ser
        275                 280                 285
Leu Met Ala Ala Leu Gly His His His His His
        290                 295                 300

<210> SEQ ID NO 57
<211> LENGTH: 300
<212> TYPE: PRT
<213> ORGANISM: Artificial Sequence
<220> FEATURE:
<223> OTHER INFORMATION: synthetic polypeptide

<400> SEQUENCE: 57

Met Ala Glu Glu Val Lys Ala Val Ser Ala Ala Leu Ser Glu Arg Ile
1               5                   10                  15
Thr Gln Leu Ala Thr Glu Leu Asn Asp Lys Ala Val Arg Ala Ala Glu
            20                  25                  30
Arg Arg Val Ala Glu Val Thr Arg Ala Ala Gly Glu Gln Thr Ala Gln
        35                  40                  45
Ala Glu Arg Glu Leu Ala Asp Ala Gln Thr Val Asp Asp Leu Glu
    50                  55                  60
Glu Lys Leu Asp Glu Leu Gln Asp Arg Tyr Asp Ser Leu Thr Leu Ala
65                  70                  75                  80
Leu Glu Ser Glu Arg Ser Leu Arg Gln Gln His Asp Val Glu Met Ala
                85                  90                  95
Gln Leu Lys Glu Glu Leu Ala Ala Glu Glu Asn Thr Arg Gln Arg
            100                 105                 110
Glu Glu Arg Tyr Gln Glu Gln Lys Thr Val Leu Gln Asp Ala Leu Asn
        115                 120                 125
Ala Glu Gln Ala Gln His Lys Asn Thr Arg Glu Asp Leu Gln Lys Arg
    130                 135                 140
Leu Glu Gln Ile Ser Ala Glu Ala Asn Ala Arg Thr Glu Glu Leu Lys
145                 150                 155                 160
Ser Glu Arg Asp Lys Val Asn Thr Leu Leu Thr Arg Leu Glu Ser Gln
                165                 170                 175
Glu Asn Ala Leu Ala Ser Glu Arg Gln Gln His Leu Ala Thr Arg Glu
            180                 185                 190
Thr Leu Gln Gln Arg Leu Glu Gln Ala Ile Ala Asp Thr Gln Ala Arg
        195                 200                 205
Ala Gly Glu Ile Ala Leu Glu Arg Asp Arg Val Ser Ser Leu Thr Ala
        210                 215                 220
Arg Leu Glu Ser Gln Glu Lys Ala Ser Ser Glu Gln Leu Val Arg Met
225                 230                 235                 240
Gly Ser Glu Ile Ala Ser Leu Thr Glu Arg Cys Thr Gln Leu Glu Asn
```

```
                        245                 250                 255
Gln Arg Asp Asp Ala Arg Leu Glu Thr Met Gly Glu Lys Glu Thr Val
            260                 265                 270
Ala Ala Leu Arg Gly Glu Ala Glu Ala Leu Lys Arg Gln Asn Gln Ser
            275                 280                 285
Leu Met Ala Ala Leu Gly His His His His His
            290                 295                 300

<210> SEQ ID NO 58
<211> LENGTH: 300
<212> TYPE: PRT
<213> ORGANISM: Artificial Sequence
<220> FEATURE:
<223> OTHER INFORMATION: synthetic polypeptide

<400> SEQUENCE: 58

Met Ala Glu Glu Val Lys Ala Val Ser Ala Ala Leu Ser Glu Arg Ile
1               5                   10                  15
Thr Gln Leu Ala Thr Glu Leu Asn Asp Lys Ala Val Arg Ala Ala Glu
            20                  25                  30
Arg Arg Val Ala Glu Val Thr Arg Ala Ala Gly Glu Gln Thr Ala Gln
        35                  40                  45
Ala Glu Arg Glu Leu Ala Asp Ala Ala Gln Thr Val Asp Asp Leu Glu
    50                  55                  60
Glu Lys Leu Asp Glu Leu Gln Asp Arg Tyr Asp Ser Leu Thr Leu Ala
65                  70                  75                  80
Leu Glu Ser Glu Arg Ser Leu Arg Gln Gln His Asp Val Glu Met Ala
                85                  90                  95
Gln Leu Lys Glu Arg Leu Ala Ala Arg Glu Asn Thr Arg Gln Arg
            100                 105                 110
Glu Glu Arg Tyr Gln Glu Gln Lys Thr Val Leu Gln Asp Ala Leu Asn
        115                 120                 125
Ala Glu Gln Ala Gln His Lys Asn Thr Arg Glu Asp Leu Gln Lys Arg
    130                 135                 140
Leu Glu Gln Ile Ser Ala Glu Ala Asn Ala Arg Thr Glu Glu Leu Lys
145                 150                 155                 160
Ser Glu Arg Asp Lys Val Asn Thr Leu Leu Thr Arg Leu Glu Ser Gln
                165                 170                 175
Glu Asn Ala Leu Ala Ser Glu Arg Gln Gln His Leu Ala Thr Arg Glu
            180                 185                 190
Thr Leu Gln Gln Arg Leu Glu Gln Ala Ile Ala Asp Thr Gln Ala Arg
        195                 200                 205
Ala Gly Glu Ile Ala Leu Glu Arg Asp Arg Val Ser Ser Leu Thr Ala
    210                 215                 220
Arg Leu Glu Ser Gln Glu Lys Ala Ser Ser Glu Gln Leu Val Arg Met
225                 230                 235                 240
Gly Ser Glu Ile Ala Ser Leu Thr Glu Arg Cys Thr Gln Leu Glu Asn
                245                 250                 255
Gln Arg Asp Asp Ala Arg Leu Glu Thr Met Gly Glu Lys Glu Thr Val
            260                 265                 270
Ala Ala Leu Arg Gly Glu Ala Glu Ala Leu Lys Arg Gln Asn Gln Ser
            275                 280                 285
Leu Met Ala Ala Leu Gly His His His His His
            290                 295                 300
```

```
<210> SEQ ID NO 59
<211> LENGTH: 300
<212> TYPE: PRT
<213> ORGANISM: Artificial Sequence
<220> FEATURE:
<223> OTHER INFORMATION: synthetic polypeptide

<400> SEQUENCE: 59

Met Ala Glu Val Lys Ala Val Ser Ala Ala Leu Ser Glu Arg Ile
1               5                   10                  15

Thr Gln Leu Ala Thr Glu Leu Asn Asp Lys Ala Val Arg Ala Ala Glu
            20                  25                  30

Arg Arg Val Ala Glu Val Thr Arg Ala Ala Gly Glu Gln Thr Ala Gln
        35                  40                  45

Ala Glu Arg Glu Leu Ala Asp Ala Ala Gln Thr Val Asp Asp Leu Glu
    50                  55                  60

Glu Lys Leu Asp Glu Leu Gln Asp Arg Tyr Asp Ser Leu Thr Leu Ala
65                  70                  75                  80

Leu Glu Ser Glu Arg Ser Leu Arg Gln Gln His Asp Val Glu Met Ala
                85                  90                  95

Gln Leu Lys Glu Arg Leu Ala Ala Ala Glu Glu Asn Thr Arg Gln Glu
            100                 105                 110

Glu Glu Arg Tyr Gln Glu Gln Lys Thr Val Leu Gln Asp Ala Leu Asn
        115                 120                 125

Ala Glu Gln Ala Gln His Lys Asn Thr Arg Glu Asp Leu Gln Lys Arg
    130                 135                 140

Leu Glu Gln Ile Ser Ala Glu Ala Asn Ala Arg Thr Glu Glu Leu Lys
145                 150                 155                 160

Ser Glu Arg Asp Lys Val Asn Thr Leu Leu Thr Arg Leu Glu Ser Gln
                165                 170                 175

Glu Asn Ala Leu Ala Ser Glu Arg Gln Gln His Leu Ala Thr Arg Glu
            180                 185                 190

Thr Leu Gln Gln Arg Leu Glu Gln Ala Ile Ala Asp Thr Gln Ala Arg
        195                 200                 205

Ala Gly Glu Ile Ala Leu Glu Arg Asp Arg Val Ser Ser Leu Thr Ala
    210                 215                 220

Arg Leu Glu Ser Gln Glu Lys Ala Ser Ser Glu Gln Leu Val Arg Met
225                 230                 235                 240

Gly Ser Glu Ile Ala Ser Leu Thr Glu Arg Cys Thr Gln Leu Glu Asn
                245                 250                 255

Gln Arg Asp Asp Ala Arg Leu Glu Thr Met Gly Glu Lys Glu Thr Val
            260                 265                 270

Ala Ala Leu Arg Gly Glu Ala Glu Leu Lys Arg Gln Asn Gln Ser
        275                 280                 285

Leu Met Ala Ala Leu Gly His His His His His His
    290                 295                 300

<210> SEQ ID NO 60
<211> LENGTH: 300
<212> TYPE: PRT
<213> ORGANISM: Artificial Sequence
<220> FEATURE:
<223> OTHER INFORMATION: synthetic polypeptide

<400> SEQUENCE: 60

Met Ala Glu Val Lys Ala Val Ser Ala Ala Leu Ser Glu Arg Ile
1               5                   10                  15
```

Thr Gln Leu Ala Thr Glu Leu Asn Asp Lys Ala Val Arg Ala Ala Glu
            20                  25                  30

Arg Arg Val Ala Glu Val Thr Arg Ala Ala Gly Glu Gln Thr Ala Gln
        35                  40                  45

Ala Glu Arg Glu Leu Ala Asp Ala Ala Gln Thr Val Asp Asp Leu Glu
    50                  55                  60

Glu Lys Leu Asp Glu Leu Gln Asp Arg Tyr Asp Ser Leu Thr Leu Ala
65                  70                  75                  80

Leu Glu Ser Glu Arg Ser Leu Arg Gln Gln His Asp Val Glu Met Ala
                85                  90                  95

Gln Leu Lys Glu Arg Leu Ala Ala Glu Glu Asn Thr Arg Gln Arg
            100                 105                 110

Arg Glu Arg Tyr Gln Glu Gln Lys Thr Val Leu Gln Asp Ala Leu Asn
        115                 120                 125

Ala Glu Gln Ala Gln His Lys Asn Thr Arg Glu Asp Leu Gln Lys Arg
    130                 135                 140

Leu Glu Gln Ile Ser Ala Glu Ala Asn Ala Arg Thr Glu Glu Leu Lys
145                 150                 155                 160

Ser Glu Arg Asp Lys Val Asn Thr Leu Leu Thr Arg Leu Glu Ser Gln
                165                 170                 175

Glu Asn Ala Leu Ala Ser Glu Arg Gln Gln His Leu Ala Thr Arg Glu
            180                 185                 190

Thr Leu Gln Gln Arg Leu Glu Gln Ala Ile Ala Asp Thr Gln Ala Arg
        195                 200                 205

Ala Gly Glu Ile Ala Leu Glu Arg Asp Arg Val Ser Ser Leu Thr Ala
    210                 215                 220

Arg Leu Glu Ser Gln Glu Lys Ala Ser Ser Glu Gln Leu Val Arg Met
225                 230                 235                 240

Gly Ser Glu Ile Ala Ser Leu Thr Glu Arg Cys Thr Gln Leu Glu Asn
                245                 250                 255

Gln Arg Asp Asp Ala Arg Leu Glu Thr Met Gly Glu Lys Glu Thr Val
            260                 265                 270

Ala Ala Leu Arg Gly Glu Ala Glu Ala Leu Lys Arg Gln Asn Gln Ser
        275                 280                 285

Leu Met Ala Ala Leu Gly His His His His His His
    290                 295                 300

<210> SEQ ID NO 61
<211> LENGTH: 300
<212> TYPE: PRT
<213> ORGANISM: Artificial Sequence
<220> FEATURE:
<223> OTHER INFORMATION: synthetic polypeptide

<400> SEQUENCE: 61

Met Ala Glu Glu Val Lys Ala Val Ser Ala Ala Leu Ser Glu Arg Ile
1               5                   10                  15

Thr Gln Leu Ala Thr Glu Leu Asn Asp Lys Ala Val Arg Ala Ala Glu
            20                  25                  30

Arg Arg Val Ala Glu Val Thr Arg Ala Ala Gly Glu Gln Thr Ala Gln
        35                  40                  45

Ala Glu Arg Glu Leu Ala Asp Ala Ala Gln Thr Val Asp Asp Leu Glu
    50                  55                  60

Glu Lys Leu Asp Glu Leu Gln Asp Arg Tyr Asp Ser Leu Thr Leu Ala
65                  70                  75                  80

```
Leu Glu Ser Glu Arg Ser Leu Arg Gln Gln His Asp Val Glu Met Ala
                85                  90                  95
Gln Leu Lys Glu Arg Leu Ala Ala Ala Glu Glu Asn Thr Arg Gln Arg
            100                 105                 110
Glu Glu Arg Tyr Gln Glu Gln Lys Thr Val Leu Gln Asp Ala Leu Asn
            115                 120                 125
Ala Glu Gln Ala Gln His Lys Asn Thr Arg Glu Asp Leu Gln Lys Arg
        130                 135                 140
Leu Glu Gln Ile Ser Ala Ala Asn Ala Arg Thr Glu Arg Leu Lys
145                 150                 155                 160
Ser Glu Arg Asp Lys Val Asn Thr Leu Leu Thr Arg Leu Glu Ser Gln
                165                 170                 175
Glu Asn Ala Leu Ala Ser Glu Arg Gln Gln His Leu Ala Thr Arg Glu
            180                 185                 190
Thr Leu Gln Gln Arg Leu Glu Gln Ala Ile Ala Asp Thr Gln Ala Arg
            195                 200                 205
Ala Gly Glu Ile Ala Leu Glu Arg Asp Arg Val Ser Ser Leu Thr Ala
        210                 215                 220
Arg Leu Glu Ser Gln Glu Lys Ala Ser Ser Glu Gln Leu Val Arg Met
225                 230                 235                 240
Gly Ser Glu Ile Ala Ser Leu Thr Glu Arg Cys Thr Gln Leu Glu Asn
                245                 250                 255
Gln Arg Asp Asp Ala Arg Leu Glu Thr Met Gly Glu Lys Glu Thr Val
            260                 265                 270
Ala Ala Leu Arg Gly Glu Ala Glu Ala Leu Lys Arg Gln Asn Gln Ser
        275                 280                 285
Leu Met Ala Ala Leu Gly His His His His His His
    290                 295                 300
```

<210> SEQ ID NO 62
<211> LENGTH: 300
<212> TYPE: PRT
<213> ORGANISM: Artificial Sequence
<220> FEATURE:
<223> OTHER INFORMATION: synthetic polypeptide

<400> SEQUENCE: 62

```
Met Ala Glu Glu Val Lys Ala Val Ser Ala Ala Leu Ser Glu Arg Ile
1               5                   10                  15
Thr Gln Leu Ala Thr Glu Leu Asn Asp Lys Ala Val Arg Ala Ala Glu
            20                  25                  30
Arg Arg Val Ala Glu Val Thr Arg Ala Ala Gly Glu Gln Thr Ala Gln
            35                  40                  45
Ala Glu Arg Glu Leu Ala Asp Ala Ala Gln Thr Val Asp Asp Leu Glu
        50                  55                  60
Glu Lys Leu Asp Glu Leu Gln Asp Arg Tyr Asp Ser Leu Thr Leu Ala
65                  70                  75                  80
Leu Glu Ser Glu Arg Ser Leu Arg Gln Gln His Asp Val Glu Met Ala
                85                  90                  95
Gln Leu Lys Glu Arg Leu Ala Ala Ala Glu Glu Asn Thr Arg Gln Arg
            100                 105                 110
Glu Glu Arg Tyr Gln Glu Gln Lys Thr Val Leu Gln Asp Ala Leu Asn
            115                 120                 125
Ala Glu Gln Ala Gln His Lys Asn Thr Arg Glu Asp Leu Gln Lys Arg
        130                 135                 140
```

```
Leu Glu Gln Ile Ser Ala Glu Ala Asn Ala Arg Thr Glu Glu Leu Lys
145                 150                 155                 160

Ser Glu Glu Asp Lys Val Asn Thr Leu Leu Thr Arg Leu Glu Ser Gln
                165                 170                 175

Glu Asn Ala Leu Ala Ser Glu Arg Gln Gln His Leu Ala Thr Arg Glu
            180                 185                 190

Thr Leu Gln Gln Arg Leu Glu Gln Ala Ile Ala Asp Thr Gln Ala Arg
        195                 200                 205

Ala Gly Glu Ile Ala Leu Glu Arg Asp Arg Val Ser Ser Leu Thr Ala
    210                 215                 220

Arg Leu Glu Ser Gln Glu Lys Ala Ser Ser Glu Gln Leu Val Arg Met
225                 230                 235                 240

Gly Ser Glu Ile Ala Ser Leu Thr Glu Arg Cys Thr Gln Leu Glu Asn
                245                 250                 255

Gln Arg Asp Asp Ala Arg Leu Glu Thr Met Gly Glu Lys Glu Thr Val
            260                 265                 270

Ala Ala Leu Arg Gly Ala Glu Ala Leu Lys Arg Gln Asn Gln Ser
        275                 280                 285

Leu Met Ala Ala Leu Gly His His His His His
    290                 295                 300

<210> SEQ ID NO 63
<211> LENGTH: 300
<212> TYPE: PRT
<213> ORGANISM: Artificial Sequence
<220> FEATURE:
<223> OTHER INFORMATION: synthetic polypeptide

<400> SEQUENCE: 63

Met Ala Glu Glu Val Lys Ala Val Ser Ala Ala Leu Ser Glu Arg Ile
1               5                   10                  15

Thr Gln Leu Ala Thr Glu Leu Asn Asp Lys Ala Val Arg Ala Ala Glu
            20                  25                  30

Arg Arg Val Ala Glu Val Thr Arg Ala Ala Gly Glu Gln Thr Ala Gln
        35                  40                  45

Ala Glu Arg Glu Leu Ala Asp Ala Ala Gln Thr Val Asp Asp Leu Glu
    50                  55                  60

Glu Lys Leu Asp Glu Leu Gln Asp Arg Tyr Asp Ser Leu Thr Leu Ala
65                  70                  75                  80

Leu Glu Ser Glu Arg Ser Leu Arg Gln Gln His Asp Val Glu Met Ala
                85                  90                  95

Gln Leu Lys Glu Arg Leu Ala Ala Ala Glu Glu Asn Thr Arg Gln Arg
            100                 105                 110

Glu Glu Arg Tyr Gln Glu Gln Lys Thr Val Leu Gln Asp Ala Leu Asn
        115                 120                 125

Ala Glu Gln Ala Gln His Lys Asn Thr Arg Glu Asp Leu Gln Lys Arg
    130                 135                 140

Leu Glu Gln Ile Ser Ala Glu Ala Asn Ala Arg Thr Glu Glu Leu Lys
145                 150                 155                 160

Ser Arg Arg Asp Lys Val Asn Thr Leu Leu Thr Arg Leu Glu Ser Gln
                165                 170                 175

Glu Asn Ala Leu Ala Ser Glu Arg Gln Gln His Leu Ala Thr Arg Glu
            180                 185                 190

Thr Leu Gln Gln Arg Leu Glu Gln Ala Ile Ala Asp Thr Gln Ala Arg
        195                 200                 205
```

```
Ala Gly Glu Ile Ala Leu Glu Arg Asp Arg Val Ser Ser Leu Thr Ala
    210                 215                 220

Arg Leu Glu Ser Gln Glu Lys Ala Ser Ser Glu Gln Leu Val Arg Met
225                 230                 235                 240

Gly Ser Glu Ile Ala Ser Leu Thr Glu Arg Cys Thr Gln Leu Glu Asn
                245                 250                 255

Gln Arg Asp Asp Ala Arg Leu Glu Thr Met Gly Glu Lys Glu Thr Val
            260                 265                 270

Ala Ala Leu Arg Gly Glu Ala Glu Ala Leu Lys Arg Gln Asn Gln Ser
        275                 280                 285

Leu Met Ala Ala Leu Gly His His His His His
        290                 295                 300
```

<210> SEQ ID NO 64
<211> LENGTH: 300
<212> TYPE: PRT
<213> ORGANISM: Artificial Sequence
<220> FEATURE:
<223> OTHER INFORMATION: synthetic polypeptide

<400> SEQUENCE: 64

```
Met Ala Glu Glu Val Lys Ala Val Ser Ala Ala Leu Ser Glu Arg Ile
1               5                   10                  15

Thr Gln Leu Ala Thr Glu Leu Asn Asp Lys Ala Val Arg Ala Ala Glu
            20                  25                  30

Arg Arg Val Ala Glu Val Thr Arg Ala Ala Gly Glu Gln Thr Ala Gln
        35                  40                  45

Ala Glu Arg Glu Leu Ala Asp Ala Ala Gln Thr Val Asp Asp Leu Glu
    50                  55                  60

Glu Lys Leu Asp Glu Leu Gln Asp Arg Tyr Asp Ser Leu Thr Leu Ala
65                  70                  75                  80

Leu Glu Ser Glu Arg Ser Leu Arg Gln Gln His Asp Val Glu Met Ala
                85                  90                  95

Gln Leu Lys Glu Arg Leu Ala Ala Ala Glu Glu Asn Thr Arg Gln Arg
            100                 105                 110

Glu Glu Arg Tyr Gln Glu Gln Lys Thr Val Leu Gln Asp Ala Leu Asn
        115                 120                 125

Ala Glu Gln Ala Gln His Lys Asn Thr Arg Glu Asp Leu Gln Lys Arg
    130                 135                 140

Leu Glu Gln Ile Ser Ala Glu Ala Asn Ala Arg Thr Glu Glu Leu Lys
145                 150                 155                 160

Ser Glu Arg Asp Lys Val Asn Thr Leu Leu Thr Arg Leu Glu Ser Gln
                165                 170                 175

Glu Asn Ala Leu Ala Ser Arg Gln Gln His Leu Ala Thr Arg Glu
            180                 185                 190

Thr Leu Gln Gln Arg Leu Glu Gln Ala Ile Ala Asp Thr Gln Ala Arg
        195                 200                 205

Ala Gly Glu Ile Ala Leu Glu Arg Asp Arg Val Ser Ser Leu Thr Ala
    210                 215                 220

Arg Leu Glu Ser Gln Glu Lys Ala Ser Ser Glu Gln Leu Val Arg Met
225                 230                 235                 240

Gly Ser Glu Ile Ala Ser Leu Thr Glu Arg Cys Thr Gln Leu Glu Asn
                245                 250                 255

Gln Arg Asp Asp Ala Arg Leu Glu Thr Met Gly Glu Lys Glu Thr Val
            260                 265                 270
```

Ala Ala Leu Arg Gly Glu Ala Glu Ala Leu Lys Arg Gln Asn Gln Ser
            275                 280                 285

Leu Met Ala Ala Leu Gly His His His His His
    290                 295                 300

<210> SEQ ID NO 65
<211> LENGTH: 300
<212> TYPE: PRT
<213> ORGANISM: Artificial Sequence
<220> FEATURE:
<223> OTHER INFORMATION: synthetic polypeptide

<400> SEQUENCE: 65

Met Ala Glu Glu Val Lys Ala Val Ser Ala Ala Leu Ser Glu Arg Ile
1               5                   10                  15

Thr Gln Leu Ala Thr Glu Leu Asn Asp Lys Ala Val Arg Ala Ala Glu
            20                  25                  30

Arg Arg Val Ala Glu Val Thr Arg Ala Ala Gly Glu Gln Thr Ala Gln
        35                  40                  45

Ala Glu Arg Glu Leu Ala Asp Ala Gln Thr Val Asp Asp Leu Glu
    50                  55                  60

Glu Lys Leu Asp Glu Leu Gln Asp Arg Tyr Asp Ser Leu Thr Leu Ala
65                  70                  75                  80

Leu Glu Ser Glu Arg Ser Leu Arg Gln Gln His Asp Val Glu Met Ala
                85                  90                  95

Gln Leu Lys Glu Arg Leu Ala Ala Glu Glu Asn Thr Arg Gln Arg
            100                 105                 110

Glu Glu Arg Tyr Gln Glu Gln Lys Thr Val Leu Gln Asp Ala Leu Asn
        115                 120                 125

Ala Glu Gln Ala Gln His Lys Asn Thr Arg Glu Asp Leu Gln Lys Arg
    130                 135                 140

Leu Glu Gln Ile Ser Ala Glu Ala Asn Ala Arg Thr Glu Glu Leu Lys
145                 150                 155                 160

Ser Glu Arg Asp Lys Val Asn Thr Leu Leu Thr Arg Leu Glu Ser Gln
                165                 170                 175

Glu Asn Ala Leu Ala Ser Glu Glu Gln Gln His Leu Ala Thr Arg Glu
            180                 185                 190

Thr Leu Gln Gln Arg Leu Glu Gln Ala Ile Ala Asp Thr Gln Ala Arg
        195                 200                 205

Ala Gly Glu Ile Ala Leu Glu Arg Asp Arg Val Ser Ser Leu Thr Ala
    210                 215                 220

Arg Leu Glu Ser Gln Glu Lys Ala Ser Ser Glu Gln Leu Val Arg Met
225                 230                 235                 240

Gly Ser Glu Ile Ala Ser Leu Thr Glu Arg Cys Thr Gln Leu Glu Asn
                245                 250                 255

Gln Arg Asp Asp Ala Arg Leu Glu Thr Met Gly Glu Lys Glu Thr Val
            260                 265                 270

Ala Ala Leu Arg Gly Glu Ala Glu Ala Leu Lys Arg Gln Asn Gln Ser
        275                 280                 285

Leu Met Ala Ala Leu Gly His His His His His
    290                 295                 300

<210> SEQ ID NO 66
<211> LENGTH: 396
<212> TYPE: PRT
<213> ORGANISM: Artificial Sequence
<220> FEATURE:

<223> OTHER INFORMATION: synthetic polypeptide

<400> SEQUENCE: 66

```
Met Leu Cys Cys Met Arg Arg Thr Lys Gln Val Glu Lys Asn Asp Glu
1               5                   10                  15

Asp Gln Lys Ile Gly Gly Ser Gly Gly Ser Arg Pro Ala Thr Tyr Glu
            20                  25                  30

Pro Glu Gln Ile Ile Glu Ala Gly Leu Ala Leu Gln Ala Glu Gly Arg
        35                  40                  45

Asn Ile Thr Gly Phe Ala Leu Arg Asn Gln Val Gly Gly Asn Pro
    50                  55                  60

Thr Arg Leu Arg Gln Ile Trp Asp Glu Tyr Gln Ala Ser Gln Ser Thr
65                  70                  75                  80

Val Val Thr Glu Pro Val Ala Glu Leu Pro Val Glu Val Ala Glu Glu
                85                  90                  95

Val Lys Ala Val Ser Ala Ala Leu Ser Glu Arg Ile Thr Gln Leu Ala
            100                 105                 110

Thr Glu Leu Asn Asp Lys Ala Val Arg Ala Ala Glu Arg Val Ala
        115                 120                 125

Glu Val Thr Arg Ala Ala Gly Glu Gln Thr Ala Gln Ala Glu Arg Glu
130                 135                 140

Leu Ala Asp Ala Ala Gln Thr Val Asp Leu Glu Glu Lys Leu Val
145                 150                 155                 160

Glu Leu Gln Asp Arg Tyr Asp Ser Leu Thr Leu Ala Leu Glu Ser Glu
                165                 170                 175

Arg Ser Leu Arg Gln Gln His Asp Val Glu Met Ala Gln Leu Lys Glu
            180                 185                 190

Arg Leu Ala Ala Ala Glu Glu Asn Thr Arg Gln Arg Arg Glu Arg Tyr
        195                 200                 205

Gln Glu Gln Lys Thr Val Leu Gln Asp Ala Leu Asn Ala Glu Gln Ala
    210                 215                 220

Gln His Lys Asn Thr Arg Glu Asp Leu Gln Lys Arg Leu Glu Gln Ile
225                 230                 235                 240

Ser Val Glu Ala Asn Ala Arg Thr Glu Glu Leu Lys Ser Glu Arg Asp
                245                 250                 255

Lys Val Asn Thr Phe Leu Thr Arg Leu Glu Ser Gln Glu Asn Ala Leu
            260                 265                 270

Ala Ser Arg Arg Gln Gln His Leu Ala Thr Arg Glu Thr Leu Gln Gln
        275                 280                 285

Arg Leu Glu Gln Ala Ile Ala Asp Thr Gln Ala Arg Ala Gly Glu Ile
    290                 295                 300

Ala Leu Glu Arg Asp Arg Val Ser Ser Leu Thr Ala Arg Leu Glu Ser
305                 310                 315                 320

Gln Glu Lys Ala Ser Ser Glu Gln Leu Val Arg Met Gly Ser Glu Ile
                325                 330                 335

Ala Ser Leu Thr Glu Arg Cys Thr Gln Leu Glu Asn Gln Arg Asp Asp
            340                 345                 350

Ala Arg Leu Glu Thr Met Gly Glu Lys Glu Thr Val Ala Ala Leu Arg
        355                 360                 365

Gly Glu Ala Glu Ala Leu Lys Arg Gln Asn Gln Ser Leu Met Ala Ala
    370                 375                 380

Leu Ser Gly Asn Lys Gln Thr Gly Gly Gln Asn Ala
385                 390                 395
```

<210> SEQ ID NO 67
<211> LENGTH: 628
<212> TYPE: PRT
<213> ORGANISM: Artificial Sequence
<220> FEATURE:
<223> OTHER INFORMATION: synthetic polypeptide

<400> SEQUENCE: 67

```
Met Arg Pro Ala Thr Tyr Glu Pro Glu Gln Ile Ile Glu Ala Gly Leu
1               5                   10                  15

Ala Leu Gln Ala Glu Gly Arg Asn Ile Thr Gly Phe Ala Leu Arg Asn
            20                  25                  30

Gln Val Gly Gly Asn Pro Thr Arg Leu Arg Gln Ile Trp Asp Glu
        35                  40                  45

Tyr Gln Ala Ser Gln Ser Thr Val Val Thr Glu Pro Val Ala Glu Leu
    50                  55                  60

Pro Val Glu Val Ala Glu Val Lys Ala Val Ser Ala Ala Leu Ser
65                  70                  75                  80

Glu Arg Ile Thr Gln Leu Ala Thr Glu Leu Asn Asp Lys Ala Val Arg
                85                  90                  95

Ala Ala Glu Arg Arg Val Ala Glu Val Thr Arg Ala Ala Gly Glu Gln
            100                 105                 110

Thr Ala Gln Ala Glu Arg Glu Leu Ala Asp Ala Ala Gln Thr Val Asp
        115                 120                 125

Asp Leu Glu Glu Lys Leu Val Glu Leu Gln Asp Arg Tyr Asp Ser Leu
    130                 135                 140

Thr Leu Ala Leu Glu Ser Glu Arg Ser Leu Arg Gln Gln His Asp Val
145                 150                 155                 160

Glu Met Ala Gln Leu Lys Glu Arg Leu Ala Ala Ala Glu Glu Asn Thr
                165                 170                 175

Arg Gln Glu Glu Glu Arg Tyr Gln Glu Gln Lys Thr Val Leu Gln Asp
            180                 185                 190

Ala Leu Asn Ala Glu Gln Ala Gln His Lys Asn Thr Arg Glu Asp Leu
        195                 200                 205

Gln Lys Arg Leu Glu Gln Ile Ser Val Glu Ala Asn Ala Arg Thr Glu
    210                 215                 220

Glu Leu Lys Ser Glu Arg Asp Lys Val Asn Thr Phe Leu Thr Arg Leu
225                 230                 235                 240

Glu Ser Gln Glu Asn Ala Leu Ala Ser Glu Glu Gln His Leu Ala
                245                 250                 255

Thr Arg Glu Thr Leu Gln Arg Leu Glu Gln Ala Ile Ala Asp Thr
            260                 265                 270

Gln Ala Arg Ala Gly Glu Ile Ala Leu Glu Arg Asp Arg Val Ser Ser
        275                 280                 285

Leu Thr Ala Arg Leu Glu Ser Gln Glu Lys Ala Ser Ser Glu Gln Leu
    290                 295                 300

Val Arg Met Gly Ser Glu Ile Ala Ser Leu Thr Glu Arg Cys Thr Gln
305                 310                 315                 320

Leu Glu Asn Gln Arg Asp Asp Ala Arg Leu Glu Thr Met Gly Glu Lys
                325                 330                 335

Glu Thr Val Ala Ala Leu Arg Gly Glu Ala Glu Ala Leu Lys Arg Gln
            340                 345                 350

Asn Gln Ser Leu Met Ala Ala Leu Ser Gly Asn Lys Gln Thr Gly Gly
        355                 360                 365
```

Gln Asn Ala Gly Gly Gly Gly Ser Gly Gly Gly Ser Gly Gly Gly
    370                 375                 380

Gly Ser Gly Gly Gly Gly Ser Gly Gly Gly Gly Ser Met Val Ser Lys
385                 390                 395                 400

Gly Glu Ala Val Ile Lys Glu Phe Met Arg Phe Lys Val His Met Glu
                405                 410                 415

Gly Ser Met Asn Gly His Glu Phe Glu Ile Glu Gly Glu Gly Glu Gly
            420                 425                 430

Arg Pro Tyr Glu Gly Thr Gln Thr Ala Lys Leu Lys Val Thr Lys Gly
        435                 440                 445

Gly Pro Leu Pro Phe Ser Trp Asp Ile Leu Ser Pro Gln Phe Met Tyr
    450                 455                 460

Gly Ser Arg Ala Phe Ile Lys His Pro Ala Asp Ile Pro Asp Tyr Tyr
465                 470                 475                 480

Lys Gln Ser Phe Pro Glu Gly Phe Lys Trp Glu Arg Val Met Asn Phe
                485                 490                 495

Glu Asp Gly Gly Ala Val Thr Val Thr Gln Asp Thr Ser Leu Glu Asp
            500                 505                 510

Gly Thr Leu Ile Tyr Lys Val Lys Leu Arg Gly Thr Asn Phe Pro Pro
        515                 520                 525

Asp Gly Pro Val Met Gln Lys Lys Thr Met Gly Trp Glu Ala Ser Thr
    530                 535                 540

Glu Arg Leu Tyr Pro Glu Asp Gly Val Leu Lys Gly Asp Ile Lys Met
545                 550                 555                 560

Ala Leu Arg Leu Lys Asp Gly Gly Arg Tyr Leu Ala Asp Phe Lys Thr
                565                 570                 575

Thr Tyr Lys Ala Lys Lys Pro Val Gln Met Pro Gly Ala Tyr Asn Val
            580                 585                 590

Asp Arg Lys Leu Asp Ile Thr Ser His Asn Glu Asp Tyr Thr Val Val
        595                 600                 605

Glu Gln Tyr Glu Arg Ser Glu Gly Arg His Ser Thr Gly Gly Met Asp
    610                 615                 620

Glu Leu Tyr Lys
625

<210> SEQ ID NO 68
<211> LENGTH: 300
<212> TYPE: PRT
<213> ORGANISM: Artificial Sequence
<220> FEATURE:
<223> OTHER INFORMATION: synthetic polypeptide

<400> SEQUENCE: 68

Met Ala Glu Glu Val Lys Ala Val Ser Ala Ala Leu Ser Glu Arg Ile
1               5                   10                  15

Thr Gln Leu Ala Thr Glu Leu Asn Asp Lys Ala Val Arg Ala Ala Glu
            20                  25                  30

Arg Arg Val Ala Glu Val Thr Arg Ala Ala Gly Glu Gln Thr Ala Gln
        35                  40                  45

Ala Glu Arg Glu Leu Ala Asp Ala Ala Gln Thr Val Asp Asp Leu Glu
    50                  55                  60

Glu Lys Leu Asp Glu Leu Gln Asp Arg Tyr Asp Ser Leu Thr Leu Ala
65                  70                  75                  80

Leu Glu Ser Glu Arg Ser Leu Arg Gln Gln His Asp Val Lys Met Ala
                85                  90                  95

Gln Leu Lys Glu Arg Leu Ala Ala Ala Glu Asn Thr Arg Gln Arg
                100                 105                 110

Glu Glu Arg Tyr Gln Glu Gln Lys Thr Val Leu Gln Asp Ala Leu Asn
            115                 120                 125

Ala Glu Gln Ala Gln His Lys Asn Thr Arg Glu Asp Leu Gln Lys Arg
        130                 135                 140

Leu Glu Gln Ile Ser Ala Glu Ala Asn Ala Arg Thr Glu Glu Leu Lys
145                 150                 155                 160

Ser Glu Arg Asp Lys Val Asn Thr Leu Leu Thr Arg Leu Glu Ser Gln
                165                 170                 175

Glu Asn Ala Leu Ala Ser Glu Arg Gln Gln His Leu Ala Thr Arg Glu
            180                 185                 190

Thr Leu Gln Gln Arg Leu Glu Gln Ala Ile Ala Asp Thr Gln Ala Arg
        195                 200                 205

Ala Gly Glu Ile Ala Leu Glu Arg Asp Arg Val Ser Ser Leu Thr Ala
210                 215                 220

Arg Leu Glu Ser Gln Glu Lys Ala Ser Ser Glu Gln Leu Val Arg Met
225                 230                 235                 240

Gly Ser Glu Ile Ala Ser Leu Thr Glu Arg Cys Thr Gln Leu Glu Asn
                245                 250                 255

Gln Arg Asp Asp Ala Arg Leu Glu Thr Met Gly Glu Lys Glu Thr Val
            260                 265                 270

Ala Ala Leu Arg Gly Glu Ala Glu Leu Lys Arg Gln Asn Gln Ser
        275                 280                 285

Leu Met Ala Ala Leu Gly His His His His His
    290                 295                 300

<210> SEQ ID NO 69
<211> LENGTH: 300
<212> TYPE: PRT
<213> ORGANISM: Artificial Sequence
<220> FEATURE:
<223> OTHER INFORMATION: synthetic polypeptide

<400> SEQUENCE: 69

Met Ala Glu Glu Val Lys Ala Val Ser Ala Ala Leu Ser Glu Arg Ile
1               5                   10                  15

Thr Gln Leu Ala Thr Glu Leu Asn Asp Lys Ala Val Arg Ala Ala Glu
            20                  25                  30

Arg Arg Val Ala Glu Val Thr Arg Ala Ala Gly Glu Gln Thr Ala Gln
        35                  40                  45

Ala Glu Arg Glu Leu Ala Asp Ala Ala Gln Thr Val Asp Asp Leu Glu
    50                  55                  60

Glu Lys Leu Asp Glu Leu Gln Asp Arg Tyr Asp Ser Leu Thr Leu Ala
65                  70                  75                  80

Leu Glu Ser Glu Arg Ser Leu Arg Gln Gln His Asp Val Glu Met Ala
                85                  90                  95

Gln Leu Glu Glu Arg Leu Ala Ala Ala Glu Glu Asn Thr Arg Gln Arg
            100                 105                 110

Glu Glu Arg Tyr Gln Glu Gln Lys Thr Val Leu Gln Asp Ala Leu Asn
        115                 120                 125

Ala Glu Gln Ala Gln His Lys Asn Thr Arg Glu Asp Leu Gln Lys Arg
    130                 135                 140

Leu Glu Gln Ile Ser Ala Glu Ala Asn Ala Arg Thr Glu Glu Leu Lys
145                 150                 155                 160

Ser Glu Arg Asp Lys Val Asn Thr Leu Leu Thr Arg Leu Glu Ser Gln
                165                 170                 175

Glu Asn Ala Leu Ala Ser Glu Arg Gln Gln His Leu Ala Thr Arg Glu
            180                 185                 190

Thr Leu Gln Gln Arg Leu Glu Gln Ala Ile Ala Asp Thr Gln Ala Arg
        195                 200                 205

Ala Gly Glu Ile Ala Leu Glu Arg Asp Arg Val Ser Ser Leu Thr Ala
    210                 215                 220

Arg Leu Glu Ser Gln Glu Lys Ala Ser Ser Glu Gln Leu Val Arg Met
225                 230                 235                 240

Gly Ser Glu Ile Ala Ser Leu Thr Glu Arg Cys Thr Gln Leu Glu Asn
                245                 250                 255

Gln Arg Asp Asp Ala Arg Leu Glu Thr Met Gly Glu Lys Glu Thr Val
            260                 265                 270

Ala Ala Leu Arg Gly Glu Ala Glu Ala Leu Lys Arg Gln Asn Gln Ser
        275                 280                 285

Leu Met Ala Ala Leu Gly His His His His His
    290                 295                 300

<210> SEQ ID NO 70
<211> LENGTH: 300
<212> TYPE: PRT
<213> ORGANISM: Artificial Sequence
<220> FEATURE:
<223> OTHER INFORMATION: synthetic polypeptide

<400> SEQUENCE: 70

Met Ala Glu Glu Val Lys Ala Val Ser Ala Ala Leu Ser Glu Arg Ile
1               5                   10                  15

Thr Gln Leu Ala Thr Glu Leu Asn Asp Lys Ala Val Arg Ala Ala Glu
            20                  25                  30

Arg Arg Val Ala Glu Val Thr Arg Ala Ala Gly Glu Gln Thr Ala Gln
        35                  40                  45

Ala Glu Arg Glu Leu Ala Asp Ala Gln Thr Val Asp Asp Leu Glu
    50                  55                  60

Glu Lys Leu Asp Glu Leu Gln Asp Arg Tyr Asp Ser Leu Thr Leu Ala
65                  70                  75                  80

Leu Glu Ser Glu Arg Ser Leu Arg Gln Gln His Asp Val Glu Met Ala
                85                  90                  95

Gln Leu Lys Glu Arg Leu Ala Ala Glu Glu Asn Thr Arg Gln Arg
            100                 105                 110

Glu Glu Arg Tyr Gln Glu Gln Lys Thr Val Leu Gln Asp Ala Leu Asn
        115                 120                 125

Ala Glu Gln Ala Gln His Lys Asn Thr Arg Glu Asp Leu Gln Lys Arg
    130                 135                 140

Leu Glu Gln Ile Ser Ala Glu Ala Asn Ala Arg Thr Glu Arg Leu Lys
145                 150                 155                 160

Ser Arg Arg Asp Lys Val Asn Thr Leu Leu Thr Arg Leu Glu Ser Gln
                165                 170                 175

Glu Asn Ala Leu Ala Ser Glu Arg Gln Gln His Leu Ala Thr Arg Glu
            180                 185                 190

Thr Leu Gln Gln Arg Leu Glu Gln Ala Ile Ala Asp Thr Gln Ala Arg
        195                 200                 205

Ala Gly Glu Ile Ala Leu Glu Arg Asp Arg Val Ser Ser Leu Thr Ala
    210                 215                 220

```
Arg Leu Glu Ser Gln Glu Lys Ala Ser Ser Glu Gln Leu Val Arg Met
225                 230                 235                 240

Gly Ser Glu Ile Ala Ser Leu Thr Glu Arg Cys Thr Gln Leu Glu Asn
            245                 250                 255

Gln Arg Asp Asp Ala Arg Leu Glu Thr Met Gly Glu Lys Glu Thr Val
            260                 265                 270

Ala Ala Leu Arg Gly Glu Ala Glu Ala Leu Lys Arg Gln Asn Gln Ser
        275                 280                 285

Leu Met Ala Ala Leu Gly His His His His His
        290                 295                 300
```

<210> SEQ ID NO 71
<211> LENGTH: 300
<212> TYPE: PRT
<213> ORGANISM: Artificial Sequence
<220> FEATURE:
<223> OTHER INFORMATION: synthetic polypeptide

<400> SEQUENCE: 71

```
Met Ala Glu Glu Val Lys Ala Val Ser Ala Ala Leu Ser Glu Arg Ile
1               5                   10                  15

Thr Gln Leu Ala Thr Glu Leu Asn Asp Lys Ala Val Arg Ala Ala Glu
            20                  25                  30

Arg Arg Val Ala Glu Val Thr Arg Ala Ala Gly Glu Gln Thr Ala Gln
        35                  40                  45

Ala Glu Arg Glu Leu Ala Asp Ala Ala Gln Thr Val Asp Asp Leu Glu
    50                  55                  60

Glu Lys Leu Asp Glu Leu Gln Asp Arg Tyr Asp Ser Leu Thr Leu Ala
65                  70                  75                  80

Leu Glu Ser Glu Arg Ser Leu Arg Gln Gln His Asp Val Glu Met Ala
            85                  90                  95

Gln Leu Lys Glu Arg Leu Ala Ala Glu Glu Asn Thr Arg Gln Arg
        100                 105                 110

Glu Glu Arg Tyr Gln Glu Gln Lys Thr Val Leu Gln Asp Ala Leu Asn
    115                 120                 125

Ala Glu Gln Ala Gln His Lys Asn Thr Arg Glu Asp Leu Gln Lys Arg
    130                 135                 140

Leu Glu Gln Ile Ser Ala Glu Ala Asn Ala Arg Thr Glu Glu Leu Lys
145                 150                 155                 160

Ser Glu Arg Asp Lys Val Asn Thr Leu Leu Thr Glu Leu Glu Ser Gln
            165                 170                 175

Glu Asn Ala Leu Ala Ser Glu Arg Gln Gln His Leu Ala Thr Arg Glu
        180                 185                 190

Thr Leu Gln Gln Arg Leu Glu Gln Ala Ile Ala Asp Thr Gln Ala Arg
    195                 200                 205

Ala Gly Glu Ile Ala Leu Glu Arg Asp Arg Val Ser Ser Leu Thr Ala
    210                 215                 220

Arg Leu Glu Ser Gln Glu Lys Ala Ser Ser Glu Gln Leu Val Arg Met
225                 230                 235                 240

Gly Ser Glu Ile Ala Ser Leu Thr Glu Arg Cys Thr Gln Leu Glu Asn
            245                 250                 255

Gln Arg Asp Asp Ala Arg Leu Glu Thr Met Gly Glu Lys Glu Thr Val
        260                 265                 270

Ala Ala Leu Arg Gly Glu Ala Glu Ala Leu Lys Arg Gln Asn Gln Ser
    275                 280                 285
```

-continued

Leu Met Ala Ala Leu Gly His His His His His
    290                 295                 300

<210> SEQ ID NO 72
<211> LENGTH: 300
<212> TYPE: PRT
<213> ORGANISM: Artificial Sequence
<220> FEATURE:
<223> OTHER INFORMATION: synthetic polypeptide

<400> SEQUENCE: 72

Met Ala Glu Glu Val Lys Ala Val Ser Ala Ala Leu Ser Glu Arg Ile
1               5                   10                  15

Thr Gln Leu Ala Thr Glu Leu Asn Asp Lys Ala Val Arg Ala Ala Glu
            20                  25                  30

Arg Arg Val Ala Glu Val Thr Arg Ala Ala Gly Glu Gln Thr Ala Gln
        35                  40                  45

Ala Glu Arg Glu Leu Ala Asp Ala Ala Gln Thr Val Asp Asp Leu Glu
    50                  55                  60

Glu Lys Leu Asp Glu Leu Gln Asp Arg Tyr Asp Ser Leu Thr Leu Ala
65                  70                  75                  80

Leu Glu Ser Glu Arg Ser Leu Arg Gln Gln His Asp Val Glu Met Ala
                85                  90                  95

Gln Leu Lys Glu Arg Leu Ala Ala Ala Glu Glu Asn Thr Arg Gln Arg
            100                 105                 110

Glu Glu Arg Tyr Gln Glu Gln Lys Thr Val Leu Gln Asp Ala Leu Asn
        115                 120                 125

Ala Glu Gln Ala Gln His Lys Asn Thr Arg Glu Asp Leu Gln Lys Arg
    130                 135                 140

Leu Glu Gln Ile Ser Ala Glu Ala Asn Ala Arg Thr Glu Glu Leu Lys
145                 150                 155                 160

Ser Glu Arg Asp Lys Val Asn Thr Leu Leu Thr Arg Leu Glu Ser Gln
                165                 170                 175

Arg Asn Ala Leu Ala Ser Glu Arg Gln Gln His Leu Ala Thr Arg Glu
            180                 185                 190

Thr Leu Gln Gln Arg Leu Glu Gln Ala Ile Ala Asp Thr Gln Ala Arg
        195                 200                 205

Ala Gly Glu Ile Ala Leu Glu Arg Asp Arg Val Ser Ser Leu Thr Ala
    210                 215                 220

Arg Leu Glu Ser Gln Glu Lys Ala Ser Ser Glu Gln Leu Val Arg Met
225                 230                 235                 240

Gly Ser Glu Ile Ala Ser Leu Thr Glu Arg Cys Thr Gln Leu Glu Asn
                245                 250                 255

Gln Arg Asp Asp Ala Arg Leu Glu Thr Met Gly Glu Lys Glu Thr Val
            260                 265                 270

Ala Ala Leu Arg Gly Glu Ala Glu Ala Leu Lys Arg Gln Asn Gln Ser
        275                 280                 285

Leu Met Ala Ala Leu Gly His His His His His
    290                 295                 300

<210> SEQ ID NO 73
<211> LENGTH: 300
<212> TYPE: PRT
<213> ORGANISM: Artificial Sequence
<220> FEATURE:
<223> OTHER INFORMATION: synthetic polypeptide

<400> SEQUENCE: 73

```
Met Ala Glu Val Lys Ala Val Ser Ala Ala Leu Ser Glu Arg Ile
1               5                   10                  15

Thr Gln Leu Ala Thr Glu Leu Asn Asp Lys Ala Val Arg Ala Ala Glu
            20                  25                  30

Arg Arg Val Ala Glu Val Thr Arg Ala Ala Gly Glu Gln Thr Ala Gln
                35                  40                  45

Ala Glu Arg Glu Leu Ala Asp Ala Ala Gln Thr Val Asp Asp Leu Glu
        50                  55                  60

Glu Lys Leu Asp Glu Leu Gln Asp Arg Tyr Asp Ser Leu Thr Leu Ala
65                  70                  75                  80

Leu Glu Ser Glu Arg Ser Leu Arg Gln Gln His Asp Val Glu Met Ala
                85                  90                  95

Gln Leu Lys Glu Arg Leu Ala Ala Ala Glu Glu Asn Thr Arg Gln Arg
            100                 105                 110

Glu Glu Arg Tyr Gln Glu Gln Lys Thr Val Leu Gln Asp Ala Leu Asn
        115                 120                 125

Ala Glu Gln Ala Gln His Lys Asn Thr Arg Glu Asp Leu Gln Lys Arg
    130                 135                 140

Leu Glu Gln Ile Ser Ala Glu Ala Asn Ala Arg Thr Glu Glu Leu Lys
145                 150                 155                 160

Ser Glu Arg Asp Lys Val Asn Thr Leu Leu Thr Arg Leu Glu Ser Gln
                165                 170                 175

Glu Asn Ala Leu Ala Ser Glu Arg Gln Gln His Leu Ala Thr Arg Glu
            180                 185                 190

Thr Leu Gln Gln Arg Leu Glu Gln Ala Ile Ala Asp Thr Gln Ala Arg
        195                 200                 205

Ala Gly Glu Ile Ala Leu Arg Arg Asp Arg Val Ser Ser Leu Thr Ala
    210                 215                 220

Arg Leu Glu Ser Gln Glu Lys Ala Ser Ser Glu Gln Leu Val Arg Met
225                 230                 235                 240

Gly Ser Glu Ile Ala Ser Leu Thr Glu Arg Cys Thr Gln Leu Glu Asn
                245                 250                 255

Gln Arg Asp Asp Ala Arg Leu Glu Thr Met Gly Glu Lys Glu Thr Val
            260                 265                 270

Ala Ala Leu Arg Gly Glu Ala Glu Ala Leu Lys Arg Gln Asn Gln Ser
        275                 280                 285

Leu Met Ala Ala Leu Gly His His His His His
    290                 295                 300

<210> SEQ ID NO 74
<211> LENGTH: 300
<212> TYPE: PRT
<213> ORGANISM: Artificial Sequence
<220> FEATURE:
<223> OTHER INFORMATION: synthetic polypeptide

<400> SEQUENCE: 74

Met Ala Glu Val Lys Ala Val Ser Ala Ala Leu Ser Glu Arg Ile
1               5                   10                  15

Thr Gln Leu Ala Thr Glu Leu Asn Asp Lys Ala Val Arg Ala Ala Glu
            20                  25                  30

Arg Arg Val Ala Glu Val Thr Arg Ala Ala Gly Glu Gln Thr Ala Gln
                35                  40                  45

Ala Glu Arg Glu Leu Ala Asp Ala Ala Gln Thr Val Asp Asp Leu Glu
        50                  55                  60
```

```
Glu Lys Leu Asp Glu Leu Gln Asp Arg Tyr Asp Ser Leu Thr Leu Ala
 65                  70                  75                  80

Leu Glu Ser Glu Arg Ser Leu Arg Gln Gln His Asp Val Glu Met Ala
                 85                  90                  95

Gln Leu Lys Glu Arg Leu Ala Ala Ala Glu Glu Asn Thr Arg Gln Arg
            100                 105                 110

Glu Glu Arg Tyr Gln Glu Gln Lys Thr Val Leu Gln Asp Ala Leu Asn
        115                 120                 125

Ala Glu Gln Ala Gln His Lys Asn Thr Arg Glu Asp Leu Gln Lys Arg
130                 135                 140

Leu Glu Gln Ile Ser Ala Glu Ala Asn Ala Arg Thr Glu Glu Leu Lys
145                 150                 155                 160

Ser Glu Arg Asp Lys Val Asn Thr Leu Leu Thr Arg Leu Glu Ser Gln
                165                 170                 175

Glu Asn Ala Leu Ala Ser Glu Arg Gln Gln His Leu Ala Thr Arg Glu
            180                 185                 190

Thr Leu Gln Gln Arg Leu Glu Gln Ala Ile Ala Asp Thr Gln Ala Arg
        195                 200                 205

Ala Gly Glu Ile Ala Leu Glu Glu Asp Arg Val Ser Ser Leu Thr Ala
210                 215                 220

Arg Leu Glu Ser Gln Glu Lys Ala Ser Ser Glu Gln Leu Val Arg Met
225                 230                 235                 240

Gly Ser Glu Ile Ala Ser Leu Thr Glu Arg Cys Thr Gln Leu Glu Asn
                245                 250                 255

Gln Arg Asp Asp Ala Arg Leu Glu Thr Met Gly Glu Lys Glu Thr Val
            260                 265                 270

Ala Ala Leu Arg Gly Glu Ala Glu Ala Leu Lys Arg Gln Asn Gln Ser
        275                 280                 285

Leu Met Ala Ala Leu Gly His His His His His
        290                 295                 300

<210> SEQ ID NO 75
<211> LENGTH: 300
<212> TYPE: PRT
<213> ORGANISM: Artificial Sequence
<220> FEATURE:
<223> OTHER INFORMATION: synthetic polypeptide

<400> SEQUENCE: 75

Met Ala Glu Glu Val Lys Ala Val Ser Ala Ala Leu Ser Glu Arg Ile
  1               5                  10                  15

Thr Gln Leu Ala Thr Glu Leu Asn Asp Lys Ala Val Arg Ala Ala Glu
             20                  25                  30

Arg Arg Val Ala Glu Val Thr Arg Ala Ala Gly Glu Gln Thr Ala Gln
         35                  40                  45

Ala Glu Arg Glu Leu Ala Asp Ala Ala Gln Thr Val Asp Asp Leu Glu
 50                  55                  60

Glu Lys Leu Asp Glu Leu Gln Asp Arg Tyr Asp Ser Leu Thr Leu Ala
 65                  70                  75                  80

Leu Glu Ser Glu Arg Ser Leu Arg Gln Gln His Asp Val Glu Met Ala
                 85                  90                  95

Gln Leu Lys Glu Arg Leu Ala Ala Ala Glu Glu Asn Thr Arg Gln Arg
            100                 105                 110

Glu Glu Arg Tyr Gln Glu Gln Lys Thr Val Leu Gln Asp Ala Leu Asn
        115                 120                 125
```

```
Ala Glu Gln Ala Gln His Lys Asn Thr Arg Glu Asp Leu Gln Lys Arg
        130                 135                 140

Leu Glu Gln Ile Ser Ala Glu Ala Asn Ala Arg Thr Glu Glu Leu Lys
145                 150                 155                 160

Ser Glu Arg Asp Lys Val Asn Thr Leu Leu Thr Arg Leu Glu Ser Gln
                165                 170                 175

Glu Asn Ala Leu Ala Ser Glu Arg Gln Gln His Leu Ala Thr Arg Glu
            180                 185                 190

Thr Leu Gln Gln Arg Leu Glu Gln Ala Ile Ala Asp Thr Gln Ala Arg
        195                 200                 205

Ala Gly Glu Ile Ala Leu Glu Arg Asp Arg Val Ser Ser Leu Thr Ala
    210                 215                 220

Glu Leu Glu Ser Gln Glu Lys Ala Ser Ser Glu Gln Leu Val Arg Met
225                 230                 235                 240

Gly Ser Glu Ile Ala Ser Leu Thr Glu Arg Cys Thr Gln Leu Glu Asn
                245                 250                 255

Gln Arg Asp Asp Ala Arg Leu Glu Thr Met Gly Glu Lys Glu Thr Val
            260                 265                 270

Ala Ala Leu Arg Gly Glu Ala Glu Ala Leu Lys Arg Gln Asn Gln Ser
        275                 280                 285

Leu Met Ala Ala Leu Gly His His His His His His
    290                 295                 300

<210> SEQ ID NO 76
<211> LENGTH: 300
<212> TYPE: PRT
<213> ORGANISM: Artificial Sequence
<220> FEATURE:
<223> OTHER INFORMATION: synthetic polypeptide

<400> SEQUENCE: 76

Met Ala Glu Glu Val Lys Ala Val Ser Ala Ala Leu Ser Glu Arg Ile
1               5                   10                  15

Thr Gln Leu Ala Thr Glu Leu Asn Asp Lys Ala Val Arg Ala Ala Glu
            20                  25                  30

Arg Arg Val Ala Glu Val Thr Arg Ala Ala Gly Glu Gln Thr Ala Gln
        35                  40                  45

Ala Glu Arg Glu Leu Ala Asp Ala Ala Gln Thr Val Asp Asp Leu Glu
    50                  55                  60

Glu Lys Leu Asp Glu Leu Gln Asp Arg Tyr Asp Ser Leu Thr Leu Ala
65                  70                  75                  80

Leu Glu Ser Glu Arg Ser Leu Arg Gln Gln His Asp Val Glu Met Ala
                85                  90                  95

Gln Leu Lys Glu Arg Leu Ala Ala Glu Glu Asn Thr Arg Gln Arg
            100                 105                 110

Glu Glu Arg Tyr Gln Glu Gln Lys Thr Val Leu Gln Asp Ala Leu Asn
        115                 120                 125

Ala Glu Gln Ala Gln His Lys Asn Thr Arg Glu Asp Leu Gln Lys Arg
    130                 135                 140

Leu Glu Gln Ile Ser Ala Glu Ala Asn Ala Arg Thr Glu Glu Leu Lys
145                 150                 155                 160

Ser Glu Arg Asp Lys Val Asn Thr Leu Leu Thr Arg Leu Glu Ser Gln
                165                 170                 175

Glu Asn Ala Leu Ala Ser Glu Arg Gln Gln His Leu Ala Thr Arg Glu
            180                 185                 190
```

-continued

```
Thr Leu Gln Gln Arg Leu Glu Gln Ala Ile Ala Asp Thr Gln Ala Arg
            195                 200                 205

Ala Gly Glu Ile Ala Leu Glu Arg Asp Arg Val Ser Ser Leu Thr Ala
        210                 215                 220

Arg Leu Glu Ser Gln Arg Lys Ala Ser Ser Glu Gln Leu Val Arg Met
225                 230                 235                 240

Gly Ser Glu Ile Ala Ser Leu Thr Glu Arg Cys Thr Gln Leu Glu Asn
                245                 250                 255

Gln Arg Asp Asp Ala Arg Leu Glu Thr Met Gly Glu Lys Glu Thr Val
            260                 265                 270

Ala Ala Leu Arg Gly Glu Ala Glu Leu Lys Arg Gln Asn Gln Ser
        275                 280                 285

Leu Met Ala Ala Leu Gly His His His His His
        290                 295                 300

<210> SEQ ID NO 77
<211> LENGTH: 300
<212> TYPE: PRT
<213> ORGANISM: Artificial Sequence
<220> FEATURE:
<223> OTHER INFORMATION: synthetic polypeptide

<400> SEQUENCE: 77

Met Ala Glu Glu Val Lys Ala Val Ser Ala Ala Leu Ser Glu Arg Ile
1               5                   10                  15

Thr Gln Leu Ala Thr Glu Leu Asn Asp Lys Ala Val Arg Ala Ala Glu
            20                  25                  30

Arg Arg Val Ala Glu Val Thr Arg Ala Ala Gly Glu Gln Thr Ala Gln
        35                  40                  45

Ala Glu Arg Glu Leu Ala Asp Ala Ala Gln Thr Val Asp Asp Leu Glu
    50                  55                  60

Glu Lys Leu Asp Glu Leu Gln Asp Arg Tyr Asp Ser Leu Thr Leu Ala
65                  70                  75                  80

Leu Glu Ser Glu Arg Ser Leu Arg Gln Gln His Asp Val Glu Met Ala
                85                  90                  95

Gln Leu Lys Glu Arg Leu Ala Ala Ala Glu Glu Asn Thr Arg Gln Arg
            100                 105                 110

Glu Glu Arg Tyr Gln Glu Gln Lys Thr Val Leu Gln Asp Ala Leu Asn
        115                 120                 125

Ala Glu Gln Ala Gln His Lys Asn Thr Arg Glu Asp Leu Gln Lys Arg
    130                 135                 140

Leu Glu Gln Ile Ser Ala Glu Ala Asn Ala Arg Thr Glu Glu Leu Lys
145                 150                 155                 160

Ser Glu Arg Asp Lys Val Asn Thr Leu Leu Thr Arg Leu Glu Ser Gln
                165                 170                 175

Glu Asn Ala Leu Ala Ser Glu Arg Gln Gln His Leu Ala Thr Arg Glu
            180                 185                 190

Thr Leu Gln Gln Arg Leu Glu Gln Ala Ile Ala Asp Thr Gln Ala Arg
        195                 200                 205

Ala Gly Glu Ile Ala Leu Glu Arg Asp Arg Val Ser Ser Leu Thr Ala
    210                 215                 220

Arg Leu Glu Ser Gln Arg Lys Ala Ser Ser Glu Gln Leu Val Arg Met
225                 230                 235                 240

Gly Ser Glu Ile Ala Ser Leu Thr Glu Glu Cys Thr Gln Leu Glu Asn
                245                 250                 255
```

```
Gln Arg Asp Asp Ala Arg Leu Glu Thr Met Gly Glu Lys Glu Thr Val
            260                 265                 270

Ala Ala Leu Arg Gly Glu Ala Glu Ala Leu Lys Arg Gln Asn Gln Ser
        275                 280                 285

Leu Met Ala Ala Leu Gly His His His His His His
    290                 295                 300

<210> SEQ ID NO 78
<211> LENGTH: 300
<212> TYPE: PRT
<213> ORGANISM: Artificial Sequence
<220> FEATURE:
<223> OTHER INFORMATION: synthetic polypeptide

<400> SEQUENCE: 78

Met Ala Glu Glu Val Lys Ala Val Ser Ala Ala Leu Ser Glu Arg Ile
1               5                   10                  15

Thr Gln Leu Ala Thr Glu Leu Asn Asp Lys Ala Val Arg Ala Ala Glu
            20                  25                  30

Arg Arg Val Ala Glu Val Thr Arg Ala Ala Gly Glu Gln Thr Ala Gln
        35                  40                  45

Ala Glu Arg Glu Leu Ala Asp Ala Ala Gln Thr Val Asp Asp Leu Glu
    50                  55                  60

Glu Lys Leu Asp Glu Leu Gln Asp Arg Tyr Asp Ser Leu Thr Leu Ala
65                  70                  75                  80

Leu Glu Ser Glu Arg Ser Leu Arg Gln Gln His Asp Val Glu Met Ala
                85                  90                  95

Gln Leu Lys Glu Arg Leu Ala Ala Ala Glu Glu Asn Thr Arg Gln Arg
            100                 105                 110

Glu Glu Arg Tyr Gln Glu Gln Lys Thr Val Leu Gln Asp Ala Leu Asn
        115                 120                 125

Ala Glu Gln Ala Gln His Lys Asn Thr Arg Glu Asp Leu Gln Lys Arg
    130                 135                 140

Leu Glu Gln Ile Ser Ala Glu Ala Asn Ala Arg Thr Glu Glu Leu Lys
145                 150                 155                 160

Ser Glu Arg Asp Lys Val Asn Thr Leu Leu Thr Arg Leu Glu Ser Gln
                165                 170                 175

Glu Asn Ala Leu Ala Ser Glu Arg Gln Gln His Leu Ala Thr Arg Glu
            180                 185                 190

Thr Leu Gln Gln Arg Leu Glu Gln Ala Ile Ala Asp Thr Gln Ala Arg
        195                 200                 205

Ala Gly Glu Ile Ala Leu Glu Arg Asp Arg Val Ser Ser Leu Thr Ala
    210                 215                 220

Arg Leu Glu Ser Gln Glu Lys Ala Ser Ser Glu Gln Leu Val Arg Met
225                 230                 235                 240

Gly Ser Glu Ile Ala Ser Leu Thr Glu Arg Cys Thr Gln Leu Arg Asn
                245                 250                 255

Gln Arg Asp Asp Ala Arg Leu Glu Thr Met Gly Glu Lys Glu Thr Val
            260                 265                 270

Ala Ala Leu Arg Gly Glu Ala Glu Ala Leu Lys Arg Gln Asn Gln Ser
        275                 280                 285

Leu Met Ala Ala Leu Gly His His His His His His
    290                 295                 300

<210> SEQ ID NO 79
```

<211> LENGTH: 300
<212> TYPE: PRT
<213> ORGANISM: Artificial Sequence
<220> FEATURE:
<223> OTHER INFORMATION: synthetic polypeptide

<400> SEQUENCE: 79

```
Met Ala Glu Glu Val Lys Ala Val Ser Ala Ala Leu Ser Glu Arg Ile
1               5                   10                  15

Thr Gln Leu Ala Thr Glu Leu Asn Asp Lys Ala Val Arg Ala Ala Glu
            20                  25                  30

Arg Arg Val Ala Glu Val Thr Arg Ala Ala Gly Glu Gln Thr Ala Gln
        35                  40                  45

Ala Glu Arg Glu Leu Ala Asp Ala Gln Thr Val Asp Asp Leu Glu
    50                  55                  60

Glu Lys Leu Asp Glu Leu Gln Asp Arg Tyr Asp Ser Leu Thr Leu Ala
65                  70                  75                  80

Leu Glu Ser Glu Arg Ser Leu Arg Gln Gln His Asp Val Glu Met Ala
                85                  90                  95

Gln Leu Lys Glu Arg Leu Ala Ala Ala Glu Glu Asn Thr Arg Gln Arg
            100                 105                 110

Glu Glu Arg Tyr Gln Glu Gln Lys Thr Val Leu Gln Asp Ala Leu Asn
        115                 120                 125

Ala Glu Gln Ala Gln His Lys Asn Thr Arg Gly Asp Leu Gln Lys Arg
    130                 135                 140

Leu Glu Gln Ile Ser Ala Glu Ala Asn Ala Arg Thr Glu Glu Leu Lys
145                 150                 155                 160

Ser Glu Arg Asp Lys Val Asn Thr Leu Leu Thr Arg Leu Glu Ser Gln
                165                 170                 175

Glu Asn Ala Leu Ala Ser Glu Arg Gln Gln His Leu Ala Thr Arg Glu
            180                 185                 190

Thr Leu Gln Gln Arg Leu Glu Gln Ala Ile Ala Asp Thr Gln Ala Arg
        195                 200                 205

Ala Gly Glu Ile Ala Leu Glu Arg Asp Arg Val Ser Ser Leu Thr Ala
    210                 215                 220

Arg Leu Glu Ser Gln Glu Lys Ala Ser Ser Glu Gln Leu Val Arg Met
225                 230                 235                 240

Gly Ser Glu Ile Ala Ser Leu Thr Glu Arg Cys Thr Gln Leu Glu Asn
                245                 250                 255

Gln Arg Asp Asp Ala Arg Leu Lys Thr Met Gly Glu Lys Glu Thr Val
            260                 265                 270

Ala Ala Leu Arg Gly Glu Ala Glu Ala Leu Lys Arg Gln Asn Gln Ser
        275                 280                 285

Leu Met Ala Ala Leu Gly His His His His His
    290                 295                 300
```

<210> SEQ ID NO 80
<211> LENGTH: 300
<212> TYPE: PRT
<213> ORGANISM: Artificial Sequence
<220> FEATURE:
<223> OTHER INFORMATION: synthetic polypeptide

<400> SEQUENCE: 80

```
Met Ala Glu Glu Val Lys Ala Val Ser Ala Ala Leu Ser Glu Arg Ile
1               5                   10                  15

Thr Gln Leu Ala Thr Glu Leu Asn Asp Lys Ala Val Arg Ala Ala Glu
```

```
                    20                  25                  30
Arg Arg Val Ala Glu Val Thr Arg Ala Ala Gly Glu Gln Thr Ala Gln
                35                  40                  45
Ala Glu Arg Glu Leu Ala Asp Ala Ala Gln Thr Val Asp Asp Leu Glu
            50                  55                  60
Glu Lys Leu Asp Glu Leu Gln Asp Arg Tyr Asp Ser Leu Thr Leu Ala
65                  70                  75                  80
Leu Glu Ser Glu Arg Ser Leu Arg Gln Gln His Asp Val Glu Met Ala
                85                  90                  95
Gln Leu Lys Glu Arg Leu Ala Ala Glu Glu Asn Thr Arg Gln Arg
            100                 105                 110
Glu Glu Arg Tyr Gln Glu Gln Lys Thr Val Leu Gln Asp Ala Leu Asn
            115                 120                 125
Ala Glu Gln Ala Gln His Lys Asn Thr Arg Glu Asp Leu Gln Lys Arg
        130                 135                 140
Leu Glu Gln Ile Ser Ala Glu Ala Asn Ala Arg Thr Glu Glu Leu Lys
145                 150                 155                 160
Ser Glu Arg Asp Lys Val Asn Thr Leu Leu Thr Arg Leu Glu Ser Gln
                165                 170                 175
Glu Asn Ala Leu Ala Ser Glu Arg Gln Gln His Leu Ala Thr Arg Glu
            180                 185                 190
Thr Leu Gln Gln Arg Leu Glu Gln Ala Ile Ala Asp Thr Gln Ala Arg
        195                 200                 205
Ala Gly Glu Ile Ala Leu Glu Arg Asp Arg Val Ser Ser Leu Thr Ala
    210                 215                 220
Arg Leu Glu Ser Gln Glu Lys Ala Ser Ser Glu Gln Leu Val Arg Met
225                 230                 235                 240
Gly Ser Glu Ile Ala Ser Leu Thr Glu Arg Cys Thr Gln Leu Glu Asn
                245                 250                 255
Gln Arg Asp Asp Ala Arg Leu Glu Thr Met Gly Lys Lys Glu Thr Val
            260                 265                 270
Ala Ala Leu Arg Gly Glu Ala Glu Ala Leu Lys Arg Gln Asn Gln Ser
        275                 280                 285
Leu Met Ala Ala Leu Gly His His His His His
    290                 295                 300

<210> SEQ ID NO 81
<211> LENGTH: 300
<212> TYPE: PRT
<213> ORGANISM: Artificial Sequence
<220> FEATURE:
<223> OTHER INFORMATION: synthetic polypeptide

<400> SEQUENCE: 81

Met Ala Glu Glu Val Lys Ala Val Ser Ala Ala Leu Ser Glu Arg Ile
1               5                   10                  15
Thr Gln Leu Ala Thr Glu Leu Asn Asp Lys Ala Val Arg Ala Ala Glu
                20                  25                  30
Arg Arg Val Ala Glu Val Thr Arg Ala Ala Gly Glu Gln Thr Ala Gln
            35                  40                  45
Ala Glu Arg Glu Leu Ala Asp Ala Ala Gln Thr Val Asp Asp Leu Glu
        50                  55                  60
Glu Lys Leu Asp Glu Leu Gln Asp Arg Tyr Asp Ser Leu Thr Leu Ala
65                  70                  75                  80
Leu Glu Ser Glu Arg Ser Leu Arg Gln Gln His Asp Val Glu Met Ala
```

```
                        85                  90                  95
Gln Leu Lys Glu Arg Leu Ala Ala Ala Glu Glu Asn Thr Arg Gln Arg
                100                 105                 110
Glu Glu Arg Tyr Gln Glu Gln Lys Thr Val Leu Gln Asp Ala Leu Asn
            115                 120                 125
Ala Glu Gln Ala Gln His Lys Asn Thr Arg Glu Asp Leu Gln Lys Arg
        130                 135                 140
Leu Glu Gln Ile Ser Ala Glu Ala Asn Ala Arg Thr Glu Glu Leu Lys
145                 150                 155                 160
Ser Glu Arg Asp Lys Val Asn Thr Leu Leu Thr Arg Leu Glu Ser Gln
                165                 170                 175
Glu Asn Ala Leu Ala Ser Glu Arg Gln Gln His Leu Ala Thr Arg Glu
                180                 185                 190
Thr Leu Gln Gln Arg Leu Glu Gln Ala Ile Ala Asp Thr Gln Ala Arg
            195                 200                 205
Ala Gly Glu Ile Ala Leu Glu Arg Asp Arg Val Ser Ser Leu Thr Ala
        210                 215                 220
Arg Leu Glu Ser Gln Glu Lys Ala Ser Ser Glu Gln Leu Val Arg Met
225                 230                 235                 240
Gly Ser Glu Ile Ala Ser Leu Thr Glu Arg Cys Thr Gln Leu Glu Asn
                245                 250                 255
Gln Arg Asp Asp Ala Arg Leu Glu Thr Met Gly Glu Glu Glu Thr Val
                260                 265                 270
Ala Ala Leu Arg Gly Glu Ala Glu Ala Leu Lys Arg Gln Asn Gln Ser
            275                 280                 285
Leu Met Ala Ala Leu Gly His His His His His
        290                 295                 300

<210> SEQ ID NO 82
<211> LENGTH: 300
<212> TYPE: PRT
<213> ORGANISM: Artificial Sequence
<220> FEATURE:
<223> OTHER INFORMATION: synthetic polypeptide

<400> SEQUENCE: 82

Met Ala Glu Glu Val Lys Ala Val Ser Ala Ala Leu Ser Glu Arg Ile
1               5                   10                  15
Thr Gln Leu Ala Thr Glu Leu Asn Asp Lys Ala Val Arg Ala Ala Glu
                20                  25                  30
Arg Arg Val Ala Glu Val Thr Arg Ala Ala Gly Glu Gln Thr Ala Gln
            35                  40                  45
Ala Glu Arg Glu Leu Ala Asp Ala Ala Gln Thr Val Asp Asp Leu Glu
        50                  55                  60
Glu Lys Leu Asp Glu Leu Gln Asp Arg Tyr Asp Ser Leu Thr Leu Ala
65                  70                  75                  80
Leu Glu Ser Glu Arg Ser Leu Arg Gln Gln His Asp Val Glu Met Ala
                85                  90                  95
Gln Leu Lys Glu Arg Leu Ala Ala Ala Glu Glu Asn Thr Arg Gln Arg
                100                 105                 110
Glu Glu Arg Tyr Gln Glu Gln Lys Thr Val Leu Gln Asp Ala Leu Asn
            115                 120                 125
Ala Glu Gln Ala Gln His Lys Asn Thr Arg Glu Asp Leu Gln Lys Arg
        130                 135                 140
Leu Glu Gln Ile Ser Ala Glu Ala Asn Ala Arg Thr Glu Glu Leu Lys
```

```
            145                 150                 155                 160
Ser Glu Arg Asp Lys Val Asn Thr Leu Leu Thr Arg Leu Glu Ser Gln
                165                 170                 175
Glu Asn Ala Leu Ala Ser Glu Arg Gln Gln His Leu Ala Thr Arg Glu
            180                 185                 190
Thr Leu Gln Gln Arg Leu Glu Gln Ala Ile Ala Asp Thr Gln Ala Arg
        195                 200                 205
Ala Gly Glu Ile Ala Leu Glu Arg Asp Arg Val Ser Ser Leu Thr Ala
    210                 215                 220
Arg Leu Glu Ser Gln Glu Lys Ala Ser Glu Gln Leu Val Arg Met
225                 230                 235                 240
Gly Ser Glu Ile Ala Ser Leu Thr Glu Arg Cys Thr Gln Leu Glu Asn
                245                 250                 255
Gln Arg Asp Asp Ala Arg Leu Lys Thr Met Gly Lys Lys Glu Thr Val
                260                 265                 270
Ala Ala Leu Arg Gly Glu Ala Glu Ala Leu Lys Arg Gln Asn Gln Ser
            275                 280                 285
Leu Met Ala Ala Leu Gly His His His His His
        290                 295                 300

<210> SEQ ID NO 83
<211> LENGTH: 300
<212> TYPE: PRT
<213> ORGANISM: Artificial Sequence
<220> FEATURE:
<223> OTHER INFORMATION: synthetic polypeptide

<400> SEQUENCE: 83

Met Ala Glu Glu Val Lys Ala Val Ser Ala Ala Leu Ser Glu Arg Ile
1               5                   10                  15
Thr Gln Leu Ala Thr Glu Leu Asn Asp Lys Ala Val Arg Ala Ala Glu
            20                  25                  30
Arg Arg Val Ala Glu Val Thr Arg Ala Ala Gly Glu Gln Thr Ala Gln
        35                  40                  45
Ala Glu Arg Glu Leu Ala Asp Ala Ala Gln Thr Val Asp Asp Leu Glu
    50                  55                  60
Glu Lys Leu Asp Glu Leu Gln Asp Arg Tyr Asp Ser Leu Thr Leu Ala
65                  70                  75                  80
Leu Glu Ser Glu Arg Ser Leu Arg Gln Gln His Asp Val Glu Met Ala
                85                  90                  95
Gln Leu Lys Glu Arg Leu Ala Ala Ala Glu Glu Asn Thr Arg Gln Arg
            100                 105                 110
Glu Glu Arg Tyr Gln Glu Gln Lys Thr Val Leu Gln Asp Ala Leu Asn
        115                 120                 125
Ala Glu Gln Ala Gln His Lys Asn Thr Arg Glu Asp Leu Gln Lys Arg
    130                 135                 140
Leu Glu Gln Ile Ser Ala Glu Ala Asn Ala Arg Thr Glu Glu Leu Lys
145                 150                 155                 160
Ser Glu Arg Asp Lys Val Asn Thr Leu Leu Thr Arg Leu Glu Ser Gln
                165                 170                 175
Glu Asn Ala Leu Ala Ser Glu Arg Gln Gln His Leu Ala Thr Arg Glu
            180                 185                 190
Thr Leu Gln Gln Arg Leu Glu Gln Ala Ile Ala Asp Thr Gln Ala Arg
        195                 200                 205
Ala Gly Glu Ile Ala Leu Glu Arg Asp Arg Val Ser Ser Leu Thr Ala
```

```
                210                 215                 220
Arg Leu Glu Ser Gln Glu Lys Ala Ser Ser Glu Gln Leu Val Arg Met
225                 230                 235                 240

Gly Ser Glu Ile Ala Ser Leu Thr Glu Arg Cys Thr Gln Leu Glu Asn
                245                 250                 255

Gln Arg Asp Asp Ala Arg Leu Glu Thr Met Gly Glu Lys Glu Thr Val
            260                 265                 270

Ala Ala Leu Arg Gly Lys Ala Glu Ala Leu Lys Arg Gln Asn Gln Ser
        275                 280                 285

Leu Met Ala Ala Leu Gly His His His His His
    290                 295                 300

<210> SEQ ID NO 84
<211> LENGTH: 300
<212> TYPE: PRT
<213> ORGANISM: Artificial Sequence
<220> FEATURE:
<223> OTHER INFORMATION: synthetic polypeptide

<400> SEQUENCE: 84

Met Ala Glu Glu Val Lys Ala Val Ser Ala Ala Leu Ser Glu Arg Ile
1               5                   10                  15

Thr Gln Leu Ala Thr Glu Leu Asn Asp Lys Ala Val Arg Ala Ala Glu
                20                  25                  30

Arg Arg Val Ala Glu Val Thr Arg Ala Ala Gly Glu Gln Thr Ala Gln
            35                  40                  45

Ala Glu Arg Glu Leu Ala Asp Ala Ala Gln Thr Val Asp Asp Leu Glu
        50                  55                  60

Glu Lys Leu Asp Glu Leu Gln Asp Arg Tyr Asp Ser Leu Thr Leu Ala
65                  70                  75                  80

Leu Glu Ser Glu Arg Ser Leu Arg Gln Gln His Asp Val Glu Met Ala
                85                  90                  95

Gln Leu Lys Glu Arg Leu Ala Ala Ala Glu Glu Asn Thr Arg Gln Arg
                100                 105                 110

Glu Glu Arg Tyr Gln Glu Gln Lys Thr Val Leu Gln Asp Ala Leu Asn
            115                 120                 125

Ala Glu Gln Ala Gln His Lys Asn Thr Arg Glu Asp Leu Gln Lys Arg
        130                 135                 140

Leu Glu Gln Ile Ser Ala Gly Ala Asn Ala Arg Thr Glu Glu Leu Lys
145                 150                 155                 160

Ser Glu Arg Asp Lys Val Asn Thr Leu Leu Thr Arg Leu Glu Ser Gln
                165                 170                 175

Glu Asn Ala Leu Ala Ser Glu Arg Gln Gln His Leu Ala Thr Arg Glu
                180                 185                 190

Thr Leu Gln Gln Arg Leu Glu Gln Ala Ile Ala Asp Thr Gln Ala Arg
            195                 200                 205

Ala Gly Glu Ile Ala Leu Glu Arg Asp Arg Val Ser Ser Leu Thr Ala
        210                 215                 220

Arg Leu Glu Ser Gln Glu Lys Ala Ser Ser Glu Gln Leu Val Arg Met
225                 230                 235                 240

Gly Ser Glu Ile Ala Ser Leu Thr Glu Arg Cys Thr Gln Leu Glu Asn
                245                 250                 255

Gln Arg Asp Asp Ala Arg Leu Glu Thr Met Gly Glu Lys Glu Thr Val
            260                 265                 270

Ala Ala Leu Arg Gly Glu Ala Glu Ala Leu Glu Arg Gln Asn Gln Ser
```

```
                  275                 280                 285
Leu Met Ala Ala Leu Gly His His His His His His
          290                 295                 300
```